United States Patent
Fujita et al.

(10) Patent No.: US 6,187,821 B1
(45) Date of Patent: Feb. 13, 2001

(54) BENZENE COMPOUND AND PHARMACEUTICAL USE THEREOF

(75) Inventors: Tetsuro Fujita, Muko; Kunitomo Adachi, Fukuoka; Toshiyuki Kohara; Masatoshi Kiuchi, both of Iruma; Kenji Chiba, Fukuoka; Koji Teshima, Iruma; Tadashi Mishina, Fukuoka, all of (JP)

(73) Assignee: Welfide Corporation, Osaka (JP)

(*) Notice: Under 35 U.S.C. 154(b), the term of this patent shall be extended for 0 days.

(21) Appl. No.: 09/309,818

(22) Filed: May 12, 1999

Related U.S. Application Data

(60) Division of application No. 08/801,390, filed on Feb. 20, 1997, now Pat. No. 5,948,820, which is a continuation-in-part of application No. PCT/JP95/01654, filed on Aug. 22, 1995.

(30) Foreign Application Priority Data

Aug. 22, 1994 (JP) .................................... 6-196888
Apr. 7, 1995 (JP) .................................... 7-82934
Jul. 7, 1995 (JP) .................................... 7-172543

(51) Int. Cl.$^7$ ........................ A61K 31/135; C07C 217/64
(52) U.S. Cl. ................... 514/653; 514/487; 514/546; 514/630; 560/29; 560/254; 564/219; 564/355
(58) Field of Search .................... 560/29, 254; 564/219, 564/355; 514/487, 546, 630, 653

(56) References Cited

U.S. PATENT DOCUMENTS

| | | | |
|---|---|---|---|
| 3,062,839 | 11/1962 | Shetty et al. | 260/347.7 |
| 3,928,572 | 12/1975 | Kluepfel et al. | 424/122 |
| 4,634,689 | 1/1987 | Witkowski et al. | 514/80 |
| 4,667,038 | 5/1987 | Clark et al. | 546/145 |
| 4,910,218 | 3/1990 | Bair | 514/443 |
| 5,039,706 | 8/1991 | Wilkerson | 514/649 |
| 5,068,247 | 11/1991 | Fujita et al. | 514/440 |
| 5,245,080 | 9/1993 | Aubard et al. | 564/346 |
| 5,604,229 | * 2/1997 | Fujita et al. | 514/255 |

FOREIGN PATENT DOCUMENTS

| | | |
|---|---|---|
| 0 083 172 | 7/1983 | (EP) . |
| 0 105 696 | 4/1984 | (EP) . |
| 167 459 | 1/1986 | (EP) . |
| 0 288 188 | 10/1988 | (EP) . |
| 0 345 775 | 12/1989 | (EP) . |
| 0 490 823 | 6/1992 | (EP) . |
| 0 520 336 | 12/1992 | (EP) . |
| 0 534 553 | 3/1993 | (EP) . |
| 1 134 687 | 11/1968 | (GB) . |
| 2 054 588 | 2/1981 | (GB) . |
| 2 091 250 | 7/1982 | (GB) . |
| 58-105946 | 6/1983 | (JP) . |
| 59-44345 | 3/1984 | (JP) . |
| 59-192962 | 11/1984 | (JP) . |
| 62-416 | 1/1986 | (JP) . |
| 63-139179 | 6/1988 | (JP) . |
| 1-104087 | 4/1989 | (JP) . |
| 92/16236 | 10/1992 | (WO) . |

OTHER PUBLICATIONS

The Merck Index, Rahway, N.J., 11th edition, Index No. 460, 1989, p. 73.
The Merck Index, Rahway, N.J., 11th edition, Index No. 451, 1989, p. 72.
The Merck Index, Rahway, N.J., 11th edition, Index No. 9684, 1989, pp. 1536–1537.
Bair, Kenneth et al., "(1–Pyrenylmethyl) amino Alcohols, a New Class of Antitumor DNA Intercalators.", J. Med. Chem., 1990, vol. 33, pp. 2385–2393.
Shetty, B. Vithal et al., "Syntheses of Some 1–Alkylamino–1,1–di (hydroxymethyl)–2–phenylethanes", J. Med. Chem., 1960, vol. 25, pp. 2057–2059.
Brunner, Henri et al., "Synthesis and antitumor activity of platinum (II) complexes . . . ", Eur. J. Med. Chem., 1990, vol. 25, pp. 35–44.
Adachi, Kunitomo et al., "Design, Synthesis, and Structure–Activity Relationships . . . ", Bioorganic & Medicinal Chemistry Letters, vol. 5, No. 8, pp. 853–856, 1995.
Fujita, Tetsuro et al., "Simple Compounds, 2–Alkyl–2–Amino–1,3–Propanediols . . . ", Bioorganic & Medicinal Chemistry Letters, vol. 5, No. 8, pp. 847–852, 1995.

* cited by examiner

*Primary Examiner*—Richard L. Raymond
(74) *Attorney, Agent, or Firm*—Evenson, McKeown, Edwards & Lenahan, P.L.L.C.

(57) ABSTRACT

A benzene compound of the formula:

(I)

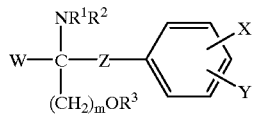

wherein each symbol is as defined in the specification; an optically active isomer or salt thereof, a medicinal composition containing the same, and an immunosuppressant containing the same as the active ingredient.

The compound, optically active isomer or salt has an excellent immunosuppressive effect and is useful as an inhibitor for the rejection reaction occurring in organ or bone marrow transplantation, and as a preventive or remedy for articular rheumatism, atopic eczema (dermatitis), Behcet's disease, uveal disease, systemic lupus erythematosus, Sjögren's syndrome, multiple sclerosis, myasthenia gravis, type I diabetes, endocrine ophthalmopathy, primary biliary, cirrhosis, Crohn's disease, glomerulonephritis, sarcoidosis, psoriasis, pemphigus, aplastic anemia, idiopathic thrombocytopenic purpura, allergy, polyarteritis nodosa, progressive systemic sclerosis, mixed connective–tissue disease, aortitis syndrome, polymyositis, dermatomyositis, Wegener's granuloma, ulcerative colitis, active chronic hepatitis, autoimmune hemolytic anemia, Evans' syndrome, bronchial asthma and pollinosis. It is useful also as an antifungal agent and hair growth stimulant.

23 Claims, No Drawings

BENZENE COMPOUND AND PHARMACEUTICAL USE THEREOF

This application is a division of application Ser. No. 08/801,390, now U.S. Pat. No. 5,948,820, filed Feb. 20, 1997 and which was a continuation-in-part of PCT/JP95/01654 filed Aug. 22, 1995.

FIELD OF THE INVENTION

The present invention relates to novel benzene compounds. In detail, the present invention relates to benzene compounds useful as immunosuppressants, optically active isomers thereof and salts thereof, and pharmaceutical use thereof.

BACKGROUND OF THE INVENTION

In recent years, cyclosporin is in use for suppressing rejection developed in transplanting organs. Inclusive of the compounds currently under development, the so-called immunosuppressants are expected to be useful as therapeutic agents for articular rheumatism and so on. Said cyclosporin, however, also possesses problems of side effects such as renal disorders.

Meanwhile, Japanese Patent Unexamined Publication No. 104087/1989 discloses that an immunosuppressive substance is obtained from a liquid culture of *Isaria sinclairii* and said substance has been confirmed to be (2S, 3R, 4R)-(E)-2-amino-3,4-dihydroxy-2-hydroxymethyl-14-oxoicosa-6-enoic acid of the formula:

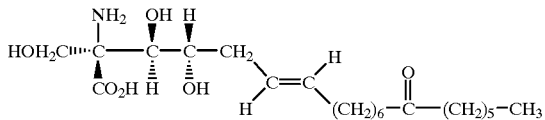

disclosed in U.S. Pat. No. 3928572. In addition, Japanese Patent Unexamined Publication No. 128347/1991 states that a series of said compound has an immunosuppressive action.

Referring to Merck Index, 11th edition, it is described that 2-amino-2-methyl-1,3-propanediol (Index No. 460), 2-amino-2-ethyl-1,3-propanediol (Index No. 451) and 2-amino-2-hydroxymethyl-1,3-propanediol (also called as tromethamine, Index No. 9684) can be used as intermediates for surface-active agents and pharmaceuticals, emulsifying agent or gas adsorbents and that tromethamine is medically usable as an alkalizer. In Japanese Patent Unexamined Publication No. 416/1987, a hair dye containing 2-amino-2-(C1–C5 alkyl)-1,3-propanediol is disclosed. U.S. Pat. No. 4,910,218 and J. Med. Chem., vol.33, 2385–2393 (1990) teach 2-amino-2-(methyl or ethyl)-1,3-propanediol as a synthetic intermediate for an antitumor agent. Also, Japanese Patent Unexamined Publication No. 192962/1984 teaches that the aforementioned 2-amino-2-(C1–C5 alkyl)-1,3-propanediol or 2-amino-1,3-propanediol can be used as a stabilizer for an antigen or antibody-sensitized latex reagent. Moreover, U.S. Pat. No. 3,062,839 teaches 2-methyl- or ethyl-amino-2-(furylmethyl, phenylmethyl or phenylmethyl substituted by lower alkyl, lower alkoxy, chloro, hydroxy or unsubstituted amine)-1,3-propanediol having a tranquilizing action and J. Org. Chem., vol.25, 2057–2059 (1960) teaches 2-methylamino-2-(phenylmethyl or phenylmethyl substituted by 2-methyl, 3-methyl, 4-methyl, 4-methoxy or 4-hydroxy)-1,3-propanediol. Eur. J. Med. Chem. vol.25, 35–44 (1990) teaches a substituted ethylenediamine such as 3-(4-methoxyethoxyphenyl)-1,2-diaminopropane, 5-phenyl-1,2-diaminopentane, 6-phenyl-1,2-diaminohexane, can be used as a ligand of a platinum (II) complex having antitumor activity. Moreover, WO92/16236 teaches sphingosine derivatives useful as membrane penetration enhancer. It has not been known, however, that these compounds have immunosuppressive actions such as suppression of rejection developed in organ transplantation, and prevention and treatment of autoimmune diseases.

WO94/08943 discloses 2-amino-1,3-propanediol compounds having immunosuppressive action. Moreover, in Bioorganic & Medicinal Chemistry Letters, vol.5, No.8, 853–856 (1995), 2-amino-2-[2-(4-octylphenyl)-ethyl]propane-1,3-diol hydrochloride (hereinafter sometimes referred to as FTY720) as a novel synthetic immunosuppressant is disclosed, and in ibid., vol.5, No.8, 847–852 (1995), 2-amino-2-tetradecylpropane-1,3-diol as an immunosuppressant is disclosed.

An object of the present invention is to provide novel benzene compounds useful as pharmaceuticals, and having superior immuno-suppressive action with less side effects.

Another object of the present invention is to provide pharmaceuticals containing said compounds.

SUMMARY OF THE INVENTION

The present invention is as follows.

(1) A benzene compound of the formula:

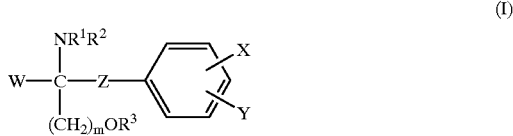

(I)

wherein

W is hydrogen; a straight- or branched chain alkyl having 1 to 6 carbon atoms; a straight- or branched chain alkenyl having 2 to 6 carbon atoms; a straight- or branched chain alkynyl having 2 to 6 carbon atoms; a phenyl which may be substituted by hydroxy; $R^4O(CH_2)_n$; or a straight- or branched chain C1–C6 alkyl substituted by 1 to 3 substituents selected from the group consisting of a halogen, a cycloalkyl and a phenyl which may be substituted by hydroxy;

X is hydrogen, a straight-chain alkyl having carbon atoms in the number of p or a straight-chain alkoxy having carbon atoms in the number of (p-1), wherein the straight-chain alkyl having carbon atoms in the number of p and the straight-chain alkoxy having carbon atoms in the number of (p-1) may have 1 to 3 substituents selected from the group consisting of an alkyl, hydroxy, an alkoxy, an acyloxy, amino, an alkylamino, an acylamino, oxo, a haloalkyl, a halogen and a phenyl which may have a substituent and wherein the phenyl which may have a substituent, may have 1 to 3 substituents selected from the group consisting of an alkyl, hydroxy, an alkoxy, an acyl, an acyloxy, amino, an alkylamino, an acylamino, a haloalkyl and a halogen;

Y is hydrogen, an alkyl, hydroxy, an alkoxy, an acyl, an acyloxy, amino, an alkylamino, an acylamino, a haloalkyl or a halogen;

Z is a single bond or a straight-chain alkylene having carbon atoms in the number of q;

p and q are the same or different and each is an integer of 1 to 20, with the proviso of 6≦p+q≦23; m is 1, 2 or 3; n is 2 or 3;

$R^1$ and $R^2$ are the same or different and each is hydrogen, an alkyl or an acyl;
$R^3$ is hydrogen, an alkyl or an acyl; and $R^4$ is hydrogen, an alkyl or an acyl, an optically active isomer thereof and a salt thereof.

(2) The benzene compound of (1), having the formula:

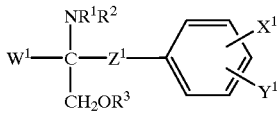

(I-a)

wherein
$W^1$ is a straight- or branched chain alkyl having 1 to 6 carbon atoms; a straight- or branched chain alkenyl having 2 to 6 carbon atoms; a straight- or branched chain alkynyl having 2 to 6 carbon atoms; or a straight- or branched chain C1–C6 alkyl substituted by 1 to 3 substituents selected from the group consisting of a halogen, a cycloalkyl and a phenyl which may be substituted by hydroxy;

$X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;

$Y^1$ is hydrogen, an alkyl, hydroxy or an alkoxy;

$Z^1$ is a straight-chain alkylene having 2 to 4 carbon atoms;

$R^1$ and $R^2$ are the same or different and each is hydrogen, an alkyl or an acyl;

and $R^3$ is hydrogen, an alkyl or an acyl, an optically active isomer thereof and a salt thereof.

(3) The benzene compound of (2), having the formula:

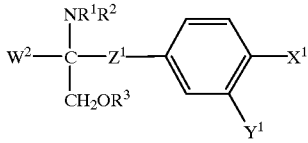

(I-b)

wherein
$W^2$ is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

$X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;

$Y^1$ is hydrogen, an alkyl, hydroxy or an alkoxy;

$Z^1$ is a straight-chain alkylene having 2 to 4 carbon atoms;

$R^1$ and $R^2$ are the same or different and each is hydrogen, an alkyl or an acyl;

and $R^3$ is hydrogen, an alkyl or an acyl, an optically active isomer thereof and a salt thereof.

(4) The benzene compound of (3), having the formula:

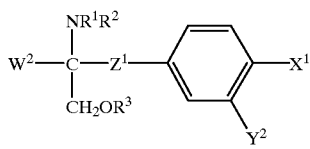

(I-c)

wherein
$W^2$ is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

$X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;

$Y^2$ is hydrogen, hydroxy or an alkoxy;

$Z^1$ is a straight-chain alkylene having 2 to 4 carbon atoms;

$R^1$ and $R^2$ are the same or different and each is hydrogen, an alkyl or an acyl;

and $R^3$ is hydrogen, an alkyl or an acyl, an optically active isomer thereof and a salt thereof.

(5) The benzene compound of (4), having the formula:

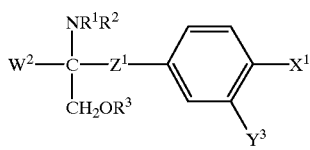

(I-d)

wherein
$W^2$ is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

$X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;

$Y^3$ is hydrogen or an alkoxy;

$Z^1$ is a straight-chain alkylene having 2 to 4 carbon atoms;

$R^1$ and $R^2$ are the same or different and each is hydrogen, an alkyl or an acyl;

and $R^3$ is hydrogen, an alkyl or an acyl, an optically active isomer thereof and a salt thereof.

(6) The benzene compound of (3), having the formula:

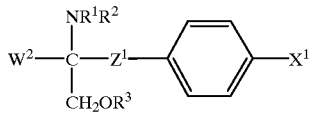

(I-e)

wherein

W² is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

X¹ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;

Z¹ is a straight-chain alkylene having 2 to 4 carbon atoms;

R¹ and R² are the same or different and each is hydrogen, an alkyl or an acyl;

and R³ is hydrogen, an alkyl or an acyl, an optically active isomer thereof and a salt thereof.

(7) The benzene compound of (6), having the formula:

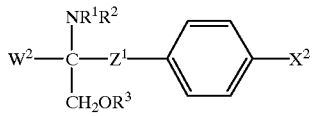

(I-f)

wherein

W² is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

X² is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;

Z¹ is a straight-chain alkylene having 2 to 4 carbon atoms;

R¹ and R² are the same or different and each is hydrogen, an alkyl or an acyl;

and R³ is hydrogen, an alkyl or an acyl, an optically active isomer thereof and a salt thereof.

(8) The benzene compound of (6), having the formula:

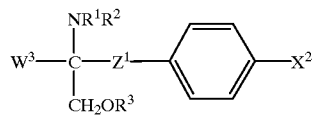

(I-g)

wherein

W³ is a straight- or branched chain alkyl having 1 to 3 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 halogens;

X² is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;

Z¹ is a straight-chain alkylene having 2 to 4 carbon atoms;

R¹ and R² are the same or different and each is hydrogen, an alkyl or an acyl;

and R³ is hydrogen, an alkyl or an acyl, an optically active isomer thereof and a salt thereof.

(9) The benzene compound of (7), having the formula:

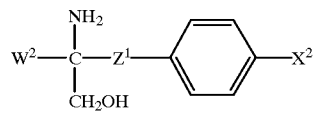

(I-h)

wherein

W² is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

X² is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo; and Z¹ is a straight-chain alkylene having 2 to 4 carbon atoms, an optically active isomer thereof and a salt thereof.

(10) The benzene compound of (8), having the formula:

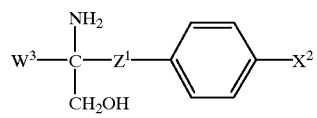

(I-i)

wherein

W³ is a straight- or branched chain alkyl having 1 to 3 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 halogens;

$X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo; and $Z^1$ is a straight-chain alkylene having 2 to 4 carbon atoms;

an optically active isomer thereof and a salt thereof.

(11) The benzene compound of (10), which is selected from the group consisting of
2-amino-2-methyl-4-(4-octylphenyl)butanol,
2-amino-2-methyl-4-(4-octanoylphenyl)butanol,
2-amino-4-[4-(1-hydroxyoctyl)phenyl]-2-methylbutanol,
2-amino-4-(4-heptyloxyphenyl)-2-methylbutanol,
(+)-2-amino-4-(4-heptyloxyphenyl)-2-methylbutanol,
(−)-2-amino-4-(4-heptyloxyphenyl)-2-methylbutanol,
2-amino-4-(4-decylphenyl)-2-methylbutanol,
2-amino-2-methyl-4-(4-nonyloxyphenyl)butanol,
2-amino-4-(4-dodecylphenyl)-2-methylbutanol,
2-amino-2-methyl-4-(4-undecyloxyphenyl)butanol,
2-amino-2-ethyl-4-(4-octylphenyl)butanol,
2-amino-2-ethyl-4-(4-octanoylphenyl)butanol,
2-amino-2-ethyl-4-[4-(1-hydroxyoctyl)phenyl]butanol,
2-amino-4-[4-(1-aminooctyl)phenyl]-2-ethylbutanol,
2-amino-2-ethyl-4-(4-heptyloxyphenyl)butanol,
2-amino-2-[2-(4-octylphenyl)ethyl]pentanol,
2-amino-2-[2-(4-octanoylphenyl)ethyl]pentanol,
2-amino-2-[2-[4-(1-hydroxyoctyl)phenyl]ethyl]pentanol,
2-amino-2-[2-[4-(1-aminooctyl)phenyl]ethyl]pentanol,
2-amino-2-[2-(4-heptyloxyphenyl)ethyl]pentanol,
(R)-2-amino-2-[2-(4-heptyloxyphenyl)ethyl]pentanol,
(S)-2-amino-2-[2-(4-heptyloxyphenyl)ethyl]pentanol,
2-amino-4-fluoro-2-[2-(4-heptyloxyphenyl)ethyl]butanol and
2-amino-2-isopropyl-4-(4-heptyloxyphenyl)butanol,
an optically active isomer thereof and a salt thereof.

(12) The benzene compound of (10), which is selected from the group consisting of
2-amino-2-methyl-4-(4-octylphenyl)butanol,
2-amino-4-(4-heptyloxyphenyl)-2-methylbutanol,
(+)-2-amino-4-(4-heptyloxyphenyl)-2-methylbutanol,
(−)-2-amino-4-(4-heptyloxyphenyl)-2-methylbutanol,
2-amino-4-(4-decylphenyl)-2-methylbutanol,
2-amino-2-methyl-4-(4-nonyloxyphenyl)butanol,
2-amino-4-(4-dodecylphenyl)-2-methylbutanol,
2-amino-2-methyl-4-(4-undecyloxyphenyl)butanol,
2-amino-2-ethyl-4-(4-heptyloxyphenyl)butanol,
2-amino-2-[2-(4-octylphenyl)ethyl]pentanol,
2-amino-2-[2-(4-octanoylphenyl)ethyl]pentanol,
2-amino-2-[2-[4-(1-hydroxyoctyl)phenyl]ethyl]pentanol,
2-amino-2-[2-(4-heptyloxyphenyl)ethyl]pentanol,
(R)-2-amino-2-[2-(4-heptyloxyphenyl)ethyl]pentanol,
(S)-2-amino-2-[2-(4-heptyloxyphenyl)ethyl]pentanol,
2-amino-4-fluoro-2-[2-(4-heptyloxyphenyl)ethyl]butanol and
2-amino-2-isopropyl-4-(4-heptyloxyphenyl)butanol,
an optically active isomer thereof and a salt thereof.

(13) The benzene compound of (10), which is selected from the group consisting of
2-amino-4-(4-heptyloxyphenyl)-2-methylbutanol,
2-amino-2-ethyl-4-(4-heptyloxyphenyl)butanol,
(R)-2-amino-2-[2-(4-heptyloxyphenyl)ethyl]pentanol and
2-amino-2-isopropyl-4-(4-heptyloxyphenyl)butanol,
an optically active isomer thereof and a salt thereof.

(14) The benzene compound of (3), having the formula:

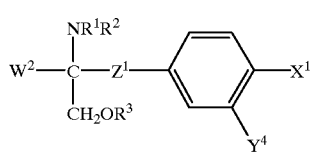

(I-j)

wherein $W^2$ is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

$X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;

$Y^4$ is hydroxy or an alkoxy;

$Z^1$ is a straight-chain alkylene having 2 to 4 carbon atoms;

$R^1$ and $R^2$ are the same or different and each is hydrogen, an alkyl or an acyl;

and $R^3$ is hydrogen, an alkyl or an acyl, an optically active isomer thereof and a salt thereof.

(15) The benzene compound of (14), having the formula:

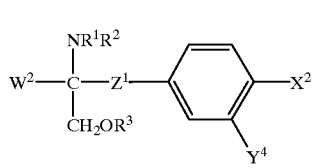

(I-k)

wherein $W^2$ is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

$X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;

$Y^4$ is hydroxy or an alkoxy;

$Z^1$ is a straight-chain alkylene having 2 to 4 carbon atoms;

$R^1$ and $R^2$ are the same or different and each is hydrogen, an alkyl or an acyl;

and $R^3$ is hydrogen, an alkyl or an acyl, an optically active isomer thereof and a salt thereof.

(16) The benzene compound of (15), having the formula:

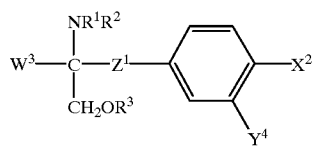

(I-l)

wherein $W^3$ is a straight- or branched chain alkyl having 1 to 3 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 halogens;

$X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;

$Y^4$ is hydroxy or an alkoxy;

$Z^1$ is a straight-chain alkylene having 2 to 4 carbon atoms;

$R^1$ and $R^2$ are the same or different and each is hydrogen, an alkyl or an acyl;

and $R^3$ is hydrogen, an alkyl or an acyl, an optically active isomer thereof and a salt thereof.

(17) The benzene compound of (14), having the formula:

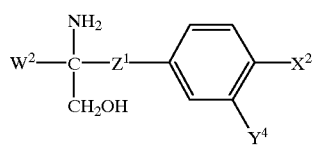

(I-m)

wherein $W^2$ is a straight- or branched chain alkyl having 1 to 4 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 substituents selected from the group consisting of a halogen, a cycloalkyl and a phenyl which may be substituted by hydroxy;

$X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;

$Y^4$ is hydroxy or an alkoxy; and $Z^1$ is a straight-chain alkylene having 2 to 4 carbon atoms, an optically active isomer thereof and a salt thereof.

(18) The benzene compound of (16), having the formula:

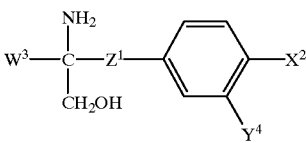

(I-n)

wherein $W^3$ is a straight- or branched chain alkyl having 1 to 3 carbon atoms; a straight- or branched chain alkenyl having 2 or 3 carbon atoms; a straight- or branched chain alkynyl having 2 or 3 carbon atoms; or a straight- or branched chain C1–C3 alkyl substituted by 1 to 3 halogens;

$X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;

$Y^4$ is hydroxy or an alkoxy; and $Z^1$ is a straight-chain alkylene having 2 to 4 carbon atoms, an optically active isomer thereof and a salt thereof.

(19) The bepzene compound of (18), which is selected from the group consisting of
2-amino-4-(4-heptyloxy-3-methoxyphenyl)-2-methylbutanol,
2-amino-4-(4-heptyloxy-3-hydroxyphenyl)-2-methylbutanol,
2-amino-2-ethyl-4-(4-heptyloxy-3-hydroxyphenyl)butanol and
2-amino-2-[2-(4-heptyloxy-3-hydroxyphenyl)ethyl]pentanol,
an optically active isomer thereof and a salt thereof.

(20) The benzene compound of (18), which is 2-amino-4-(4-heptyloxy-3-methoxyphenyl)-2-methylbutanol, an optically active isomer thereof and a salt thereof.

(21) The benzene compound of (1), having the formula:

(I-o)

wherein $X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;

$Y^1$ is hydrogen, an alkyl, hydroxy or an alkoxy;

$Z^1$ is a straight-chain alkylene having 2 to 4 carbon atoms;

m is 1, 2 or 3; n is 2 or 3;

$R^1$ and $R^2$ are the same or different and each is hydrogen, an alkyl or an acyl;

$R^3$ is hydrogen, an alkyl or an acyl; and $R^4$ is hydrogen, an alkyl or an acyl, an optically active isomer thereof and a salt thereof.

(22) The benzene compound of (21), having the formula:

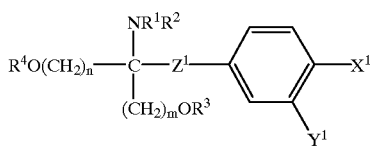

(I-p)

wherein
X$^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
Y$^1$ is hydrogen, an alkyl, hydroxy or an alkoxy;
Z$^1$ is a straight-chain alkylene having 2 to 4 carbon atoms;
m is 1, 2 or 3; n is 2 or 3;
R$^1$ and R$^2$ are the same or different and each is hydrogen, an alkyl or an acyl;
R$^3$ is hydrogen, an alkyl or an acyl; and
R$^4$ is hydrogen, an alkyl or an acyl,
an optically active isomer thereof and a salt thereof.

(23) The benzene compound of (22), having the formula:

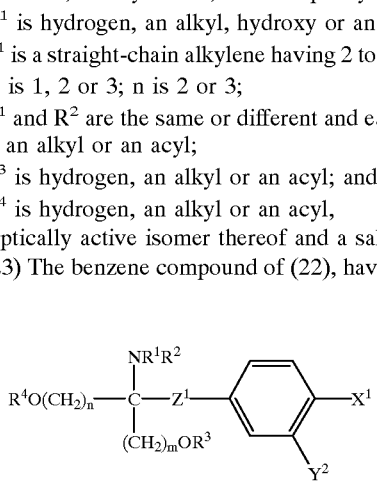

(I-q)

wherein
X$^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
Y$^2$ is hydrogen, hydroxy or an alkoxy;
Z$^1$ is a straight-chain alkylene having 2 to 4 carbon atoms;
m is 1, 2 or 3; n is 2 or 3;
R$^1$ and R$^2$ are the same or different and each is hydrogen, an alkyl or an acyl;
R$^3$ is hydrogen, an alkyl or an acyl; and
R$^4$ is hydrogen, an alkyl or an acyl,
an optically active isomer thereof and a salt thereof.

(24) The benzene compound of (23), having the formula:

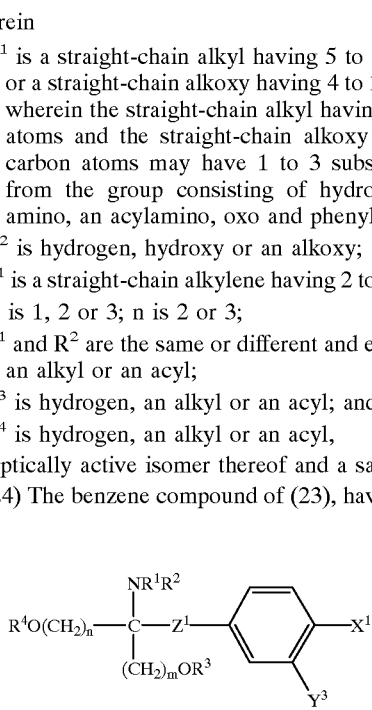

(I-r)

wherein
X$^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
Y$^3$ is hydrogen or an alkoxy;
Z$^1$ is a straight-chain alkylene having 2 to 4 carbon atoms;
m is 1, 2 or 3; n is 2 or 3;
R$^1$ and R$^2$ are the same or different and each is hydrogen, an alkyl or an acyl;
R$^3$ is hydrogen, an alkyl or an acyl; and
R$^4$ is hydrogen, an alkyl or an acyl,
an optically active isomer thereof and a salt thereof.

(25) The benzene compound of (22), having the formula:

(I-s)

wherein
X$^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
Z$^1$ is a straight-chain alkylene having 2 to 4 carbon atoms;
m is 1, 2 or 3; n is 2 or 3;
R$^1$ and R$^2$ are the same or different and each is hydrogen, an alkyl or an acyl;
R$^3$ is hydrogen, an alkyl or an acyl; and
R$^4$ is hydrogen, an alkyl or an acyl,
an optically active isomer thereof and a salt thereof.

(26) The benzene compound of (25), having the formula:

(I-t)

wherein
X$^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;
Z$^1$ is a straight-chain alkylene having 2 to 4 carbon atoms;
m is 1, 2 or 3 ; n is 2 or 3;
R$^1$ and R$^2$ are the same or different and each is hydrogen, an alkyl or an acyl;
R$^3$ is hydrogen, an alkyl or an acyl; and
R$^4$ is hydrogen, an alkyl or an acyl,
an optically active isomer thereof and a salt thereof.

(27) The benzene compound of (26), having the formula:

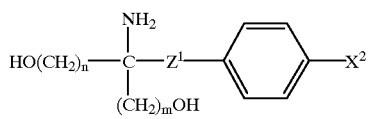

(I-u)

wherein
- $X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;
- $Z^1$ is a straight-chain alkylene having 2 to 4 carbon atoms;
- m is 1, 2 or 3; and n is 2 or 3, an optically active isomer thereof and a salt thereof.

(28) The benzene compound of (27), which is selected from the group consisting of
2-amino-2-[3-(4-heptylphenyl)propyl]butane-1,4-diol,
2-amino-2-[3-(4-nonylphenyl)propyl]butane-1,4-diol,
2-amino-2-[3-(4-undecylphenyl)propyl]butane-1,4-diol,
2-amino-2-[2-(4-octylphenyl)ethyl]butane-1,4-diol,
2-amino-2-[2-(4-decylphenyl)ethyl]butane-1,4-diol,
2-amino-2-[2-(4-dodecylphenyl)ethyl]butane-1,4-diol,
2-amino-2-[2-(4-heptyloxyphenyl)ethyl]butane-1,4-diol,
2-amino-2-[2-(4-octylphenyl)ethyl]pentane-1,5-diol,
3-amino-3-[2-(4-octylphenyl)ethyl]pentane-1,5-diol and
3-amino-3-[2-(4-octylphenyl)ethyl]hexane-1,6-diol,
an optically active isomer thereof and a salt thereof.

(29) The benzene compound of (27), which is selected from the group consisting of
2-amino-2-[3-(4-heptylphenyl)propyl]butane-1,4-diol,
2-amino-2-[3-(4-nonylphenyl)propyl]butane-1,4-diol,
2-amino-2-[3-(4-undecylphenyl)propyl]butane-1,4-diol,
2-amino-2-[2-(4-octylphenyl)ethyl]butane-1,4-diol,
2-amino-2-[2-(4-decylphenyl)ethyl]butane-1,4-diol,
2-amino-2-[2-(4-dodecylphenyl)ethyl]butane-1,4-diol,
2-amino-2-[2-(4-heptyloxyphenyl)ethyl]butane-1,4-diol,
2-amino-2-[2-(4-octylphenyl)ethyl]pentane-1,5-diol and
3-amino-3-[2-(4-bctylphenyl)ethyl]hexane-1,6-diol,
an optically active isomer thereof and a salt thereof.

(30) The benzene compound of (27), which is
2-amino-2-[3-(4-nonylphenyl)propyl]butane-1,4-diol,
an optically active isomer thereof and a-salt thereof.

(31) The benzene compound of (1), having the formula:

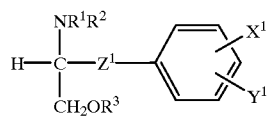

(I-v)

wherein
- $X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
- $Y^1$ is hydrogen, an alkyl, hydroxy or an alkoxy;
- $Z^1$ is a straight-chain alkylene having 2 to 4 carbon atoms;
- $R^1$ and $R^2$ are the same or different and each is hydrogen, an alkyl or an acyl;
- and $R^3$ is hydrogen, an alkyl or an acyl, an optically active isomer thereof and a salt thereof.

(32) The benzene compound of (31), having the formula:

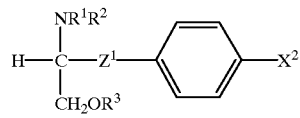

(I-w)

wherein
- $X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;
- $Z^1$ is a straight-chain alkylene having 2 to 4 carbon atoms;
- $R^1$ and $R^2$ are the same or different and each is hydrogen, an alkyl or an acyl;
- and $R^3$ is hydrogen, an alkyl or an acyl, an optically active isomer thereof and a salt thereof.

(33) The benzene compound of (32), having the formula:

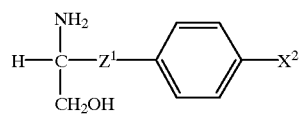

(I-x)

wherein
- $X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo; and
- $Z^1$ is a straight-chain alkylene having 2 to 4 carbon atoms, an optically active isomer thereof and a salt thereof.

(34) The benzene compound of (33), which is selected from the group consisting of
2-amino-4-(4-octylphenyl)butanol,
2-amino-4-(4-heptyloxyphenyl)butanol and
2-amino-5-(4-hexyloxyphenyl)pentanol,
an optically active isomer thereof and a salt thereof.

(35) The benzene compound of (1), having the formula:

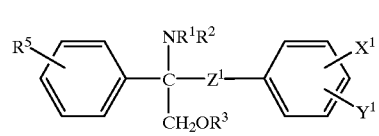

(I-y)

wherein
- $X^1$ is a straight-chain alkyl having 5 to 19 carbon atoms or a straight-chain aikoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;

$Y^1$ is hydrogen, an alkyl, hydroxy or an alkoxy;

$Z^1$ is a straight-chain alkylene having 2 to 4 carbon atoms;

$R^1$ and $R^2$ are the same or different and each is hydrogen, an alkyl or an acyl;

$R^3$ is hydrogen, an alkyl or an acyl; and $R^5$ is hydrogen or hydroxy, an optically active isomer thereof and a salt thereof.

(36) The benzene compound of (35), having the formula:

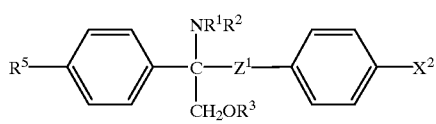

(I-z)

wherein $X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;

$Z^1$ is a straight-chain alkylene having 2 to 4 carbon atoms;

$R^1$ and $R^2$ are the same or different and each is hydrogen, an alkyl or an acyl;

$R^3$ is hydrogen, an alkyl or an acyl; and $R^5$ is hydrogen or hydroxy, an optically active isomer thereof and a salt thereof.

(37) The benzene compound of (36), having the formula:

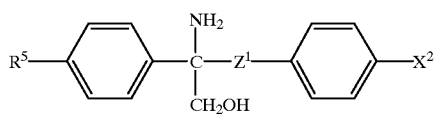

(I-aa)

wherein $X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;

$Z^1$ is a straight-chain alkylene having 2 to 4 carbon atoms; and $R^5$ is hydrogen or hydroxy, an optically active isomer thereof and a salt thereof.

(38) The benzene compound of (6), which is 2-amino-2-ethyl-4-(4-(4-phenylbutyloxy)phenyl)butanol, an optically active isomer thereof, a salt thereof or a hydrate thereof.

(39) The benzene compound of (38), which is (−)-2-amino-2-ethyl-4-(4-(4-phenyibutyloxy)phenyl)butanol hydrochloride.

(40) A pharmaceutical composition comprising any one of the compounds of (1) to (39).

(41) A method for immunosuppression of an immune system of a mammal, which comprises administering to a mammal a therapeutically effective amount of a benzene compound of any one of (1) to (39).

(42) The method according to (41), wherein the immunosuppression is suppression of rejection in an organ or bone marrow transplantation.

(43) The method according to (42), wherein the suppression of rejection in an organ or bone marrow transplantation is prevention or treatment of graft-versus-host diseases.

(44) The method according to (41), wherein the immunosuppression is the prevention or treatment of an autoimmune disease.

(45) The method according to (44), wherein the autoimmune disease is rheumatoid arthritis.

(46) The method according to (44), wherein the autoimmune disease is psoriasis or atopic dermatitis.

(47) The method according to (44), wherein the autoimmune disease is bronchial asthma or pollinosis.

(48) The method according to (44), wherein the autoimmune disease is Behget's disease or uveitis.

(49) The method according to (44), wherein the autoimmune disease is systemic lupus erythematosus.

(50) The method according to (44), wherein the autoimmune disease is multiple sclerosis.

In present invention, compounds of the general formula:

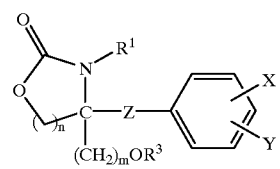

(a)

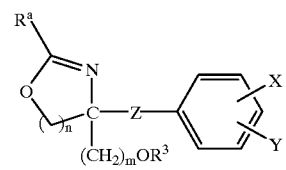

(b)

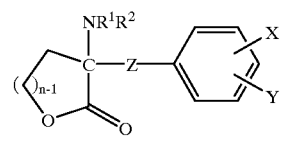

(c)

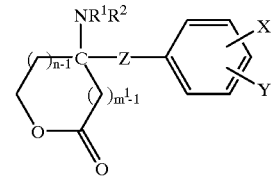

(d)

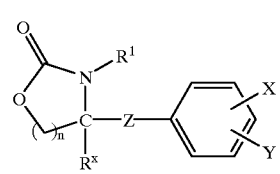

(e)

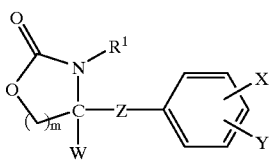
(f)

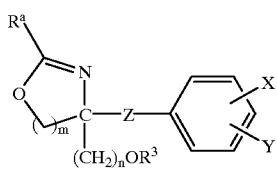
(g)

wherein $R^a$ is hydrogen, an alkyl (e.g. methyl, ethyl, propyl, butyl), $R^x$ is carboxy, alkoxycarbonyl (e.g. methoxycarbonyl, ethoxycarbonyl), aldehyde, vinyl, $m^1$ is 2 or 3, and $R^1$, $R^2$, $R^3$, X, Y, Z, W, m and n are those mentioned above, are useful as synthetic intermediates.

The groups represented by the respective symbols in the present specification are explained in the following.

The straight- or branched chain alkyl having 1 to 6 carbon atoms at W or $W^1$ is exemplified by methyl, ethyl, propyl, isopropyl, butyl, isobutyl, tert-butyl, pentyl, isopentyl, hexyl and isohexyl. Preferred is a straight- or branched chain alkyl having 1 to 4 carbon atoms, particularly preferred is a straight- or branched chain alkyl having 1 to 3 carbon atoms.

The straight- or branched chain alkyl having 1 to 4 carbon atoms at $W^2$ is exemplified by methyl, ethyl, propyl, isopropyl, butyl, isobutyl and tert-butyl.

The straight- or branched chain alkyl having 1 to 3 carbon atoms at $W^3$ is exemplified by methyl, ethyl, propyl and isopropyl.

The straight- or branched chain alkenyl having 2 to 6 carbon atoms at W is exemplified by vinyl, allyl, 1-propenyl, 2-butenyl, 3-butenyl, 4-pentenyl and 5-hexenyl. Preferred is a straight- or branched chain alkenyl having 2 or 3 carbon atoms.

The straight- or branched chain alkenyl having 2 or 3 carbon atoms at $W^2$ or $W^3$ is exemplified by vinyl, allyl and 1-propenyl.

The straight- or branched chain alkynyl having 2 to 6 carbon atoms at W is exemplified by propargyl, 2-butynyl, 3-butynyl, 4-pentynyl and 5-hexynyl. Preferred is a straight- or branched chain alkynyl having 2 or 3 carbon atoms.

The straight- or branched chain alkynyl having 2 or 3 carbon atoms at $W^2$ or $W^3$ is exemplified by propargyl.

The phenyl which may be substituted by hydroxy at W is exemplified by phenyl, 4-hydroxyphenyl, 3-hydroxyphenyl and 2-hydroxyphenyl.

The straight- or branched chain C1–C6 alkyl substituted by 1 to 3 substituents selected from the group consisting of a halogen (fluorine, chlorine, bromine, iodine), a cycloalkyl (e.g. cyclopropyl, cyclobutyl, cyclopentyl, cyclohexyl, cycloheptyl) and a phenyl which may be substituted by hydroxy at W or $W^1$ is exemplified by fluoromethyl, 2-fluoroethyl, chloromethyl, 2-chloroethyl, 2-bromoethyl, 2,2,2-trifluoroethyl, 3-fluoropropyl, 3,3,3-trifluoropropyl, 4-fluorobutyl, 5-fluoropentyl, 6-fluorohexyl, cyclopropylmethyl, cyclobutylmethyl, cyclohexylmethyl, benzyl, 2-phenylethyl, 3-phenylpropyl, 4-hydroxybenzyl, 3,4-dihydroxybenzyl and 3,4,5-trihydroxybenzyl. Preferred is a straight- or branched chain C1–C3 alkyl substituted by 1 to 3 substituents selected from the group consisting of a halogen, a cycloalkyl and a phenyl which may be substituted by hydroxy, particularly preferred is a straight- or branched chain C1–C3 alkyl which is substituted by 1 to 3 halogens.

The straight- or branched chain C1–C3 alkyl substituted by 1 to 3 substituents selected from the group consisting of a halogen, a cycloalkyl and a phenyl which may be substituted by hydroxy at $W^2$ is exemplified by fluoromethyl, 2-fluoroethyl, chloromethyl, 2-chloroethyl, 2-bromoethyl, 2,2,2-trifluoroethyl, 3-fluoropropyl, 3,3,3-trifluoropropyl, cyclopropylmethyl, cyclobutylmethyl, cyclohexylmethyl, benzyl, 2-phenylethyl, 3-phenylpropyl, 4-hydroxybenzyl, 3,4-dihydroxybenzyl and 3,4,5-trihydroxybenzyl.

The straight- or branched chain C1–C3 alkyl substituted by 1 to 3 halogens at $W^3$ is exemplified by fluoromethyl; 2-fluoroethyl, chloromethyl, 2-chloroethyl, 2-bromoethyl, 2,2,2-trifluoroethyl, 3-fluoropropyl, 3,3,3-trifluoropropyl.

The straight-chain alkyl having carbon atoms in the number of p at X is a straight-chain alkyl having 1 to 20 carbon atoms and is exemplified by methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and icosyl. Preferred is a straight-chain alkyl having 5 to 19 carbon atoms, particularly preferred is a straight-chain alkyl having 7 to 12 carbon atoms.

The straight-chain alkyl having 5 to 19 carbon atoms at $X^1$ is exemplified by pentyl, hexyl, heptyl, octyl, nonyl, decyl, undecyl, dodecyl, tridecyl, tetradecyl, pentadecyl, hexadecyl, heptadecyl, octadecyl and nonadecyl.

The straight-chain alkyl having 7 to 12 carbon atoms at $X^2$ is exemplified by heptyl, octyl, nonyl, decyl, undecyl and dodecyl.

The straight-chain alkoxy having carbon atoms in the number of (P-1) at X is a straight-chain alkoxy having 1 to 19 carbon atoms and is exemplified by methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy and icosyloxy. Preferred is a straight-chain alkoxy having 4 to 18 carbon atoms, particularly preferred is a straight-chain alkoxy having 6 to 11 carbon atoms.

The straight-chain alkoxy having 4 to 18 carbon atoms at $X^1$ is exemplified by butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy and octadecyloxy.

The straight-chain alkoxy having 6 to 11 carbon atoms at $X^2$ is exemplified by hexyloxy, heptyloxy, octyloxy, nonyloxy, decyloxy and undecyloxy.

The alkyl as a substituent at X is a straight- or branched chain alkyl having 1 to 6 carbon atoms and is exemplified by methyl, ethyl, propyl, isopropyl, butyl, isobutyl, tert-butyl, pentyl and hexyl. The said alkyl may be substituted by a phenyl which may have 1 to 3 substituents selected from the group consisting of an alkyl, hydroxy, an acyl, an acyloxy, amino, an alkylamino, a haloalkyl and a halogen.

The alkoxy as a substituent at X is a straight- or branched chain alkoxy having 1 to 6 carbon atoms and is exemplified by methoxy, ethoxy, propoxy, isopropoxy, butoxy, isobutoxy, sec-butoxy, tert-butoxy, pentyloxy, isopentyloxy, tert-pentyloxy and hexyloxy.

The acyloxy as a substituent at X, $X^1$ or $X^2$ is that where the acyl moiety is a straight- or branched chain alkanoyl having 2 to 20 carbon atoms and includes, for example, acetoxy, propionyloxy, butyryloxy, isobutyryloxy, pivaloyloxy; pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, nonadecanoyloxy and icosanoyloxy.

The alkylamino as a substituent at X is that where the alkyl moiety is a straight- or branched chain alkyl having 1 to 6 carbon atoms and includes, for example, methylamino, ethylamino, propylamino, isopropylamino, butylamino, isobutylamino, sec-butylamino, tert-butylamino, pentylamino, isopentylamino, tert-pentylamino and hexylamino.

The acylamino as a substituent at X, $X^1$ or $X^2$ is that where the acyl moiety is a straight- or branched chain alkanoyl, alkoxycarbonyl or aralkoxycarbonyl having 1 to 20 carbon atoms and includes, for example, formylamino, acetylamino, propionylamino, butyrylamino, isobutyrylamino, pentanoylamino, pivaloylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, nonadecanoylamino, icosadecanoylamino, methoxycarbonylamino, ethoxycarbonylamino, propoxycarbonylamino, isopropoxycarbonylamino, butoxycarbonylamino, isobutoxycarbonylamino, tert-butoxycarbonylamino and benzyloxycarbonylamino.

The haloalkyl as a substituent at X is that where the alkyl moiety is a straight- or branched chain alkyl having 1 to 6 carbon atoms and includes, for example, fluoromethyl, trifluoromethyl, chloromethyl, 2,2,2-trifluoroethyl, perfluoroethyl, 3-chloropropyl, 3-fluoropropyl, 4-chlorobutyl, 4-fluorobutyl, 5-chloropentyl, 6-chlorohexyl and 6-fluorohexyl.

The halogen as a substituent at X is exemplified by fluorine, chlorine, bromine, iodine.

The acyl as a substituent of a phenyl which may have a substituent at X is an alkanoyl or aroyl which may have a substituent, where the alkanoyl is a straight- or branched chain alkanoyl having 1 to 20 carbon atoms and includes, for example, formyl, acetyl, propionyl, butyryl, isobutyryl, pentanoyl, hexanoyl, heptanoyl, octanoyl, nonanoyl, decanoyl, undecanoyl, dodecanoyl, tridecanoyl, tertadecanoyl, pentadecanoyl, hexadecanoyl, heptadecanoyl, octadecanoyl, nonadecanoyl and icosanoyl, and which may have phenyl as a substituent. Examples thereof include phenylacetyl and phenylpropionyl. The aroyl includes benzoyl.

The alkyl, alkoxy, acyloxy, alkylamino, acylamino, haloalkyl and halogen as a substituent of a phenyl which may have a substituent at X are respectively the same as the aforementioned alkyl, alkoxy, acyloxy, alkylamino, acylamino, haloalkyl and halogen as a substituent at X.

The acyl, acyloxy, alkylamino, acylamino, haloalkyl and halogen at Y, the alkyl at Y or $Y^1$ or the alkoxy at $Y^1$, $y^2$, $Y^3$ or $Y^4$ are respectively the same as the aforementioned acyl, acyloxy, alkylamino, acylamino, haloalkyl, halogen, alkyl and alkoxy as a substituent of a phenyl which may have a substituent at X.

The straight-chain alkylene having carbon atoms in the number of q at Z is a straight-chain alkylene having 1 to 20 carbon atoms and is exemplified by methylene, ethylene, trimethylene, tetramethylene, pentamethylene, hexamethylene, heptamethylene, octamethylene, nonamethylene, decamethylene, undecamethylene, dodecamethylene, tridecamethylene, tertadecamethylene, pentadecamethylene, hexadecamethylene, heptadecamethylene, octadecamethylene, nonadecamethylene and icosamethylene. Preferred is a straight-chain alkylene having 2 to 4 carbon atoms.

The straight-chain alkylene having 2 to 4 carbon atoms at $Z^1$ is exemplified by ethylene, trimethylene and tetramethylene.

The alkyl at $R^1$ and $R^2$ is the same as the aforementioned alkyl as a substituent at X.

The acyl at $R^1$ and $R^2$ is an alkanoyl, aroyl, alkoxycarbonyl or aralkyloxycarbonyl which may have a substituent, where the alkanoyl is a straight- or branched chain alkanoyl having 1 to 20 carbon atoms and includes, for example, formyl, acetyl, propionyl, butyryl, isobutyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl, and which may have phenyl as a substituent. Examples thereof include phenylacetyl and phenylpropionyl. The aroyl includes benzoyl. The alkoxycarbonyl is that the alkoxy moiety is a straight- or branched chain alkoxy having 1 to 20 carbon atoms and includes, for example, methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, tert-pentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl, tridecyloxycarbonyl, tetradecyloxycarbonyl, pentadecyloxycarbonyl, hexadecyloxycarbonyl, heptadecyloxycarbonyl, octadecyloxycarbonyl, nonadecyloxycarbonyl and icosyloxycarbonyl. The aralkyloxycarbonyl includes benzyloxycarbponyl.

The alkyl at $R^3$ is the same as the aforementioned alkyl as a substituent at X.

The acyl at $R^3$ is the same as the aforementioned acyl at $R^1$ and $R^2$.

The alkyl at $R^4$ is the same as the aforementioned alkyl as a substituent at X.

The acyl at $R^4$ is the same as the aforementioned acyl at $R^1$ and $R^2$.

Examples of the salts of the compound (I) include salts with inorganic acids, such as hydrochloride, hydrobromide, sulfate and phosphate, salts with organic acid, such as acetate, fumarate, maleate, benzoate, citrate, succinate, malate, methanesulfonate, benzenesulfonate and tartrate. When the salts of the compound (I) are used as pharmaceuticals, preferred are these pharmaceutically acceptable salts. The compounds of the present invention also encompass hydrate and solvates.

When the compounds of the present invention have one or more asymmetric centers in the molecules, various optical isomers are obtained. The present invention also encompasses optical isomers, racemates, diastereomers and the mixture thereof. Moreover, when the compounds of the present invention include geometric isomers, the present invention encompasses cis-compounds, trans-compounds and the mixture thereof.

The preferable compounds of the present invention are shown in the following tables. In the table, Me means methyl, Et means ethyl, n-Pr means n-propyl, i-Pr means isopropyl, c-Pr means cyclopropyl, n-Bu means n-butyl, Ac means acetyl, Ph means phenyl, $C_6H_4$ means phenylene and Boc means tert-butoxycarbonyl.

TABLE 1

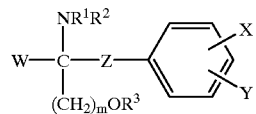

| R¹ | R² | R³ | m | W | Z | X | Y |
|---|---|---|---|---|---|---|---|
| H | H | H | 1 | Me | (CH$_2$)$_2$ | 4-(CH$_2$)$_7$CH$_3$ | H |
| H | H | H | 1 | Me | (CH$_2$)$_2$ | 4-CO(CH$_2$)$_6$CH$_3$ | H |
| H | H | H | 1 | Me | (CH$_2$)$_2$ | 4-CH(OH)(CH$_2$)$_6$CH$_3$ | H |
| H | H | H | 1 | Me | (CH$_2$)$_2$ | 4-CH(NH$_2$)(CH$_2$)$_6$CH$_3$ | H |
| H | H | H | 1 | Me | (CH$_2$)$_2$ | 4-O(CH$_2$)$_6$CH$_3$ | H |
| Ac | H | Ac | 1 | Me | (CH$_2$)$_2$ | 4-(CH$_2$)$_7$CH$_3$ | H |
| Ac | H | Ac | 1 | Me | (CH$_2$)$_2$ | 4-O(CH$_2$)$_6$CH$_3$ | H |
| H | H | H | 1 | Me | (CH$_2$)$_2$ | 4-(CH$_2$)$_8$CH$_3$ | H |
| H | H | H | 1 | Me | (CH$_2$)$_2$ | 4-O(CH$_2$)$_7$CH$_3$ | H |
| Ac | H | Ac | 1 | Me | (CH$_2$)$_2$ | 4-(CH$_2$)$_8$CH$_3$ | H |
| Ac | H | Ac | 1 | Me | (CH$_2$)$_2$ | 4-O(CH$_2$)$_7$CH$_3$ | H |
| H | H | H | 1 | Me | (CH$_2$)$_2$ | 4-(CH$_2$)$_9$CH$_3$ | H |
| H | H | H | 1 | Me | (CH$_2$)$_2$ | 4-O(CH$_2$)$_8$CH$_3$ | H |
| Ac | H | Ac | 1 | Me | (CH$_2$)$_2$ | 4-(CH$_2$)$_9$CH$_3$ | H |
| Ac | H | Ac | 1 | Me | (CH$_2$)$_2$ | 4-O(CH$_2$)$_8$CH$_3$ | H |
| H | H | H | 1 | Me | (CH$_2$)$_2$ | 4-(CH$_2$)$_{10}$CH$_3$ | H |
| H | H | H | 1 | Me | (CH$_2$)$_2$ | 4-O(CH$_2$)$_9$CH$_3$ | H |
| Ac | H | Ac | 1 | Me | (CH$_2$)$_2$ | 4-(CH$_2$)$_{10}$CH$_3$ | H |
| Ac | H | Ac | 1 | Me | (CH$_2$)$_2$ | 4-O(CH$_2$)$_9$CH$_3$ | H |
| H | H | H | 1 | Me | (CH$_2$)$_2$ | 4-(CH$_2$)$_{11}$CH$_3$ | H |
| H | H | H | 1 | Me | (CH$_2$)$_2$ | 4-O(CH$_2$)$_{10}$CH$_3$ | H |
| Ac | H | Ac | 1 | Me | (CH$_2$)$_2$ | 4-(CH$_2$)$_{11}$CH$_3$ | H |
| Ac | H | Ac | 1 | Me | (CH$_2$)$_2$ | 4-O(CH$_2$)$_{10}$CH$_3$ | H |
| H | H | H | 1 | Me | (CH$_2$)$_2$ | 4-O(CH$_2$)$_3$Ph | H |
| Ac | H | Ac | 1 | Me | (CH$_2$)$_2$ | 4-O(CH$_2$)$_3$Ph | H |
| H | H | H | 1 | Me | (CH$_2$)$_2$ | 4-O(CH$_2$)$_4$Ph | H |
| Ac | H | Ac | 1 | Me | (CH$_2$)$_2$ | 4-O(CH$_2$)$_4$Ph | H |
| H | H | H | 1 | Me | (CH$_2$)$_2$ | 4-O(CH$_2$)$_5$Ph | H |
| Ac | H | Ac | 1 | Me | (CH$_2$)$_2$ | 4-O(CH$_2$)$_5$Ph | H |
| H | H | H | 1 | Me | (CH$_2$)$_2$ | 4-O(CH$_2$)$_6$Ph | H |
| Ac | H | Ac | 1 | Me | (CH$_2$)$_2$ | 4-O(CH$_2$)$_6$Ph | H |

TABLE 2

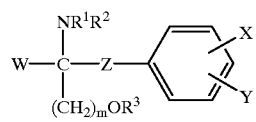

| R¹ | R² | R³ | m | W | Z | X | Y |
|---|---|---|---|---|---|---|---|
| H | H | H | 1 | Me | (CH$_2$)$_2$ | 3-O(CH$_2$)$_6$CH$_3$ | H |
| Ac | H | Ac | 1 | Me | (CH$_2$)$_2$ | 3-O(CH$_2$)$_6$CH$_3$ | H |
| H | H | H | 1 | Me | (CH$_2$)$_2$ | 3-O(CH$_2$)$_7$CH$_3$ | H |
| Ac | H | Ac | 1 | Me | (CH$_2$)$_2$ | 3-O(CH$_2$)$_7$CH$_3$ | H |
| H | H | H | 1 | Me | (CH$_2$)$_2$ | 3-O(CH$_2$)$_8$CH$_3$ | H |
| Ac | H | Ac | 1 | Me | (CH$_2$)$_2$ | 3-O(CH$_2$)$_8$CH$_3$ | H |
| H | H | H | 1 | Me | (CH$_2$)$_2$ | 3-O(CH$_2$)$_9$CH$_3$ | H |
| Ac | H | Ac | 1 | Me | (CH$_2$)$_2$ | 3-O(CH$_2$)$_9$CH$_3$ | H |
| H | H | H | 1 | Me | (CH$_2$)$_2$ | 3-O(CH$_2$)$_{10}$CH$_3$ | H |
| Ac | H | Ac | 1 | Me | (CH$_2$)$_2$ | 3-O(CH$_2$)$_{10}$CH$_3$ | H |
| H | H | H | 1 | Me | (CH$_2$)$_2$ | 2-O(CH$_2$)$_6$CH$_3$ | H |
| Ac | H | Ac | 1 | Me | (CH$_2$)$_2$ | 2-O(CH$_2$)$_6$CH$_3$ | H |
| H | H | H | 1 | Me | (CH$_2$)$_2$ | 2-O(CH$_2$)$_7$CH$_3$ | H |
| Ac | H | Ac | 1 | Me | (CH$_2$)$_2$ | 2-O(CH$_2$)$_7$CH$_3$ | H |
| H | H | H | 1 | Me | (CH$_2$)$_2$ | 2-O(CH$_2$)$_8$CH$_3$ | H |
| Ac | H | Ac | 1 | Me | (CH$_2$)$_2$ | 2-O(CH$_2$)$_8$CH$_3$ | H |
| H | H | H | 1 | Me | (CH$_2$)$_2$ | 2-O(CH$_2$)$_9$CH$_3$ | H |
| Ac | H | Ac | 1 | Me | (CH$_2$)$_2$ | 2-O(CH$_2$)$_9$CH$_3$ | H |
| H | H | H | 1 | Me | (CH$_2$)$_2$ | 2-O(CH$_2$)$_{10}$CH$_3$ | H |
| Ac | H | Ac | 1 | Me | (CH$_2$)$_2$ | 2-O(CH$_2$)$_{10}$CH$_3$ | H |
| H | H | H | 1 | Me | (CH$_2$)$_2$ | 4-O(CH$_2$)$_6$CH$_3$ | 3-OMe |
| Ac | H | Ac | 1 | Me | (CH$_2$)$_2$ | 4-O(CH$_2$)$_6$CH$_3$ | 3-OMe |
| H | H | H | 1 | Me | (CH$_2$)$_2$ | 4-O(CH$_2$)$_7$CH$_3$ | 3-OMe |
| Ac | H | Ac | 1 | Me | (CH$_2$)$_2$ | 4-O(CH$_2$)$_7$CH$_3$ | 3-OMe |
| H | H | H | 1 | Me | (CH$_2$)$_2$ | 4-O(CH$_2$)$_8$CH$_3$ | 3-OMe |

TABLE 2-continued

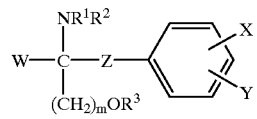

| R¹ | R² | R³ | m | W | Z | X | Y |
|---|---|---|---|---|---|---|---|
| Ac | H | Ac | 1 | Me | (CH$_2$)$_2$ | 4-O(CH$_2$)$_8$CH$_3$ | 3-OMe |
| H | H | H | 1 | Me | (CH$_2$)$_2$ | 4-O(CH$_2$)$_9$CH$_3$ | 3-OMe |
| Ac | H | Ac | 1 | Me | (CH$_2$)$_2$ | 4-O(CH$_2$)$_9$CH$_3$ | 3-OMe |
| H | H | H | 1 | Me | (CH$_2$)$_2$ | 4-O(CH$_2$)$_{10}$CH$_3$ | 3-OMe |
| Ac | H | Ac | 1 | Me | (CH$_2$)$_2$ | 4-O(CH$_2$)$_{10}$CH$_3$ | 3-OMe |
| H | H | H | 1 | Et | (CH$_2$)$_2$ | 4-(CH$_2$)$_7$CH$_3$ | H |

TABLE 3

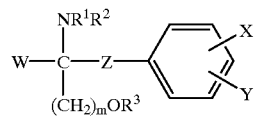

| R¹ | R² | R³ | m | W | Z | X | Y |
|---|---|---|---|---|---|---|---|
| H | H | H | 1 | Et | (CH$_2$)$_2$ | 4-CO(CH$_2$)$_6$CH$_3$ | H |
| H | H | H | 1 | Et | (CH$_2$)$_2$ | 4-CH(OH)(CH$_2$)$_6$CH$_3$ | H |
| H | H | H | 1 | Et | (CH$_2$)$_2$ | 4-CH(NH$_2$)(CH$_2$)$_6$CH$_3$ | H |
| H | H | H | 1 | Et | (CH$_2$)$_2$ | 4-O(CH$_2$)$_6$CH$_3$ | H |
| Ac | H | Ac | 1 | Et | (CH$_2$)$_2$ | 4-(CH$_2$)$_7$CH$_3$ | H |
| Ac | H | Ac | 1 | Et | (CH$_2$)$_2$ | 4-O(CH$_2$)$_6$CH$_3$ | H |
| H | H | H | 1 | Et | (CH$_2$)$_2$ | 4-(CH$_2$)$_8$CH$_3$ | H |
| H | H | H | 1 | Et | (CH$_2$)$_2$ | 4-O(CH$_2$)$_7$CH$_3$ | H |
| Ac | H | Ac | 1 | Et | (CH$_2$)$_2$ | 4-(CH$_2$)$_8$CH$_3$ | H |
| Ac | H | Ac | 1 | Et | (CH$_2$)$_2$ | 4-O(CH$_2$)$_7$CH$_3$ | H |
| H | H | H | 1 | Et | (CH$_2$)$_2$ | 4-(CH$_2$)$_9$CH$_3$ | H |
| H | H | H | 1 | Et | (CH$_2$)$_2$ | 4-O(CH$_2$)$_8$CH$_3$ | H |
| Ac | H | Ac | 1 | Et | (CH$_2$)$_2$ | 4-(CH$_2$)$_9$CH$_3$ | H |
| Ac | H | Ac | 1 | Et | (CH$_2$)$_2$ | 4-O(CH$_2$)$_8$CH$_3$ | H |
| H | H | H | 1 | Et | (CH$_2$)$_2$ | 4-(CH$_2$)$_{10}$CH$_3$ | H |
| H | H | H | 1 | Et | (CH$_2$)$_2$ | 4-O(CH$_2$)$_9$CH$_3$ | H |
| Ac | H | Ac | 1 | Et | (CH$_2$)$_2$ | 4-(CH$_2$)$_{10}$CH$_3$ | H |
| Ac | H | Ac | 1 | Et | (CH$_2$)$_2$ | 4-O(CH$_2$)$_9$CH$_3$ | H |
| H | H | H | 1 | Et | (CH$_2$)$_2$ | 4-(CH$_2$)$_{11}$CH$_3$ | H |
| H | H | H | 1 | Et | (CH$_2$)$_2$ | 4-O(CH$_2$)$_{10}$CH$_3$ | H |
| Ac | H | Ac | 1 | Et | (CH$_2$)$_2$ | 4-(CH$_2$)$_{11}$CH$_3$ | H |
| Ac | H | Ac | 1 | Et | (CH$_2$)$_2$ | 4-O(CH$_2$)$_{10}$CH$_3$ | H |
| H | H | H | 1 | Et | (CH$_2$)$_2$ | 4-O(CH$_2$)$_3$Ph | H |
| Ac | H | Ac | 1 | Et | (CH$_2$)$_2$ | 4-O(CH$_2$)$_3$Ph | H |
| H | H | H | 1 | Et | (CH$_2$)$_2$ | 4-O(CH$_2$)$_4$Ph | H |
| Ac | H | Ac | 1 | Et | (CH$_2$)$_2$ | 4-O(CH$_2$)$_4$Ph | H |
| H | H | H | 1 | Et | (CH$_2$)$_2$ | 4-O(CH$_2$)$_5$Ph | H |
| Ac | H | Ac | 1 | Et | (CH$_2$)$_2$ | 4-O(CH$_2$)$_5$Ph | H |
| H | H | H | 1 | Et | (CH$_2$)$_2$ | 4-O(CH$_2$)$_6$Ph | H |
| Ac | H | Ac | 1 | Et | (CH$_2$)$_2$ | 4-O(CH$_2$)$_6$Ph | H |
| H | H | H | 1 | Et | (CH$_2$)$_2$ | 4-O(CH$_2$)$_6$CH$_3$ | 3-OMe |

TABLE 4

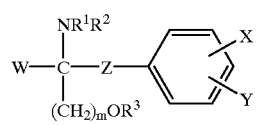

| R¹ | R² | R³ | m | W | Z | X | Y |
|---|---|---|---|---|---|---|---|
| Ac | H | Ac | 1 | Et | (CH$_2$)$_2$ | 4-O(CH$_2$)$_6$CH$_3$ | 3-OMe |
| H | H | H | 1 | Et | (CH$_2$)$_2$ | 4-O(CH$_2$)$_7$CH$_3$ | 3-OMe |
| Ac | H | Ac | 1 | Et | (CH$_2$)$_2$ | 4-O(CH$_2$)$_7$CH$_3$ | 3-OMe |
| H | H | H | 1 | Et | (CH$_2$)$_2$ | 4-O(CH$_2$)$_8$CH$_3$ | 3-OMe |
| Ac | H | Ac | 1 | Et | (CH$_2$)$_2$ | 4-O(CH$_2$)$_8$CH$_3$ | 3-OMe |

TABLE 4-continued

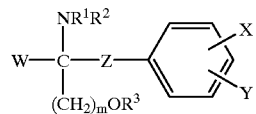

| R¹ | R² | R³ | m | W | Z | X | Y |
|---|---|---|---|---|---|---|---|
| H | H | H | 1 | Et | $(CH_2)_2$ | 4-$O(CH_2)_9CH_3$ | 3-OMe |
| Ac | H | Ac | 1 | Et | $(CH_2)_2$ | 4-$O(CH_2)_9CH_3$ | 3-OMe |
| H | H | H | 1 | Et | $(CH_2)_2$ | 4-$O(CH_2)_{10}CH_3$ | 3-OMe |
| Ac | H | Ac | 1 | Et | $(CH_2)_2$ | 4-$O(CH_2)_{10}CH_3$ | 3-OMe |
| H | H | H | 1 | $(CH_2)_2F$ | $(CH_2)_2$ | 4-$(CH_2)_7CH_3$ | H |
| H | H | H | 1 | $(CH_2)_2F$ | $(CH_2)_2$ | 4-$CO(CH_2)_6CH_3$ | H |
| H | H | H | 1 | $(CH_2)_2F$ | $(CH_2)_2$ | 4-$CH(OH)(CH_2)_6CH_3$ | H |
| H | H | H | 1 | $(CH_2)_2F$ | $(CH_2)_2$ | 4-$CH(NH_2)(CH_2)_6CH_3$ | H |
| H | H | H | 1 | $(CH_2)_2F$ | $(CH_2)_2$ | 4-$O(CH_2)_6CH_3$ | H |
| H | H | H | 1 | $(CH_2)_2F$ | $(CH_2)_2$ | 4-$O(CH_2)_6CH_3$ | 3-OMe |
| H | H | H | 1 | $(CH_2)_2F$ | $(CH_2)_2$ | 4-$(CH_2)_8CH_3$ | H |
| H | H | H | 1 | $(CH_2)_2F$ | $(CH_2)_2$ | 4-$O(CH_2)_7CH_3$ | H |
| H | H | H | 1 | $(CH_2)_2F$ | $(CH_2)_2$ | 4-$(CH_2)_9CH_3$ | H |
| H | H | H | 1 | $(CH_2)_2F$ | $(CH_2)_2$ | 4-$O(CH_2)_8CH_3$ | H |
| H | H | H | 1 | $(CH_2)_2F$ | $(CH_2)_2$ | 4-$(CH_2)_{10}CH_3$ | H |
| H | H | H | 1 | $(CH_2)_2F$ | $(CH_2)_2$ | 4-$O(CH_2)_9CH_3$ | H |
| H | H | H | 1 | $(CH_2)_2F$ | $(CH_2)_2$ | 4-$(CH_2)_{11}CH_3$ | H |
| H | H | H | 1 | $(CH_2)_2F$ | $(CH_2)_2$ | 4-$O(CH_2)_{10}CH_3$ | H |
| H | H | H | 1 | $CH_2F$ | $(CH_2)_2$ | 4-$(CH_2)_7CH_3$ | H |
| H | H | H | 1 | $CH_2F$ | $(CH_2)_2$ | 4-$O(CH_2)_6CH_3$ | H |
| H | H | H | 1 | $CH_2F$ | $(CH_2)_2$ | 4-$(CH_2)_8CH_3$ | H |
| H | H | H | 1 | $CH_2F$ | $(CH_2)_2$ | 4-$O(CH_2)_7CH_3$ | H |
| H | H | H | 1 | $CH_2F$ | $(CH_2)_2$ | 4-$(CH_2)_9CH_3$ | H |
| H | H | H | 1 | $CH_2F$ | $(CH_2)_2$ | 4-$O(CH_2)_8CH_3$ | H |
| H | H | H | 1 | $CH_2F$ | $(CH_2)_2$ | 4-$(CH_2)_{10}CH_3$ | H |
| H | H | H | 1 | $CH_2F$ | $(CH_2)_2$ | 4-$O(CH_2)_9CH_3$ | H |

TABLE 5

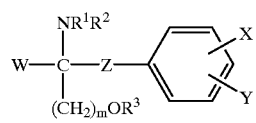

| R¹ | R² | R³ | m | W | Z | X | Y |
|---|---|---|---|---|---|---|---|
| H | H | H | 1 | $CH_2F$ | $(CH_2)_2$ | 4-$(CH_2)_{11}CH_3$ | H |
| H | H | H | 1 | $CH_2F$ | $(CH_2)_2$ | 4-$O(CH_2)_{10}CH_3$ | H |
| H | H | H | 1 | $(CH_2)_2Cl$ | $(CH_2)_2$ | 4-$(CH_2)_7CH_3$ | H |
| H | H | H | 1 | $(CH_2)_2Cl$ | $(CH_2)_2$ | 4-$CO(CH_2)_6CH_3$ | H |
| H | H | H | 1 | $(CH_2)_2Cl$ | $(CH_2)_2$ | 4-$CH(OH)(CH_2)_6CH_3$ | H |
| H | H | H | 1 | $(CH_2)_2Cl$ | $(CH_2)_2$ | 4-$CH(NH_2)(CH_2)_6CH_3$ | H |
| H | H | H | 1 | $(CH_2)_2Cl$ | $(CH_2)_2$ | 4-$O(CH_2)_6CH_3$ | H |
| H | H | H | 1 | $(CH_2)_2Cl$ | $(CH_2)_2$ | 4-$(CH_2)_8CH_3$ | H |
| H | H | H | 1 | $(CH_2)_2Cl$ | $(CH_2)_2$ | 4-$O(CH_2)_7CH_3$ | H |
| H | H | H | 1 | $(CH_2)_2Cl$ | $(CH_2)_2$ | 4-$(CH_2)_9CH_3$ | H |
| H | H | H | 1 | $(CH_2)_2Cl$ | $(CH_2)_2$ | 4-$O(CH_2)_8CH_3$ | H |
| H | H | H | 1 | $(CH_2)_2Cl$ | $(CH_2)_2$ | 4-$(CH_2)_{10}CH_3$ | H |
| H | H | H | 1 | $(CH_2)_2Cl$ | $(CH_2)_2$ | 4-$O(CH_2)_9CH_3$ | H |
| H | H | H | 1 | $(CH_2)_2Cl$ | $(CH_2)_2$ | 4-$(CH_2)_{11}CH_3$ | H |
| H | H | H | 1 | $(CH_2)_2Cl$ | $(CH_2)_2$ | 4-$O(CH_2)_{10}CH_3$ | H |
| H | H | H | 1 | $(CH_2)_2Br$ | $(CH_2)_2$ | 4-$(CH_2)_7CH_3$ | H |
| H | H | H | 1 | $(CH_2)_2Br$ | $(CH_2)_2$ | 4-$O(CH_2)_6CH_3$ | H |
| H | H | H | 1 | $(CH_2)_2Br$ | $(CH_2)_2$ | 4-$(CH_2)_8CH_3$ | H |
| H | H | H | 1 | $(CH_2)_2Br$ | $(CH_2)_2$ | 4-$O(CH_2)_7CH_3$ | H |
| H | H | H | 1 | $(CH_2)_2Br$ | $(CH_2)_2$ | 4-$(CH_2)_9CH_3$ | H |
| H | H | H | 1 | $(CH_2)_2Br$ | $(CH_2)_2$ | 4-$O(CH_2)_8CH_3$ | H |
| H | H | H | 1 | $(CH_2)_2Br$ | $(CH_2)_2$ | 4-$(CH_2)_{10}CH_3$ | H |
| H | H | H | 1 | $(CH_2)_2Br$ | $(CH_2)_2$ | 4-$O(CH_2)_9CH_3$ | H |
| H | H | H | 1 | $(CH_2)_2Br$ | $(CH_2)_2$ | 4-$(CH_2)_{11}CH_3$ | H |
| H | H | H | 1 | $(CH_2)_2Br$ | $(CH_2)_2$ | 4-$O(CH_2)_{10}CH_3$ | H |
| H | H | H | 1 | $(CH_2)_3F$ | $(CH_2)_2$ | 4-$(CH_2)_7CH_3$ | H |
| H | H | H | 1 | $(CH_2)_3F$ | $(CH_2)_2$ | 4-$O(CH_2)_6CH_3$ | H |
| H | H | H | 1 | $(CH_2)_3F$ | $(CH_2)_2$ | 4-$(CH_2)_8CH_3$ | H |
| H | H | H | 1 | $(CH_2)_3F$ | $(CH_2)_2$ | 4-$O(CH_2)_7CH_3$ | H |

TABLE 5-continued

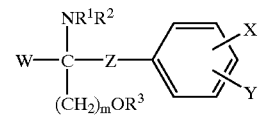

| R¹ | R² | R³ | m | W | Z | X | Y |
|---|---|---|---|---|---|---|---|
| H | H | H | 1 | $(CH_2)_3F$ | $(CH_2)_2$ | 4-$(CH_2)_9CH_3$ | H |
| H | H | H | 1 | $(CH_2)_3F$ | $(CH_2)_2$ | 4-$O(CH_2)_8CH_3$ | H |

TABLE 6

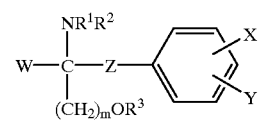

| R¹ | R² | R³ | m | W | Z | X | Y |
|---|---|---|---|---|---|---|---|
| H | H | H | 1 | $(CH_2)_3F$ | $(CH_2)_2$ | 4-$(CH_2)_{10}CH_3$ | H |
| H | H | H | 1 | $(CH_2)_3F$ | $(CH_2)_2$ | 4-$O(CH_2)_9CH_3$ | H |
| H | H | H | 1 | $(CH_2)_3F$ | $(CH_2)_2$ | 4-$(CH_2)_{11}CH_3$ | H |
| H | H | H | 1 | $(CH_2)_3F$ | $(CH_2)_2$ | 4-$O(CH_2)_{10}CH_3$ | H |
| H | H | H | 1 | n-Pr | $(CH_2)_2$ | 4-$(CH_2)_3CH_3$ | H |
| H | H | H | 1 | n-Pr | $(CH_2)_2$ | 4-$O(CH_2)_2CH_3$ | H |
| H | H | H | 1 | n-Pr | $(CH_2)_2$ | 4-$CO(CH_2)_2CH_3$ | H |
| H | H | H | 1 | n-Pr | $(CH_2)_2$ | 4-$(CH_2)_6CH_3$ | H |
| H | H | H | 1 | n-Pr | $(CH_2)_2$ | 4-$O(CH_2)_5CH_3$ | H |
| H | H | H | 1 | n-Pr | $(CH_2)_2$ | 4-$CO(CH_2)_5CH_3$ | H |
| H | H | H | 1 | n-Pr | $(CH_2)_2$ | 4-$(CH_2)_7CH_3$ | H |
| H | H | H | 1 | n-Pr | $(CH_2)_2$ | 4-$O(CH_2)_6CH_3$ | H |
| H | H | H | 1 | n-Pr | $(CH_2)_2$ | 4-$CO(CH_2)_6CH_3$ | H |
| H | H | H | 1 | n-Pr | $(CH_2)_2$ | 4-$CH(OH)(CH_2)_6CH_3$ | H |
| H | H | H | 1 | n-Pr | $(CH_2)_2$ | 4-$CH(NH_2)(CH_2)_6CH_3$ | H |
| H | H | H | 1 | n-Pr | $(CH_2)_2$ | 4-$CH(OAc)(CH_2)_6CH_3$ | H |
| H | H | H | 1 | n-Pr | $(CH_2)_2$ | 4-$CH(NHAc)(CH_2)_6CH_3$ | H |
| Ac | H | Ac | 1 | n-Pr | $(CH_2)_2$ | 4-$(CH_2)_7CH_3$ | H |
| Ac | H | Ac | 1 | n-Pr | $(CH_2)_2$ | 4-$O(CH_2)_6CH_3$ | H |
| Ac | H | Ac | 1 | n-Pr | $(CH_2)_2$ | 4-$CO(CH_2)_6CH_3$ | H |
| Ac | H | Ac | 1 | n-Pr | $(CH_2)_2$ | 4-$CH(OH)(CH_2)_6CH_3$ | H |
| Ac | H | Ac | 1 | n-Pr | $(CH_2)_2$ | 4-$CH(NH_2)(CH_2)_6CH_3$ | H |
| Ac | H | Ac | 1 | n-Pr | $(CH_2)_2$ | 4-$CH(OAc)(CH_2)_6CH_3$ | H |
| Ac | H | Ac | 1 | n-Pr | $(CH_2)_2$ | 4-$CH(NHAc)(CH_2)_6CH_3$ | H |
| H | H | H | 1 | n-Pr | $(CH_2)_3$ | 4-$(CH_2)_6CH_3$ | H |
| H | H | H | 1 | n-Pr | $(CH_2)_3$ | 4-$O(CH_2)_5CH_3$ | H |
| H | H | H | 1 | n-Pr | $(CH_2)_3$ | 4-$CO(CH_2)_5CH_3$ | H |
| H | H | H | 1 | n-Pr | $(CH_2)_4$ | 4-$(CH_2)_5CH_3$ | H |
| H | H | H | 1 | n-Pr | $(CH_2)_4$ | 4-$O(CH_2)_4CH_3$ | H |
| H | H | H | 1 | n-Pr | $(CH_2)_4$ | 4-$CO(CH_2)_4CH_3$ | H |
| H | H | H | 1 | n-Pr | $(CH_2)_{10}$ | H | H |

TABLE 7

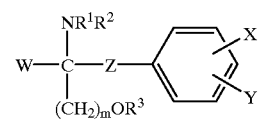

| R¹ | R² | R³ | m | W | Z | X | Y |
|---|---|---|---|---|---|---|---|
| H | H | H | 1 | n-Pr | $(CH_2)_2$ | 4-$(CH_2)_8CH_3$ | H |
| H | H | H | 1 | n-Pr | $(CH_2)_2$ | 4-$O(CH_2)_7CH_3$ | H |
| H | H | H | 1 | n-Pr | $(CH_2)_2$ | 4-$(CH_2)_9CH_3$ | H |
| H | H | H | 1 | n-Pr | $(CH_2)_2$ | 4-$O(CH_2)_8CH_3$ | H |
| H | H | H | 1 | n-Pr | $(CH_2)_2$ | 4-$(CH_2)_{10}CH_3$ | H |
| H | H | H | 1 | n-Pr | $(CH_2)_2$ | 4-$O(CH_2)_9CH_3$ | H |
| H | H | H | 1 | n-Pr | $(CH_2)_2$ | 4-$(CH_2)_{11}CH_3$ | H |
| H | H | H | 1 | n-Pr | $(CH_2)_2$ | 4-$O(CH_2)_{10}CH_3$ | H |
| H | H | H | 1 | n-Pr | $(CH_2)_2$ | 4-$(CH_2)_{12}CH_3$ | H |

TABLE 7-continued

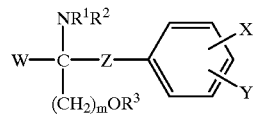

| R¹ | R² | R³ | m | W | Z | X | Y |
|----|----|----|---|---|---|---|---|
| H | H | H | 1 | n-Pr | $(CH_2)_2$ | 4-$O(CH_2)_{11}CH_3$ | H |
| H | H | H | 1 | n-Pr | $(CH_2)_2$ | 4-$(CH_2)_{13}CH_3$ | H |
| H | H | H | 1 | n-Pr | $(CH_2)_2$ | 4-$O(CH_2)_{12}CH_3$ | H |
| H | H | H | 1 | n-Pr | $(CH_2)_2$ | 4-$(CH_2)_{14}CH_3$ | H |
| H | H | H | 1 | n-Pr | $(CH_2)_2$ | 4-$O(CH_2)_{13}CH_3$ | H |
| H | H | H | 1 | n-Pr | $(CH_2)_2$ | 4-$(CH_2)_{15}CH_3$ | H |
| H | H | H | 1 | n-Pr | $(CH_2)_2$ | 4-$O(CH_2)_{14}CH_3$ | H |
| H | H | H | 1 | n-Pr | $(CH_2)_2$ | 4-$(CH_2)_{16}CH_3$ | H |
| H | H | H | 1 | n-Pr | $(CH_2)_2$ | 4-$O(CH_2)_{15}CH_3$ | H |
| H | H | H | 1 | n-Pr | $(CH_2)_2$ | 4-$(CH_2)_{17}CH_3$ | H |
| H | H | H | 1 | n-Pr | $(CH_2)_2$ | 4-$O(CH_2)_{16}CH_3$ | H |
| H | H | H | 1 | n-Pr | $(CH_2)_2$ | 4-$(CH_2)_{18}CH_3$ | H |
| H | H | H | 1 | n-Pr | $(CH_2)_2$ | 4-$O(CH_2)_{17}CH_3$ | H |
| H | H | H | 1 | n-Pr | $(CH_2)_2$ | 4-$(CH_2)_4Ph$ | H |
| H | H | H | 1 | n-Pr | $(CH_2)_2$ | 4-$(CH_2)_5Ph$ | H |
| H | H | H | 1 | n-Pr | $(CH_2)_2$ | 4-$(CH_2)_6Ph$ | H |
| H | H | H | 1 | n-Pr | $(CH_2)_2$ | 4-$O(CH_2)_3Ph$ | H |
| H | H | H | 1 | n-Pr | $(CH_2)_2$ | 4-$O(CH_2)_4Ph$ | H |
| H | H | H | 1 | n-Pr | $(CH_2)_2$ | 4-$O(CH_2)_5Ph$ | H |
| H | H | H | 1 | n-Pr | $(CH_2)_2$ | 4-$O(CH_2)_6Ph$ | H |
| H | H | H | 1 | n-Pr | $(CH_2)_2$ | 3-$O(CH_2)_6CH_3$ | H |
| H | H | H | 1 | n-Pr | $(CH_2)_2$ | 3-$O(CH_2)_8CH_3$ | H |

TABLE 8

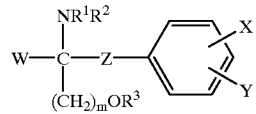

| R¹ | R² | R³ | m | W | Z | X | Y |
|----|----|----|---|---|---|---|---|
| H | H | H | 1 | n-Pr | $(CH_2)_2$ | 3-$O(CH_2)_9CH_3$ | H |
| H | H | H | 1 | n-Pr | $(CH_2)_2$ | 3-$O(CH_2)_{10}CH_3$ | H |
| H | H | H | 1 | n-Pr | $(CH_2)_2$ | 2-$O(CH_2)_6CH_3$ | H |
| H | H | H | 1 | n-Pr | $(CH_2)_2$ | 2-$O(CH_2)_7CH_3$ | H |
| H | H | H | 1 | n-Pr | $(CH_2)_2$ | 2-$O(CH_2)_8CH_3$ | H |
| H | H | H | 1 | n-Pr | $(CH_2)_2$ | 2-$O(CH_2)_9CH_3$ | H |
| H | H | H | 1 | n-Pr | $(CH_2)_2$ | 4-$O(CH_2)_6CH_3$ | 3-OMe |
| H | H | H | 1 | n-Pr | $(CH_2)_2$ | 4-$O(CH_2)_7CH_3$ | 3-OMe |
| H | H | H | 1 | n-Pr | $(CH_2)_2$ | 4-$O(CH_2)_8CH_3$ | 3-OMe |
| H | H | H | 1 | n-Pr | $(CH_2)_2$ | 4-$O(CH_2)_{10}CH_3$ | 3-OMe |
| H | H | H | 1 | Me | $(CH_2)_2$ | 4-$O(CH_2)_6CH_3$ | 3-OH |
| H | H | H | 1 | Me | $(CH_2)_2$ | 4-$O(CH_2)_7CH_3$ | 3-OH |
| H | H | H | 1 | Me | $(CH_2)_2$ | 4-$O(CH_2)_8CH_3$ | 3-OH |
| H | H | H | 1 | Me | $(CH_2)_2$ | 4-$O(CH_2)_9CH_3$ | 3-OH |
| H | H | H | 1 | Me | $(CH_2)_2$ | 4-$O(CH_2)_{10}CH_3$ | 3-OH |
| H | H | H | 1 | Et | $(CH_2)_2$ | 4-$O(CH_2)_6CH_3$ | 3-OH |
| H | H | H | 1 | Et | $(CH_2)_2$ | 4-$O(CH_2)_7CH_3$ | 3-OH |
| H | H | H | 1 | Et | $(CH_2)_2$ | 4-$O(CH_2)_8CH_3$ | 3-OH |
| H | H | H | 1 | Et | $(CH_2)_2$ | 4-$O(CH_2)_9CH_3$ | 3-OH |
| H | H | H | 1 | Et | $(CH_2)_2$ | 4-$O(CH_2)_{10}CH_3$ | 3-OH |
| H | H | H | 1 | n-Pr | $(CH_2)_2$ | 4-$O(CH_2)_6CH_3$ | 3-OH |
| H | H | H | 1 | n-Pr | $(CH_2)_2$ | 4-$O(CH_2)_7CH_3$ | 3-OH |
| H | H | H | 1 | n-Pr | $(CH_2)_2$ | 4-$O(CH_2)_8CH_3$ | 3-OH |
| H | H | H | 1 | n-Pr | $(CH_2)_2$ | 4-$O(CH_2)_9CH_3$ | 3-OH |
| H | H | H | 1 | n-Pr | $(CH_2)_2$ | 4-$O(CH_2)_{10}CH_3$ | 3-OH |
| H | H | H | 1 | $(CH_2)_2F$ | $(CH_2)_2$ | 4-$O(CH_2)_6CH_3$ | 3-OH |
| H | H | H | 1 | $(CH_2)_2F$ | $(CH_2)_2$ | 4-$O(CH_2)_7CH_3$ | 3-OH |
| H | H | H | 1 | $(CH_2)_2F$ | $(CH_2)_2$ | 4-$O(CH_2)_8CH_3$ | 3-OH |
| H | H | H | 1 | $(CH_2)_2F$ | $(CH_2)_2$ | 4-$O(CH_2)_9CH_3$ | 3-OH |
| H | H | H | 1 | $(CH_2)_2F$ | $(CH_2)_2$ | 4-$O(CH_2)_{10}CH_3$ | 3-OH |
| H | H | H | 1 | i-Pr | $(CH_2)_2$ | 4-$(CH_2)_7CH_3$ | H |

TABLE 9

| R¹ | R² | R³ | m | W | Z | X | Y |
|----|----|----|---|---|---|---|---|
| H | H | H | 1 | i-Pr | $(CH_2)_2$ | 4-$O(CH_2)_6CH_3$ | H |
| Ac | H | Ac | 1 | i-Pr | $(CH_2)_2$ | 4-$(CH_2)_7CH_3$ | H |
| Ac | H | Ac | 1 | i-Pr | $(CH_2)_2$ | 4-$O(CH_2)_6CH_3$ | H |
| H | H | H | 1 | i-Pr | $(CH_2)_2$ | 4-$(CH_2)_8CH_3$ | H |
| H | H | H | 1 | i-Pr | $(CH_2)_2$ | 4-$O(CH_2)_7CH_3$ | H |
| Ac | H | Ac | 1 | i-Pr | $(CH_2)_2$ | 4-$(CH_2)_8CH_3$ | H |
| Ac | H | Ac | 1 | i-Pr | $(CH_2)_2$ | 4-$O(CH_2)_7CH_3$ | H |
| H | H | H | 1 | i-Pr | $(CH_2)_2$ | 4-$(CH_2)_9CH_3$ | H |
| H | H | H | 1 | i-Pr | $(CH_2)_2$ | 4-$O(CH_2)_8CH_3$ | H |
| Ac | H | Ac | 1 | i-Pr | $(CH_2)_2$ | 4-$(CH_2)_9CH_3$ | H |
| Ac | H | Ac | 1 | i-Pr | $(CH_2)_2$ | 4-$O(CH_2)_8CH_3$ | H |
| H | H | H | 1 | i-Pr | $(CH_2)_2$ | 4-$(CH_2)_{10}CH_3$ | H |
| H | H | H | 1 | i-Pr | $(CH_2)_2$ | 4-$O(CH_2)_9CH_3$ | H |
| Ac | H | Ac | 1 | i-Pr | $(CH_2)_2$ | 4-$(CH_2)_{10}CH_3$ | H |
| Ac | H | Ac | 1 | i-Pr | $(CH_2)_2$ | 4-$O(CH_2)_9CH_3$ | H |
| H | H | H | 1 | i-Pr | $(CH_2)_2$ | 4-$(CH_2)_{11}CH_3$ | H |
| H | H | H | 1 | i-Pr | $(CH_2)_2$ | 4-$O(CH_2)_{10}CH_3$ | H |
| Ac | H | Ac | 1 | i-Pr | $(CH_2)_2$ | 4-$(CH_2)_{11}CH_3$ | H |
| Ac | H | Ac | 1 | i-Pr | $(CH_2)_2$ | 4-$O(CH_2)_{10}CH_3$ | H |
| H | H | H | 1 | n-Bu | $(CH_2)_2$ | 4-$(CH_2)_7CH_3$ | H |
| H | H | H | 1 | n-Bu | $(CH_2)_2$ | 4-$O(CH_2)_6CH_3$ | H |
| Ac | H | Ac | 1 | n-Bu | $(CH_2)_2$ | 4-$(CH_2)_7CH_3$ | H |
| Ac | H | Ac | 1 | n-Bu | $(CH_2)_2$ | 4-$O(CH_2)_6CH_3$ | H |
| H | H | H | 1 | n-Bu | $(CH_2)_2$ | 4-$(CH_2)_8CH_3$ | H |
| H | H | H | 1 | n-Bu | $(CH_2)_2$ | 4-$O(CH_2)_7CH_3$ | H |
| Ac | H | Ac | 1 | n-Bu | $(CH_2)_2$ | 4-$(CH_2)_8CH_3$ | H |
| Ac | H | Ac | 1 | n-Bu | $(CH_2)_2$ | 4-$O(CH_2)_7CH_3$ | H |
| H | H | H | 1 | n-Bu | $(CH_2)_2$ | 4-$(CH_2)_9CH_3$ | H |
| H | H | H | 1 | n-Bu | $(CH_2)_2$ | 4-$O(CH_2)_8CH_3$ | H |
| Ac | H | Ac | 1 | n-Bu | $(CH_2)_2$ | 4-$(CH_2)_9CH_3$ | H |
| Ac | H | Ac | 1 | n-Bu | $(CH_2)_2$ | 4-$O(CH_2)_8CH_3$ | H |

TABLE 10

| R¹ | R² | R³ | m | W | Z | X | Y |
|----|----|----|---|---|---|---|---|
| H | H | H | 1 | n-Bu | $(CH_2)_2$ | 4-$(CH_2)_{10}CH_3$ | H |
| H | H | H | 1 | n-Bu | $(CH_2)_2$ | 4-$O(CH_2)_9CH_3$ | H |
| Ac | H | Ac | 1 | n-Bu | $(CH_2)_2$ | 4-$(CH_2)_{10}CH_3$ | H |
| Ac | H | Ac | 1 | n-Bu | $(CH_2)_2$ | 4-$O(CH_2)_9CH_3$ | H |
| H | H | H | 1 | n-Bu | $(CH_2)_2$ | 4-$(CH_2)_{11}CH_3$ | H |
| H | H | H | 1 | n-Bu | $(CH_2)_2$ | 4-$O(CH_2)_{10}CH_3$ | H |
| Ac | H | Ac | 1 | n-Bu | $(CH_2)_2$ | 4-$(CH_2)_{11}CH_3$ | H |
| Ac | H | Ac | 1 | n-Bu | $(CH_2)_2$ | 4-$O(CH_2)_{10}CH_3$ | H |
| H | H | H | 1 | $CH_2=CHCH_2$ | $(CH_2)_2$ | 4-$(CH_2)_7CH_3$ | H |
| H | H | H | 1 | $CH_2=CHCH_2$ | $(CH_2)_2$ | 4-$O(CH_2)_6CH_3$ | H |
| Ac | H | Ac | 1 | $CH_2=CHCH_2$ | $(CH_2)_2$ | 4-$(CH_2)_7CH_3$ | H |
| Ac | H | Ac | 1 | $CH_2=CHCH_2$ | $(CH_2)_2$ | 4-$O(CH_2)_6CH_3$ | H |
| H | H | H | 1 | $CH_2=CHCH_2$ | $(CH_2)_2$ | 4-$(CH_2)_8CH_3$ | H |
| H | H | H | 1 | $CH_2=CHCH_2$ | $(CH_2)_2$ | 4-$O(CH_2)_7CH_3$ | H |
| Ac | H | Ac | 1 | $CH_2=CHCH_2$ | $(CH_2)_2$ | 4-$(CH_2)_8CH_3$ | H |
| Ac | H | Ac | 1 | $CH_2=CHCH_2$ | $(CH_2)_2$ | 4-$O(CH_2)_7CH_3$ | H |
| H | H | H | 1 | $CH_2=CHCH_2$ | $(CH_2)_2$ | 4-$(CH_2)_9CH_3$ | H |
| H | H | H | 1 | $CH_2=CHCH_2$ | $(CH_2)_2$ | 4-$O(CH_2)_8CH_3$ | H |
| Ac | H | Ac | 1 | $CH_2=CHCH_2$ | $(CH_2)_2$ | 4-$(CH_2)_9CH_3$ | H |
| Ac | H | Ac | 1 | $CH_2=CHCH_2$ | $(CH_2)_2$ | 4-$O(CH_2)_8CH_3$ | H |
| H | H | H | 1 | $CH_2=CHCH_2$ | $(CH_2)_2$ | 4-$(CH_2)_{10}CH_3$ | H |
| H | H | H | 1 | $CH_2=CHCH_2$ | $(CH_2)_2$ | 4-$O(CH_2)_9CH_3$ | H |
| Ac | H | Ac | 1 | $CH_2=CHCH_2$ | $(CH_2)_2$ | 4-$(CH_2)_{10}CH_3$ | H |
| Ac | H | Ac | 1 | $CH_2=CHCH_2$ | $(CH_2)_2$ | 4-$O(CH_2)_9CH_3$ | H |
| H | H | H | 1 | $CH_2=CHCH_2$ | $(CH_2)_2$ | 4-$(CH_2)_{11}CH_3$ | H |

TABLE 10-continued

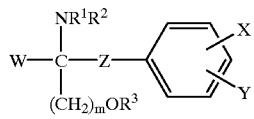

| R¹ | R² | R³ | m | W | Z | X | Y |
|---|---|---|---|---|---|---|---|
| H | H | H | 1 | CH$_2$=CHCH$_2$ | (CH$_2$)$_2$ | 4-O(CH$_2$)$_{10}$CH$_3$ | H |
| Ac | H | Ac | 1 | CH$_2$=CHCH$_2$ | (CH$_2$)$_2$ | 4-(CH$_2$)$_{11}$CH$_3$ | H |
| Ac | H | Ac | 1 | CH$_2$=CHCH$_2$ | (CH$_2$)$_2$ | 4-O(CH$_2$)$_{10}$CH$_3$ | H |
| H | H | H | 1 | c-Pr—CH$_2$ | (CH$_2$)$_2$ | 4-(CH$_2$)$_7$CH$_3$ | H |
| H | H | H | 1 | c-Pr—CH$_2$ | (CH$_2$)$_2$ | 4-O(CH$_2$)$_6$CH$_3$ | H |
| Ac | H | Ac | 1 | c-Pr—CH$_2$ | (CH$_2$)$_2$ | 4-(CH$_2$)$_7$CH$_3$ | H |

TABLE 11

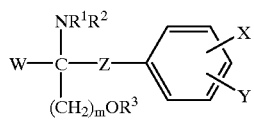

| R¹ | R² | R³ | m | W | Z | X | Y |
|---|---|---|---|---|---|---|---|
| Ac | H | Ac | 1 | c-Pr—CH$_2$ | (CH$_2$)$_2$ | 4-O(CH$_2$)$_6$CH$_3$ | H |
| H | H | H | 1 | c-Pr—CH$_2$ | (CH$_2$)$_2$ | 4-(CH$_2$)$_8$CH$_3$ | H |
| H | H | H | 1 | c-Pr—CH$_2$ | (CH$_2$)$_2$ | 4-O(CH$_2$)$_7$CH$_3$ | H |
| Ac | H | Ac | 1 | c-Pr—CH$_2$ | (CH$_2$)$_2$ | 4-(CH$_2$)$_8$CH$_3$ | H |
| Ac | H | Ac | 1 | c-Pr—CH$_2$ | (CH$_2$)$_2$ | 4-O(CH$_2$)$_7$CH$_3$ | H |
| H | H | H | 1 | c-Pr—CH$_2$ | (CH$_2$)$_2$ | 4-(CH$_2$)$_9$CH$_3$ | H |
| H | H | H | 1 | c-Pr—CH$_2$ | (CH$_2$)$_2$ | 4-O(CH$_2$)$_8$CH$_3$ | H |
| Ac | H | Ac | 1 | c-Pr—CH$_2$ | (CH$_2$)$_2$ | 4-(CH$_2$)$_9$CH$_3$ | H |
| Ac | H | Ac | 1 | c-Pr—CH$_2$ | (CH$_2$)$_2$ | 4-O(CH$_2$)$_8$CH$_3$ | H |
| H | H | H | 1 | c-Pr—CH$_2$ | (CH$_2$)$_2$ | 4-(CH$_2$)$_{10}$CH$_3$ | H |
| H | H | H | 1 | c-Pr—CH$_2$ | (CH$_2$)$_2$ | 4-O(CH$_2$)$_9$CH$_3$ | H |
| Ac | H | Ac | 1 | c-Pr—CH$_2$ | (CH$_2$)$_2$ | 4-(CH$_2$)$_{10}$CH$_3$ | H |
| Ac | H | Ac | 1 | c-Pr—CH$_2$ | (CH$_2$)$_2$ | 4-O(CH$_2$)$_9$CH$_3$ | H |
| H | H | H | 1 | c-Pr—CH$_2$ | (CH$_2$)$_2$ | 4-(CH$_2$)$_{11}$CH$_3$ | H |
| H | H | H | 1 | c-Pr—CH$_2$ | (CH$_2$)$_2$ | 4-O(CH$_2$)$_{10}$CH$_3$ | H |
| Ac | H | Ac | 1 | c-Pr—CH$_2$ | (CH$_2$)$_2$ | 4-(CH$_2$)$_{11}$CH$_3$ | H |
| Ac | H | Ac | 1 | c-Pr—CH$_2$ | (CH$_2$)$_2$ | 4-O(CH$_2$)$_{10}$CH$_3$ | H |
| H | H | H | 1 | CH≡CCH$_2$ | (CH$_2$)$_2$ | 4-(CH$_2$)$_7$CH$_3$ | H |
| H | H | H | 1 | CH≡CCH$_2$ | (CH$_2$)$_2$ | 4-O(CH$_2$)$_6$CH$_3$ | H |
| Ac | H | Ac | 1 | CH≡CCH$_2$ | (CH$_2$)$_2$ | 4-(CH$_2$)$_7$CH$_3$ | H |
| Ac | H | Ac | 1 | CH≡CCH$_2$ | (CH$_2$)$_2$ | 4-O(CH$_2$)$_6$CH$_3$ | H |
| H | H | H | 1 | CH≡CCH$_2$ | (CH$_2$)$_2$ | 4-(CH$_2$)$_8$CH$_3$ | H |
| H | H | H | 1 | CH≡CCH$_2$ | (CH$_2$)$_2$ | 4-O(CH$_2$)$_7$CH$_3$ | H |
| Ac | H | Ac | 1 | CH≡CCH$_2$ | (CH$_2$)$_2$ | 4-(CH$_2$)$_8$CH$_3$ | H |
| Ac | H | Ac | 1 | CH≡CCH$_2$ | (CH$_2$)$_2$ | 4-O(CH$_2$)$_7$CH$_3$ | H |
| H | H | H | 1 | CH≡CCH$_2$ | (CH$_2$)$_2$ | 4-(CH$_2$)$_9$CH$_3$ | H |
| H | H | H | 1 | CH≡CCH$_2$ | (CH$_2$)$_2$ | 4-(CH$_2$)$_8$CH$_3$ | H |
| Ac | H | Ac | 1 | CH≡CCH$_2$ | (CH$_2$)$_2$ | 4-(CH$_2$)$_9$CH$_3$ | H |
| Ac | H | Ac | 1 | CH≡CCH$_2$ | (CH$_2$)$_2$ | 4-O(CH$_2$)$_8$CH$_3$ | H |
| H | H | H | 1 | CH≡CCH$_2$ | (CH$_2$)$_2$ | 4-(CH$_2$)$_{10}$CH$_3$ | H |
| H | H | H | 1 | CH≡CCH$_2$ | (CH$_2$)$_2$ | 4-O(CH$_2$)$_9$CH$_3$ | H |

TABLE 12

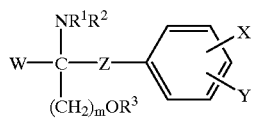

| R¹ | R² | R³ | m | W | Z | X | Y |
|---|---|---|---|---|---|---|---|
| Ac | H | Ac | 1 | CH≡CCH$_2$ | (CH$_2$)$_2$ | 4-(CH$_2$)$_{10}$CH$_3$ | H |
| Ac | H | Ac | 1 | CH≡CCH$_2$ | (CH$_2$)$_2$ | 4-O(CH$_2$)$_9$CH$_3$ | H |
| H | H | H | 1 | CH≡CCH$_2$ | (CH$_2$)$_2$ | 4-(CH$_2$)$_{11}$CH$_3$ | H |
| H | H | H | 1 | CH≡CCH$_2$ | (CH$_2$)$_2$ | 4-O(CH$_2$)$_{10}$CH$_3$ | H |
| Ac | H | Ac | 1 | CH≡CCH$_2$ | (CH$_2$)$_2$ | 4-(CH$_2$)$_{11}$CH$_3$ | H |

TABLE 12-continued

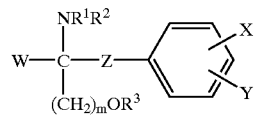

| R¹ | R² | R³ | m | W | Z | X | Y |
|---|---|---|---|---|---|---|---|
| Ac | H | Ac | 1 | CH≡CCH$_2$ | (CH$_2$)$_2$ | 4-O(CH$_2$)$_{10}$CH$_3$ | H |
| H | H | H | 1 | CH$_2$=CH | (CH$_2$)$_2$ | 4-(CH$_2$)$_7$CH$_3$ | H |
| H | H | H | 1 | CH$_2$=CH | (CH$_2$)$_2$ | 4-O(CH$_2$)$_6$CH$_3$ | H |
| H | H | H | 1 | CH$_2$=CH | (CH$_2$)$_2$ | 4-(CH$_2$)$_8$CH$_3$ | H |
| H | H | H | 1 | CH$_2$=CH | (CH$_2$)$_2$ | 4-O(CH$_2$)$_7$CH$_3$ | H |
| H | H | H | 1 | CH$_2$=CH | (CH$_2$)$_2$ | 4-(CH$_2$)$_9$CH$_3$ | H |
| H | H | H | 1 | CH$_2$=CH | (CH$_2$)$_2$ | 4-O(CH$_2$)$_8$CH$_3$ | H |
| H | H | H | 1 | CH$_2$=CH | (CH$_2$)$_2$ | 4-(CH$_2$)$_{10}$CH$_3$ | H |
| H | H | H | 1 | CH$_2$=CH | (CH$_2$)$_2$ | 4-O(CH$_2$)$_9$CH$_3$ | H |
| H | H | H | 1 | CH$_2$=CH | (CH$_2$)$_2$ | 4-(CH$_2$)$_{11}$CH$_3$ | H |
| H | H | H | 1 | CH$_2$=CH | (CH$_2$)$_2$ | 4-O(CH$_2$)$_{10}$CH$_3$ | H |
| H | H | H | 1 | (CH$_3$)$_2$CHCH$_2$ | (CH$_2$)$_2$ | 4-(CH$_2$)$_7$CH$_3$ | H |
| H | H | H | 1 | (CH$_3$)$_2$CHCH$_2$ | (CH$_2$)$_2$ | 4-O(CH$_2$)$_6$CH$_3$ | H |
| H | H | H | 1 | (CH$_3$)$_2$CHCH$_2$ | (CH$_2$)$_2$ | 4-(CH$_2$)$_8$CH$_3$ | H |
| H | H | H | 1 | (CH$_3$)$_2$CHCH$_2$ | (CH$_2$)$_2$ | 4-O(CH$_2$)$_7$CH$_3$ | H |
| H | H | H | 1 | (CH$_3$)$_2$CHCH$_2$ | (CH$_2$)$_2$ | 4-(CH$_2$)$_9$CH$_3$ | H |
| H | H | H | 1 | (CH$_3$)$_2$CHCH$_2$ | (CH$_2$)$_2$ | 4-O(CH$_2$)$_8$CH$_3$ | H |
| H | H | H | 1 | (CH$_3$)$_2$CHCH$_2$ | (CH$_2$)$_2$ | 4-(CH$_2$)$_{10}$CH$_3$ | H |
| H | H | H | 1 | (CH$_3$)$_2$CHCH$_2$ | (CH$_2$)$_2$ | 4-O(CH$_2$)$_9$CH$_3$ | H |
| H | H | H | 1 | (CH$_3$)$_2$CHCH$_2$ | (CH$_2$)$_2$ | 4-(CH$_2$)$_{11}$CH$_3$ | H |
| H | H | H | 1 | (CH$_3$)$_2$CHCH$_2$ | (CH$_2$)$_2$ | 4-O(CH$_2$)$_{10}$CH$_3$ | H |
| H | H | H | 1 | CH$_2$=CH(CH$_2$)$_2$ | (CH$_2$)$_2$ | 4-(CH$_2$)$_7$CH$_3$ | H |
| H | H | H | 1 | CH$_2$=CH(CH$_2$)$_2$ | (CH$_2$)$_2$ | 4-O(CH$_2$)$_6$CH$_3$ | H |
| H | H | H | 1 | CH$_2$=CH(CH$_2$)$_2$ | (CH$_2$)$_2$ | 4-(CH$_2$)$_8$CH$_3$ | H |
| H | H | H | 1 | CH$_2$=CH(CH$_2$)$_2$ | (CH$_2$)$_2$ | 4-O(CH$_2$)$_9$CH$_3$ | H |
| H | H | H | 1 | CH$_2$=CH(CH$_2$)$_2$ | (CH$_2$)$_2$ | 4-(CH$_2$)$_9$CH$_3$ | H |

TABLE 13

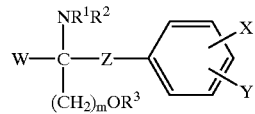

| R¹ | R² | R³ | m | W | Z | X | Y |
|---|---|---|---|---|---|---|---|
| H | H | H | 1 | CH$_2$=CH(CH$_2$)$_2$ | (CH$_2$)$_2$ | 4-O(CH$_2$)$_8$CH$_3$ | H |
| H | H | H | 1 | CH$_2$=CH(CH$_2$)$_2$ | (CH$_2$)$_2$ | 4-(CH$_2$)$_{10}$CH$_3$ | H |
| H | H | H | 1 | CH$_2$=CH(CH$_2$)$_2$ | (CH$_2$)$_2$ | 4-O(CH$_2$)$_9$CH$_3$ | H |
| H | H | H | 1 | CH$_2$=CH(CH$_2$)$_2$ | (CH$_2$)$_2$ | 4-(CH$_2$)$_{11}$CH$_3$ | H |
| H | H | H | 1 | CH$_2$=CH(CH$_2$)$_2$ | (CH$_2$)$_2$ | 4-O(CH$_2$)$_{10}$CH$_3$ | H |
| H | H | H | 1 | CH$_3$C≡CCH$_2$ | (CH$_2$)$_2$ | 4-(CH$_2$)$_7$CH$_3$ | H |
| H | H | H | 1 | CH$_3$C≡CCH$_2$ | (CH$_2$)$_2$ | 4-O(CH$_2$)$_6$CH$_3$ | H |
| H | H | H | 1 | CH$_3$C≡CCH$_2$ | (CH$_2$)$_2$ | 4-(CH$_2$)$_8$CH$_3$ | H |
| H | H | H | 1 | CH$_3$C≡CCH$_2$ | (CH$_2$)$_2$ | 4-O(CH$_2$)$_7$CH$_3$ | H |
| H | H | H | 1 | CH$_3$C≡CCH$_2$ | (CH$_2$)$_2$ | 4-(CH$_2$)$_9$CH$_3$ | H |
| H | H | H | 1 | CH$_3$C≡CCH$_2$ | (CH$_2$)$_2$ | 4-O(CH$_2$)$_8$CH$_3$ | H |
| H | H | H | 1 | CH$_3$C≡CCH$_2$ | (CH$_2$)$_2$ | 4-(CH$_2$)$_{10}$CH$_3$ | H |
| H | H | H | 1 | CH$_3$C≡CCH$_2$ | (CH$_2$)$_2$ | 4-O(CH$_2$)$_9$CH$_3$ | H |
| H | H | H | 1 | CH$_3$C≡CCH$_2$ | (CH$_2$)$_2$ | 4-CH$_2$)$_{11}$CH$_3$ | H |
| H | H | H | 1 | CH$_3$C≡CCH$_2$ | (CH$_2$)$_2$ | 4-O(CH$_2$)$_{10}$CH$_3$ | H |
| H | H | H | 1 | (CH$_2$)$_4$CH$_3$ | (CH$_2$)$_2$ | 4-(CH$_2$)$_7$CH$_3$ | H |
| H | H | H | 1 | (CH$_2$)$_4$CH$_3$ | (CH$_2$)$_2$ | 4-O(CH$_2$)$_6$CH$_3$ | H |
| H | H | H | 1 | (CH$_2$)$_4$CH$_3$ | (CH$_2$)$_2$ | 4-(CH$_2$)$_8$CH$_3$ | H |
| H | H | H | 1 | (CH$_2$)$_4$CH$_3$ | (CH$_2$)$_2$ | 4-O(CH$_2$)$_7$CH$_3$ | H |
| H | H | H | 1 | (CH$_2$)$_4$CH$_3$ | (CH$_2$)$_2$ | 4-(CH$_2$)$_9$CH$_3$ | H |
| H | H | H | 1 | (CH$_2$)$_4$CH$_3$ | (CH$_2$)$_2$ | 4-O(CH$_2$)$_8$CH$_3$ | H |
| H | H | H | 1 | (CH$_2$)$_4$CH$_3$ | (CH$_2$)$_2$ | 4-(CH$_2$)$_{10}$CH$_3$ | H |
| H | H | H | 1 | (CH$_2$)$_4$CH$_3$ | (CH$_2$)$_2$ | 4-O(CH$_2$)$_9$CH$_3$ | H |
| H | H | H | 1 | (CH$_2$)$_4$CH$_3$ | (CH$_2$)$_2$ | 4-(CH$_2$)$_{11}$CH$_3$ | H |
| H | H | H | 1 | (CH$_2$)$_4$CH$_3$ | (CH$_2$)$_2$ | 4-O(CH$_2$)$_{10}$CH$_3$ | H |
| H | H | H | 1 | (CH$_3$)$_2$CH(CH$_2$)$_2$ | (CH$_2$)$_2$ | 4-(CH$_2$)$_7$CH$_3$ | H |
| H | H | H | 1 | (CH$_3$)$_2$CH(CH$_2$)$_2$ | (CH$_2$)$_2$ | 4-O(CH$_2$)$_6$CH$_3$ | H |
| H | H | H | 1 | (CH$_3$)$_2$CH(CH$_2$)$_2$ | (CH$_2$)$_2$ | 4-(CH$_2$)$_8$CH$_3$ | H |
| H | H | H | 1 | (CH$_3$)$_2$CH(CH$_2$)$_2$ | (CH$_2$)$_2$ | 4-O(CH$_2$)$_7$CH$_3$ | H |

TABLE 13-continued

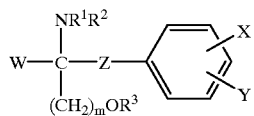

| R¹ | R² | R³ | m | W | Z | X | Y |
|----|----|----|---|---|---|---|---|
| H | H | H | 1 | (CH₃)₂CH(CH₂)₂ | (CH₂)₂ | 4-(CH₂)₉CH₃ | H |
| H | H | H | 1 | (CH₃)₂CH(CH₂)₂ | (CH₂)₂ | 4-O(CH₂)₈CH₃ | H |

TABLE 14

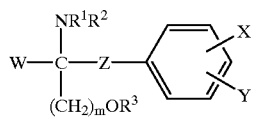

| R¹ | R² | R³ | m | W | Z | X | Y |
|----|----|----|---|---|---|---|---|
| H | H | H | 1 | (CH₃)₂CH(CH₂)₂ | (CH₂)₂ | 4-(CH₂)₁₀CH₃ | H |
| H | H | H | 1 | (CH₃)₂CH(CH₂)₂ | (CH₂)₂ | 4-O(CH₂)₉CH₃ | H |
| H | H | H | 1 | (CH₃)₂CH(CH₂)₂ | (CH₂)₂ | 4-(CH₂)₁₁CH₃ | H |
| H | H | H | 1 | (CH₃)₂CH(CH₂)₂ | (CH₂)₂ | 4-O(CH₂)₁₀CH₃ | H |
| H | H | H | 1 | (CH₂)₅CH₃ | (CH₂)₂ | 4-(CH₂)₇CH₃ | H |
| H | H | H | 1 | (CH₂)₅CH₃ | (CH₂)₂ | 4-O(CH₂)₆CH₃ | H |
| H | H | H | 1 | (CH₂)₅CH₃ | (CH₂)₂ | 4-(CH₂)₈CH₃ | H |
| H | H | H | 1 | (CH₂)₅CH₃ | (CH₂)₂ | 4-O(CH₂)₇CH₃ | H |
| H | H | H | 1 | (CH₂)₅CH₃ | (CH₂)₂ | 4-(CH₂)₉CH₃ | H |
| H | H | H | 1 | (CH₂)₅CH₃ | (CH₂)₂ | 4-O(CH₂)₈CH₃ | H |
| H | H | H | 1 | (CH₂)₅CH₃ | (CH₂)₂ | 4-(CH₂)₁₀CH₃ | H |
| H | H | H | 1 | (CH₂)₅CH₃ | (CH₂)₂ | 4-O(CH₂)₉CH₃ | H |
| H | H | H | 1 | (CH₂)₅CH₃ | (CH₂)₂ | 4-(CH₂)₁₁CH₃ | H |
| H | H | H | 1 | (CH₂)₅CH₃ | (CH₂)₂ | 4-O(CH₂)₁₀CH₃ | H |
| H | H | H | 1 | (CH₃)₂CH(CH₂)₃ | (CH₂)₂ | 4-(CH₂)₇CH₃ | H |
| H | H | H | 1 | (CH₃)₂CH(CH₂)₃ | (CH₂)₂ | 4-O(CH₂)₆CH₃ | H |
| H | H | H | 1 | (CH₃)₂CH(CH₂)₃ | (CH₂)₂ | 4-(CH₂)₈CH₃ | H |
| H | H | H | 1 | (CH₃)₂CH(CH₂)₃ | (CH₂)₂ | 4-O(CH₂)₇CH₃ | H |
| H | H | H | 1 | (CH₃)₂CH(CH₂)₃ | (CH₂)₂ | 4-(CH₂)₉CH₃ | H |
| H | H | H | 1 | (CH₃)₂CH(CH₂)₃ | (CH₂)₂ | 4-O(CH₂)₈CH₃ | H |
| H | H | H | 1 | (CH₃)₂CH(CH₂)₃ | (CH₂)₂ | 4-(CH₂)₁₀CH₃ | H |
| H | H | H | 1 | (CH₃)₂CH(CH₂)₃ | (CH₂)₂ | 4-O(CH₂)₉CH₃ | H |
| H | H | H | 1 | (CH₃)₂CH(CH₂)₃ | (CH₂)₂ | 4-(CH₂)₁₁CH₃ | H |
| H | H | H | 1 | (CH₃)₂CH(CH₂)₃ | (CH₂)₂ | 4-O(CH₂)₁₀CH₃ | H |
| H | H | H | 1 | Ph | (CH₂)₂ | 4-(CH₂)₇CH₃ | H |
| H | H | H | 1 | Ph | (CH₂)₂ | 4-O(CH₂)₆CH₃ | H |
| H | H | H | 1 | Ph | (CH₂)₂ | 4-(CH₂)₈CH₃ | H |
| H | H | H | 1 | Ph | (CH₂)₂ | 4-O(CH₂)₇CH₃ | H |
| H | H | H | 1 | Ph | (CH₂)₂ | 4-(CH₂)₉CH₃ | H |
| H | H | H | 1 | Ph | (CH₂)₂ | 4-O(CH₂)₈CH₃ | H |
| H | H | H | 1 | Ph | (CH₂)₂ | 4-(CH₂)₁₀CH₃ | H |

TABLE 15

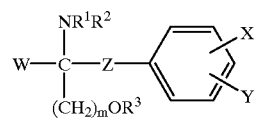

| R¹ | R² | R³ | m | W | Z | X | Y |
|----|----|----|---|---|---|---|---|
| H | H | H | 1 | Ph | (CH₂)₂ | 4-O(CH₂)₉CH₃ | H |
| H | H | H | 1 | Ph | (CH₂)₂ | 4-(CH₂)₁₁CH₃ | H |
| H | H | H | 1 | Ph | (CH₂)₂ | 4-O(CH₂)₁₀CH₃ | H |
| H | H | H | 1 | C₆H₄-4-OH | (CH₂)₂ | 4-(CH₂)₇CH₃ | H |
| H | H | H | 1 | C₆H₄-4-OH | (CH₂)₂ | 4-O(CH₂)₆CH₃ | H |
| H | H | H | 1 | C₆H₄-4-OH | (CH₂)₂ | 4-(CH₂)₈CH₃ | H |
| H | H | H | 1 | C₆H₄-4-OH | (CH₂)₂ | 4-O(CH₂)₇CH₃ | H |
| H | H | H | 1 | C₆H₄-4-OH | (CH₂)₂ | 4-(CH₂)₉CH₃ | H |
| H | H | H | 1 | C₆H₄-4-OH | (CH₂)₂ | 4-O(CH₂)₈CH₃ | H |
| H | H | H | 1 | C₆H₄-4-OH | (CH₂)₂ | 4-(CH₂)₁₀CH₃ | H |
| H | H | H | 1 | C₆H₄-4-OH | (CH₂)₂ | 4-O(CH₂)₉CH₃ | H |
| H | H | H | 1 | C₆H₄-4-OH | (CH₂)₂ | 4-(CH₂)₁₁CH₃ | H |
| H | H | H | 1 | C₆H₄-4-OH | (CH₂)₂ | 4-O(CH₂)₁₀CH₃ | H |
| H | H | H | 1 | CH₂Ph | (CH₂)₂ | 4-(CH₂)₇CH₃ | H |
| H | H | H | 1 | CH₂Ph | (CH₂)₂ | 4-O(CH₂)₆CH₃ | H |
| H | H | H | 1 | CH₂Ph | (CH₂)₂ | 4-(CH₂)₈CH₃ | H |
| H | H | H | 1 | CH₂Ph | (CH₂)₂ | 4-O(CH₂)₇CH₃ | H |
| H | H | H | 1 | CH₂Ph | (CH₂)₂ | 4-(CH₂)₉CH₃ | H |
| H | H | H | 1 | CH₂Ph | (CH₂)₂ | 4-O(CH₂)₈CH₃ | H |
| H | H | H | 1 | CH₂Ph | (CH₂)₂ | 4-(CH₂)₁₀CH₃ | H |
| H | H | H | 1 | CH₂Ph | (CH₂)₂ | 4-O(CH₂)₉CH₃ | H |
| H | H | H | 1 | CH₂Ph | (CH₂)₂ | 4-(CH₂)₁₁CH₃ | H |
| H | H | H | 1 | CH₂Ph | (CH₂)₂ | 4-O(CH₂)₁₀CH₃ | H |
| H | H | H | 1 | CH₂—C₆H₄-4-OH | (CH₂)₂ | 4-(CH₂)₇CH₃ | H |
| H | H | H | 1 | CH₂—C₆H₄-4-OH | (CH₂)₂ | 4-O(CH₂)₆CH₃ | H |
| H | H | H | 1 | CH₂—C₆H₄-4-OH | (CH₂)₂ | 4-(CH₂)₈CH₃ | H |
| H | H | H | 1 | CH₂—C₆H₄-4-OH | (CH₂)₂ | 4-O(CH₂)₇CH₃ | H |
| H | H | H | 1 | CH₂—C₆H₄-4-OH | (CH₂)₂ | 4-(CH₂)₉CH₃ | H |
| H | H | H | 1 | CH₂—C₆H₄-4-OH | (CH₂)₂ | 4-O(CH₂)₈CH₃ | H |
| H | H | H | 1 | CH₂—C₆H₄-4-OH | (CH₂)₂ | 4-(CH₂)₁₀CH₃ | H |
| H | H | H | 1 | CH₂—C₆H₄-4-OH | (CH₂)₂ | 4-O(CH₂)₉CH₃ | H |

TABLE 16

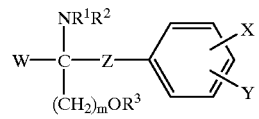

| R¹ | R² | R³ | m | W | Z | X | Y |
|---|---|---|---|---|---|---|---|
| H | H | H | 1 | CH₂—C₆H₄-4-OH | (CH₂)₂ | 4-(CH₂)₁₁CH₃ | H |
| H | H | H | 1 | CH₂—C₆H₄-4-OH | (CH₂)₂ | 4-O(CH₂)₁₀CH₃ | H |
| H | H | H | 1 | (CH₂)₂OH | (CH₂)₂ | 4-(CH₂)₆CH₃ | H |
| H | H | H | 1 | (CH₂)₂OH | (CH₂)₂ | 4-(CH₂)₇CH₃ | H |
| MeOCO | H | H | 1 | (CH₂)₂OH | (CH₂)₂ | 4-(CH₂)₇CH₃ | H |
| Ac | H | Ac | 1 | (CH₂)₂OAc | (CH₂)₂ | 4-CO(CH₂)₆CH₃ | H |
| H | H | H | 1 | (CH₂)₂OH | (CH₂)₂ | 4-CO(CH₂)₆CH₃ | H |
| H | H | H | 1 | (CH₂)₂OH | (CH₂)₂ | 4-CH(OH)(CH₂)₆CH₃ | H |
| H | H | H | 1 | (CH₂)₂OH | (CH₂)₂ | 4-CH(NH₂)(CH₂)₆CH₃ | H |
| Ac | H | Ac | 1 | (CH₂)₂OAc | (CH₂)₂ | 4-(CH₂)₇CH₃ | H |
| H | H | H | 1 | (CH₂)₂OH | (CH₂)₂ | 4-(CH₂)₈CH₃ | H |
| H | H | H | 1 | (CH₂)₂OH | (CH₂)₂ | 4-(CH₂)₉CH₃ | H |
| MeOCO | H | Ac | 1 | (CH₂)₂OAc | (CH₂)₂ | 4-CO(CH₂)₈CH₃ | H |
| H | H | H | 1 | (CH₂)₂OH | (CH₂)₂ | 4-CO(CH₂)₈CH₃ | H |
| H | H | H | 1 | (CH₂)₂OH | (CH₂)₂ | 4-CH(OH)(CH₂)₈CH₃ | H |
| H | H | H | 1 | (CH₂)₂OH | (CH₂)₂ | 4-CH(NH₂)(CH₂)₈CH₃ | H |
| MeOCO | H | Ac | 1 | (CH₂)₂OAc | (CH₂)₂ | 4-(CH₂)₉CH₃ | H |
| Ac | H | Ac | 1 | (CH₂)₂OAc | (CH₂)₂ | 4-(CH₂)₉CH₃ | H |
| H | H | H | 1 | (CH₂)₂OH | (CH₂)₂ | 4-(CH₂)₁₀CH₃ | H |
| H | H | H | 1 | (CH₂)₂OH | (CH₂)₂ | 4-(CH₂)₁₁CH₃ | H |
| Ac | H | Ac | 1 | (CH₂)₂OAc | (CH₂)₂ | 4-(CH₂)₁₁CH₃ | H |
| Ac | H | Ac | 1 | (CH₂)₂OAc | (CH₂)₂ | 4-CO(CH₂)₁₀CH₃ | H |
| H | H | H | 1 | (CH₂)₂OH | (CH₂)₂ | 4-CO(CH₂)₁₀CH₃ | H |
| H | H | H | 1 | (CH₂)₂OH | (CH₂)₂ | 4-CH(OH)(CH₂)₁₀CH₃ | H |
| H | H | H | 1 | (CH₂)₂OH | (CH₂)₂ | 4-CH(NH₂)(CH₂)₁₀CH₃ | H |
| H | H | H | 1 | (CH₂)₂OH | (CH₂)₂ | 4-(CH₂)₁₂CH₃ | H |
| H | H | H | 1 | (CH₂)₂OH | (CH₂)₂ | 4-(CH₂)₁₃CH₃ | H |
| H | H | H | 1 | (CH₂)₂OH | (CH₂)₂ | 4-(CH₂)₁₄CH₃ | H |
| H | H | H | 1 | (CH₂)₂OH | (CH₂)₂ | 4-(CH₂)₁₅CH₃ | H |
| H | H | H | 1 | (CH₂)₂OH | (CH₂)₂ | 4-(CH₂)₁₆CH₃ | H |
| H | H | H | 1 | (CH₂)₂OH | (CH₂)₂ | 4-(CH₂)₁₇CH₃ | H |

TABLE 17

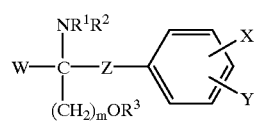

| R¹ | R² | R³ | m | W | Z | X | Y |
|---|---|---|---|---|---|---|---|
| H | H | H | 1 | (CH₂)₂OH | (CH₂)₂ | 4-(CH₂)₁₈CH₃ | H |
| H | H | H | 1 | (CH₂)₂OH | (CH₂)₂ | 4-O—(CH₂)₅CH₃ | H |
| H | H | H | 1 | (CH₂)₂OH | (CH₂)₂ | 4-O—(CH₂)₆CH₃ | H |
| H | H | H | 1 | (CH₂)₂OH | (CH₂)₂ | 4-O—(CH₂)₇CH₃ | H |
| H | H | H | 1 | (CH₂)₂OH | (CH₂)₂ | 4-O—(CH₂)₆CH₃ | 3-OMe |
| H | H | H | 1 | (CH₂)₂OH | (CH₂)₂ | 4-O—(CH₂)₇CH₃ | 3-OMe |
| H | H | H | 1 | (CH₂)₂OH | (CH₂)₂ | 4-O—(CH₂)₆CH₃ | 3-OH |
| H | H | H | 1 | (CH₂)₂OH | (CH₂)₂ | 4-O—(CH₂)₇CH₃ | 3-OH |
| H | H | H | 1 | (CH₂)₂OH | (CH₂)₂ | 4-O—(CH₂)₈CH₃ | H |
| H | H | H | 1 | (CH₂)₂OH | (CH₂)₂ | 4-O—(CH₂)₉CH₃ | H |
| H | H | H | 1 | (CH₂)₂OH | (CH₂)₂ | 4-O—(CH₂)₁₀CH₃ | H |
| H | H | H | 1 | (CH₂)₂OH | (CH₂)₂ | 4-O—(CH₂)₁₁CH₃ | H |
| H | H | H | 1 | (CH₂)₂OH | (CH₂)₂ | 4-O—(CH₂)₁₂CH₃ | H |
| H | H | H | 1 | (CH₂)₂OH | (CH₂)₂ | 4-O—(CH₂)₁₃CH₃ | H |
| H | H | H | 1 | (CH₂)₂OH | (CH₂)₂ | 4-O—(CH₂)₁₄CH₃ | H |
| H | H | H | 1 | (CH₂)₂OH | (CH₂)₂ | 4-O—(CH₂)₁₅CH₃ | H |
| H | H | H | 1 | (CH₂)₂OH | (CH₂)₂ | 4-O—(CH₂)₁₆CH₃ | H |
| H | H | H | 1 | (CH₂)₂OH | (CH₂)₂ | 4-O—(CH₂)₁₇CH₃ | H |
| H | H | H | 1 | (CH₂)₂OH | (CH₂)₂ | 4-O—(CH₂)₄Ph | H |
| H | H | H | 1 | (CH₂)₂OH | (CH₂)₂ | 4-O—(CH₂)₅Ph | H |
| H | H | H | 1 | (CH₂)₂OH | (CH₂)₂ | 4-O—(CH₂)₆Ph | H |
| H | H | H | 1 | (CH₂)₂OH | (CH₂)₂ | 4-O—(CH₂)₇Ph | H |
| H | H | H | 1 | (CH₂)₂OH | (CH₂)₂ | 2-O—(CH₂)₆CH₃ | H |
| H | H | H | 1 | (CH₂)₂OH | (CH₂)₂ | 2-O—(CH₂)₈CH₃ | H |

TABLE 17-continued

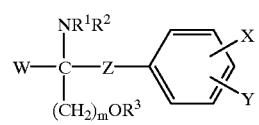

| R¹ | R² | R³ | m | W | Z | X | Y |
|---|---|---|---|---|---|---|---|
| H | H | H | 1 | (CH₂)₂OH | (CH₂)₂ | 2-O—(CH₂)₁₀CH₃ | H |
| H | H | H | 1 | (CH₂)₂OH | (CH₂)₂ | 3-O—(CH₂)₆CH₃ | H |
| H | H | H | 1 | (CH₂)₂OH | (CH₂)₂ | 3-O—(CH₂)₇CH₃ | H |
| H | H | H | 1 | (CH₂)₂OH | (CH₂)₂ | 3-O—(CH₂)₉CH₃ | H |
| H | H | H | 1 | (CH₂)₂OH | (CH₂)₃ | 4-(CH₂)₅CH₃ | H |
| H | H | H | 1 | (CH₂)₂OH | (CH₂)₃ | 4-(CH₂)₆CH₃ | H |
| Ac | H | Ac | 1 | (CH₂)₂OAc | (CH₂)₃ | 4-(CH₂)₆CH₃ | H |

TABLE 18

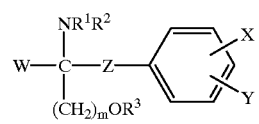

| R¹ | R² | R³ | m | W | Z | X | Y |
|---|---|---|---|---|---|---|---|
| Ac | H | Ac | 1 | (CH₂)₂OAc | (CH₂)₃ | 4-CO(CH₂)₅CH₃ | H |
| H | H | H | 1 | (CH₂)₂OH | (CH₂)₃ | 4-CO(CH₂)₅CH₃ | H |
| H | H | H | 1 | (CH₂)₂OH | (CH₂)₃ | 4-CH(OH)(CH₂)₅CH₃ | H |

TABLE 18-continued

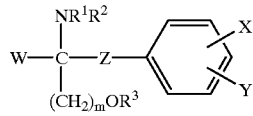

| R¹ | R² | R³ | m | W | Z | X | Y |
|---|---|---|---|---|---|---|---|
| H | H | H | 1 | $(CH_2)_2OH$ | $(CH_2)_3$ | $4\text{-}CH(NH_2)(CH_2)_5CH_3$ | H |
| H | H | H | 1 | $(CH_2)_2OH$ | $(CH_2)_3$ | $4\text{-}(CH_2)_7CH_3$ | H |
| H | H | H | 1 | $(CH_2)_2OH$ | $(CH_2)_3$ | $4\text{-}(CH_2)_8CH_3$ | H |
| Ac | H | Ac | 1 | $(CH_2)_2OAc$ | $(CH_2)_3$ | $4\text{-}(CH_2)_8CH_3$ | H |
| Ac | H | Ac | 1 | $(CH_2)_2OAc$ | $(CH_2)_3$ | $4\text{-}CO(CH_2)_7CH_3$ | H |
| H | H | H | 1 | $(CH_2)_2OH$ | $(CH_2)_3$ | $4\text{-}(CH_2)_9CH_3$ | H |
| H | H | H | 1 | $(CH_2)_2OH$ | $(CH_2)_3$ | $4\text{-}(CH_2)_{10}CH_3$ | H |
| Ac | H | Ac | 1 | $(CH_2)_2OAc$ | $(CH_2)_3$ | $4\text{-}(CH_2)_{10}CH_3$ | H |
| Ac | H | Ac | 1 | $(CH_2)_2OAc$ | $(CH_2)_3$ | $4\text{-}CO(CH_2)_9CH_3$ | H |
| H | H | H | 1 | $(CH_2)_2OH$ | $(CH_2)_3$ | $4\text{-}(CH_2)_{11}CH_3$ | H |
| H | H | H | 1 | $(CH_2)_2OH$ | $(CH_2)_3$ | $4\text{-}(CH_2)_{12}CH_3$ | H |
| H | H | H | 1 | $(CH_2)_2OH$ | $(CH_2)_3$ | $4\text{-}O\text{-}(CH_2)_5CH_3$ | H |
| H | H | H | 1 | $(CH_2)_2OH$ | $(CH_2)_3$ | $4\text{-}O\text{-}(CH_2)_6CH_3$ | H |
| H | H | H | 1 | $(CH_2)_2OH$ | $(CH_2)_3$ | $4\text{-}O\text{-}(CH_2)_7CH_3$ | H |
| H | H | H | 1 | $(CH_2)_2OH$ | $(CH_2)_3$ | $4\text{-}O\text{-}(CH_2)_8CH_3$ | H |
| H | H | H | 1 | $(CH_2)_2OH$ | $(CH_2)_3$ | $4\text{-}O\text{-}(CH_2)_9CH_3$ | H |
| H | H | H | 1 | $(CH_2)_2OH$ | $(CH_2)_3$ | $4\text{-}O\text{-}(CH_2)_{10}CH_3$ | H |
| H | H | H | 1 | $(CH_2)_2OH$ | $(CH_2)_3$ | $4\text{-}O\text{-}(CH_2)_{11}CH_3$ | H |
| H | H | H | 1 | $(CH_2)_2OH$ | $(CH_2)_3$ | $4\text{-}O\text{-}(CH_2)_{12}CH_3$ | H |
| H | H | H | 1 | $(CH_2)_2OH$ | $(CH_2)_4$ | $4\text{-}(CH_2)_4CH_3$ | H |
| H | H | H | 1 | $(CH_2)_2OH$ | $(CH_2)_4$ | $4\text{-}(CH_2)_5CH_3$ | H |
| H | H | H | 1 | $(CH_2)_2OH$ | $(CH_2)_4$ | $4\text{-}(CH_2)_6CH_3$ | H |
| H | H | H | 1 | $(CH_2)_2OH$ | $(CH_2)_4$ | $4\text{-}(CH_2)_7CH_3$ | H |
| H | H | H | 1 | $(CH_2)_2OH$ | $(CH_2)_4$ | $4\text{-}(CH_2)_8CH_3$ | H |
| H | H | H | 1 | $(CH_2)_2OH$ | $(CH_2)_4$ | $4\text{-}(CH_2)_9CH_3$ | H |
| H | H | H | 1 | $(CH_2)_2OH$ | $(CH_2)_4$ | $4\text{-}(CH_2)_{10}CH_3$ | H |
| H | H | H | 1 | $(CH_2)_2OH$ | $(CH_2)_4$ | $4\text{-}(CH_2)_{11}CH_3$ | H |
| H | H | H | 1 | $(CH_2)_3OH$ | $(CH_2)_2$ | $4\text{-}(CH_2)_6CH_3$ | H |

TABLE 19

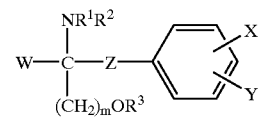

| R¹ | R² | R³ | m | W | Z | X | Y |
|---|---|---|---|---|---|---|---|
| H | H | H | 1 | $(CH_2)_3OH$ | $(CH_2)_2$ | $4\text{-}(CH_2)_7CH_3$ | H |
| Ac | H | Ac | 1 | $(CH_2)_3OAc$ | $(CH_2)_2$ | $4\text{-}(CH_2)_7CH_3$ | H |
| Ac | H | Ac | 1 | $(CH_2)_3OAc$ | $(CH_2)_2$ | $4\text{-}CO(CH_2)_6CH_3$ | H |
| H | H | H | 1 | $(CH_2)_3OH$ | $(CH_2)_2$ | $4\text{-}CO(CH_2)_6CH_3$ | H |
| H | H | H | 1 | $(CH_2)_3OH$ | $(CH_2)_2$ | $4\text{-}CH(OH)(CH_2)_6CH_3$ | H |
| H | H | H | 1 | $(CH_2)_3OH$ | $(CH_2)_2$ | $4\text{-}CH(NH_2)(CH_2)_6CH_3$ | H |
| H | H | H | 1 | $(CH_2)_3OH$ | $(CH_2)_2$ | $4\text{-}(CH_2)_8CH_3$ | H |
| H | H | H | 1 | $(CH_2)_3OH$ | $(CH_2)_2$ | $4\text{-}(CH_2)_9CH_3$ | H |
| Ac | H | Ac | 1 | $(CH_2)_3OAc$ | $(CH_2)_2$ | $4\text{-}(CH_2)_9CH_3$ | H |
| Ac | H | Ac | 1 | $(CH_2)_3OAc$ | $(CH_2)_2$ | $4\text{-}CO(CH_2)_8CH_3$ | H |
| H | H | H | 1 | $(CH_2)_3OH$ | $(CH_2)_2$ | $4\text{-}CO(CH_2)_8CH_3$ | H |
| H | H | H | 1 | $(CH_2)_3OH$ | $(CH_2)_2$ | $4\text{-}(CH_2)_{10}CH_3$ | H |
| H | H | H | 1 | $(CH_2)_3OH$ | $(CH_2)_2$ | $4\text{-}(CH_2)_{11}CH_3$ | H |
| Ac | H | Ac | 1 | $(CH_2)_3OAc$ | $(CH_2)_2$ | $4\text{-}(CH_2)_{11}CH_3$ | H |
| Ac | H | Ac | 1 | $(CH_2)_3OAc$ | $(CH_2)_2$ | $4\text{-}CO(CH_2)_{10}CH_3$ | H |
| H | H | H | 1 | $(CH_2)_3OH$ | $(CH_2)_2$ | $4\text{-}CO(CH_2)_{10}CH_3$ | H |
| H | H | H | 1 | $(CH_2)_3OH$ | $(CH_2)_2$ | $4\text{-}(CH_2)_{12}CH_3$ | H |
| H | H | H | 1 | $(CH_2)_3OH$ | $(CH_2)_2$ | $4\text{-}(CH_2)_{13}CH_3$ | H |
| H | H | H | 1 | $(CH_2)_3OH$ | $(CH_2)_3$ | $4\text{-}(CH_2)_6CH_3$ | H |
| H | H | H | 1 | $(CH_2)_3OH$ | $(CH_2)_3$ | $4\text{-}(CH_2)_8CH_3$ | H |
| H | H | H | 1 | $(CH_2)_3OH$ | $(CH_2)_3$ | $4\text{-}(CH_2)_{10}CH_3$ | H |
| H | H | H | 1 | $(CH_2)_3OH$ | $(CH_2)_4$ | $4\text{-}(CH_2)_5CH_3$ | H |
| H | H | H | 1 | $(CH_2)_3OH$ | $(CH_2)_4$ | $4\text{-}(CH_2)_7CH_3$ | H |
| H | H | H | 1 | $(CH_2)_3OH$ | $(CH_2)_4$ | $4\text{-}(CH_2)_9CH_3$ | H |
| H | H | H | 1 | $(CH_2)_3OH$ | $(CH_2)_2$ | $4\text{-}O\text{-}(CH_2)_5CH_3$ | H |
| H | H | H | 1 | $(CH_2)_3OH$ | $(CH_2)_2$ | $4\text{-}O\text{-}(CH_2)_6CH_3$ | H |
| Ac | H | Ac | 1 | $(CH_2)_3OAc$ | $(CH_2)_2$ | $4\text{-}O\text{-}(CH_2)_6CH_3$ | H |
| Ac | H | Ac | 1 | $(CH_2)_3OAc$ | $(CH_2)_2$ | $4\text{-}O\text{-}(CH_2)_6CH_3$ | 3-OMe |
| H | H | H | 1 | $(CH_2)_3OH$ | $(CH_2)_2$ | $4\text{-}O\text{-}(CH_2)_6CH_3$ | 3-OMe |

TABLE 19-continued

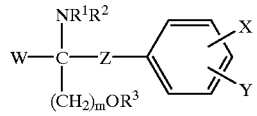

| R¹ | R² | R³ | m | W | Z | X | Y |
|----|----|----|---|---|---|---|---|
| H | H | H | 1 | (CH$_2$)$_3$OH | (CH$_2$)$_2$ | 4-O—(CH$_2$)$_6$CH$_3$ | 3-OH |
| H | H | H | 1 | (CH$_2$)$_3$OH | (CH$_2$)$_2$ | 4-O—(CH$_2$)$_7$CH$_3$ | H |

TABLE 20

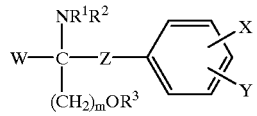

| R¹ | R² | R³ | m | W | Z | X | Y |
|----|----|----|---|---|---|---|---|
| H | H | H | 1 | (CH$_2$)$_3$OH | (CH$_2$)$_2$ | 4-O—(CH$_2$)$_8$CH$_3$ | H |
| Ac | H | Ac | 1 | (CH$_2$)$_3$OAc | (CH$_2$)$_2$ | 4-O—(CH$_2$)$_8$CH$_3$ | H |
| Ac | H | Ac | 1 | (CH$_2$)$_3$OAc | (CH$_2$)$_2$ | 4-O—(CH$_2$)$_8$CH$_3$ | 3-OMe |
| H | H | H | 1 | (CH$_2$)$_3$OH | (CH$_2$)$_2$ | 4-O—(CH$_2$)$_8$CH$_3$ | 3-OMe |
| H | H | H | 1 | (CH$_2$)$_3$OH | (CH$_2$)$_2$ | 4-O—(CH$_2$)$_8$CH$_3$ | 3-OH |
| H | H | H | 1 | (CH$_2$)$_3$OH | (CH$_2$)$_2$ | 4-O—(CH$_2$)$_9$CH$_3$ | H |
| H | H | H | 1 | (CH$_2$)$_3$OH | (CH$_2$)$_2$ | 4-O—(CH$_2$)$_{10}$CH$_3$ | H |
| Ac | H | Ac | 1 | (CH$_2$)$_3$OAc | (CH$_2$)$_2$ | 4-O—(CH$_2$)$_{10}$CH$_3$ | H |
| Ac | H | Ac | 1 | (CH$_2$)$_3$OAc | (CH$_2$)$_2$ | 4-O—(CH$_2$)$_{10}$CH$_3$ | 3-OMe |
| H | H | H | 1 | (CH$_2$)$_3$OH | (CH$_2$)$_2$ | 4-O—(CH$_2$)$_{10}$CH$_3$ | 3-OMe |
| H | H | H | 1 | (CH$_2$)$_3$OH | (CH$_2$)$_2$ | 4-O—(CH$_2$)$_{10}$CH$_3$ | 3-OH |
| H | H | H | 1 | (CH$_2$)$_3$OH | (CH$_2$)$_2$ | 4-O—(CH$_2$)$_{11}$CH$_3$ | H |
| H | H | H | 1 | (CH$_2$)$_3$OH | (CH$_2$)$_2$ | 4-O—(CH$_2$)$_{12}$CH$_3$ | H |
| H | H | H | 1 | (CH$_2$)$_3$OH | (CH$_2$)$_2$ | 4-O—(CH$_2$)$_4$Ph | H |
| Ac | H | Ac | 1 | (CH$_2$)$_3$OAc | (CH$_2$)$_2$ | 4-O—(CH$_2$)$_4$Ph | H |
| H | H | H | 1 | (CH$_2$)$_3$OH | (CH$_2$)$_2$ | 4-O—(CH$_2$)$_4$Ph | 3-OMe |
| H | H | H | 1 | (CH$_2$)$_3$OH | (CH$_2$)$_2$ | 4-O—(CH$_2$)$_4$Ph | 3-OH |
| H | H | H | 1 | (CH$_2$)$_3$OH | (CH$_2$)$_2$ | 4-O—(CH$_2$)$_5$Ph | H |
| H | H | H | 1 | (CH$_2$)$_3$OH | (CH$_2$)$_2$ | 4-O—(CH$_2$)$_6$Ph | H |
| H | H | H | 2 | (CH$_2$)$_2$OH | (CH$_2$)$_2$ | 4-(CH$_2$)$_6$CH$_3$ | H |
| H | H | H | 2 | (CH$_2$)$_2$OH | (CH$_2$)$_2$ | 4-(CH$_2$)$_7$CH$_3$ | H |
| H | H | H | 2 | (CH$_2$)$_2$OH | (CH$_2$)$_2$ | 4-CO(CH$_2$)$_6$CH$_3$ | H |
| H | H | H | 2 | (CH$_2$)$_2$OH | (CH$_2$)$_2$ | 4-CH(OH)(CH$_2$)$_6$CH$_3$ | H |
| H | H | H | 2 | (CH$_2$)$_2$OH | (CH$_2$)$_2$ | 4-CH(NH$_2$)(CH$_2$)$_6$CH$_3$ | H |
| H | H | H | 2 | (CH$_2$)$_2$OH | (CH$_2$)$_2$ | 4-(CH$_2$)$_8$CH$_3$ | H |
| H | H | H | 2 | (CH$_2$)$_2$OH | (CH$_2$)$_2$ | 4-(CH$_2$)$_9$CH$_3$ | H |
| H | H | H | 2 | (CH$_2$)$_2$OH | (CH$_2$)$_2$ | 4-(CH$_2$)$_{10}$CH$_3$ | H |
| H | H | H | 2 | (CH$_2$)$_2$OH | (CH$_2$)$_2$ | 4-(CH$_2$)$_{11}$CH$_3$ | H |
| H | H | H | 2 | (CH$_2$)$_2$OH | (CH$_2$)$_2$ | 4-(CH$_2$)$_{12}$CH$_3$ | H |
| H | H | H | 2 | (CH$_2$)$_2$OH | (CH$_2$)$_2$ | 4-(CH$_2$)$_{13}$CH$_3$ | H |
| H | H | H | 2 | (CH$_2$)$_2$OH | (CH$_2$)$_3$ | 4-(CH$_2$)$_6$CH$_3$ | H |

TABLE 21

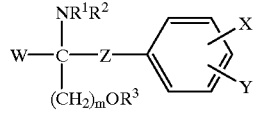

| R¹ | R² | R³ | m | W | Z | X | Y |
|----|----|----|---|---|---|---|---|
| H | H | H | 2 | (CH$_2$)$_2$OH | (CH$_2$)$_3$ | 4-(CH$_2$)$_8$CH$_3$ | H |
| H | H | H | 2 | (CH$_2$)$_2$OH | (CH$_2$)$_3$ | 4-(CH$_2$)$_{10}$CH$_3$ | H |
| H | H | H | 2 | (CH$_2$)$_2$OH | (CH$_2$)$_4$ | 4-(CH$_2$)$_5$CH$_3$ | H |
| H | H | H | 2 | (CH$_2$)$_2$OH | (CH$_2$)$_4$ | 4-(CH$_2$)$_7$CH$_3$ | H |

TABLE 21-continued $$\text{W}-\underset{(CH_2)_mOR^3}{\overset{NR^1R^2}{\underset{|}{C}}}-Z-\text{C}_6H_3(X)(Y)$$

| R¹ | R² | R³ | m | W | Z | X | Y |
|---|---|---|---|---|---|---|---|
| H | H | H | 2 | (CH₂)₂OH | (CH₂)₄ | 4-(CH₂)₉CH₃ | H |
| H | H | H | 2 | (CH₂)₂OH | (CH₂)₂ | 4-O—(CH₂)₅CH₃ | H |
| H | H | H | 2 | (CH₂)₂OH | (CH₂)₂ | 4-O—(CH₂)₆CH₃ | H |
| H | H | H | 2 | (CH₂)₂OH | (CH₂)₂ | 4-O—(CH₂)₆CH₃ | 3-OMe |
| H | H | H | 2 | (CH₂)₂OH | (CH₂)₂ | 4-O—(CH₂)₆CH₃ | 3-OH |
| H | H | H | 2 | (CH₂)₂OH | (CH₂)₂ | 4-O—(CH₂)₇CH₃ | H |
| H | H | H | 2 | (CH₂)₂OH | (CH₂)₂ | 4-O—(CH₂)₈CH₃ | H |
| H | H | H | 2 | (CH₂)₂OH | (CH₂)₂ | 4-O—(CH₂)₉CH₃ | H |
| H | H | H | 2 | (CH₂)₂OH | (CH₂)₂ | 4-O—(CH₂)₁₀CH₃ | H |
| H | H | H | 2 | (CH₂)₂OH | (CH₂)₂ | 4-O—(CH₂)₁₁CH₃ | H |
| H | H | H | 2 | (CH₂)₂OH | (CH₂)₂ | 4-O—(CH₂)₁₂CH₃ | H |
| H | H | H | 2 | (CH₂)₂OH | (CH₂)₂ | 4-O—(CH₂)₄Ph | H |
| H | H | H | 2 | (CH₂)₂OH | (CH₂)₂ | 4-O—(CH₂)₅Ph | H |
| H | H | H | 2 | (CH₂)₂OH | (CH₂)₂ | 4-O—(CH₂)₆Ph | H |
| H | H | H | 3 | (CH₂)₂OH | (CH₂)₂ | 4-(CH₂)₆CH₃ | H |
| H | H | H | 2 | (CH₂)₃OH | (CH₂)₂ | 4-(CH₂)₇CH₃ | H |
| Ac | H | Ac | 2 | (CH₂)₃OAc | (CH₂)₂ | 4-(CH₂)₇CH₃ | H |
| H | H | H | 2 | (CH₂)₃OH | (CH₂)₂ | 4-CO(CH₂)₆CH₃ | H |
| H | H | H | 2 | (CH₂)₃OH | (CH₂)₂ | 4-CH(OH)(CH₂)₆CH₃ | H |
| H | H | H | 2 | (CH₂)₃OH | (CH₂)₂ | 4-CH(NH₂)(CH₂)₆CH₃ | H |
| Boc | H | H | 2 | (CH₂)₃OH | (CH₂)₂ | 4-(CH₂)₇CH₃ | H |
| H | H | H | 2 | (CH₂)₃OH | (CH₂)₂ | 4-(CH₂)₈CH₃ | H |
| H | H | H | 2 | (CH₂)₃OH | (CH₂)₂ | 4-(CH₂)₉CH₃ | H |
| H | H | H | 2 | (CH₂)₃OH | (CH₂)₂ | 4-(CH₂)₁₀CH₃ | H |
| H | H | H | 2 | (CH₂)₃OH | (CH₂)₂ | 4-(CH₂)₁₁CH₃ | H |
| H | H | H | 2 | (CH₂)₃OH | (CH₂)₂ | 4-(CH₂)₁₂CH₃ | H |
| H | H | H | 2 | (CH₂)₃OH | (CH₂)₂ | 4-(CH₂)₁₃CH₃ | H |

TABLE 22

$$\text{W}-\underset{(CH_2)_mOR^3}{\overset{NR^1R^2}{\underset{|}{C}}}-Z-\text{C}_6H_3(X)(Y)$$

| R¹ | R² | R³ | m | W | Z | X | Y |
|---|---|---|---|---|---|---|---|
| H | H | H | 2 | (CH₂)₃OH | (CH₂)₃ | 4-(CH₂)₆CH₃ | H |
| H | H | H | 2 | (CH₂)₃OH | (CH₂)₃ | 4-(CH₂)₈CH₃ | H |
| H | H | H | 2 | (CH₂)₃OH | (CH₂)₃ | 4-(CH₂)₁₀CH₃ | H |
| H | H | H | 2 | (CH₂)₃OH | (CH₂)₄ | 4-(CH₂)₅CH₃ | H |
| H | H | H | 2 | (CH₂)₃OH | (CH₂)₄ | 4-(CH₂)₇CH₃ | H |
| H | H | H | 2 | (CH₂)₃OH | (CH₂)₄ | 4-(CH₂)₉CH₃ | H |
| H | H | H | 2 | (CH₂)₃OH | (CH₂)₂ | 4-O—(CH₂)₅CH₃ | H |
| H | H | H | 2 | (CH₂)₃OH | (CH₂)₂ | 4-O—(CH₂)₆CH₃ | H |
| H | H | H | 2 | (CH₂)₃OH | (CH₂)₂ | 4-O—(CH₂)₆CH₃ | 3-OMe |
| H | H | H | 2 | (CH₂)₃OH | (CH₂)₂ | 4-O—(CH₂)₆CH₃ | 3-OH |
| H | H | H | 2 | (CH₂)₃OH | (CH₂)₂ | 4-O—(CH₂)₇CH₃ | H |
| H | H | H | 2 | (CH₂)₃OH | (CH₂)₂ | 4-O—(CH₂)₈CH₃ | H |
| H | H | H | 2 | (CH₂)₃OH | (CH₂)₂ | 4-O—(CH₂)₉CH₃ | H |
| H | H | H | 2 | (CH₂)₃OH | (CH₂)₂ | 4-O—(CH₂)₁₀CH₃ | H |
| H | H | H | 2 | (CH₂)₃OH | (CH₂)₂ | 4-O—(CH₂)₁₁CH₃ | H |
| H | H | H | 2 | (CH₂)₃OH | (CH₂)₂ | 4-O—(CH₂)₁₂CH₃ | H |
| H | H | H | 2 | (CH₂)₃OH | (CH₂)₂ | 4-O—(CH₂)₄Ph | H |
| H | H | H | 2 | (CH₂)₃OH | (CH₂)₂ | 4-O—(CH₂)₅Ph | H |
| H | H | H | 2 | (CH₂)₃OH | (CH₂)₂ | 4-O—(CH₂)₆Ph | H |
| H | H | H | 3 | (CH₂)₃OH | (CH₂)₂ | 4-(CH₂)₇CH₃ | H |
| H | H | H | 3 | (CH₂)₃OH | (CH₂)₂ | 4-CO(CH₂)₆CH₃ | H |
| H | H | H | 3 | (CH₂)₃OH | (CH₂)₂ | 4-CH(OH)(CH₂)₆CH₃ | H |
| H | H | H | 3 | (CH₂)₃OH | (CH₂)₂ | 4-CH(NH₂)(CH₂)₆CH₃ | H |
| H | H | H | 3 | (CH₂)₃OH | (CH₂)₂ | 4-O(CH₂)₆CH₃ | H |
| H | H | H | 3 | (CH₂)₃OH | (CH₂)₂ | 4-O(CH₂)₆CH₃ | 3-OMe |
| H | H | H | 3 | (CH₂)₃OH | (CH₂)₂ | 4-O(CH₂)₆CH₃ | 3-OH |

TABLE 22-continued

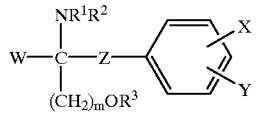

| R¹ | R² | R³ | m | W | Z | X | Y |
|---|---|---|---|---|---|---|---|
| H | H | H | 1 | H | $(CH_2)_2$ | 4-$(CH_2)_6CH_3$ | H |
| H | H | H | 1 | H | $(CH_2)_2$ | 4-$(CH_2)_7CH_3$ | H |
| Ac | H | H | 1 | H | $(CH_2)_2$ | 4-$(CH_2)_7CH_3$ | H |
| Ac | H | Ac | 1 | H | $(CH_2)_2$ | 4-$(CH_2)_7CH_3$ | H |
| Ac | H | Ac | 1 | H | $(CH_2)_2$ | 4-$CO(CH_2)_6CH_3$ | H |

TABLE 23

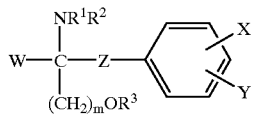

| R¹ | R² | R³ | m | W | Z | X | Y |
|---|---|---|---|---|---|---|---|
| H | H | H | 1 | H | $(CH_2)_2$ | 4-$CO(CH_2)_6CH_3$ | H |
| H | H | H | 1 | H | $(CH_2)_2$ | 4-$CH(OH)(CH_2)_6CH_3$ | H |
| H | H | H | 1 | H | $(CH_2)_2$ | 4-$CH(NH_2)(CH_2)_6CH_3$ | H |
| H | H | H | 1 | H | $(CH_2)_2$ | 4-$(CH_2)_8CH_3$ | H |
| H | H | H | 1 | H | $(CH_2)_2$ | 4-$(CH_2)_9CH_3$ | H |
| Ac | H | H | 1 | H | $(CH_2)_2$ | 4-$(CH_2)_9CH_3$ | H |
| Ac | H | Ac | 1 | H | $(CH_2)_2$ | 4-$(CH_2)_9CH_3$ | H |
| Ac | H | Ac | 1 | H | $(CH_2)_2$ | 4-$CO(CH_2)_8CH_3$ | H |
| H | H | H | 1 | H | $(CH_2)_2$ | 4-$(CH_2)_{10}CH_3$ | H |
| H | H | H | 1 | H | $(CH_2)_2$ | 4-$(CH_2)_{11}CH_3$ | H |
| Ac | H | H | 1 | H | $(CH_2)_2$ | 4-$(CH_2)_{11}CH_3$ | H |
| Ac | H | Ac | 1 | H | $(CH_2)_2$ | 4-$(CH_2)_{11}CH_3$ | H |
| Ac | H | Ac | 1 | H | $(CH_2)_2$ | 4-$CO(CH_2)_{10}CH_3$ | H |
| H | H | H | 1 | H | $(CH_2)_2$ | 4-$(CH_2)_{12}CH_3$ | H |
| H | H | H | 1 | H | $(CH_2)_2$ | 4-$(CH_2)_{13}CH_3$ | H |
| H | H | H | 1 | H | $(CH_2)_2$ | 4-$(CH_2)_{14}CH_3$ | H |
| H | H | H | 1 | H | $(CH_2)_2$ | 4-$(CH_2)_{15}CH_3$ | H |
| H | H | H | 1 | H | $(CH_2)_2$ | 4-$(CH_2)_{16}CH_3$ | H |
| H | H | H | 1 | H | $(CH_2)_2$ | 4-$(CH_2)_{17}CH_3$ | H |
| H | H | H | 1 | H | $(CH_2)_2$ | 4-$(CH_2)_{18}CH_3$ | H |
| H | H | H | 1 | H | $(CH_2)_2$ | 4-O—$(CH_2)_5CH_3$ | H |
| H | H | H | 1 | H | $(CH_2)_2$ | 4-O—$(CH_2)_6CH_3$ | H |
| Ac | H | Ac | 1 | H | $(CH_2)_2$ | 4-O—$(CH_2)_6CH_3$ | H |
| Ac | H | H | 1 | H | $(CH_2)_2$ | 4-O—$(CH_2)_6CH_3$ | H |
| H | H | H | 1 | H | $(CH_2)_2$ | 4-O—$(CH_2)_6CH_3$ | 3-OMe |
| H | H | H | 1 | H | $(CH_2)_2$ | 4-O—$(CH_2)_6CH_3$ | 3-OH |
| Ac | H | Ac | 1 | H | $(CH_2)_2$ | 4-O—$(CH_2)_6CH_3$ | 3-OMe |
| H | H | H | 1 | H | $(CH_2)_2$ | 4-O—$(CH_2)_7CH_3$ | H |
| H | H | H | 1 | H | $(CH_2)_2$ | 4-O—$(CH_2)_8CH_3$ | H |
| Ac | H | Ac | 1 | H | $(CH_2)_2$ | 4-O—$(CH_2)_8CH_3$ | H |
| Ac | H | H | 1 | H | $(CH_2)_2$ | 4-O—$(CH_2)_8CH_3$ | H |
| H | H | H | 1 | H | $(CH_2)_2$ | 4-O—$(CH_2)_8CH_3$ | 3-OMe |
| Ac | H | Ac | 1 | H | $(CH_2)_2$ | 4-O—$(CH_2)_8CH_3$ | 3-OMe |

TABLE 24

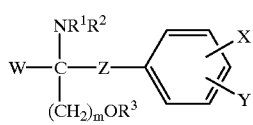

| R¹ | R² | R³ | m | W | Z | X | Y |
|---|---|---|---|---|---|---|---|
| H | H | H | 1 | H | $(CH_2)_2$ | 4-O—$(CH_2)_9CH_3$ | H |
| H | H | H | 1 | H | $(CH_2)_2$ | 4-O—$(CH_2)_{10}CH_3$ | H |
| Ac | H | Ac | 1 | H | $(CH_2)_2$ | 4-O—$(CH_2)_{10}CH_3$ | H |

TABLE 24-continued

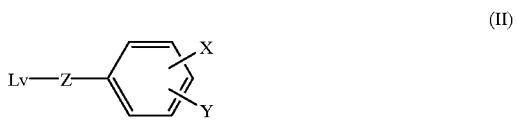

| R¹ | R² | R³ | m | W | Z | X | Y |
|---|---|---|---|---|---|---|---|
| Ac | H | H | 1 | H | $(CH_2)_2$ | 4-O—$(CH_2)_{10}CH_3$ | H |
| H | H | H | 1 | H | $(CH_2)_2$ | 4-O—$(CH_2)_{10}CH_3$ | 3-OMe |
| Ac | H | Ac | 1 | H | $(CH_2)_2$ | 4-O—$(CH_2)_{10}CH_3$ | 3-OMe |
| H | H | H | 1 | H | $(CH_2)_2$ | 4-O—$(CH_2)_{11}CH_3$ | H |
| H | H | H | 1 | H | $(CH_2)_2$ | 4-O—$(CH_2)_{12}CH_3$ | H |
| H | H | H | 1 | H | $(CH_2)_2$ | 4-O—$(CH_2)_4Ph$ | H |
| Ac | H | Ac | 1 | H | $(CH_2)_2$ | 4-O—$(CH_2)_4Ph$ | H |
| Ac | H | H | 1 | H | $(CH_2)_2$ | 4-O—$(CH_2)_4Ph$ | H |
| H | H | H | 1 | H | $(CH_2)_2$ | 4-O—$(CH_2)_4Ph$ | 3-OMe |
| Ac | H | Ac | 1 | H | $(CH_2)_2$ | 4-O—$(CH_2)_4Ph$ | 3-OMe |
| H | H | H | 1 | H | $(CH_2)_2$ | 4-O—$(CH_2)_5Ph$ | H |
| H | H | H | 1 | H | $(CH_2)_2$ | 4-O—$(CH_2)_6Ph$ | H |
| H | H | H | 1 | H | $(CH_2)_2$ | 4-O—$(CH_2)_7Ph$ | H |
| H | H | H | 1 | H | $(CH_2)_3$ | 4-$(CH_2)_6CH_3$ | H |
| H | H | H | 1 | H | $(CH_2)_3$ | 4-$(CH_2)_8CH_3$ | H |
| H | H | H | 1 | H | $(CH_2)_3$ | 4-$(CH_2)_{10}CH_3$ | H |
| H | H | H | 1 | H | $(CH_2)_4$ | 4-$(CH_2)_5CH_3$ | H |
| H | H | H | 1 | H | $(CH_2)_4$ | 4-$(CH_2)_7CH_3$ | H |
| H | H | H | 1 | H | $(CH_2)_4$ | 4-$(CH_2)_9CH_3$ | H |
| H | H | H | 1 | H | $(CH_2)_{10}$ | H | H |
| H | H | H | 1 | H | $(CH_2)_{13}$ | H | H |
| H | H | H | 1 | H | $(CH_2)_3$ | 4-O—$(CH_2)_4CH_3$ | H |
| H | H | H | 1 | H | $(CH_2)_3$ | 4-O—$(CH_2)_5CH_3$ | H |
| Ac | H | Ac | 1 | H | $(CH_2)_3$ | 4-O—$(CH_2)_5CH_3$ | H |
| Ac | H | H | 1 | H | $(CH_2)_3$ | 4-O—$(CH_2)_5CH_3$ | H |
| H | H | H | 1 | H | $(CH_2)_3$ | 4-O—$(CH_2)_6CH_3$ | H |
| H | H | H | 1 | H | $(CH_2)_4$ | 4-O—$(CH_2)_4CH_3$ | H |
| H | H | H | 1 | H | $(CH_2)_4$ | 4-O—$(CH_2)_6CH_3$ | H |
| H | H | H | 1 | H | $(CH_2)_4$ | 4-O—$(CH_2)_8CH_3$ | H |

The compound of the present invention can be produced according to the following methods.

Method A

A compound of the formula: (II) [hereinafter referred to as Compound (II)]:

$$Lv—Z—\text{Ar}(X)(Y) \quad (II)$$

wherein Z, X and Y are as defined above. Lv is a leaving group widely employed in the field of organic synthetic chemistry, such as fluorine, chlorine, bromine, iodine, methanesulfonyloxy, p-toluenesulfonyloxy or trifluoromethanesulfonyloxy, or when X or Y has a functional group (e.g. amino, hydroxy, oxo), the functional group may be protected if necessary; is condensed, in the presence of a base, with a compound of the formula (III) [hereinafter referred to as Compound (III)]:

(III)

wherein $R^c$ is lower alkyl, for example, methyl, ethyl, propyl, isopropyl, butyl, tert-butyl; to give a compound of the formula (IV) [hereinafter referred to as Compound (IV)]:

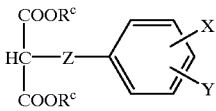
(IV)

wherein X, Y, Z and $R^c$ are as defined above; which is subjected to condensation with a compound of the formula (V) [hereinafter referred to as Compound (V)]:

$$P^1O(CH_2)_n\text{—}Lv \quad (V)$$

wherein $P^1$ is a hydroxy-protecting group widely employed in the field of organic synthetic chemistry, such as acetyl benzoyl, benzyl, trimethylsilyl, tert-butyldimethylsilyl, tert-butyldiphenylsilyl, methoxymethyl, methoxyethoxymethyl or tetrahydropyranyl, and n and Lv are as defined above; in the presence of a base, to give a compound of the formula (VI) [hereinafter referred to as Compound (VI)]:

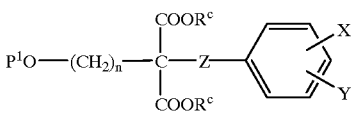
(VI)

wherein X, Y, Z, $R^c$, n and $P^1$ are as defined above. The ester compound obtained is then subjected to hydrolysis and the Curtius rearrangement a reaction, to give a compound of the formula (VII) [hereinafter referred to as Compound (VII)]:

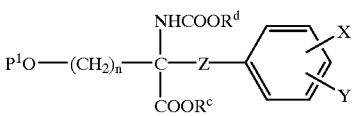
(VII)

wherein $R^d$ is alkyl group or aralkyl group, for example, methyl, ethyl, propyl, isopropyl, butyl, tert-butyl, benzyl, and X, Y, Z, $R^c$, n and $P^1$ are as defined above; which is subjected to reduction of ester and protection/deprotection, if necessary, to give compound(s) of the formula (VIII-a) and/or (VIII-b) [hereinafter referred to as Compound (VIII-a) and/or (VIII-b)]:

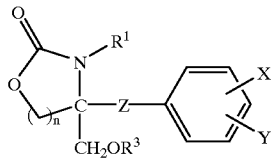
(VIII-a)

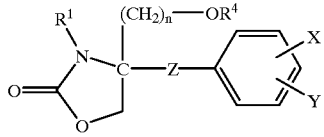
(VIII-b)

wherein X, Y, Z, $R^1$, $R^3$, $R^4$ and n are as defined above; followed by treatment with an alkali and protection/deprotection, if necessary, to give a compound of the formula (I-1) [hereinafter referred to as Compound (I-1)]:

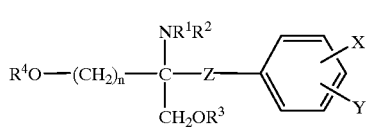
(I-1)

wherein X, Y, Z, $R^1$, $R^2$, $R^3$, $R^4$ and n are as defined above.

Examples of the base to be used in the condensation of Compound (II) and Compound (III) include sodium methoxide, sodium ethoxide, sodium hydride, potassium hydride, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the Compound (IV) can be purified by a method known in the field of organic synthetic chemistry, such as solvent extraction, recrystallization, chromatography or a method using an ion exchange resin.

The condensation of the second process in the present method is carried out under the above-mentioned conditions.

Examples of the base to be used in the hydrolysis of Compound (VI) include sodium hydroxide, potassium hydroxide, lithium hydroxide and barium hydroxide.

Examples of the organic solvent to be used in hydrolysis include methanol, ethanol, tert-butyl alcohol, tetrahydrofuran, ethylene glycol dimethyl ether, dimethylformamide and dimethyl sulfoxide, and a mixed solvent with water thereof can be used if necessary.

The hydrolysis generally proceeds at a temperature of from −20° C. to 80° C. and a lower or higher temperature than said temperature range may be selected on demand.

The hydrolysis is generally carried out for 30 minutes to 2 days and a longer or shorter reaction period than the indicated period may be selected on demand.

After the hydrolysis is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the Curtius rearrangement reaction include hönig base such as triethylamine or diisopropylethylamine, provided that carboxylic acid in the reaction substrate form a salt, none of the aforementioned base need to be used.

Examples of the activating agent to be used in the Curtius rearrangement reaction include methyl chloroformate, ethyl chloroformate, isopropyl chloroformate, isobutyl chloroformate and phenyl chloroformate.

Examples of the azidation agent to be used in the Curtius rearrangement reaction include sodium azide and diphenylphosphoric azide, provided that diphenylphosphoric azide is used, both the aforementioned base and activating agent are not necessary to employ.

The solvent to be used in the Curtius rearrangement reaction is preferably non-protonic solvent at the first half of the reaction and is exemplified by tetrahydrofuran, acetone, diethyl ether, ethylene glycol dimethyl ether, dimethylformamide, dimethyl sulfoxide, dioxane, metylene chloride, chloroform, dichloroethane and acetonitrile, and is exemplified, at the latter half of the reaction, by methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane, acetonitrile and benzyl alcohol.

The Curtius rearrangement reaction generally proceeds at a temperature of from −20° C. to 150° C. and a lower or higher temperature than said temperature range may be selected on demand.

The Curtius rearrangement reaction is generally carried out for 30 minutes to 10 hours and a longer or shorter reaction period than the indicated period may be selected on demand.

After the Curtius rearrangement reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent in the reduction of ester include metallic reducing reagent such as diborane, sodium borohydride, lithium borohydride or lithium alminum hydride.

Examples of the organic solvent to be used in the reduction include methanol, ethanol, tert-butyl alcohol, tetrahydrofuran, diethyl ether and ethylene glycol dimethyl ether.

The reduction generally proceeds at a temperature of from −100° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the alkali to be used in the alkaline treatment of Compound (VIII-a) and/or (VIII-b) include sodium hydroxide and potassium hydroxide.

Examples of the solvent to be used in the present reaction include methanol, ethanol, tert-butyl alcohol, tetrahydrofuran, diethyl ether, ethylene glycol dimethyl ether, water and a mixture thereof.

The reaction generally proceeds at a temperature of from 50° C. to the refluxing temperature of the solvent to be used and a lower or higher temperature than said temperature range may be selected on demand.

The reaction is generally carried out for 30 minutes to 12 hours and a longer or shorter reaction period than the indicated period may be selected on demand.

After the reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

In the present method, Compound (I-1) also can be produced directly without through Compound (VII) to Compound (VIII-a) and/or (VIII-b).

Method B

The Compound (VI) in Method A also can be produced according to the following method.

Namely, Compound (III) and Compound (V) are condensed in the presence of a base to give a compound of the formula (IX) [hereinafter referred to as Compound (IX)]:

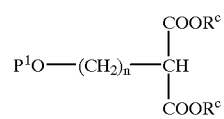

(IX)

wherein $R^c$, $P^1$ and n are as defined above; which is subjected to condensation, in the presence of a base, with Compound (II) to give Compound (VI). Each condensation reaction in the present method is also carried out under the same conditions of the condensation in Method A.

Method C

Compound (VI) to be produced according to Method A is deprotected selectively and is then treated with an acid or a base to give a compound of the formula (X) [hereinafter referred to as Compound (X)]:

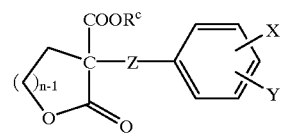

(X)

wherein X, Y, Z, $R^c$ and n are as defined above; which is subjected to hydrolysis and then Curtius rearrangement reaction, and is further protected/deprotected, if necessary, to give a compound of the formula ($X^1$) [hereinafter referred to as Compound (XI)]:

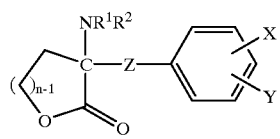

wherein X, Y, Z, $R^1$, $R^2$ and n are as defined above; which is subjected to reduction and is protected/deprotected, if necessary, to give Compound (I-1).

Examples of the base to be used in the hydrolysis include sodium hydroxide, potassium hydroxide, lithium hydroxide and barium hydroxide.

Examples of the solvent to be used in the hydrolysis include water, methanol, ethanol, tert-butyl alcohol, tetrahydrofuran, ethylene glycol dimethyl ether, dimethylformamide and dimethyl sulfoxide.

The hydrolysis generally proceeds at a temperature of from −20° C. to 80° C. and a lower or higher temperature than said temperature range may be selected on demand.

The hydrolysis is generally carried out for 30 minutes to 2 days and a longer or shorter reaction period than the indicated period may be selected on demand.

After the reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the Curtius rearrangement reaction include hönig base such as triethylamine or diisopropylethylamine, provided that carboxylic acid in the reaction substrate form a salt, none of the aforementioned base need to be used.

Examples of the activating agent to be used in the Curtius rearrangement reaction include methyl chloroformate, ethyl chloroformate, isopropyl chloroformate, isobutyl chloroformate and phenyl chloroformate.

Examples of the azidation agent to be used in the Curtius rearrangement reaction include sodium azide and diphenylphosphoric azide, provided that diphenylphosphoric azide is used, both the aforementioned base and activating agent are not necessary to employ.

The solvent to be used in the Curtius rearrangement reaction is preferably non-protonic solvent at the first half of the reaction and is exemplified by tetrahydrofuran, acetone, diethyl ether, ethylene glycol dimethyl ether, dimethylformamide, dimethyl sulfoxide, dioxane, metylene chloride, chloroform, dichloroethane and acetonitrile, and is exemplified, at the latter half of the reaction, by methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane, acetonitrile and benzyl alcohol.

The Curtius rearrangement reaction generally proceeds at a temperature of from −20° C. to 150° C. and a lower or higher temperature than said temperature range may be selected on demand.

The Curtius rearrangement reaction is generally carried out for 30 minutes to 10 hours and the longer or shorter reaction period than a indicated period may be selected on demand.

After the Curtius rearrangement reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent in the reduction include metallic reducing reagent such as diborane, sodium borohydride, lithium borohydride or lithium alminum hydride.

Examples of the organic solvent to be used in the reduction include methanol, ethanol, tert-butyl alcohol, tetrahydrofuran, diethyl ether and ethylene glycol dimethyl ether.

The reduction generally proceeds at a temperature of from −100° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method D

Compound (XI) in Method C also can be produced according to the following method.

Namely, a compound of the formula (XII-a) [hereinafter referred to as Compound (XII-a)]:

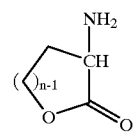

wherein n is as defined above; and benzophenoneimine are condensed to give a compound of the formula (XII-b) [hereinafter referred to as Compound (XII-b)]:

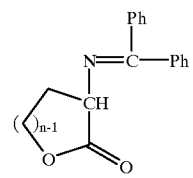

wherein Ph is phenyl and n is as defined above; and Compound (XII-b) and Compound (II) are condensed, in the presence of a base, to give a compound of the formula (XIII) [hereinafter referred to as Compound (XIII)]:

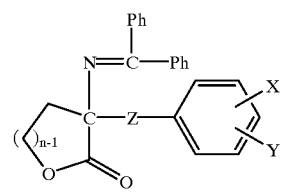

wherein X, Y, Z, Ph and n are as defined above; which is subjected to hydrolysis and protection/deprotection, if necessary, to give Compound (XI).

Examples of the organic solvent to be used in the condensation with benzophenoneimine include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 50° C. and a lower or higher temperature than said temperature range may be selected on demand.

The condensation is generally carried out for 30 minutes to 24 hours and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the condensation with Compound (II) include sodium methoxide, sodium ethoxide, sodium hydride, potassium hydride, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −100° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reagent to be used in the hydrolysis include hydrochloric acid, sulfuric acid, acetic acid and trifluoroacetic acid.

Examples of the solvent to be used in the hydrolysis include water, methanol, ethanol, tert-butyl alcohol, tetrahydrofuran, ethylene glycol dimethyl ether, dimethylformamide and dimethyl sulfoxide.

The hydrolysis generally proceeds at a temperature of from −20° C. to 80° C. and a lower or higher temperature than said temperature range may be selected on demand.

The hydrolysis is generally carried out for 30 minutes to 5 hours and a longer or shorter reaction period than the indicated period may be selected on demand.

After the hydrolysis is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method E

A compound of the formula (XIV) [hereinafter referred as to Compound (XIV)]:

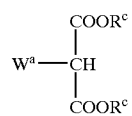

(XIV)

wherein $W^a$ is a straight- or branched chain alkyl having 1 to 6 carbon atoms; a straight- or branched chain alkenyl having 2 to 6 carbon atoms; a straight- or branched chain alkynyl having 2 to 6 carbon atoms; a phenyl which may be substituted by hydroxy; or a straight- or branched chain C1–C6 alkyl substituted by 1 to 3 substituents selected from the group consisting of a halogen, a cycloalkyl and a phenyl which may be substituted by hydroxy, $R^c$ is as defined above, when $W^a$ has hydroxy, the hydroxy may be protected if necessary; is condensed, in the presence of a base, with Compound (II) to give a compound of the formula (XV) [hereinafter referred as to Compound (XV)]:

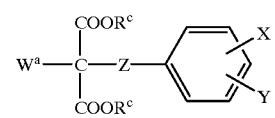

(XV)

wherein $W^a$, X, Y, Z and $R^c$ are as defined above; which is hydrolyzed, followed by Curtius rearrangement reaction to give a compound of the formula (XVI) [hereinafter referred as to Compound (XVI)]:

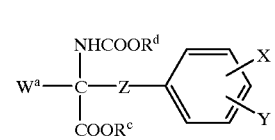

(XVI)

wherein $W^a$, X, Y, Z, $R^c$ and $R^d$ are as defined above. The ester compound obtained is reduced and subjected to protection/deprotection, if necessary, to give a compound of the formula (XVII) [hereinafter referred as to Compound (XVII)]:

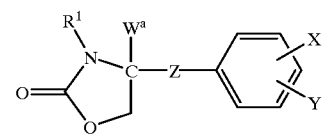

(XVII)

wherein $W^a$, X, Y, Z and $R^1$ are as defined above; followed by treatment with an alkali and protection/deprotection, if necessary, to give a compound of the formula (I-2) [hereinafter referred as to Compound (I-2)]:

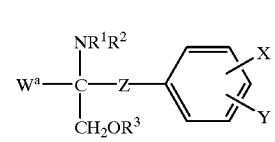

(I-2)

wherein $W^a$, X, Y, Z, $R^1$, $R^2$ and $R^3$ are as defined above.

Examples of the base to be used in the condensation with Compound (II) include sodium methoxide, sodium ethoxide, sodium hydride, potassium hydride, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the hydrolysis of Compound (XV) include sodium hydroxide, potassium hydroxide, lithium hydroxide and barium hydroxide.

Examples of the organic solvent to be used in hydrolysis include methanol, ethanol, tert-butyl alcohol, tetrahydrofuran, ethylene glycol dimethyl ether, dimethylformamide and dimethylsulfoxide, and a mixed solvent with water thereof can be used if necessary.

The hydrolysis generally proceeds at a temperature of from −20° C. to 80° C. and a lower or higher temperature than said temperature range may be selected on demand.

The hydrolysis is generally carried out for 30 minutes to 2 days and a longer or shorter reaction period than the indicated period may be selected on demand.

After the hydrolysis is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the Curtius rearrangement reaction include honig base such as triethylamine or diisopropylethylamine, provided that carboxylic acid in the reaction substrate form a salt, none of the aforementioned base need to be used.

Examples of the activating agent to be used in the Curtius rearrangement reaction include methyl chloroformate, ethyl chloroformate, isopropyl chloroformate, isobutyl chloroformate and phenyl chloroformate.

Examples of the azidation agent to be used in the Curtius rearrangement reaction include sodium azide and diphenylphosphoric azide, provided that diphenylphosphoric azide is used, both the aforementioned base and activating agent are not necessary to employ.

Examples of the solvent to be used in the Curtius rearrangement reaction is preferably non-protonic solvent at the first half of the reaction and is exemplified by tetrahydrofuran, acetone, diethyl ether, ethylene glycol dimethyl ether, dimethylformamide, dimethyl sulfoxide, dioxane, methylene chloride, chloroform, dichloroethane and acetonitrile, and is exemplified, at the latter half of the reaction, by methanol, ethanol, tertbutyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane, acetonitrile and benzyl alcohol.

The Curtius rearrangement reaction generally proceeds at a temperature of from −20° C. to 150° C. and a lower or higher temperature than said temperature range may be selected on demand.

The Curtius rearrangement reaction is generally carried out for 30 minutes to 10 hours and a longer or shorter reaction period than the indicated period may be selected on demand.

After the Curtius rearrangement reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent to be used in the reduction of Compound (XVI) include metallic reducing reagent such as sodium borohydride, lithium borohydride or alminum hydride.

Examples of the organic solvent to be used in the reduction include methanol, ethanol, tert-butyl alcohol, tetrahydrofuran, diethyl ether and ethylene glycol dimethyl ether. The reduction generally proceeds at a temperature of from −20° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the alkali to be used in the alkaline treatment of Compound (XVII) include sodium hydroxide and potassium hydroxide.

Examples of the organic solvent to be used in the present reaction include methanol, ethanol, tert-butyl alcohol, tetrahydrofuran, diethyl ether, ethylene glycol dimethyl ether, water and a mixture thereof The present reaction generally proceeds at a temperature of from 50° C. to the refluxing temperature of the solvent to be used and a lower or higher temperature than said temperature range may be selected on demand.

The present reaction is generally carried out for 30 minutes to 12 hours and a longer or shorter reaction period than the indicated period may be selected on demand.

After the present reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

In the present method, Compound (I-2) also can be produced directly from Compound (XVI) without through Compound (XVII).

Method F

Compound (XIV) also can be produced according to the following method.

Namely, a compound of the formula (XVIII) [hereinafter referred to as Compound (XVIII)]:

$$W^a—Lv \qquad (XIII)$$

wherein $W^a$ and Lv are as defined above; and Compound (III) are condensed in the presence of a base, to give Compound (XIV).

Examples of the base to be used in the condensation of Compound (XVIII) and Compound (III) include sodium methoxide, sodium ethoxide, sodium hydride, potassium hydride, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method G

Compound (XV) in Method F also can be produced according to the following method.

Namely, Compound (IV) and Compound (XVIII) are condensed in the presence of a base to give Compound (XV).

Examples of the base to be used in the condensation of Compound (IV) and Compound (XVIII) include sodium methoxide, sodium ethoxide, sodium hydride, potassium hydride, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method H

A compound of the formula (XIX) [hereinafter referred to as Compound (XIX)]:

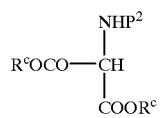

(XIX)

wherein $P^2$ is an amino-protecting group widely employed in the field of organic synthetic chemistry, such as acetyl, benzoyl, benzyl, tert-butoxycarbonyl or benzyloxycarbonyl, $R^c$ is as defined above; and Compound (II) are condensed in the presence of a base to give a compound of the formula (XX) [hereinafter referred to as Compound (XX)]:

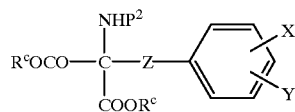

(XX)

wherein X, Y, Z, $P^2$ and Rc are as defined above; which is subjected to hydrolysis and then decarboxylation at the same time, followed by protection/deprotection, if necessary, to give a compound of the formula (XXI) [hereinafter referred to as Compound (XXI)]:

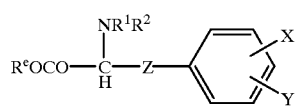

(XXI)

wherein $R^e$ is hydrogen or an carboxyl-protecting group widely employed in the field of organic synthetic chemistry, such as methyl, ethyl, tert-butyl or benzyl, and X, Y, Z, $R^1$ and $R^2$ are as defined above; the carboxyl compound obtained is reduced and then subjected to protection/deprotection, if necessary, to give a compound of the formula (I-3) [hereinafter referred to as Compound (I-3)];

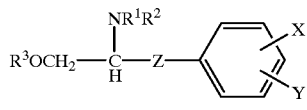

(I-3)

wherein X, Y, Z, $R^1$, $R^2$ and $R^3$ are as defined above.

Examples of the base to be used in the condensation with Compound (II) include sodium methoxide, sodium ethoxide, sodium hydride, potassium hydride, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reagent to be used in the hydrolysis and decarboxylation of Compound (XX) include hydrochloric acid, sulfuric acid, acetic acid and trifluoroacetic acid.

Examples of the solvent to be used in hydrolysis and decarboxylation include water, methanol, ethanol, tert-butyl alcohol, tetrahydrofuran, ethylene glycol dimethyl ether, dimethylformamide and dimethyl sulfoxide.

The hydrolysis and decarboxylation generally proceeds at a temperature of from −20° C. to 150° C. and a lower or higher temperature than said temperature range may be selected on demand.

The hydrolysis and decarboxylation is generally carried out for 30 minutes to 2 days and a longer or shorter reaction period than the indicated period may be selected on demand.

After the hydrolysis and decarboxylation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent to be used in the reduction of Compound (XXI) include borane, metallic reducing reagent such as sodium borohydride, lithium borohydride and lithium alminum hydride.

Examples of the organic solvent to be used in the reduction include methanol, ethanol, tert-butyl alcohol, tetrahydrofuran, diethyl ether and ethylene glycol dimethyl ether.

The reduction generally proceeds at a temperature of from −20° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method I

A compound of the formula (XXII) [hereinafter referred to as Compound (XXII)]:

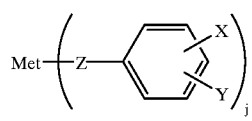

(XXII)

wherein Met is a metal widely employed in the field of organic synthetic chemistry, such as lithium, magnesium chloride, magnesium bromide, magnesium iodide, copper, lithium copper and nickel, j is an integer of 1 to 3, X, Y and Z are as defined above, or when X or Y has a functional group (e.g. amino, hydroxy, oxo), the functional group may be protected if necessary; is subjected to addition with a compound of the formula (XXIII) [hereinafter referred to as Compound (XXIII)]:

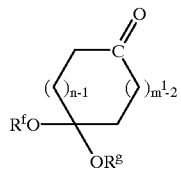

(XXIII)

wherein $R^f$ and $R^g$ are a lower alkyl (e.g. methyl, ethyl, propyl, isopropyl, butyl) and $R^f$ and $R^g$ may together form an alkylene (e.g. ethylene, propylene), $m^1$ and n are as defined above; to give a compound of the formula (XXIV) [hereinafter referred to as Compound (XXIV)]:

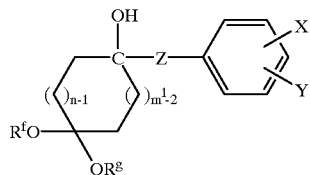

(XXIV)

wherein $R^f$, $R^g$, X, Y, Z, $m^1$ and n are as defined above; which is subjected to Ritter reaction and then hydrolysis to give a compound of the formula (XXV) [hereinafter referred to as Compound (XXV)]:

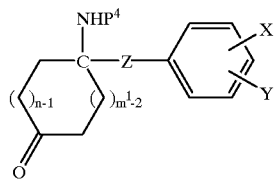

(XXV)

wherein $P^4$ is an acyl such as formyl, acetyl or benzoyl, and X, Y, Z, $m^1$ and n are as defined above; followed by Baeyer-Villiger reaction and then protection/deprotection, if necessary, to give a compound of the formula (XXVI) [hereinafter referred to as Compound (XXVI)]:

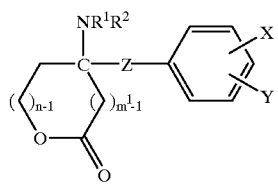

(XXVI)

wherein X, Y, Z, $R^1$, $R^2$, $m^1$ and n are as defined above; and Compound (XXVI) is reduced and then subjected to protection/deprotection, if necessary, to give a compound of the formula (I-4) [hereinafter referred to as Compound (I-4)]:

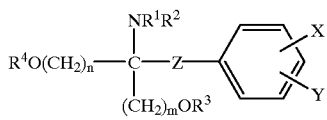

(I-4)

wherein X, Y, Z, $R^1$, $R^2$, $R^3$, $R^4$, m and n are as defined above.

Examples of the organic solvent to be used in the addition with Compound (XXIII) include tetrahydrofuran, diethyl ether, ethylene glycol dimethyl ether, dimethylformamide, dimethyl sulfoxide, benzene, toluene, xylene, dioxane, methylene chloride, chloroform and dichloroethane.

The addition generally proceeds at a temperature of from −20° C. to 100° C. and a lower or higher temperature than said temperature range may be selected on demand.

The addition is generally carried out for 30 minutes to 2 days and a longer or shorter reaction period than the indicated period may be selected on demand.

After the addition is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reagent to be used in the Ritter reaction of Compound (XXIV) include hydrogen cyanide, acetonitrile and benzonitrile.

Examples of the organic solvent to be used in the Ritter reaction include acetic acid, tetrahydrofuran, diethyl ether, ethylene glycol dimethyl ether, dimethylformamide, dimethyl sulfoxide, benzene, toluene, xylene, dioxane, methylene chloride, chloroform and dichloroethane.

Examples of the acid catalyst to be used in the Ritter reaction include a strong acid such as sulfuric acid or trifluoroacetic acid.

The Ritter reaction generally proceeds at a temperature of from −20° C. to 80° C. and a lower or higher temperature than said temperature range may be selected on demand.

The Ritter reaction is generally carried out for 30 minutes to 24 hours and a longer or shorter reaction period than the indicated period may be selected on demand.

After the Ritter reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reagent to be used in the hydrolysis include hydrochloric acid, sulfic acid, acetic acid and trifluoroacetic acid.

Examples of the solvent to be used in the hydrolysis include water, methanol, ethanol, isopropyl alcohol, tert-butyl alcohol, acetone, tetrahydrofuran, ethylene glycol dimethyl ether, dimethylformamide and dimethyl sulfoxide.

The hydrolysis generally proceeds at a temperature of from −20° C. to 100° C. and a lower or higher temperature than said temperature range may be selected on demand.

The condensation is generally carried out for 30 minutes to 5 hours and a longer or shorter reaction period than the indicated period may be selected on demand.

After the hydrolysis is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the oxidizing agent to be used in the Baeyer-Villiger reaction of Compound (XXV) include peracetic acid, hydrogen peroxide and metachloroperbenzoic acid.

Examples of the organic solvent to be used in the Baeyer-Villiger reaction include tetrahydrofuran, diethyl ether, ethylene glycol dimethyl ether, dimethylformamide, dimethyl sulfoxide, benzene, toluene, xylene, dioxane, methylene chloride, chloroform, carbon tetrachloride and dichloroethane.

The Baeyer-Villiger reaction generally proceeds at a temperature of from 0° C. to 100° C. and a lower or higher temperature than said temperature range may be selected on demand.

The Baeyer-Villiger reaction is generally carried out for 30 minutes to 24 hours and a longer or shorter reaction period than the indicated period may be selected on demand.

After the Baeyer-Villiger reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent to be used in the reduction of Compound (XXVI) include borane, metallic reducing reagent such as sodium borohydride, lithium borohydride or lithium aluminum hydride.

Examples of the solvent to be used in the reduction include water, methanol, ethanol, isopropyl alcohol, tert-butyl alcohol, tetrahydrofuran, diethyl ether and ethylene glycol dimethyl ether.

The reduction generally proceeds at a temperature of from −100° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method J

Compound (I-4) also can be produced according to the following method. Namely, a compound of the formula (XXVII) [hereinafter referred to as Compound (XXVII)]:

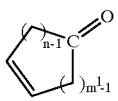

(XXVII)

wherein $m^1$ and n are as defined above; is subjected to addition with Compound (XXII) to give a compound of the formula (XXVIII) [hereinafter referred to as Compound (XXVIII)]:

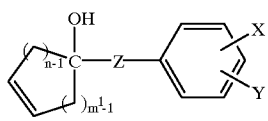

(XXVIII)

wherein X, Y, Z, $m^1$ and n are as defined above; which is subjected to Ritter reaction to give a compound of the formula (XXIX) [hereinafter referred to as Compound (XXIX)]:

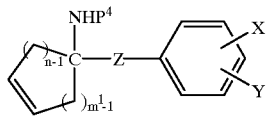

(XXIX)

wherein X, Y. Z, $P^4$, $m^1$ and n are as defined above; the double bond in the compound obtained is subjected to oxidative cleavage reaction and then reduction and/or protection/deprotection, if necessary, to give Compound (I:4).

Examples of the organic solvent to be used in the addition with Compound (XXII) include tetrahydrofuran, diethyl ether, ethylene glycol dimethyl ether, dimethylformamide, dimethyl sulfoxide, benzene, toluene, xylene, dioxane, methylene chloride, chloroform and dichloroethane.

The addition generally proceeds at a temperature of from −20° C. to 100° C. and a lower or higher temperature than said temperature range may be selected on demand.

The addition is generally carried out for 30 minutes to 2 days and a longer or shorter reaction period than the indicated period may be selected on demand.

After the addition is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reagent to be used in the Ritter reaction of Compound (XXVIII) include hydrogen cyanide, acetonitrile and benzonitrile.

Examples of the organic solvent to be used in the Ritter reaction include acetic acid, tetrahydrofuran, diethyl ether, ethylene glycol dimethyl ether, dimethylformamide, dimethyl sulfoxide, benzene, toluene, xylene, dioxane, methylene chloride, chloroform and dichloroethane.

Examples of the acid catalyst to be used in the Ritter reaction include a strong acid such as sulfuric acid or trifluoroacetic acid.

The Ritter reaction generally proceeds at a temperature of from −20° C. to 80° C. and a lower or higher temperature than said temperature range may be selected on demand.

The Ritter reaction is generally carried out for 30 minutes to 24 hours and a longer or shorter reaction period than the indicated period may be selected on demand.

After the Ritter reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reagent to be used in the oxidative cleavage reaction of Compound (XXIX) include ozone, potassium permanganate, osumic acid-sodium metaperiodate and osumic acid-lead tetraacetate.

Examples of the solvent to be used in the oxidative cleavage reaction include water, methanol, ethanol, isopropyl alcohol, tert-butyl alcohol, acetone, acetic acid, tetrahydrofuran, diethyl ether, ethylene glycol dimethyl ether, ethyl acetate, dimethylformamide, dimethyl sulfoxide, benzene, toluene, xylene, dioxane, methylene chloride, chloroform, dichloroethane and pyridine.

The oxidative cleavage reaction generally proceeds at a temperature of from −100° C. to 80° C. and a lower or higher temperature than said temperature range may be selected on demand.

The oxidative cleavage reaction is generally carried out for 30 minutes to 24 hours and a longer or shorter reaction period than the indicated period may be selected on demand.

After the oxidative cleavage reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method K

A compound of the formula (XXX) [hereinafter referred to as Compound (XXX)]:

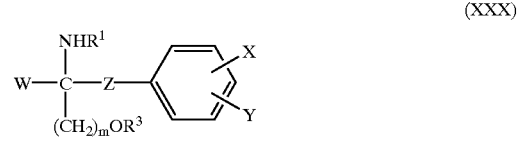

(XXX)

wherein W, X, Y, Z, $R^1$, $R^3$ and m are as defined above, is divided into an optically active isomer thereof and, if necessary, is subjected to protection/deprotection to give a compound of the formula (XXX-a) or (XXX-b):

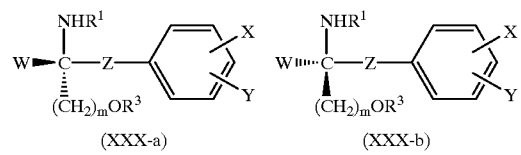

(XXX-a)  (XXX-b)

wherein W, X, Y, Z, $R^1$, $R^3$ and m are as defined above.

A method dividing into an optically active isomer is inclusive of the following methods: (1) a salt, an ester or an acid amide of Compound (XXX) is formed with an optically active acid such as (+)- or (−)-tartaric acid, (+)- or (−)-mandelic acid, (+)- or (−)-malic acid, (+)- or (−)-dibenzoyltartaric acid, (+)- or (−)-aspartic acid, (S)- or (R)-1-phenylethanesulfonic acid, (+)- or (−)-10-camphorsulfonic acid or (S)- or (R)-α-methoxy-α-trifluoromethylphenyl-acetic acid, and is subjected to recrystallization or chromatography; (2) Compound (XXX) is directly subjected to high performance liquid chromatography using a chiral carrier [e.g. CROWNPAK CR (trademark, Daicel Chemical Industries); or (3) Compound (XXX) is subjected to N-acylation with 3,5-dinitrobenzoyl chloride etc. and then is subjected to high performance liquid chromatography using a chiral carrier [e.g. CHIRALCEL OD (trademark, Daicel Chemical Industries), CHIRALCEL OG (trademark, Daicel Chemical Industries), CHIRALCEL OF (trademark, Daicel Chemical Industries)].

After the reaction is carried out under the above-mentioned conditions or after removing the protecting group on demand, the object compound can be purified by a method known in the field of organic synthetic chemistry, such as solvent extraction, recrystallization, chromatography or a method using an ion exchange resin.

Method L

Compound (I-3) also can be produced according to the following method.

Namely, a compound of the formula (XXXI) [hereinafter referred to as Compound (XXXI)] derived from an amino acid:serine or an ester thereof:

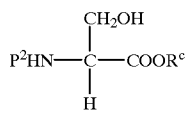

(XXXI)

wherein $R^c$ and $P^2$ are as defined above; is reacted, in the presence of an acid catalyst, with 2,2-dimethoxypropane to give a compound of the formula [hereinafter referred to as Compound (XXXII)]:

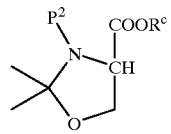

(XXXII)

wherein $R^c$ and $P^2$ are as defined above. The carboxyl acid or ester of the compound obtained is reduced to give a compound of the formula (XXXIII) [hereinafter referred to as Compound (XXXIII)]:

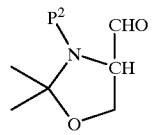

(XXXIII)

wherein $P^2$ is as defined above; which is condensed, in the presence of a base, with a compound of the formula (XXXIV) [hereinafter referred to as compound (XXXIV)]:

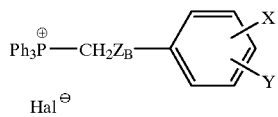

(XXXIV)

wherein Hal is a halogen such as chlorine, bromine or iodine, $Z_B$ is a single bond or a straight-chain alkylene having carbon atoms in the number of (q-1), X and Y are as defined above; to give a compound of the formula (XXXV) [hereinafter referred to as Compound (XXXV)]:

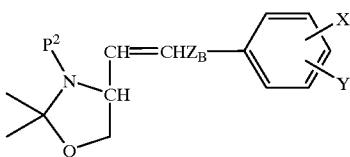

(XXXV)

wherein X, Y, $Z_B$ and $P^2$ are as defined above; and Compound (XXXV) is reduced to give a compound of the formula (XXXVI) [hereinafter referred to as Compound (XXXVI)]:

(XXXVI)

wherein X, Y, $Z_B$ and $P^2$ are as defined above; which is subjected to protection/deprotection to give a compound of the formula (I-3).

Compound (XXXI) can be produced according to a method widely employed in the field of organic synthetic chemistry such as reacting serine or an ester thereof with acetyl chloride, benzoyl chloride, di-tert-butyl oxalate or benzyl chloroformate etc.

Examples of the acid catalyst using in the production of Compound (XXXII) include p-toluenesulfonic acid and borone trifluoride ether complex.

Examples of the organic solvent to be used in the present reaction include tetrahydrofuran, diethyl ether, dimethylformamide, dimethyl sulfoxide, benzene, toluene, xylene, dioxane, methylene chloride, chloroform, dichloroethane and acetonitrile.

The present reaction generally proceeds at a temperature of from room temperature to 80° C. and a lower or higher temperature than said temperature range may be selected on demand.

The present reaction is generally carried out for 5 hours to 24 hours and a longer or shorter reaction period than the indicated period may be selected on demand.

After the reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

The reduction of the carboxylic acid or ester can be carried out according to (1) a method using a reducing agent such as diisobutyl aluminum hydride or lithium aluminum hydride, (2) a method using reducing agent such as lithium aluminum hydride, sodium aluminum bis(2-methoxyethoxy) hydride, lithium aluminum trimethoxy hydride or lithium aluminum triethoxy hydride after amidation using ammonia or N, O-dimethylhydroxylamine. When an reduction isomer obtained is an alcohol, the alcohol can be oxidated to give the aldehyde using Swern oxidation or pyridinium chlorochromate (PCC) oxidation.

Examples of the organic solvent to be used in the reduction include hexane, benzene, toluene, methylene chloride, tetrahydrofaran and diethyl ether.

The reduction generally proceeds at a temperature of from −78° C. to 100° C. and a lower or higher temperature than said temperature range may be selected on demand.

The reduction is generally carried out for 5 hours to 24 hours and a longer or shorter reaction period than the indicated period may be selected on demand.

After the reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the condensation with Compound (XXXIV) include sodium hydroxide, sodium methoxide, sodium ethoxide, potassium tert-butoxide, sodium hydride, potassium hydride, lithium diisopropylamide, butyl lithium, lithium hexamethyldisilazane, triethylamine, diisopropylethylamine, pyridine and 1,8-diazabicyclo[4.3.0]undec-5-ene.

Examples of the solvent to be used in the condensation include water, methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a lower or higher temperature than said temperature range may be selected on demand.

The condensation is generally carried out for 30 minutes to 24 hours and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent to be used in the reduction of a double bond include a metallic reducing reagent such as lithium borohydride or lithium aluminum hydride, transition metal (palladium-carbon, platinum oxide, Raney nickel, rhodium or ruthenium) for catalytic reduction.

Examples of the organic solvent to be used in the reduction include methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide.

The reduction generally proceeds at a temperature of from −20° C. to 80° C. and a lower or higher temperature than said temperature range may be selected on demand.

The reduction is generally carried out for 30 minutes to 24 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Moreover, Compound (XXXVI) is treated with an acid catalyst such as p-toluenesulfonic acid in a solvent such as methanol, or with trifluoroacetic acid, and then removed the protecting group on demand, the objective compound can be purified by a method known in the field of organic synthetic chemistry, such as solvent extraction, recrystallization, chromatography or a method using an ion exchange resin.

Method M

Using a method shown in from Method A to Method L and from Method P to Method V as mentioned later, a compound of the formula (XXXVII) [hereinafter referred to as Compound (XXXVII)]:

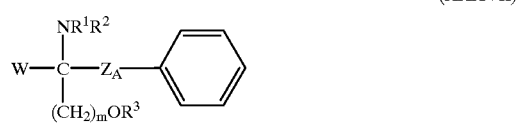

(XXXVII)

wherein $Z_A$ is a single bond or a straight-chain alkyl having carbon atoms in the number of r, r is an integer of from 1 to 20, W, $R^1$, $R^2$, $R^3$ and m are as defined above, and when W has a functional group (e.g. hydroxy), the functional group may be protected if necessary; can be produced.

The present method is the method to produce Compound (I) using Compound (XXXVII) as a starting material. Namely, Compound (XXXVI) and a compound of the formula (XXXVIII) [hereinafter referred to as Compound (XXXVIII)]:

$X_A COCl$                               (XXXVIII)

wherein $X_A$ is a straight-chain alkyl having carbon atoms in the number of (p-1) (p is as defined above), the said straight-chain alkyl may have 1 to 3 substituents selected from the group consisting of an alkyl, hydroxy, an alkoxy, an acyloxy, amino, an alkylamino, an acylamino, oxo, a haloalkyl, a halogen and a phenyl which may have substituents, and when $X_A$ has a functional group (e.g. amino, hydroxy, oxo), the functional group may be protected if necessary; is subjected to Friedel–Crafts reaction in the presence of an acid, and protection/deprotection, if necessary, to give a compound of the formula (I-5):

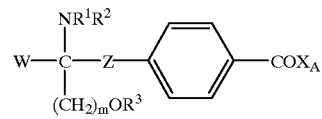

(I-5)

wherein W, Z, $X_A$, $R^1$, $R^2$, $R^3$ and m are as defined above.

Examples of the acid to be used in the Friedel-Crafts reaction include aluminum chloride, aluminum bromide, titanium chloride, sulfuric acid, zinc chloride, ferric chloride, hydrogen fluoride and phosphoric acid.

Examples of the organic solvent to be used in the Friedel-Crafts reaction include tetrahydrofuran, diethyl ether, ethylene glycol dimethyl ether, dimethylformamide, dimethyl sulfoxide, methylene chloride, chloroform, dichloroethane, acetonitrile, nitromethane and carbon disulfide. The present reaction may be carried out without a solvent if necessary.

The Friedel-Crafts reaction generally proceeds at a temperature of from −20° C. to 100° C. and a lower or higher temperature than said temperature range may be selected on demand.

The Friedel-Crafts reaction is generally carried out for 30 minutes to 24 hours and a longer or shorter reaction period than the indicated period may be selected on demand.

After the Friedel-Crafts reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method N

Compound (I-5) obtained in Method L is subjected to reduction and then protection/deprotection, if necessary, to give a compound of the formula (I-6) [hereinafter referred to as Compound (I-6)]:

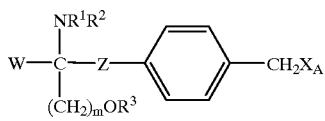

(I-6)

wherein W, Z, $X_A$, $R^1$, $R^2$, $R^3$ and m are as defined above.

In the reduction, Clemmensen reaction or Wolff-Kishner reaction widely employed in the field of organic synthetic chemistry can be used, but the following reaction is especially useful for the present reaction.

Examples of the reagent to be used in the reduction include triethylsilane.

Examples of the organic solvent to be used in the reduction include trifluoroacetic acid, methanol, ethanol, tert-butyl alcohol, tetrahydrofuran, ethylene glycol dimethyl ether, dimethylformamide, dimethyl sulfoxide, methylene chloride, chloroform, dichloroethane, acetonitrile and nitromethane.

The reduction generally proceeds at a temperature of from 0° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method O

Using a method shown in from Method A to Method L and from Method P to Method V as mentioned later, a compound of the formula (XXXIX) [hereinafter referred to as Compound (XXXIX)]:

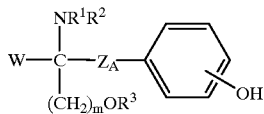

(XXXIX)

wherein W, $Z_A$, $R^1$, $R^2$, $R^3$ and m are as defined above, and when W has a functional group (e.g. hydroxy), the functional group may be protected if necessary; can be produced.

The present method is the method to produce Compound (I) using Compound (XXXIX) as a starting material. Namely, Compound (XXXIX) and a compound of the formula (XL) [hereinafter referred to as Compound (XL)]:

$X_A$—Lv  (XL)

wherein $X_A$ and Lv are as defined above, and when $X_A$ has a functional group (e.g. amino, hydroxy, oxo), the functional group may be protected if necessary; are subjected to condensation in the presence of a base, and then protection/deprotection, if necessary, to give a compound of the formula (I-7) [hereinafter referred to as Compound (I-7)]:

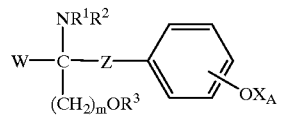

(I-7)

wherein W, Z, $X_A$, $R^1$, $R^2$, $R^3$ and m are as defined above.

Examples of the base to be used in the condensation include sodium methoxide, sodium ethoxide, sodium hydride, potassium hydride, lithium diisopropylamide, lithium hexamethyldisilazane, diisopropylethylamine, 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method P

The present method is especially useful for the production of a compound of the formula (I) wherein W is an alkyl substituted by a halogen. Namely, Compound (I-1) is subjected to protection/deprotection, if necessary, and then condensation with triethyl orthoacetate [$CH_3C(OCH_2CH_3)_3$] to give a compound of the formula (XLI) [hereinafter referred to as Compound (XLI)]:

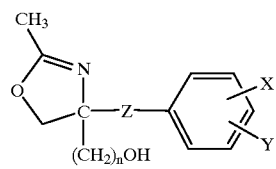

(XLI)

wherein X, Y, Z and n are as defined above. The free hydroxyl group in the compound obtained is halogenated, and protection/deprotection, if necessary, is subjected to give a compound of the formula (I-8) [hereinafter referred to as Compound (I-8)]:

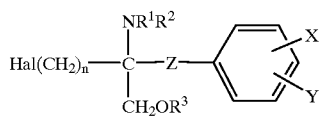

(I-8)

wherein $R^1$, $R^2$, $R^3$, X, Y, Z, n and Hal are as defined above.

Examples of the organic solvent to be used in the condensation of Compound (I-1) and triethyl orthoacetate include tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from 20° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the halogenating reagent to be used in the halogenation include a reagent widely employed in the field of organic synthetic chemistry, for example, hydrogen halide such as hydrochloric acid, hydrobromic acid or hydriodic acid, phosphorous halide such as phosphorous chloride, phosphorous bromide, phosphorous pentachloride or phosphorous oxychloride, halogen such as chlorine, bromine or iodine, metal halide such as sodium bromide, sodium iodide, or potassium iodide, ,thionyl chloride, carbon tetrachloride-triphenylphosphine and carbon tetrabromide-triphenylphosphine. The following reagent is especially useful as the halogenating reagent to be used in the halogenation of Compound (XLI). Namely, examples of the halogenating reagent include N-chlorosuccinimidetriphenylphosphine for the chlorination, N-bromosuccinimide-triphenylphosphine for the bromination, and paratosyl fluoride-tetrabutylammonium fluoride for the fluorination.

Examples of the organic solvent to be used in the halogenation include tetrahydrofuran, diethyl ether, ethylene glycol dimethyl ether, dimethylformamide, dimethyl sulfoxide, benzene, toluene, xylene dioxane, methylene chloride, chloroform, carbon tetrachloride, dichloroethane and acetonitrile. Methylene chloride is preferred in the chlorination and bromination, and tetrahydrofuran is preferred in the fluorination.

The halogenation generally proceeds at a temperature of from 20° C. to 80° C. and a lower or higher temperature than said temperature range may be selected on demand.

The halogenation is generally carried out for 30 minutes to 2 days and a longer or shorter reaction period than the indicated period may be selected on demand.

After the halogenation is carried out under the above-mentioned conditions or after removing the protecting group on demand, the objective compound can be purified by a method known in the field of organic synthetic chemistry, such as solvent extraction, recrystallization chromatography or a method using an ion exchange resin.

Method Q

The present method is especially useful for the production of a compound of the formula (I) wherein W is 1-alkenyl such as vinyl. Namely, by using the manufacturing process disclosed in WO94/08943 or the method reported in Bioorganic & Medicinal Chemistry Letters, Vol.5, No.8, 853–856 (1995) and by performing a selective protection, a compound of the formula(XLII) [hereinafter referred to as Compound (XLII)]:

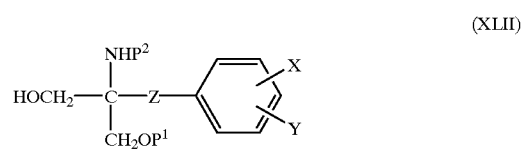

wherein X, Y, Z, $P^1$ and $P^2$ are as defined above; can be produced, Compound (XLII) is oxidized and subjected to protection/deprotection, if necessary, to give a compound of the formula (XLIII) [hereinafter referred to as Compound (XLIII)]:

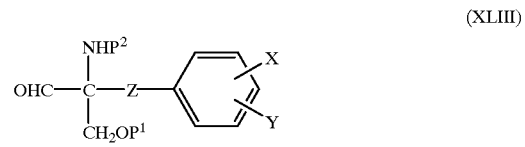

wherein X, Y, Z, $P^1$ and $P^2$ are as defined above; which is condensed, in the presence of a base, with a compound of the formula (XLIV) [hereinafter referred to as Compound (XLIV)]:

wherein $R^i$ is hydrogen or a straight- or branched chain alkyl having 1 to 5 carbon atoms (e.g. methyl, ethyl, propyl, isopropyl, butyl, isobutyl, pentyl, isopentyl), Hal is as defined above; and then subjected to protection/deprotection, if necessary, to give a compound of the formula (I-9) [hereinafter referred to as Compound (I-9)]:

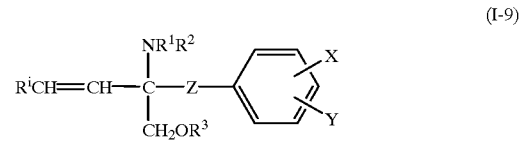

wherein $R^1$, $R^2$, $R^3$, X, Y, Z and $R^i$ are as defined above.

As a method for oxidizing alcohol to aldehyde, Collins oxidation, Jones oxidation, pyridinium chlorochromate (PCC) oxidation, pyridinium dichromate (PDC) oxidation and Swern oxidation widely employed in the field of organic synthetic chemistry are useful.

Collins oxidation is carried out using chromium (VI) oxide-pyridine complex prepared from chromium (VI) oxide and pyridine in a solvent such as methylene chloride. Collins oxidation generally proceeds at a temperature of from 0° C. to 70° C. and a lower or higher temperature than said temperature range may be selected on demand. Collins oxidation is generally carried out for 10 minutes to 24 hours and a longer or shorter reaction period than the indicated period may be selected on demand.

Jones oxidation is carried out using a solution of chromium (VI) oxide in a dilute sulfuric acid in a solvent such as acetone. Jones oxidation generally proceeds at a temperature of from 0° C. to 70° C. and a lower or higher temperature than said temperature range may be selected on demand. Jones oxidation is generally carried out for 10 minutes to 24 hours and a longer or shorter reaction period than the indicated period may be selected on demand.

The oxidation with pyridinium chlorochromate or pyridinium dichromate is carried out in a solvent such as methylene chloride or benzene. The oxidation generally proceeds at a temperature of from 0° C. to 80° C. and a lower or higher temperature than said temperature range may be selected on demand. The oxidation is generally carried out for 10 minutes to 24 hours and a longer or shorter reaction period than the indicated period may be selected on demand.

Swern oxidation is carried out using dimethyl sulfoxide-oxalyl chloride in a solvent such as methylene chloride and treating with a base such as triethylamine. Swern oxidation generally proceeds at a temperature of from −78° C. to room temperature and a lower or higher temperature than said temperature range may be selected on demand. Swern oxidation is generally carried out for 10 minutes to 24 hours and a longer or shorter reaction period than the indicated period may be selected on demand.

After the oxidation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the condensation include sodium methoxide, sodium ethoxide, sodium hydride, potassium hydride, n-butyl lithium, tert-butyl lithium, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −78° C. to 100° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Compound (II) can be produced according to the following method.

Method R

Compound (II) wherein X is a straight-chain alkyl having carbon atoms in the number of p, which may have 1 to 3 substituents selected from the group consisting of an alkyl, hydroxy, an alkoxy, an acyloxy, amino, an alkylamino, an acylamino, oxo, a haloalkyl, a halogen and a phenyl which may have substituents, the said group is substituted at the p-position of the substituent Lv—Z, Y is hydrogen, and Lv is a halogen, can be produced according to the following method. Namely, a compound of the formula (XLV) hereinafter referred to as Compound(XLV)]:

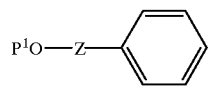
(XLV)

wherein $P^1$ and Z are as defined above; and a compound of the formula (XLVI) [hereinafter referred to as Compound (XLVI)]:

$$X_A COCl \quad (XLVI)$$

wherein $X_A$ is as defined above, when $X_A$ has a functional group (e.g. amino, hydroxy, oxo), the functional group may be protected if necessary; are, in the presence of an acid, subjected to Friedel-Crafts reaction to give a compound of the formula (XLVII) [hereinafter referred to as Compound (XLVII)]:

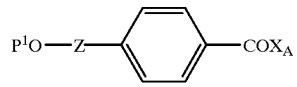
(XLVII)

wherein $P^1$, $X_A$ and Z are as defined above; which is reduced and subjected to protection/deprotection, if necessary, to give a compound of the formula (XLVIII) [hereinafter referred to as Compound (XLVIII)]:

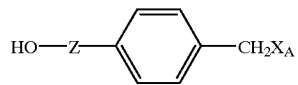
(XLVIII)

wherein $X_A$ and Z are as defined above; which is halogenated and subjected to protection/deprotection, if necessary, to give a compound of the formula (XLIX) [hereinafter referred to as Compound (XLIX)]:

(XLIX)

wherein Hal, $X_A$ and Z are as defined above.

Examples of the acid to be used in the Friedel-Crafts reaction include aluminum chloride, aluminum bromide, titanium chloride, sulfuric acid, zinc chloride, ferric chloride, hydrogen fluoride and phosphoric acid.

Examples of the organic solvent to be used in the Friedel-Crafts reaction include tetrahydrofuran, diethyl ether, ethylene glycol dimethyl ether, dimethylformamide, dimethyl sulfoxide, methylene chloride, chloroform, dichloroethane, acetonitrile, nitromethane and carbon disulfide. The present reaction may be carried out without a solvent if necessary.

The Friedel-Crafts reaction generally proceeds at a temperature of from −20° C. to 100° C. and a lower or higher temperature than said temperature range may be selected on demand.

The Friedel-Crafts reaction is generally carried out for 30 minutes to 24 hours and a longer or shorter reaction period than the indicated period may be selected on demand.

After the Friedel-Crafts reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

In the reduction, Clemmensen reaction or Wolff-Kishner reaction widely employed in the field of organic synthetic chemistry can be used, but the following reaction is especially useful for the present reaction.

Examples of the reagent to be used in the reduction include triethylsilane.

Examples of the organic solvent to be used in the reduction include trifluoroacetic acid, methanol, ethanol, tert-butyl alcohol, tetrahydrofuran, ethylene glycol dimethyl ether, dimethylformamide, dimethyl sulfoxide, methylene chloride, chloroform, dichloroethane, acetonitrile and nitromethane.

The reduction generally proceeds at a temperature of from 0° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the halogenating agent to be used in the halogenation of Compound (XLVIII) include hydrogen halide such as hydrochloric acid, hydrobromic acid or hydriodic acid, phosphorous halide such as phosphorous chloride, phosphorous bromide, phosphorous pentachloride or phosphorous oxychloride, halogen such as chlorine, bromine or iodine, metal halide such as sodium bromide, sodium iodide or potassium iodide, thionyl chloride, carbon tetrachloride-triphenylphosphine, carbon tetrabromide-triphenylphosphine, N-chlorosuccinimide and N-bromosuccinimide. In the present reaction, iodine is preferably used in the presence of triphenylphosphine-imidazole or sodium iodide is preferably used. Moreover, the halogenation also can be carried out converting the hydroxyl into the corresponding methanesulfonyloxy by reacting with methanesulfonyl chloride, and then followed by reacting a halogenating agent such as sodium iodide.

Examples of the solvent to be used in the halogenation include water, diethyl ether, tetrahydrofuran, ethylene glycol dimethyl ether, dimethylformamide, dimethyl sulfoxide, hexamethylphosphoric triamide, methylene chloride, chloroform, dichloroethane, acetonitrile, benzene, toluene, xylene, acetone and 2-butanone.

The halogenation generally proceeds at a temperature of from 0° C. to 100° C. and a lower or higher temperature than said temperature range may be selected on demand.

The halogenation is generally carried out for an hour to 12 hours and a longer or shorter reaction period than the indicated period may be selected on demand.

After the halogenation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Compound (XLVII) is halogenated and subjected to protection/deprotection, if necessary, to give a compound of the formula (L) [hereinafter referred to as Compound (L)]:

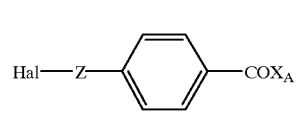

(L)

wherein Hal, $X_A$ and Z are as defined above.

The halogenation of Compound (XLVII) is carried out the same as the halogenation of Compound (XLVIII).

Method S

Compound (II) wherein X is a straight-chain alkoxy having carbon atoms in the number of (p-1) which may have 1 to 3 substituents selected from the group consisting of an alkyl, hydroxy, an alkoxy, an acyloxy, amino, an alkylamino, an acylamino, oxo, a haloalkyl, a halogen and a phenyl which may have substituents, and Lv is a halogen, can be produced according to the following method. Namely, a compound of the formula (LI) [hereinafter referred to as Compound (LI)]:

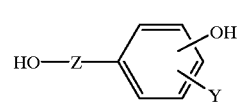

(LI)

wherein Y and Z are as defined above, when Y has a functional group (e.g. amino, hydroxy, oxo), the functional group may be protected if necessary; and Compound (XL) are condensed in the presence of a base to give a compound of the formula (LII) [hereinafter referred to as Compound (LII)]:

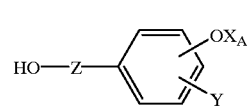

(LII)

wherein $X_A$, Y and Z are as defined above, when $X_A$ has a functional group (e.g. amino, hydroxy, oxo), the functional group may be protected if necessary; which is halogenated and subjected to protection/deprotection, if necessary, to give a compound of the formula (LIII) [hereinafter referred to as Compound (LIII)]:

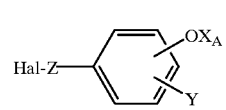

(LIII)

wherein Hal, $X_A$, Y and Z are as defined above.

Examples of the base to be used in the condensation include sodium methoxide, sodium ethoxide, sodium hydride, potassium hydride, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −20° C. to 150° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the halogenating agent to be used in the halogenation of Compound (LII) include hydrogen halide such as hydrochloric acid, hydrobromic acid or hydroiodic acid, phosphorous halide such as phosphorous chloride, phosphorous bromide, phosphorous pentachloride or phosphorous oxychloride, halogen such as chlorine, bromine or iodine, metal halide such as sodium bromide, sodium iodide or potassium iodide, thionyl chloride, carbon tetrachloride-triphenylphosphine, carbon tetrabromide-triphenylphosphine, N-chlorosuccinimide and N-bromosuccinimide. In the present reaction, iodine is preferably used in the presence of triphenylphosphine-imidazole or sodium iodide is preferably used. Moreover, the halogenation also can be carried out converting the hydroxyl into the corresponding methanesulfonyloxy by reacting with methanesulfonyl chloride, and then followed by reacting a halogenating agent such as sodium iodide.

Examples of the solvent to be used in the halogenation include water, diethyl ether, tetrahydrofuran, ethylene glycol dimethyl ether, dimethylformamide, dimethyl sulfoxide, hexamethylphosphoric triamide, methylene chloride, chloroform, dichloroethane, acetonitrile, benzene, toluene, xylene, acetone and 2-butanone.

The halogenation generally proceeds at a temperature of from 0° C. to 100° C. and a lower or higher temperature than said temperature range may be selected on demand.

The halogenation is generally carried out for an hour to 12 hours and a longer or shorter reaction period than the indicated period may be selected on demand.

After the halogenation is carried out under the above-mentioned conditions or after removing the protecting group on demand, the objective compound can be purified by a method known in the field of organic synthetic chemistry, such as solvent extraction, recrystallization chromatography or a method using an ion exchange resin.

Method T

Compound (I-5) is subjected to reduction and protection/deprotection, if necessary, to give a compound of the formula (I-10) [hereinafter referred to as Compound (I-10)]:

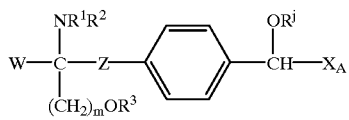

(I-10)

wherein $R^j$ is hydrogen, an alkyl or an acyl and W, $X_A$, Z, $R^1$, $R^2$, $R^3$ and m are as defined above, and when W and $X_A$ have a functional group (e.g. amino, hydroxy, oxo), the functional group may be protected if necessary.

Examples of the reducing agent to be used in the reduction include sodium borohydride, lithium borohydride, lithium aluminum hydride, aluminum diisobutyl hydride, lithium aluminum hydride trimethoxy, lithium aluminum hydride tri-tert-butyl and diborane.

Examples of the organic solvent to be used in the reduction include methanol, ethanol, tert-butyl alcohol, tetrahydrofuran, diethyl ether, ethylene glycol dimethyl ether, acetone and methyl ethyl ketone.

The reduction generally proceeds at a temperature of from −100° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method U

Compound (I-10) obtained in Method T is subjected to Mitsunobu reaction with a phthalimide or hydrogen azide [Synthesis, 1 (1981)] to give an each compound of the formula (LIV) or formula (LV) [hereinafter referred to as Compound (LIV) or Compound (LV)]:

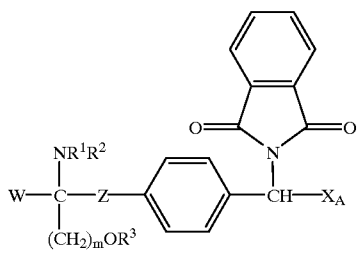

(LIV)

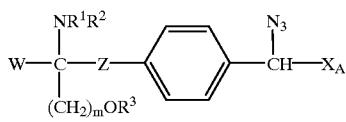

(LV)

wherein W, $X_A$, Z, $R^1$, $R^2$, $R^3$ and m are as defined above, when W and $X_A$ have a functional group (e.g. amino, hydroxy, oxo), the functional group may be protected if necessary. Compound (LIV) is treated with a base or Compound (LV) is subjected to reduction, and the each compound obtained is subjected-to protection/deprotection, if necessary, to give a compound of the formula (I-11) [hereinafter referred to as Compound (I-11)]:

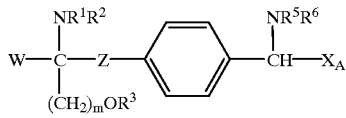

(I-11)

wherein $R^5$ and $R^6$ are the same or different and each is hydrogen, an alkyl or an acyl, and W, $X_A$, Z, $R^1$, $R^2$, $R^3$ and m are as defined above.

Examples of the reagent to be used in the Mitsunobu reaction include azodicarboxylic acid ester (e.g. ethyl azodicarboxylate)-triphenylphosphine.

The hydrogen azide to be used in the Mitsunobu reaction can be produced by treating metal azide such as sodium azide or lithium azide in sulfuric acid or treating trimethyl-silylazide with methanol in a solvent such as tetrahydrofuran if necessary.

The Mitsunobu reaction generally proceeds at a temperature of from −20° C. to 40° C. and a lower or higher temperature than said temperature range may be selected on demand.

The Mitsunobu reaction is generally carried out for an hour to 24 hours and a longer or shorter reaction period than the indicated period may be selected on demand.

After the Mitsunobu reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the reaction of Compound (LIV) include hydrazine hydrate, methylhydrazine and phenylhydrazine.

Examples of the organic solvent to be used in the present reaction include methanol, ethanol, propanol, isopropyl alcohol and butanol.

The reaction generally proceeds at a temperature of from 50° C. to the refluxing temperature of the solvent to be used and a lower or higher temperature than said temperature range may be selected on demand.

The present reaction is generally-carried out for an hour to 10 hours and a longer or shorter reaction period than the indicated period may be selected on demand.

After the present reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent to be used in the reduction of Compound (LV) include metallic reducing reagent such as sodium borohydride, lithium borohydride or lithium aluminum hydride, transition metal such as Lindlar catalyst (palladium, calcium carbonate), palladium carbon, Raney nickel, platinum oxide, rhodium or ruthenium for catalytic reduction.

Examples of the organic solvent to be used in the reduction of Compound (LV) include methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide.

The reduction generally proceeds at a temperature of from −20° C. to 80° C. and a lower or higher temperature than said temperature range may be selected on demand.

The reduction is generally carried out for an hour to 24 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method V

In Compound (VII) wherein n is 2, the protecting group ($P^1$) is removed selectively and the compound obtained is subjected to an alkaline treatment or treating by heating to give a compound of the formula (LVI) [hereinafter referred to as Compound (LVI)]:

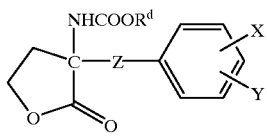

(LVI)

wherein X, Y, Z and $R^d$ are as defined above; which is, in the presence of a base, subjected to alcoholysis to give a compound of the formula (LVII) [hereinafter referred to as Compound (LVII)]:

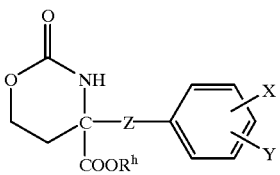

(LVII)

wherein $R^h$ is a lower alkyl such as methyl or ethyl, and X, Y and Z are as defined above. The ester compound obtained is subjected to reduction, and then oxidation if necessary to give a compound of the formula (LVIII) [hereinafter referred to as Compound (LVIII)]:

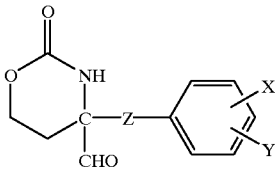

(LVIII)

wherein X, Y and Z are as defined above; which is condensed, in the presence of a base, with a compound of the formula (XLIV) wherein $R^i$ is hydrogen, and subjected to protection/deprotection, if necessary, to give a compound of the formula (LIX) [hereinafter referred to as Compound (LIX)]:

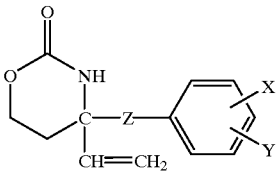

(LIX)

wherein X, Y and Z are as defined above; the double bond in the compound obtained is subjected to hydration and then the cyclic urethane thereof is hydrolyzed, and subjected to protection/deprotection, if necessary, to give a compound of the formula (I-12) [hereinafter referred to as Compound (I-12)]:

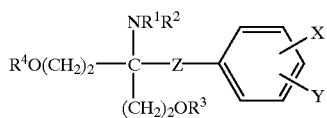
(I-12)

wherein $R^1$, $R^2$, $R^3$, $R^4$, X, Y and Z are as defined above.

Examples of the base to be used in the alcoholysis include sodium methoxide, sodium ethoxide, triethylamine, diisopropylethylamine, 1,8-diazabicyclo[4.3.0]undec-5-ene.

Examples of the organic solvent to be used in the alcoholysis include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

After the alcoholysis is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent to be used in the reduction of ester include diisobutyl aluminum hydride, lithium aluminum hydride, sodium borohydride and lithium borohydride. When the reduction isomer obtained is alcohol, as a method for oxidizing alcohol to aldehyde, Collins oxidation, Jones oxidation, PCC oxidation and Swern oxidation widely employed in the field of organic synthetic chemistry are useful.

Examples of the organic solvent to be used in the reduction include hexane, benzene, toluene, methylene chloride, methanol, ethanol, tert-butyl alcohol, tetrahydrofuran, diethyl ether and ethylene glycol dimethyl ether.

The reduction generally proceeds at a temperature of from −78° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the condensation include sodium methoxide, sodium ethoxide, sodium hydride, potassium hydride, n-butyl lithium, tert-butyl lithium, lithium diisopropylamide, lithium hexamethyldisilazane, diisopropylethylamine and 1,8-diazabicyclo[4.3.0]undec-5-ene.

Examples of the organic solvent to be used in the condensation include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The condensation generally proceeds at a temperature of from −78° C. to 100° C. and a lower or higher temperature than said temperature range may be selected on demand.

The condensation is generally carried out for 30 minutes to 2 days and a longer or shorter reaction period than the indicated period may be selected on demand.

After the condensation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

The two steps reaction comprising hydroboration and then oxidation is especially useful for the hydration.

Examples of the reagent to be used in the hydroboration include diborane and 9-borabicyclo[3.3.1]nonane (9-BBN).

Examples of the organic solvent to be used in the hydroboration include tetrahydrofuran, diethyl ether, ethylene glycol dimethyl ether, benzene, toluene, xylene, dioxane, methylene chloride, chloroform and dichloroethane.

The hydroboration generally proceeds at a temperature of from −78° C. to 50° C. and a lower or higher temperature than said temperature range may be selected on demand.

The hydroboration is generally carried out for 30 minutes to 2 days and a longer or shorter reaction period than the indicated period may be selected on demand.

In the oxidation carried out in after-treatment of hydroboration, a peracid such as hydrogen peroxide is usually used and the reaction is carried out in an aqueous alkaline solution such as sodium hydroxide.

The oxidation generally proceeds at a temperature of from 0° C. to 50° C. and a lower or higher temperature than said temperature range may be selected on demand.

The hydroboration is generally carried out for 30 minutes to 24 hours and a longer or shorter reaction period than the indicated period may be selected on demand.

After the two steps reaction of hydroboration and oxidation is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the hydrolysis include sodium hydroxide, potassium hydroxide, lithium hydroxide and barium hydroxide.

Examples of the organic solvent to be used in the hydrolysis include methanol, ethanol, tert-butyl alcohol, tetrahydrofuran, ethylene glycol dimethyl ether, dimethylformamide and dimethyl sulfoxide, and a mixed solvent thereof with water can be used if necessary.

The hydrolysis generally proceeds at a temperature of from −20° C. to 80° C. and a lower or higher temperature than said temperature range may be selected on demand.

The hydrolysis is generally carried out for 30 minutes to 2 days and a longer or shorter reaction period than the indicated period may be selected on demand.

After the hydrolysis is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method W

The compound of the formula [hereinafter referred to as Compound (LX)]:

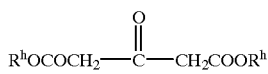

(LX)

wherein $R^h$ is as defined above, is subjected to carbonyl-protection, and the obtained carbonyl-protecting compound is reduced, then protected with a suitable hydroxy protecting reagent such as benzyl halide (benzyl chloride, benzyl bromide or benzyl iodide) and then subjected to carbonyl-deprotection to give the compound (LXI):

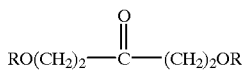

(LXI)

wherein R is a hydroxy protecting group such as benzyl; which is subjected to addition with the compound of the formula [hereinafter referred to as Compound (LXII)]:

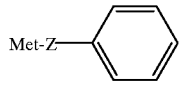

(LXII)

wherein Met and Z are as defined above, to give the compound of the formula [hereinafter referred to as Compound (LXIII)]:

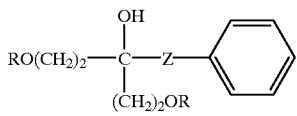

(LXIII)

wherein R and Z are defined above; which is subjected to Ritter reaction and then protection/deprotection, if necessary, to give the compound of the formula [hereinafter referred to as Compound (LXIV)]:

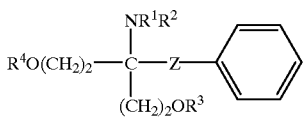

(LXIV)

wherein $R^1$, $R^2$, $R^3$, $R^4$ and Z are as defined above.

The carbonyl protecting reaction of Compound (LX) is carried out by a method known in the field of organic synthetic chemistry. The reaction is, for example, carried out by treating with ethylene glycol in the presence of acid catalyst such as p-toluenesulfonic acid in a solvent such as benzene, toluene, xylene, methylene chloride, chloroform or hexane.

The reaction generally proceeds at a temperature of from 0° C. to the refluxing temperature of the solvent to be used and a lower or higher temperature than said temperature range may be selected on demand.

The reaction is generally carried out for 30 minutes to 2 days and a longer or shorter reaction period than the indicated period may be selected on demand.

After the reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reducing agent in the reduction include metallic reducing reagent such as diborane, sodium borohydride, lithium borohydride or lithium. Aluminum hydride.

Examples of the organic solvent to be used in the reduction include methanol, ethanol, tert-butyl alcohol, tetrahydrofuran, diethyl ether and ethylene glycol dimethyl ether.

The reduction generally proceeds at a temperature of from –100° C. to 80° C. and a lower or higher temperature than said temperature range may be selected on demand.

The reduction is generally carried out for 30 minutes to 10 hours and a longer or shorter reaction period than the indicated period may be selected on demand.

After the reduction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the base to be used in the protection of hydroxy include sodium methoxide, sodium ethoxide, sodium hydride, potassium hydride, lithium diisopropylamide, lithium hexamethyldisilazane, diisopropylethylamine and 1,8-diazabicyclo[4.3.0]undec-5-ene.

Examples of the organic solvent to be used in the protection include methanol, ethanol, tert-butyl alcohol, tetrahydrofuran, diethyl ether, ethylene glycol dimethyl ether, dimethylformamide, dimethyl sulfoxide, benzene, toluene, xylene, dioxane, methylene chloride, chloroform, dichloroethane and acetonitrile.

The protection generally proceeds at a temperature of from –20° C. to 150° C. and a lower or higher temperature than said temperature range may be selected on demand.

The protection is generally carried out for 30 minutes to 2 days and a longer or shorter reaction period than the indicated period may be selected on demand.

After the protection is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the organic solvent to be used in the addition with Compound (LXII) include tetrahydrofuran, diethyl ether, ethylene glycol dimethyl ether, dimethylformamide, dimethyl sulfoxide, benzene, toluene, xylene, dioxane, methylene chloride, chloroform and dichloroethane.

The addition generally proceeds at a temperature of from –20° C. to 100° C. and a lower or higher temperature than said temperature range may be selected on demand.

The addition is generally carried out for 30 minutes to 2 days and a longer or shorter reaction period than the indicated period may be selected on demand.

After the addition is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Examples of the reagent to be used in the Ritter reaction of Compound (LXIII) include hydrogen cyanide, acetonitrile and benzonitrile.

Examples of the organic solvent to be used in the Ritter reaction include acetic acid, tetrahydrofuran, diethyl ether, ethylene glycol dimethyl ether, dimethylformamide, dimethyl sulfoxide, benzene, toluene, xylene, dioxane, methylene chloride, chloroform and dichloroethane.

Examples of the acid catalyst to be used in the Ritter reaction include a strong acid such as sulfuric acid or trifluoroacetic acid.

The Ritter reaction generally proceeds at a temperature of from −20° C. to 80° C. and a lower or higher temperature than said temperature range may be selected on demand.

The Ritter reaction is generally carried out for 30 minutes to 24 hours and a longer or shorter reaction period than the indicated period may be selected on demand.

After the Ritter reaction is carried out under the above-mentioned conditions or after removing the protecting group on demand, the objective compound can be purified by a method known in the field of organic synthetic chemistry, such as solvent extraction, recrystallization, chromatography or a method using an ion exchange resin.

Method X

In Method W, the same method is carried out using the compound of the formula [hereinafter referred to as Compound (LXV)] instead of Compound (LX):

$$W^b\text{—COCH}_2\text{COOR}^h \qquad (LXV)$$

wherein $W^b$ is methyl or ethyl and $R^h$ is as defined above, to give the compound of the formula [hereinafter referred to as Compound (LXVI)]:

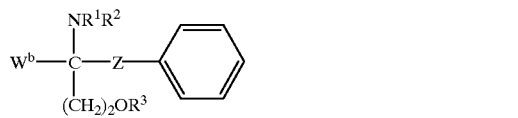

(LXVI)

wherein $W^b$, $R^1$, $R^2$, $R^3$ and Z are as defined above.

Method Y

In Method W and X, the same method is carried out using the Compound (XXII) instead of Compound (LXII), to give the compound of the formula

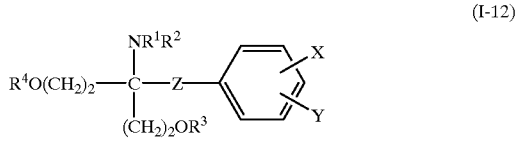

(I-12)

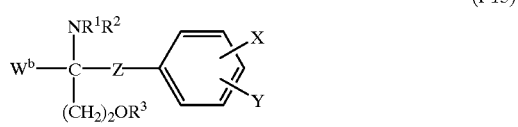

(I-13)

wherein $R^1$, $R^2$, $R^3$, $R^4$, $W^b$, Z, X and Y are as defined above.

The benzene compounds of the present invention, optically isomers thereof and salts thereof can be used for the prevention or treatment of various indications such as immunosuppression in organs or bone marrow transplantation, various autoimmune diseases or various allergy diseases. Namely, the compounds of the present invention have pharmacological activities such as immunosuppressive activity or antimicrobial activity and therefore are useful for the prevention or treatment of resistance to transplantation or transplantation rejection of organs or tissues (such as heart, kidney, liver, lung, bone marrow, cornea, pancreas, intestinum tenue, limb, muscle, nervus, fatty marrow, duodenum, skin or pancreatic islet cell etc., including xenotransplantation), graft-versus-host diseases by bone marrow transplantation, autoimmune diseases such as rheumatoid arthritis, systemic lupus erythematosus, nephrotic syndrome lupus, Hashimoto's thyroiditis, multiple sclerosis, myasthenia gravis, type I diabetes mellitus, type II adult onset diabetes mellitus, uveitis, nephrotic syndrome, steroid-dependent and steroid-resistant nephrosis, palmoplantar pustulosis, allergic encephalomyelitis, glomerulonephritis, etc., and infectious diseases caused by pathogenic microorganisms.

The compounds of the present invention are useful for treating inflammatory, proliferative and hyperproliferative skin diseases and cutaneous manifestations of immunologically-mediated illnesses such as psoriasis, psoriatic arthritis, atopic eczema (atopic dermatitis), contact dermatitis and further eczematous dermatitises, seborrheic dermatitis, lichen planus, pemphigus, bullous pemphigoid, epidermolysis bullosa, urticaria, angioedemas, vasculitides, erythemas, cutaneous eosinophilias, acne, alopecia areata, eosinophilic fasciitis, and atherosclerosis.

More particularly, the compounds of the present invention are useful in hair revitalizing, such as in the treatment of female or male pattern alopecia, or senile alopecia, by providing epilation prevention, hair germination, and/or a promotion of hair generation and hair growth.

The compounds of the present invention are further useful in the treatment of respiratory diseases, for example, sarcoidosis, fibroid lung, idiopathic interstitial pneumonia, and reversible obstructive airways disease, including conditions such as asthma, including bronchial asthma, infantile asthma, allergic asthma, intrinsic asthma, extrinsic asthma and dust asthma, particularly chronic or inveterate asthma (for example late asthma and airway hyperreponsiveness), bronchitis and the like.

The compounds of the present invention may also be useful for treating hepatic injury associated with ischemia.

The compounds of the present invention are also indicated in certain eye diseases such as conjunctivitis, keratoconjunctivitis, keratitis, vernal conjunctivitis, uveitis associated with Behget's disease, herpetic keratitis, conical cornea, dystorphia epithelialis corneae, keratoleukoma, ocular pemphigus, Mooren's ulcer, scleritis, Graves' ophthalmopathy, severe intraocular inflammation and the like.

The compounds of the present invention are also useful for preventing or treating inflammation of mucosa or blood vessels (such as leukotriene $B_4$-mediated diseases, gastric ulcers, vascular damage caused by ischemic diseases and thrombosis, ischemic bowel disease, inflammatory bowel disease (e.g. Crohn's disease and ulcerative colitis) necrotizing enterocolitis), or intestinal lesions associated with thermal burns.

Further, the compounds of the present invention are also useful for treating or preventing renal diseases including interstitial nephritis, Goodpasture's syndrome, hemolytic uremic syndrome and diabetic nephropathy; nervous diseases selected from multiple myositis, Guillain-Barré syndrome, Ménière's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, vitiligo vulgaris, ichthyosis vulgaris, photoallergic sensitivity and cutaneous T cell lymphoma; circulatory diseases including arteriosclerosis, aortitis, polyarteritis nodosa and myocardosis; collagen disease including scleroderma, Wegener's granuloma and Sjögren' syndrome; adiposis; eosinophilic fasciitis; periodontal disease; nephrotic syndrome; hemolytic uremic syndrome; and muscular dystrophy.

Further, the compounds of the present invention are indicated in the treatment of diseases including intestinal inflammations or allergies such as Coeliac disease, proctitis, eosinophilic gastroenteritis, mastocytosis, Crohn's disease or ulcerative colitis; and food related allergic diseases which have symptomatic manifestation remote from the gastrointestinal tract, for example migraine, rhinitis and eczema.

The compounds of the present invention also have liver regenerating activity and/or activity in promoting hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compounds of the present invention are also indicated for use as antimicrobial agents, and thus may be used in the treatment of diseases caused by pathogenic microorganisms and the like.

Further, the compounds of the present invention can be used in the prevention or treatment of malignant rheumatoid arthritis, amyloidosis, fulminant hepatitis, Shy-Drager syndrome, pustular psoriasis, Behget's disease, systemic lupus erythematosus, endocrine opthalmopathy, progressive systemic sclerosis, mixed connective tissue disease, aortitis syndrome, Wegener's gramulomatosis, active chronic hepatitis, Evans syndrome, pollinosis, idiopathic hypoparathyroidism, Addison disease (autoimmune adrenalitis), autoimmune orchitis, autoimmune oophoritis, cold hemagglutinin, paroxysmal cold hemoglobinuria, pernicious anemia, adult T cell leukemia, autoimmune atrophic gastritis, lupoid hepatitis, tubulointerstitial nephritis, membranous nephritis, amyotrophic lateral sclerosis, rheumatic fever, postmyocardial infarction syndrome and sympathetic ophthalmitis.

The compounds of the present invention have antiftngal effect and are useful as a antifungal agent. Also, the compounds protected with a protecting group are useful as intermediates for the synthesis of the compounds having superior pharmacological actions.

When these compounds are used as pharmaceuticals, an effective amount thereof is generally admixed with carrier, excipient, diluent and so on and formulated into powders, capsules, tablets, injections, topical administration preparations or the like for the administration to patients. A lyophilized preparation may be produced by a method known per se.

While the dose of these compounds varies depending on disease, symptom, body weight, sex, age and so on, they may be administered, for example, to an adult daily by 0.01–10 mg (potency) in a single to several times divided doses when suppressing rejection in kidney transplantation.

Moreover, the compounds of the present invention can be used as a suppressant of rejection in organ or bone marrow transplantation in combination with other immunosuppressant(s), steroid(s) (prednisolone, methylprednisolone, dexamethasone, hydrocortisone and the like) or nonsteroidal anti-inflammatory agent. As the other immunosuppressant, preferred is particularly selected from azathiprine, brequinar sodium, deoxyspergualin, mizoribine, mycophenolate 2-morphorinoethyl, cyclosporin, rapamycin, tacrolimus monohydrate, leflunomide and OKT-3.

BEST MODE FOR EMBODYING THE INVENTION

The present invention is hereinafter explained in detail by illustrating examples, to which the present invention is construed not to limited.

WORKING EXAMPLE 1

2-Amino-4-(4-heptyloxyphenyl)-2-methylbutanol hydrochloride (1) Diethyl 2-methyl-2-[2-(4-benzyloxyphenyl)ethyl]malonate Sodium hydride (2.6 g) and diethyl methylmalonate (10.3 g) were added to dimethylformamide (80 ml) and the mixture was stirred at room temperature for 30 minutes. A solution of 2-(4-benzyloxyphenyl)ethyl iodide (20.0 g) in dimethylformamide (30 ml) was dropwise added thereto, and the mixture was stirred at room temperature for an hour. The reaction mixture was poured into ice-water and extracted with ethyl acetate. The ethyl acetate layer was washed with a saturated aqueous brine and dried over anhydrous sodium sulfate. The solvent was distilled away and the residue obtained was purified by silica gel column chromatography (eluent; ethyl acetate:n-hexane=1:9) to give the subject compound (13.7 g) as white crystals, melting at 50–51° C.

Rf value: 0.28 (ethyl acetate:n-hexane=1:9)

$^1$H-NMR (CDCl$_3$) δ: 1.26 (6H, t, J=7.1 Hz), 1.48 (3H, s), 2.13 (2H, m), 2.51 (2H, m), 4.16 (4H, q, J=7.1 Hz), 5.04 (2H, s), 6.90 (2H, d, J=8.5 Hz), 7.10 (2H, d, J=8.5 Hz), 7.32–7.44 (5H, m)

IR (cm$^{-1}$): 2987, 1728, 1173, 743

MS (EI): 384 (M$^+$)

Elemental analysis

| | |
|---|---|
| Calculated | C; 71.85, H; 7.34 |
| Found | C; 71.79, H; 7.39 |

(2) Potassium 2-ethoxycarbonyl-2-methyl-4-(4-benzyloxyphenyl)butanoate

A solution of potassium hydroxide (1.45 g) in ethanol (25 ml) was dropwise added to a solution of diethyl 2-methyl-2-[2-( 4-benzyloxyhpenyl)ethyl]malonate (10.0 g) in ethanol (25 ml) and the mixture was stirred at room temperature for 7 hours. The reaction mixture was ice-cooled and the solvent of the filtrate obtained by filtration was distilled away. The residue obtained was suspended in ether (50 ml) and collected by filtration to give the subject compound (5.01 g) as white crystals, melting at 183–184° C.

Rf value: 0.51 (n-hexane:ethyl acetate:acetic acid= 49:49:2)

$^1$H-NMR (DMSO-d$_6$) δ: 1.13 (3H, t, J=7.3 Hz), 1.15 (3H, s), 1.77 (1H, ddd, J=13.2, 12.7, 4.7 Hz), 1.86 (1H, ddd, J=13.2, 12.7, 4.4 Hz), 2.21 (1H, ddd, J=14.4, 12.7, 4.4 Hz), 2.44 (1H, ddd, J=14.4, 12.7, 4.7 Hz), 3.93 (2H, m), 5.04 (2H, s), 6.88 (2H, d, J=8.3 Hz), 7.03 (2H, d, J=8.3 Hz), 7.30–7.43 (5H, m).

(3) Ethyl 2-methyl-2-methoxycarbonylamino-4-(4-benzyloxyphenyl)butanoate

A solution of ethyl chloroformate (1.38 g) in tetrahydrofuran (25 ml) was dropwise added at −10° C. to a solution of potassium 2-ethoxycarbonyl-2-methyl-4-(4-benzyloxyphenyl)butanoate (5.0 g) in tetrahydrofuran (150 ml) and the mixture was stirred at −10° C. for 40 minutes. A solution of sodium azide (0.98 g) in water (2 ml) was dropwise added thereto and the whole mixture was stirred at −10° C. for 30 minutes. The reaction mixture was poured into ice-water and extracted with dichloromethane. The dichloromethane layer was dried over anhydrous sodium sulfate and the solvent was distilled away. The residue obtained was dissolved in benzene (150 ml) and the solution was refluxed under heating for an hour while stirring. Methanol (150 ml) and p-toluenesulfonic acid monohydrate (50 mg) were added thereto and the mixture was refluxed under heating for 6 hours while stirring. The solvent was distilled away and the residue obtained was purified by silica gel column chromatography (eluent; ethyl acetate:n-hexane=1:4) to give the subject compound (4.22 g) as an oily substance.

Rf value: 0.29 (ethyl acetete:n-hexane=1:4)

$^1$H-NMR(CDCl$_3$) δ: 1.27 (3H, t, J=6.4 Hz), 1.60 (3H, s), 2.07 (1H, m), 2.33 (1H, m), 2.53 (2H, m), 3.65 (3H, s), 4.16 (2H, m), 5.03 (2H, s), 5.68 (1H, br. s), 6.87 (2H, d, J=8.8 Hz), 7.05 (2H, d, J=8.8 Hz), 7.29–7.43 (5H, m)

IR (cm$^{-1}$): 3420, 2984, 1733, 1511, 1241, 1077

MS (EI): 385 (M$^+$).

(4) 4-[2-(4-Benzyloxyphenyl)ethyl]-4-methyl-2-oxazolidinone

Lithium borohydride (0.48 g) was added to a solution of ethyl 2-methyl-2-methoxycarbonylamino-4-(4-benzyloxyphenyl)butanoate (4.22 g) in tetrahydrofuran (110 ml) and the mixture was refluxed under heating for 30 minutes while stirring. 2M hydrochloric acid (11 ml) and water (400 ml) were added thereto under ice-cooling and the mixture was extracted with dichloromethane. The dichloromethane layer was dried over anhydrous sodium sulfate and the solvent was distilled away. The powder obtained was recrystallized from dichloromethane and isopropyl ether to give the subject compound (2.72 g) as a white powder, melting at 165–166° C.

Rf value: 0.19 (ethyl acetate:n-hexane=2:3)

$^1$H-NMR(CDCl$_3$) δ: 1.41 (3H, s), 1.89 (2H, m), 2.62 (2H, m), 4.06 (1H, d, J=8.6 Hz), 4.17 (1H, d, J=8.6 Hz), 4.84 (1H, br. s), 5.05 (2H, s), 6.92 (2H, d, J=8.6 Hz), 7.09 (2H, d, J=8.6 Hz), 7.32–7.44 (5H, m)

IR (cm$^{-1}$): 3231,2965, 1763, 1514, 1255, 1041, 743

MS (EI): 311 (M$^+$).

(5) 4-[2-(4-Hydroxyphenyl)ethyl]-4-methyl-2-oxazolidinone.

A solution of 4-[2-(4-benzyloxyphenyl)ethyl]-4-methyl-2-oxazolidinone (2.72 g) in 10% aqueous 1,4-dioxane (110 ml) was added to a suspension of 10% palladium hydroxide-carbon (0.3 g) in 10% aqueous 1,4-dioxane (40 ml) and the suspension was stirred under a hydrogen atmosphere at room temperature for 12 hours. The reaction mixture was filtered off and the solvent was distilled away. The powder obtained was recrystallized from ethanol and isopropyl ether to give the subject compound (1.50 g) as a white powder, melting at 156–157° C.

Rf value: 0.22 (ethyl acetate:n-hexane=1:1)

$^1$H-NMR (DMSO-d$_6$) δ: 1.23 (3H, s), 1.68 (2H, dd, J=8.7, 8.3 Hz), 2.44 (2H, m), 3.92 (1H, d, J=8.6 Hz), 4.10 (1H, d, J=8.6 Hz), 6.65 (2H, d, J=8.6 Hz), 6.97 (2H, d, J=8.6 Hz), 7.78 (1H, br. s), 9.12 (1H, s)

IR (cm$^{-1}$): 3299, 3117, 1728, 1516, 1038

MS (EI): 221 (M$^+$)

Elemental analysis

| Calculated | C; 65.14, H; 6.83, N; 6.33 |
| Found | C; 65.17, H; 6.98, N; 6.28 |

(6) 4-[2-(4-Heptyloxyphenyl)ethyl]-4-methyl-2-oxazolidinone

A solution of heptyl bromide (0.45 g) in tetrahydrofuran (4 ml) was added to a solution of sodium ethoxide (0.19 g) and 4-[2-(4-hydroxyphenyl)ethyl]-4-methyl-2-oxazolidinone (0.50 g) in ethanol (12 ml) and the mixture was refluxed under heating for 7 hours while stirring. The reaction mixture was concentrated, poured into ice-water and extracted with ethyl acetate. The ethyl acetate layer was washed with water and dried over anhydrous sodium sulfate. The solvent was distilled away and the residue obtained was purified by silica gel column chromatograpgy (eluent; ethyl acetate:n-hexane=2:3) to give the subject compound (0.56 g) as a white powder, melting at 56–59° C.

Rf value: 0.52 (ethyl acetate:n-hexane=1:1)

$^1$H-NMR (CDCl$_3$) δ: 0.89 (3H, t, J=6.9 Hz), 1.26–1.44 (8H, m), 1.40 (3H, s), 1.77 (2H, m), 1.88 (2H, m), 2.62 (2H, m), 3.92 (2H, t, J=6.6 Hz), 4.06 (1H, d, J=8.6 Hz), 4.17 (1H, d, J=8.6 Hz), 5.04 (1H, br. s), 6.82 (2H, d, J=8.7 Hz), 7.07 (2H, d, J=8.7 Hz)

IR (cm$^{-1}$): 3253, 2931, 1733, 1511, 1242, 1038

MS (EI): 319(M$^+$)

Elemental analysis

| Calculated | C; 71.44, H; 9.15, N; 4.38 |
| Found | C; 71.30, H; 9.10, N; 4.35 |

(7) 2-Amino-2-methyl-4-(4-heptyloxyphenyl)butanol hydrochloride

A 5 M aqueous potassium hydroxide solution (55 ml) and tetrahydrofuran (15 ml) were added to a solution of 4-[2-(4-heptyloxyphenyl)ethyl]-4-methyl-2-oxazolidinone (0.49 g) in methanol (40 ml) and the mixture was refluxed under heating for 9 hours while stirring. The reaction mixture was concentrated, poured into ice water and extracted with ethyl acetate. The ethyl acetate layer was washed with a saturated aqueous brine solution and dried over anhydrous sodium sulfate. The solvent was distilled away and the residue obtained was recrystallized from ethanol and ethyl acetate to give the subject compound (0.34 g) as white crystals, melting at 162–163° C.

Rf value: 0.29 (chloroform:methanol=4:1)

$^1$H-NMR (DMSO-d$_6$) δ: 0.86 (3H, t, J=6.8 Hz), 1.18 (3H, s), 1.26–1.38 (8H, m), 1.64–1.78 (4H, m), 2.49 (2H, m), 3.39 (2H, m), 3.90 (2H, t, J=6.6 Hz), 5.51 (1H, t, J=4.9 Hz), 6.83 (2H, d, J=8.5 Hz), 7.09 (2H, d, J=8.5 Hz), 7.77 (3H, br. s)

IR (cm$^{-1}$): 3374, 3025, 2933, 1518, 1242, 1060

MS (EI): 293 (M—HCl)$^{+}$). Elemental analysis

| | |
|---|---|
| Calculated | C; 65.53, H; 9.78, N; 4.25 |
| Found | C; 65.21, H; 9.94, N; 4.18 |

WORKING EXAMPLE 2

2-Amino-2-[3-(4-undecylphenyl)propyl]butane-1,4-diol (1) 2-Diphenylmethyleneamino-γ-butyrolactone A solution of 2-amimo-γ-butyrolactone hydrobromide (5.0 g) and benzophenoneimine (4.6 ml) in methylene chloride was stirred at room temperature overnight. Ammonium bromide was filtered off and the filtrate was concentrated. The residue obtained was purified by silica gel column chromatography (eluent; ethyl acetate:n-hexane=1:3) to give the subject compound (6.98 g) as white crystals, melting at 98–101° C.

Rf value: 0.59 (ethyl acetate:n-hexane=1:1)

$^1$H-NMR(CDCl$_3$) δ: 2.40 (1H, m), 2.61 (1H, m), 4.22 (1H, m), 4.30 (1H, t, J=8.3Hz), 4.56 (1H, dt, J=8.8, 3.4Hz), 7.32–7.65 (10H, m)

IR(cm$^{-1}$): 1775, 1627, 1450

MS(EI): 265(M$^+$)

Elemental analysis

| | |
|---|---|
| Calculated | C; 76.96, H; 5.70, N; 5.28 |
| Found | C; 77.32, H; 5.85, N; 5.22 |

(2) 2-Cinnamyl-2-diphenylmethyleneamino-γ-butyrolactone

To a solution of lithium diisopropylamide in tetrahydrofuran (450 ml) prepared from butyl lithium (1.6M, 59 ml) and diisopropylamine (13.7 ml), a solution of 2-diphenylmethyleneamino-γ-butyrolactone (22.62 g) in tetrahydrofuran (100 ml) was dropwise added at −78° C. under a nitrogen atmosphere. After stirring at −78° C. for 30 minutes, a solution of cinnamyl bromide (13.2 ml) in hexamethylenephosphoric triamidd (178 ml) was dropwise added thereto. The whole mixture was heated to room temperature and stirred at room temperature for 2 hours. The reaction mixture was poured into an aqueous ammonium chloride solution and extracted with ethyl acetate. The ethyl acetate layer was dried over anhydrous sodium sulfate and the solvent was distilled away. The residue obtained was purified by silica gel column chromatography (eluent; ethyl acetate:n-hexane=1:3) to give the subject compound (23.26 g) as white crystals, melting at 138–140° C.

Rf value: 0.39 (ethyl acetete:n-hexane=1:3)

$^1$H-NMR(CDCl$_3$) δ: 2.26 (1H, ddd, J=4.8, 8.3, 13.7Hz), 2.37 (1H, ddd, J=7.3, 8.8, 13.7 Hz), 2.78 (2H, m), 3.90 (1H, ddd, J=8.8, 8.8, 3.9Hz), 4.03 (1H, ddd, J=8.8, 8.8, 8.8 Hz), 6.30 (1H, dt, J=15.6, 7.8 Hz), 6.48 (1H, d, J=15.6 Hz), 7.20–7.63 (15H, m)

IR(cm$^{-1}$): 1754, 1626

MS(EI): 381 (M$^+$)

Elemental analysis

| | |
|---|---|
| Calculated | C; 81.86, H; 6.08, N; 3.67 |
| Found | C; 82.00, H; 6.03, N; 3.65 |

(3) 2-Acetamido-2-cinnamyl-γ-butyrolactone

2M Hydrochloric acid (26 ml) was added to a solution of 2-cinnamyl-2-diphenylmethyleneamino-γ-butyrolactone (13.51 g) in tetrahydrofuran (100 ml) and the mixture was left standing at room temperature for an hour. The organic solvent was distilled away and the residue was diluted with water (100 ml). Ethyl acetate (100 ml), potassium hydrogencarbonate (14.19 g) and acetyl chloride (3.8 ml) were added thereto, and the mixture was vigorously stirred at room temperature for an hour. After the organic layer was separated, the aqueous layer was extracted with ethyl acetate (100 ml) and the extract was combined with the foregoing organic layer. The combined organic layer was dried over anhydrous sodium sulfate and the solvent was distilled away. The crude crystals obtained were recrystallized form ethyl acetate and n-hexane (1:6) to give the subject compound (8.20 g) as white crystals, melting at 132–134° C.

Rf value: 0.41 (ethyl acetate)

$^1$H-NMR(CDCl$_3$) δ: 2.00 (3H, s), 2.57 (1H, ddd, J=2.9, 7.8, 10.7 Hz), 2.73 (3H, m), 4.26 (1H, ddd, J=8.6, 8.6, 8.6 Hz), 4.52 (1H, ddd, J=2.9, 9.3, 9.3 Hz), 5.93 (1H, br.s), 6.14 (1H, ddd, J=7.8, 7.8, 15.6 Hz), 6.60 (1H, d, J=15.6 Hz), 7.31 (5H, m)

IR(cm$^{-1}$): 3322, 1761, 1671, 1541

MS(EI): 259(M$^+$)

Elemental analysis

| | |
|---|---|
| Calculated | C; 69.48, H; 6.61, N; 5.40 |
| Found | C; 69.51, H; 6.62, N; 5.39 |

(4) 2-Acetamido-2-(3-phenylpropyl)-γ-butyrolactone

2-Acetamido-2-cinnamyl-γ-butyrolactone (7.50 g) was dissolved in ethanol (100 ml) and the mixture was subjected to catalytic reduction in the presence of 10% palladium-carbon (708 mg) under a hydrogen pressure of 10 atom. The catalyst was filtered off and the solvent was distilled away. The residue obtained was purified by silica gel column chromatography (eluent; ethyl acetate:n-hexane=2:1) to give the subject compound (7.56 g) as a colorless oily substance.

Rf value: 0.38 (ethyl acetate)

$^1$H-NMR(CDCl$_3$) δ: 1.73 (3H, m), 1.95 (1H, m), 1.97 (3H, s), 2.47 (1H, ddd, J=2.9, 7.8, 13.1 Hz), 2.65 (3H, m), 4.21 (1H, ddd, J=7.4, 9.2, 9.2 Hz), 4.47 (1H, ddd, J=2.9, 9.2, 9.2 Hz), 5.86 (1H, br.s), 7.20 (5H, m)

IR(cm$^{-1}$): 3321,3026, 1771, 1656

MS(EI): 261(M$^+$)

(5) 3-Acetamido-3-acetoxymethyl-6-phenylhexyl acetate

A solution of 2-acetamido-2-(3-phenylpropyl)-γ-butyrolactone (8.27 g) in tetrahydrofuran (20 ml) was dropwise added at 0° C. to a solution of lithium borohydride (1.4 g) in tetrahydrofuran (100 ml). After stirring at 50° C. for 2 hours, the reaction was stopped with 2M hydrochloric acid. The mixture was diluted with water (200 ml) and extracted with ethyl acetate. The ethyl acetate layer was dried over anhydrous sodium sulfate and the solvent was distilled away. The residue obtained was dissolved in pyridine (30 ml) and acetic anhydride (20 ml) and the mixture was left standing at room temperature overnight. The resulting mixture was poured into ice-water (200 ml) and extracted with ethyl acetate. The ethyl acetate layer was washed with 2M hydrochloric acid and a saturated brine, dried over anhydrous sodium sulfate and the solvent was distilled away. The residue obtained was purified by silica gel column chromatography (eluent; ethyl acetate:n-hexane=3:1) to give the subject compound (8.25 g) as a colorless oily substance.

Rf value: 0.60 (ethyl acetate)

$^1$H-NMR(CDCl$_3$) δ: 1.60 (2H, m), 1.80 (2H, m), 1.94 (3H, s), 2.02 (3H, s), 2.03 (3H, s), 2.16 (2H, m), 4.11 (2H, t, J=6.8 Hz), 4.24 (2H, 2d, J=11.2 Hz), 5.52 (1H, br.s), 7.15–7.30 (5H, m)

IR(cm$^{-1}$): 3308, 1741, 1654, 1604

MS(EI): 349(M$^+$).

(6) 3-Acetamido-3-acetoxymethyl-6-(4-undecanoylphenyl) hexyl acetate

To a suspension of aluminum chloride (4.58 g) in dichloroethane (30 ml), a solution of undecanoyl chloride (3.52 g) in dichloroethane (15 ml) was dropwise added over 10 minutes. After stirring at room temperature for 30 minutes, a solution of 3-acetamido-3-acetoxymethyl-6-phenylhexyl acetate (2.0 g) in dichloroethane (15 ml) was dropwise added thereto. After stirring at room temperature for 10 minutes, the reaction mixture was poured into water and extracted with chloroform. The chloroform layer was dried over anhydrous sodium sulfate and the solvent was distilled away. The residue obtained was purified by silica gel column chromatography (eluent; ethyl acetate:n-hexane=1:1, and then 3:1) to give the subject compound (2.60 g) as a colorless oily substance.

Rf value: 0.67 (ethyl acetate)

$^1$H-NMR(CDCl$_3$) δ: 0.88 (3H, t, J=6.8 Hz), 1.26 (16H, m), 1.71 (2H, m), 1.82 (2H, m), 1.95 (3H, s), 2.03 (3H, s), 2.04 (3H, s), 2.12 (2H, t, J=6.8 Hz), 2.66 (2H, m), 2.93 (2H, t, J=6.7 Hz), 4.11 (2H, d, J=6.4 Hz), 4.24 (2H, s), 5.58 (1H, br.s), 7.25 (2H, d, J=7.8 Hz), 7.88 (2H, d, J=7.8 Hz)

IR(cm$^{-1}$): 3323, 2927, 2855, 1741, 1680

MS(EI): 517(M$^+$).

(7) 3-Acetamido-3-acetoxymethyl-6-(4-undecylphenyl) hexyl acetate

To a solution of 3- acetamido-3-acetoxymethyl-6-(4-undecanoylphenyl)hexyl acetate (505.4 mg) in trifluoroacetic acid (1.0 ml), triethylsilane (0.31 ml) was dropwise added at 0° C. and the mixture was stirred at room temperature for 2 hours. The reaction mixture was poured into a saturated potassium hydrogencarbonate solution (50 ml) and extracted with chloroform. The chloroform layer was dried over anhydrous sodium sulfate and the solvent was distilled away. The residue obtained was purified by silica gel column chromatography (eluent; ethyl acetate:n-hexane=1:1) to give the subject compound (294.8 mg) as a colorless oily substance.

Rf value: 0.28 (ethyl acetate:n-hexane=1:1)

$^1$H-NMR(CDCl$_3$) δ: 0.88 (3H, t, J=6.6 Hz), 1.28 (18H, m), 1.56 (4H, m), 1.78 (2H, m), 1.94 (3H, s), 2.02 (3H, s), 2.03 (3H, s), 2.12 (2H, m), 2.56 (4H, m), 4.10 (2H, t, J=6.8 Hz), 4.25 (2H, m), 5.48 (1H, s), 7.06 (1H, d, J=7.8 Hz), 7.09 (1H, d, J=7.8 Hz)

IR(cm$^{-1}$): 3307, 2926, 2855, 1743, 1658

MS(EI): 503(M$^+$).

(8) 2-Amino-2-[3-(4-undecylphenyl)propyl]butane-1,4-diol

3-Acetamido-3-acetoxymethyl-6-(4-undecylphenyl) hexyl acetate (1.70 g) and lithium hydroxide monohydrate (1.42 g) were dissolved in methanol (17 ml) and water (17 ml), and the mixture was refluxed under heating for 3 hours while stirring. The reaction mixture was diluted with water (100 ml) and extracted with ethyl acetate. The ethyl acetate layer was dried over anhydrous sodium sulfate and the solvent was distilled away. The crude crystals obtained were recrystallized from ether-hexane-ethyl acetate (2:2:1) to give the subject compound (330 mg) as white crystals, melting at 73–76° C.

$^1$H-NMR(CDCl$_3$) δ: 0.88 (3H, t, J=6.6 Hz), 1.25, 1.30 (20H, 2br.s), 1.57 (8H, m), 2.57 (4H, m), 3.36 (1H, d, J=10.8 Hz), 3.45 (1H, d, J=10.8 Hz), 3.73 (1H, m), 3.81 (1H, m), 7.08 (4H, br.s)

IR(cm$^{-1}$): 3315, 2923, 2852, 1516

MS(EI): 377(M$^+$)

Elemental analysis

| Calculated | C; 76.34, H; 11.48, N; 3.71 |
| Found | C; 76.07, H; 11.54, N; 3.60 |

WORKING EXAMPLE 3

2-Amino-2-[3-(4-nonylphenyl)propyl]butane-1,4-diol

The subject compound, melting at 71–73° C., was produced in the same manner as working example 2 using nonanoyl chloride instead of undecanoyl chloride in working example 2 (6).

$^1$H-DNMR(CDCl$_3$) δ: 0.88 (3H, t, J=6.8 Hz), 1.26, 1.30 (14H, 2br.s), 1.57 (10H, m), 2.57 (2H, t, J=8.1 Hz), 2.58 (2H, t, J=8.1 Hz), 3.36 (1H, d, J=10.7 Hz), 3.45 (1H, d, J=10.7 Hz), 3.73 (1H, m), 3.82 (1H, m), 7.07 (2H, d, J=8.8 Hz), 7.10 (2H, d, J=8.8 Hz)

MS(EI): 350[(M+1)$^+$];

Elemental analysis

| Calculated | C; 75.59, H; 11.25, N; 4.01 |
| Found | C; 75.43, H; 11.25; N; 3.93 |

WORKING EXAMPLE 4

2-Amino-2-[3-(4-heptylphenyl)propyl]butane-1,4-diol

The subject compound, melting at 68–71° C., was produced in the same manner as working example 2 using heptanoyl chloride instead of undecanoyl chloride in working example 2 (6).

$^1$H-NMR(CDCl$_3$) δ: 0.88 (3H, t, J=6.8 Hz), 1.29 (10H, m), 1.59 (10H, m), 2.57 (2H, t, J=8.0 Hz), 2.58 (2H, t, J=8.0 Hz), 3.36 (1H, d, J=10.7 Hz), 3.45 (1H, d, J=10.7 Hz), 3.73 (1H, m), 3.81 (1H, m), 7.07 (2H, d, J=9.4 Hz), 7.10 (2H, d, J=9.4 Hz)

MS(EI): 321(M$^+$)

Elemental analysis

| Calculated | C; 74.72, H; 10.97, N; 4.36 |
| Found | C; 74.71, H; 10.97, N; 4.22 |

WORKING EXAMPLE 5

3-Amino-3-[2-(4-octylphenyl)ethyl]hexane-1,6-diol (1) 8-Hydroxy-8-(2-phenylethyl)-1,4-dioxaspiro[4.5]decane To a solution of phenylethyl magnesium bromide in tetrahydrofuran (250 ml) prepared from phenylethyl bromide (17.3 ml) and magnesium (3.0 g), a solution of 1,4-cyclohexadione monoethylene ketal (15.2 g) in tetrahydrofuran (30 ml) was dropwise added at room temperature over 20 minutes under a nitrogen atmosphere. Moreover, the mixture was stirred at room temperature for 30 minutes and a saturated aqueous ammonium chloride solution (20 ml) was added to the reaction solution. The oily layer was separated and the solvent was distilled away. The residue obtained was dissolved in ethyl acetate, the ethyl acetate layer was washed with water and a saturated brine and dried anhydrous over magnesium sulfate. The solvent was distilled away and the residue obtained was purified by silica gel chromatography (eluent; ethyl acetate:n-hexane=1:3) to give 1/10 hydrate of the subject compound (12.8 g) as white crystals, melting at 109–110° C.

$^1$H-NMR(CDCl$_3$) δ: 1.12 (1H, s), 1.57–1.67 (2H, m), 1.69–1.76 (2H, m), 1.73–1.83 (4H, m), 1.86–1.96 (2H, m), 2.67–2.74 (2H, m), 3.92–4.00 (4H, m), 7.25–7.35 (5H, m)

IR(cm$^{-1}$): 3472, 2948, 2888, 1491, 1454

MS(EI): 262(M$^+$)

Elemental analysis

| Calculated | C; 72.75, H; 8.47 |
|---|---|
| Found | C; 72.70, H; 8.47 |

(2) 4-Acetamido-4-(2-phenylethyl)cyclohexan-1-one

To a solution of 8-hydroxy-8-(2-phenylethyl)-1,4-dioxaspiro[4.5]decane (12.8 g) in acetonitrile (200 ml), a concentrated sulfuric acid (5.7 ml) was dropwise added under ice-cooling over 3 minutes. The reaction mixture was left standing at room temperature for 2 days, poured into a saturated aqueous sodium hydrogencarbonate solution under ice-cooling and extracted with ethyl acetate. The ethyl acetate layer was washed with water and a saturated brine and dried over anhydrous magnesium sulfate. The solvent was distilled away under reduced pressure to give 8-acetamido-8-(2-phenylethyl)-1,4-dioxaspiro[4.5]decane as a crude product. The crude product was dissolved in tetrahydrofuran (140 ml) without purifying and thereto was added a 0.1N aqueous hydrochloric acid solution (30 ml) at room temperature and the mixture was allowed to stand overnight. The mixture was carefully poured into a ice-cooled saturated aqueous sodium hydrogen-carbonate solution and extracted with ethyl acetate. The ethyl acetate layer was washed with water and a saturated brine, dried over anhydrous magnesium sulfate and the solvent was distilled away to give crude crystals. The crystals were recrystallized from a mixed solvent (1:1) of 1,2-dimethoxyethane-diisopropyl ether to give 1/5 hydrate of the subject compound (5.1 g) as white crystals, melting at 140–143° C.

$^1$H-NMR(CDCl$_3$) δ: 1.82–1.92 (2H, m), 1.97 (3H, s), 2.19 (2H, dd, J=7.8, 8.8 Hz), 2.29–2.38 (2H, m), 2.40–2.59 (4H, m), 2.63 (2H, dd, J=7.8, 8.8 Hz), 5.27 (1H, s), 7.15–7.34 (5H, m)

IR(cm$^{-1}$): 3282, 3082, 2928, 1715, 1648, 1560, 1457, 697

MS(EI): 259(M$^+$)

Elemental analysis

| Calculated | C; 73.08, H; 8.20, N; 5.33 |
|---|---|
| Found | C; 73.31, H; 8.21, N; 5.13 |

(3) 4-Acetamido-4-(2-phenylethyl)-6-hexanolide

To a solution of 4-acetamido-4-(2-phenylethyl)cyclohexan-1-one (4.3 g) in methylene chloride (60 ml), metachloroperbenzoic acid (3.4 g) and potassium hydrogencarbonate (2.0 g) were added at room temperature and the mixture was refluxed under heating for 18 hours. After cooling, a 5% aqueous sodium thiosulfate solution (5.0 ml) was added thereto to reduce an excess amount of metachloroperbenzoic acid. The methylene chloride layer and the aqueous layer was separated and the aqueous layer was extracted with chloroform. The oily layers were combined, washed with water and a saturated brine and dried over anhydrous magnesium sulfate. The solvent was distilled away and the residue obtained was purified by silica gel chromatography (eluent; chloroform-methanol=10:1) to give crude crystals. The crystals were recrystallized from ethyl acetate to give 1/10 hydrate of the subject compound (2.7 g) as white crystals, melting at 165–167° C.

$^1$H-NMR(CDCl$_3$) δ: 1.76 (1H, t, J=13.2 Hz), 1.87 (1H, dd, J=16.1, 10.2 Hz), 1.96 (3H, s), 2.07–2.12 (1H, m), 2.17–2.24 (1H, m), 2.38 (1H, dd, J=15.1, 8.3 Hz), 2.56 (4H, t, J=8.3 Hz), 2.67 (1H, dd, J=15.1, 5.8 Hz), 2.78 (1H, t, J=13.2 Hz), 4.18 (1H, ddd, J=13.6, 6.3, 2.0 Hz), 4.33 (1H, dd, J=13.6, 9.7 Hz), 5.02 (1H, s), 7.14–7.32 (5H, m)

IR(cm$^{-1}$): 3294, 1731, 1648, 1560, 1452, 1294, 1182, 699

MS(EI): 276(M$^+$+1)

Elemental analysis

| Calculated | C; 69.34, H; 7.71, N; 5.05 |
|---|---|
| Found | C; 69.05, H; 7.74, N; 4.98 |

(4) 3-Acetamido-6-acetoxy-3-(2-phenylethyl)hexyl acetate

To a solution of lithium borohydride (220 mg) in tetrahydrofuran (100 ml), under a nitrogen atmosphere, a solution of 4-acetamido-4-(2-phenylethyl)-6-hexanolide (1.4 g) in tetrahydrofuran (30 ml) was dropwise added over 10 minutes and the mixture was further refluxed under heating for 1.5 hours. After cooling, the reaction mixture was neutralized with a saturated aqueous ammonium chloride solution and the solvent was distilled away under reduced pressure. The residue obtained was dissolved in ethyl acetate and the mixture was washed with water and a saturated brine. The mixture was dried over anhydrous magnesium sulfate and the solvent was distilled away to give 3-acetamido-3-(2-phenylethyl)hexane-1,6-diol as a crude product. The product was dissolved in pyridine (20 ml) without purifying, and acetic anhydride (10 ml) was added to the mixture at room temperature. The whole mixture was allowed to stand overnight. The solvent was distilled away under reduced pressure and the residue obtained was purified by silica gel chromatography (eluent; chloroform-ethyl acetate=2:1) to give the subject compound (0.50 g) as a colorless oily substance.

$^1$H-NMR(CDCl$_3$) δ: 1.59–1.75 (4H, m), 1.77–1.82 (1H, m), 1.88–1.96 (1H, m), 1.94 (3H, s), 2.05 (3H, s), 2.06 (3H, s), 2.16 (2H, t, J=6.8 Hz), 2.56 (2H, t, J=8.8 Hz), 4.08 (2H, t, J=6.3 Hz), 4.14 (2H, t, J=6.8 Hz), 7.15–7.30 (5H, m)

IR(cm$^{-1}$): 3308, 2958, 1733, 1652, 1553, 1456, 1240, 1035, 702

MS(EI): 363(M$^+$).

(5) 3-Acetamido-6-acetoxy-3-[2-(4-octanoylphenyl)ethyl]hexyl acetate

To a suspension of anhydrous aluminum chloride (1.4 g) in 1,2-dichloroetane (20 ml), octanoyl chloride was carefully added at room temperature and the suspension was stirred until anhydrous aluminum chloride was entirely dissolved. To the reaction solution, a solution of 3-acetamido-6-acetoxy-3-(2-phenylethyl)hexyl acetate (780 mg) in 1,2-dichloroethane (10 ml) was dropwise added at room temperature over 10 minutes. The reaction temperature raised to 70° C. and the mixture was stirred for 30 minutes. After cooling, the reaction solution was poured into ice-water and extracted with chloroform. The chloroform layer was washed with water and a saturated brine, dried over anhydrous magnesium sulfate and the solvent was distilled away. The residue obtained was purified by silica gel chromatography (eluent; hexane-ethyl acetate=1:1) to give the subject compound (780 mg) as a yellowish oily substance.

$^1$H-NMR(CDCl$_3$) δ: 0.88 (3H, t, J=6.8 Hz), 1.22–1.42 (10H, m), 1.60–2.23 (8H, m), 1.94 (3H, s), 2.05 (3H, s), 2.06 (3H, s), 2.61 (2H, t, J=7.8 Hz), 2.94 (2H, t, J=6.9 Hz), 5.52 (1H, s), 7.26 (2H, d, J=7.9 Hz), 7.88 (2H, d, J=7.9 Hz)

IR(cm$^{-1}$): 3321, 2931, 2857, 1738, 1683, 1652, 1538, 1239, 1036

MS(EI): 489 (M$^+$).

(6) 3-Acetamido-6-acetoxy-3-[2-(4-octylphenyl)ethyl]hexyl acetate

To a solution of 3-acetamido-6-acetoxy-3-[2-(4-octanoylphenyl)ethyl]hexyl acetate (720 mg) in triiluoroacetic acid (15 ml), triethylsilane (0.53 ml) was added at room temperature. After stirring for an hour, the reaction solution was poured into ice-water and potassium carbonate was carefully added to the mixture to neutralize. The mixture was extracted with ethyl acetate and the extract was washed with water and a saturated brine and dried over anhydrous magnesium sulfate. The solvent was distilled away and the residue obtained was purified by silica gel chromatography (eluent; hexane-ethyl acetate=1:1) to give the subject compound (450 mg) as a colorless oily substance.

$^1$H-NMR(CDCl$_3$) δ: 0.88 (3H, t, J=6.8 Hz), 1.22–1.36 (10H, m), 1.53–1.68 (4H, m), 1.72–1.80 (1H, m), 1.82–1.97 (2H, m), 1.90 (3H, s), 2.04 (3H, s), 2.06 (3H, s), 2.17 (2H, t, J=6.8 Hz), 2.45–2.60 (4H, m), 4.07 (2H, t, J=604 Hz), 4.14 (2H, t, J=6.8 Hz), 5.14 (1H, s), 7.09 (4H, s)

IR(cm$^{-1}$): 3313, 2927, 2855, 1733, 1661, 1557, 1456, 1367, 1240, 1037

MS(EI): 475(M$^+$).

(7) 3-Amino-3-[2-(4-octylphenyl)ethyl]hexane-1,6-diol

To a solution of 3-acetamido-6-acetoxy-3-[2-(4-octylphenyl)ethyl]hexyl acetate (400 mg) in methanol-water (1:1) (12 ml), lithium hydroxide monohydrate (360 mg) was added at room temperature and the mixture was refluxed under heating for 4 hours. After cooling, the mixture was neutralized with ammonium chloride and the solvent was distilled away under reduced pressure. The residue obtained was extracted with chloroform, the extract was washed with water and a saturated brine and dried over anhydrous magnesium sulfate. The solvent was distilled away to give the subject compound (290 mg) as a yellowish oily substance.

$^1$H-NMR(CDCl$_3$) δ: 0.88 (3H, t, J=6.8 Hz), 1.36–1.98 (12H, m), 1.50–1.85 (8H, m), 1.75 (2H, t, J=4.9 Hz), 2.44–2.64 (4H, m), 3.64 (2H, t, J=5.3 Hz), 3.85 (2H, t, J=5.9 Hz), 7.09 (4H, s)

IR(cm$^{-1}$): 3348, 2926, 2855, 2854, 1457, 1057

MS(EI): 349(M$^+$).

WORKING EXAMPLE 6

2-Amino-4-(4-octylphenyl)butanol hydrochloride (1) 2-(4-Octylphenyl)ethyl iodide To a solution of 2-(4-octylphenyl)ethanol (25 g) in ether (200 ml)-acetonitrile (100 ml), imidazole (11 g) and triphenylphosphine (36 g) were added and the mixture was stirred at 0° C. for an hour. Iodine (38 g) was added to the solution and the whole mixture was stirred at 0° C. for 2 hours. Silica gel was added to the reaction solution and the mixture was filtered off. The precipitate was washed with a mixed solution of hexane-ethyl acetate (2:1). The filtrate and the solvent employed at washing were combined and concentrated. The residue was purified by silica gel chromatography (eluent; hexane-ethyl acetate=2:1) to give the subject compound (37 g).

Rf value: 0.85 (hexane-ethyl acetate=4:1)

MS: 344(M$^+$)

$^1$H-NMR(400MHz, CDCl$_3$) δ: 0.88 (3H, t, J=8 Hz), 1.10–1.40 (10H, m), 1.50–1.65 (2H, m), 2.57 (2H, t, J=8 Hz), 3.14 (2H, t, J=8 Hz), 3.33 (2H, t, J=8 Hz), 7.09 (2H, d, J=8 Hz), 7.13 (2H, d, J=8 Hz);

(2) Diethyl 2-acetamido-2-[2-(4-octylphenyl)ethyl] malonate

To a suspension of sodium hydride (6 g) in dimethylformamide (100 ml), a solution of ethyl acetamidomalonate (33 g) in dimethylformamide (100 ml) was added under ice-cooling and the mixture was stirred at room temperature for 2 hours. A solution of 2-(4-octylphenyl)ethyl iodide (37 g) in dimethyl-formamide (100 ml) was added to the mixture under ice-cooling. The mixture was stirred for 2 hours at the same temperature and left standing overnight. The resultant mixture was poured into water and extracted with ethyl acetate. The extract was washed With a saturated brine and dried over magnesium sulfate. The solvent was distilled away under reduced pressure and the residue was purified by silica gel chromatography (eluent; hexane-ethyl acetate= 3:1) to give the subject compound (25 g).

Rf value: 0.40 (hexane-ethyl acetate=2:1)

$^1$H-NMR(400 MHz, CDCl$_3$) δ: 0.88 (3H, t, J=8 Hz), 1.20–1.30 (10H, m), 1.24 (6H, t, J=8 Hz), 1.50–1.62 (2H, m), 1.97 (3H, s), 2.45 (2H, dd, J=12, 8 Hz), 2.54 (2H, t, J=8 Hz), 2.68 (2H, dd, J=12, 8 Hz), 4.14–4.26 (4H, m), 6.75 (1H, s), 7.05 (2H, d, J=8 Hz), 7.08 (2H, d, J=8 Hz);

(3) 2-Amino-4-(4-octylphenyl)butanoic acid hydrochloride

Diethyl 2-acetamido-2-[2-(4-octylphenyl)ethyl]malonate (20 g) was added to a 5N aqueous hydrochloric acid solution (350 ml) and the mixture was refluxed under heating for 6.5 hours. Ethanol (45 ml) was added to the mixture and the whole mixture was further refluxed under heating for 1.5 hours. The reaction mixture was concentrated under reduced pressure to give the subject compound (20 g). MS: 292(M$^+$).

$^1$H-NMR(400 MHz, DMSO-d$_6$) δ: 0.84 (3H, t, J=8 Hz), 1.17–1.32 (10H, m), 1.46–1.58 (2H, m), 1.96–2.11 (2H, m), 2.49 (2H, t, J=4 Hz), 2.48–2.62 (1H, m), 2.63–2.76 (1H, m), 3.83–3.94 (1H, m), 7.06–7.12 (4H, m), 8.33–8.44 (2H, br.s), 8.48–8.58 (1H, br.s);

(4) Methyl 2-amino-4-(4-octylphenyl)butyrate hydrochloride

To a solution of 2-Amino-4-(4-octylphenyl)butanoic acid hydrochloride (20 g) in methanol (500 ml), thionyl chloride (7.2 ml) was added under ice-cooling and the mixture was left standing overnight. The reaction mixture was concentrated under reduced pressure to give the subject compound (16 g). MS: 305(M$^+$).

$^1$H-NMR(400 MHz, DMSO-d$_6$) δ: 0.84 (3H, t, J=8 Hz), 1.14–1.31 (10H, m), 1.45–1.57 (2H, m), 1.97–2.10 (2H, m), 2.49 (2H, t, J=4 Hz), 2.49–2.63 (1H, m), 2.63–2.74 (1H, m), 3.73 (3H, s), 3.94–4.06 (1H, m), 7.10 (4H, s), 8.43–8.62 (3H, br.s);

(5) Methyl 2-acetamido-4-(4-octylphenyl)butyrate

To a solution of methyl 2-amino-4-(4-octylphenyl) butyrate hydrochloride (16 g) in methylene chloride (300 ml), triethylamine (16 ml) and acetyl chloride (3.8 ml) were added and the mixture was stirred at room temperature for an hour. Then, methylene chloride (500 ml) was further added to the mixture, the whole mixture was washed with a dilute hydrochloric acid, an aqueous sodium hydrogencarbonate solution and a saturated brine in order and dried over magnesium sulfate. The solvent was distilled away under reduced pressure and the residue was purified by silica gel chromatography (eluent; hexane-ethyl acetate=1:2) to give the subject compound (11 g). MS: 348($M^+$+1).

$^1$H-NMR(400 MHz, CDCl$_3$) δ: 0.88 (3H, t, J=8 Hz), 1.19–1.36 (10H, m), 1.48–1.62 (2H, m), 2.02 (3H, s), 1.94–2.06 (lH, m), 2.13–2.23 (1H, m), 2.56 (2H, t, J=8 Hz), 2.47–2.70 (2H, m), 3.72 (3H, s), 4.63–4.72 (lH, m), 5.87–5.98 (1H, m), 7.07 (2H, d, J=8 Hz), 7.09 (2H, d, J=8 Hz);

(6) 2-Acetamido-4-(4-octylphenyl)butanol

To a suspension of lithium abluminum hydride (1.2 g) in tetrahydrofuran (100 ml), a solution of methyl 2-acetamido-4-(4-octylphenyl)butyrate (11 g) in tetrahydrofuran (200 ml) was added and the suspension was stirred at room temperature for 30 minutes. An aqueous tetrahydrofuran (70%, 10 ml) was added to the solution and the mixture was left standing overnight. Magnesium sulfate was added to the mixture, the precipitate was filtered off and the solvent was distilled away under reduced pressure. The residue was dissolved in ethyl acetate, the solution was washed with a dilute hydrochloric acid, an aqueous sodium hydrogencarbonate solution and a saturated brine in order and dried over sodium sulfate. The solvent was distilled away under reduced pressure to give the subject compound (6.6 g). MS: 319($M^+$).

$^1$H-NMR(400 MHz, CDCl$_3$) δ: 0.88 (3H, t, J=8 Hz), 1.20–1.38 (10H, m), 1.52–1.62 (2H, m), 1.75–1.96 (2H, m), 1.96 (3H, s), 2.48 (1H, t, J=8 Hz), 2.56 (2H, t, J=8 Hz), 2.64 (2H, t, J=8 Hz), 3.58–3.64 (1H, m), 3.69–3.74 (1H, m), 3.92–4.03 (1H, m), 5.46–5.58 (1H, m), 7.08 (2H, d, J=8 Hz), 7.11 (2H, d, J=8 Hz);

(7) 2-Amino-4-(4-octylphenyl)butanol hydrochloride

Methyl 2-amino-4-(4-octylphenyl)butyrate hydrochloride (1.0 g) obtained in aforementioned (5) was added to an aqueous ammonia solution (20 ml), and the mixture was extracted with ethyl acetate. The extract was washed with water and a saturated brine, dried over sodium sulfate and the solvent was distilled away under reduced pressure. A solution of the obtained residue in tetrahydrofuran (20 ml) was added to a suspension of lithium aluminum hydride (0.35 g) in tetrahydrofuran (10 ml) under ice-cooling and the mixture was stirred at room temperature for an hour. An aqueous tetrahydrofuran (80%, 10 ml) was added to the mixture and the whole mixture was left standing overnight. Celite was added thereto, the precipitate was filtered off and the solvent was distilled away under reduced pressure. The residue was dissolved in ethyl acetate, and the solution was washed with water and a saturated brine and dried over magnesium sulfate. The solvent was distilled away under reduced pressure. Thereto was added a solution of 26% hydrochloric acid in ethanol to crystallize and the crystals were recrystallized from methanol-ethyl acetate to give the subject compound (0.43 g), melting at 96–97° C. MS: 277($M^+$).

$^1$H-NMR(400 MHz, CDCl$_3$) δ: 0.84 (3H, t, J=8 Hz), 1.18–1.32 (10H, m), 1.45–1.58 (2H, m), 1.70–1.85 (2H, m), 2.45–2.55 (2H, m), 2.60 (2H, t, J=8 Hz), 3.02 (1H, br.s), 3.40–3.48 (1H, m), 3.56–3.64 (1H, m), 5.30 (1H, t, J=8 Hz), 7.10 (4H, s), 7.85 (3H, br.s)

Elemental analysis

| | |
|---|---|
| Calculated | C; 68.87, H; 10.28, N; 4.46 |
| Found | C; 68.58, H; 10.34, N; 4.48 |

IR(KBr): 3331, 3012, 2924, 2853, 1614, 1515, 1498 (cm$^{-1}$)

Working example 7:2-Methoxycarbonylamino-2-[2-(4-octylphenyl)ethyl]-butane1,4-diol (1) Diethyl 2-(2-tert-butyldiphenylsilyloxyethyl)-2-(2-phenylethyl)malonate Sodium hydride (60%, 2.13 g) and diethyl 2-(2-tert-butyldiphenylsilyloxyethyl)malonate (13.40 g) were added to dimethylformamide (70 ml) and the mixture was stirred at room temperature for 30 minutes. Thereto was dropwise added a solution of 2-phenylethyl iodide (20.81 g) in dimethylformamide (20 ml) and the whole mixture was stirred at room temperature for 5 hours. The reaction mixture was poured into ice-water and extracted with ethyl acetate. The ethyl acetate layer was washed with a saturated brine and dried over anhydrous sodium sulfate. The solvent was distilled away and the residue obtained was purified by silica gel column chromatography to give the subject compound (18.70 g) as a colorless oily substance.

Rf value: 0.46 (ethyl acetate:hexane=1:5)

$^1$H-NMR(CDCl$_3$) δ: 1.04 (9H, s), 1.11 (6H, t, J=7.3 Hz), 2.18 (2H, m), 2.33 (2H, t, J=7.3 Hz), 2.43 (2H, m), 4.15 (6H, m), 7.07 (2H, d, J=6.8 Hz), 7.15–7.43 (9H, m), 7.65 (4H, m)

IR(neat): 2962, 2933, 1732 cm$^{-1}$.

(2) 2-Ethoxycarbonyl-2-(2-phenylethyl)-γ-butyrolactone

To a solution of diethyl 2-(2-tert-butyldiphenylsilyloxyethyl)-2-(2-phenylethyl)malonate (5.570 g) in tetrahydrofuran (10 ml), a 1M solution of tetrabutylammonium fluoride in tetrahydrofuran (10.2 ml) was added and the mixture was stirred at room temperature for 18 hours. After the reaction mixture was concentrated, water (100 ml) was added to the resultant mixture and the solution was extracted with ethyl acetate. The ethyl acetate layer was washed with a saturated brine and dried over anhydrous sodium sulfate. The solvent was distilled away and the residue obtained was purified by silica gel column chromatography to give the subject compound (2.09 g) as a colorless oily substance.

Rf value: 0.17 (ethyl acetate:hexane=1:5)

$^1$H-NMR(CDCl$_3$) δ: 1.31 (3H, t, J=7.3 Hz), 2.08 (1H, m), 2.27 (1H, dt, J=12.7, 8.8 Hz), 2.43 (1H, m), 2.60 (1H, m), 2.77 (2H, m), 4.24 (2H, q, J=7.3 Hz), 4.36 (2H, m), 7.28 (3H, m), 7.20 (2H, m)

IR(neat): 2983, 2931, 1775, 1732 cm$^{-1}$

MS(EI): 262($M^+$).

(3) 2-(2-Phenylethyl)-γ-butyrolactone-2-carboxylic acid

To a solution of 2-ethoxycarbonyl-2-(2-phenylethyl)-γ-butyrolactone (2.01 g) in acetone (32 ml), a 0.25N aqueous sodium hydroxide solution (32 ml) was dropwise added under ice-cooling. After the mixture was stirred at room temperature for an hour, 2N hydrochloric acid was added thereto and the mixture was extracted with ethyl acetate. The ethyl acetate layer was washed with a saturated brine and dried over anhydrous sodium sulfate. The solvent was distilled away and the crude crystals obtained were washed with hexane a few times to give the subject compound (1.53 g) as white crystals, melting at 131–134° C.

Rf value: 0.21 (acetic acid:ethyl acetate:hexane=2:49:49)

$^1$H-NMR(CDCl$_3$) δ: 2.10 (1H, m), 2.38 (2H, m), 2.64 (1H, dt, J=4.9, 11.7 Hz), 2.82 (2H, m), 4.41 (2H, m), 4.60 (1H, br.s), 7.20 (2H, m), 7.27 (3H, m)

MS(EI): 234 ($M^+$).

(4) 2-Methoxycarbonylamino-2-(2-phenylethyl)-γ-butyrolactone

To a solution of 2-(2-phenylethyl)-γ-butyrolactone-2-carboxylic acid (1.4617 g) in acetone (30 ml), triethylamine (1.04 ml) was added at −20° C. The mixture was stirred for 15 minutes, ethyl chloroformate (0.66 ml) was added thereto. After the mixture was stirred for 30 minutes, sodium azide (490 mg) was dissolved in water (5 ml) and the solution was added to the mixture, and the whole mixture was stirred for an hour. The reaction mixture was diluted with water (50 ml) and extracted with chloroform. The chloroform layer was washed with a saturated brine and dried over anhydrous sodium sulfate. The solvent was distilled away, the residue obtained (acid azide) was dissolved in benzene (10 ml) and the mixture was refluxed under heating for an hour. Methanol (10 ml) was further added thereto and the mixture was refluxed under heating for an hour. The solvent was distilled away and the residue obtained was purified by silica gel column chromatography to give the subject compound (1.7607 g) as a colorless oily substance.

Rf value: 0.48 (ethyl acetate:hexane=1:1)
$^1$H-NMR(CDCl$_3$) δ: 2.04 (1H, m), 2.26 (1H, m), 2.74 (2H, t, J=8.8 Hz), 3.67 (3H, s), 4.28 (1H, dt, J=7.3, 6.9 Hz), 4.50 (1H, dt, J=1.9, 9.2 Hz), 5.27 (1H, s), 7.19 (2H, m), 7.28 (3H, m)
IR(neat): 3343, 3027, 1775, 1717 cm$^{-1}$
MS(EI): 232([M-OMe]$^+$).

(5) 2-Methoxycarbonylamino-2-[2-(4-octanoylphenyl)ethyl]-γ-butyrolactone

2-Methoxycarbonylamino-2-(2-phenylethyl)-γ-butyrilactone (1.5479 g) was subjected to Friedel-Crafts reaction using octanoyl chloride in the same manner as working example 2 (6) to give the subject compound (790 mg) as a colorless oily substance.

Rf value: 0.36 (ethyl acetate:hexane=1:1)
$^1$H-NMR(CDCl$_3$) δ: 0.88 (3H, t, J=6.8 Hz), 1.30 (8H, m), 1.71 (1H, m), 2.05 (1H, m), 2.30 (1H, m), 2.59 (1H, m), 3.66 (3H, s), 4.29 (1H, m), 4.50 (1H, m), 5.31 (1H, s), 7.26 (2H, d, J=8.3 Hz), 7.89 (2H, d, J=8.3 Hz)
IR(neat): 3342, 2929, 2857, 1776, 1722 cm$^{-1}$
MS(EI): 389(M$^+$);

(6) 2-Methoxycarbonylamino-2-[2-(4-octylphenyl)ethyl]-γ-butyrolactone

2-Methoxycarbonylamino-2-[2-(4-octanoylphenyl)ethyl]-γ-butyrolactone (832.1 mg) was subjected to reduction in the same manner as working example 2 (7) to give the subject compound (579.4 mg) as white crystals, melting at 93–95° C.

Rf value: 0.50 (ethyl acetate:hexane=1:1)
$^1$H-NMR(CDCl$_3$) δ: 0.88 (3H, t, J=7.3 Hz), 1.28 (12H, m), 1.56 (2H,; m), 2.03 (1H, m), 2.21 (1H, m), 2.56 (2H, t, J=7.8 Hz), 2.68 (2H, t, J=8.3 Hz), 3.66 (3H, s), 4.28 (1H, m), 4.49 (1H, m), 5.24 (1H, s), 7.08 (2H, d, J=8.3 Hz), 7.11 (2H, d, J=8.3 Hz)
IR(KBr): 3271,2926, 2855, 1772, 1721 cm$^{-1}$
MS(EI): 377(M$^+$)
Elemental analysis

| | |
|---|---|
| Calculated | C; 70.37, H; 8.86, N; 3.73 |
| Found | C; 70.40, H; 8.82, N; 3.66 |

(7) 2-Methoxycarbonylamino-2-[2-(4-octylphenyl)ethyl]butane-1,4-diol

2-Methoxycatbonylamino-2-[2-(4-octylphenyl)ethyl]-γ-butyrolactone (489.4 mg) was subjected to reduction in the same manner as working example 2 (5) to give the subject compound (342.8 mg) as a colorless oily substance.

Rf value: 0.56 (ethyl acetate)
$^1$H-NMR(CDCl$_3$) δ: 0.88 (3H, t, J=7.3 Hz), 1.27 (12H, m), 1.57 (2H, m), 2.13 (2H, m), 2.57 (4H, m), 3.68 (3H, m), 3.72 (2H, m), 3.82 (2H, s), 5.50 (1H, s), 7.09 (4H, s)
IR(neat): 3342, 2927, 2856, 1705, 1515 cm$^{-1}$
MS(EI): 380 ([M+1]$^+$).

WORKING EXAMPLE 8

3-Acetamido-3-acetoxymethyl-5-(4-octanoylphenyl) pentyl acetate (1) 3-Acetoxymethyl-3-methoxycarbonylamino-5-phenylpentyl acetate 2-Methoxycarbonylamino-2-(2-phenylethyl)-γ-butyrolactone (10.56 g) was subjected to reduction and acetylated in the same manner as working example 2 (5) to give the subject compound (6.73 g) as a colorless oily substance.

Rf value: 0.70 (ethyl acetate:hexane=1:1)
$^1$H-NMR(CDCl$_3$) δ: 2.04 (3H, s), 2.06 (2H, m), 2.17 (2H, t, J=7.3 Hz), 2.61 (2H, m), 3.64 (3H, s), 4.19 (2H, t, J=6.3 Hz), 4.28 (2H, s), 4.88 (1H, s), 7.18 (3H, m), 7.28 (2H, m)
IR(neat): 3355, 2956, 1740 cm$^{-1}$
MS(EI): 351 (M$^+$).

(2) 3-Acetamido-3-acetoxymethyl-5-phenylpentyl acetate

To a solution of 3-acetoxymethyl-3-methoxycarbonylamino-5-phenylpentyl acetate (3.678 g) in dichloromethane (22 ml), trimethylsilyl iodide (0.70 ml) was added and the mixture was left standing at room temperature for 30 minutes. Methanol (10 ml) was added thereto to discontinue the reaction and the solvent was distilled away. The residue obtained was acetylated in a usual manner to give the subject compound (1.1137 g) as a colorless oily substance.

Rf value: 0.46 (ethyl acetate)
$^1$H-NMR(CDCl$_3$) δ: 1.94 (3H, s), 2.05 (3H, s), 2.11 (3H, s), 2.22 (2H, t, J=6.9 Hz), 2.60 (2, m), 4.18 (2H, t, J=6.9 Hz), 4.33 (2H, dd, J=12.7, 11.7 Hz), 5.59 (1H, s), 7.19 (3H, m), 7.28 (2H, m)
IR(neat): 3308, 2965, 1739, 1658 cm$^{-1}$
MS(EI): 335 (M$^+$).

(3) 3-Acetamido-3-acetoxymethyl-5-(4-octanoylphenyl) pentyl acetate

3-Acetamido-3-acetoxymethyl-5-phenylpentyl acetate (1.00 g) was subjected to Friedel-Crafts reaction using octanoyl chloride in the same manner as working example 2 (6) to give the subject compound (0.94 g) as a colorless oily substance.

Rf value: 0.11 (ethyl acetate:hexane=1:1)
$^1$H-NMR(CDCl$_3$) δ: 0.88 (3H, t, J=7.3 Hz), 1.32 (10H, m), 1.56 (2H, m), 1.72 (2H, m), 1.97 (3H, s), 2.05 (3H, s), 2.12 (3H, s), 2.19 (2H, m), 2.63 (2H, m), 2.93 (2H, t, J=7.3 Hz), 4.18 (2H, t, J=6.4 Hz), 4.32 (2H, s), 5.66 (1H, s), 7.26 (2H, d, J=8.3 Hz), 7.87 (2H, d, J=8.3 Hz)
IR(neat): 3363, 2931,2858, 1741, 1679 cm$^{-1}$;

WORKING EXAMPLE 9

3-Acetamido-3-acetoxymethyl-5-(4-octylphenyl) pentyl acetate

3-Acetamido-3-acetoxymethyl-5-(4-octanoylphenyl) pentyl acetate (912.5 mg) was reduced in the same manner as working example 2 (7) to give the subject compound (646.4 mg) as a colorless oily substance.

Rf value: 0.18 (ethyl acetate:hexane=1:1)

¹H-NMR(CDCl₃) δ: 0.88 (3H, t, J=6.8 Hz), 1.27 (10H, m), 1.58 (2H, m), 1.93 (3H, s), 2.04 (3H, s), 2.10 (3H, s), 2.22 (2H, t, J=6.8 Hz), 2.55 (4H, m), 4.15 (2H, t, J=6.9 Hz), 4.30 (2H, m), 5.55 (1H, s), 7.02 (4H, s)

IR(neat): 3308, 2928, 2856, 1744, 1658 cm⁻¹

MS(EI): 447(M⁺).

WORKING EXAMPLE 10

2-Amino-2-[2-(4-octylphenyl)ethyl]butane-1,4-diol ⅕ hydrate

3-Acetamido-3-acetoxymethyl-5-(4-octylphenyl)pentyl acetate was hydrolyzed in the same manner as working example 2 (8) to give the subject compound, melting at 75–76° C.

Rf value: 0.47 (chloroform:methanol:acetic acid:water= 70:20:6:4) ¹H-NMR(DMSO-d₆) δ: 0.84 (3H, t, J=6.9 Hz), 1.25 (12H, m), 1.50 (6H, m), 3.18 (2H, s), 3.54 (2H, t, J=6.9 Hz), 4.59 (1H, s), 7.05 (4H, s)

IR(KBr): 3367, 3296, 2927, 2854 cm⁻¹

MS(EI): 321(M⁺)

Elemental analysis

| | |
|---|---|
| Calculated | C; 78.89, H; 10.97, N; 4.31 |
| Found | C; 74.11, H; 11.10, N; 4.24 |

WORKING EXAMPLE 11

3-Acetoxymethyl-3-methoxycarbonylamino-5-(4-decanoylphenyl)pentyl acetate

3-Acetoxymethyl-3-methoxycarbonylamino-5-phenylpentyl acetate (1.99 g) was subjected to Friedel-Crafts reaction using decanoyl chloride in the same manner as working example 2 (6) to give the subject compound (2.33 g) as white crystals, melting at 75–77° C.

Rf value: 0.25 (ethyl acetate:hexane=1:2)

¹H-NMR(CDCl₃) δ: 0.88 (3H, t, J=7.3 Hz), 1.26 (10H, m), 1.58 (2H, m), 1.71 (2H, m), 2.04 (3H, s), 2.11 (3H, s), 2.19 (4H, m), 2.66 (2H, dd, J=7.3, 9.7 Hz), 2.93 (2H, t, J=7.8 Hz), 3.65 (3H, s), 4.20 (2H, t, J=6.6 Hz), 4.28 (2H, s), 4.92 (1H, s), 7.27 (2H, d, J=8.5 Hz), 7.88 (2H, d, J=8.5 Hz)

IR(KBr): 3338, 2917, 2851, 1742, 1698, 1684 cm⁻¹

MS(EI): 505(M⁺)

Elemental analysis

| | |
|---|---|
| Calculated | C; 66.51, H; 8.57, N; 2.77 |
| Found | C; 66.29, H; 8.76, N; 2.71 |

WORKING EXAMPLE 12

3-Acetoxymethyl-3-methoxycarbonylamino-5-(4-decylphenyl)pentyl acetate

3-Acetoxymethyl-3-methoxycarbonylamino-5-(4-decanoylphenyl)pentyl acetate (2.25 g) was subjected to reduction in the same manner as working example 2 (7) to give the subject compound (1.26 g) as white crystals, melting at 79–81° C.

Rf value: 0.51 (ethyl acetate:hexane=1:2)

¹H-NMR(CDCl₃) δ: 0.88 (3H, t, J=6.8 Hz), 1.27 (14H, m), 1.58 (2H, m), 2.01 (2H, m), 2.04 (3H, s), 2.10 (3H, s), 2.16 (2H, t, J=6.3 Hz), 2.57 (4H, m), 3.64 (3H, s), 4.19 (2H, t, J=6.8 Hz), 4.28 (2H, s), 4.85 (1H, s), 7.08 (4H, 2d, J=8.3 Hz)

IR(KBr): 3332, 2920, 2850, 1742, 1698, 1545 cm⁻¹

MS(EI): 491(M⁺)

Elemental analysis

| | |
|---|---|
| Calculated | C; 68.40, H; 9.22, N; 2.85 |
| Found | C; 68.18, H; 9.14, N; 2.93 |

WORKING EXAMPLE 13

3-Acetamido-3-acetoxymethyl-5-(4-decylphenyl) pentyl acetate

3-Acetoxymethyl-3-methoxycarbonylamino-5-(4-decylphenyl)pentyl acetate (1.0844 g) was treated in the same manner as working example 8 (2) to give the subject compound (1.1137 g) as a colorless oily substance.

Rf value: 0.64 (ethyl acetate)

¹H-NMR(CDCl₃) δ: 0.88 (3H, t, J=6.8 Hz), 1.28 (14H, m), 1.55 (2H, m), 1.93 (3H, s), 2.04 (3H, s), 2.08 (2H, m), 2.10 (3H, s), 2.22 (2H, t, J=6.8 Hz), 2.56 (4H, m), 4.17 (2H, t, J=6.8 Hz), 4.33 (2H, 2d, Jgem=11.7 Hz), 5.54 (1H, s); 7.08 (4H, s)

IR(neat): 3307, 2927, 2855, 1744, 1658 cm⁻¹

MS(EI): 475(M⁺).

WORKING EXAMPLE 14

2-Amino-2-[2-(4-decylphenyl)ethyl]butane-1,4-diol

3-Acetamido-3-acetoxymethyl-5-(4-decylphenyl)pentyl acetate was hydrolyzed in the same manner as working example 2 (8) to give the subject compound, melting at 69–72° C.

¹H-NMR(DMSO-d₆) δ: 0.84 (3H, t, J=6.8 Hz), 1.23 (16H, m), 1.50 (6H, m), 3.19 (2H, s), 3.54 (2H, t, J=6.9 Hz), 4.59 (1H, s), 7.06 (4H, s)

IR(KBr): 3360, 3265, 2922, 2851, 1575 cm⁻¹

MS(EI): 349 (M⁺)

Elemental analysis

| | |
|---|---|
| Calculated | C; 75.59, H; 11.25, N; 4.01 |
| Found | C; 75.61, H; 11.21, N; 3.97 |

WORKING EXAMPLE 15

3-Acetamido-3-acetoxymethyl-5-(4-dodecanoylphenyl)pentyl acetate

3-Acetamido-3-acetoxymethyl-5-phenylpentyl acetate (1.0 g) was subjected to Friedel-Crafts reaction using dodecanoyl chloride in the same manner as working example 2 (6) to give the subject compound (690 mg) as white crystals, melting at 87–88° C.

Rf value: 0.13 (ethyl acetate:hexane=1:1)

¹H-NMR(CDCl₃) δ: 0.88 (3H, t, J=6.8 Hz), 1.26 (16H, m), 1.72 (2H, m), 1.97 (3H, s), 2.05 (3H, s), 2.11 (3H, s), 2.20 (4H, m), 2.65 (2H, m), 2.92 (2H, t, J=7.8 Hz), 4.18 (2H, t, J=6.5 Hz), 4.33 (2H, s), 5.66 (1H, s), 7.26 (2H, d, J=8.3 Hz), 7.88 (2H, d, J=8.3 Hz)

IR(KBr): 3305, 2917, 2851, 1740, 1684, 1652 cm$^{-1}$

MS(EI): 517(M$^+$)

Elemental analysis

| Calculated | C; 69.60, H; 9.15, N; 2.71 |
|---|---|
| Found | C; 69.10, H; 9.32, N; 2.71 |

WORKING EXAMPLE 16

3-Acetamido-3-acetoxymethyl-5-(4-dodecylphenyl) pentyl acetate

3-Acetamido-3-acetoxymethyl-5-(4-dodecanoylphenyl) pentyl acetate (660 mg) was subjected to reduction in the same manner as working example 2 (7) to give the subject compound (611.6 mg) as white crystals, melting at 75–77° C.

Rf value: 0.24 (ethyl acetate:hexane=1:1)

$^1$H-NMR(CDCl$_3$) δ: 0.88 (3H, t, J=6.8 Hz), 1.25 (18H, m), 1.56 (2H, m), 1.93 (3H, s), 2.04 (3H, s), 2.08 (3H, s), 2.22 (2H, t, J=6.3 Hz), 2.56 (4H, m), 4.17 (2H, t, J=6.8 Hz), 4.33 (2H, m), 5.54 (1H, s), 7.08 (4H, s)

IR(KBr): 3296, 2918, 2849, 1738, 1652 cm$^{-1}$

MS(EI): 503(M$^+$)

Elemental analysis

| Calculated | C; 71.51, H; 9.80, N; 2.78 |
|---|---|
| Found | C; 71.11, H; 9.94, N; 2.77 |

WORKING EXAMPLE 17

2-Amino-2-[2-(4-dodecylphenyl)ethyl]butane-1,4-diol

3-Acetamido-3-acetoxymethyl-5-(4-dodecylphenyl) pentyl acetate was hydrolyzed in the same manner as working example 2 (8) to give the subject compound, melting at 75–77° C. IR(KBr): 3360, 3264, 2922, 2850, 1574, 1516, 1470 cm$^{-1}$ Elemental analysis

| Calculated | C; 76.34, H; 11.48, N; 3.71 |
|---|---|
| Found | C; 76.10, H; 11.55, N; 3.71 |

WORKING EXAMPLE 18

2-Acetamido-5-(4-hexyloxyphenyl)pentanol

The same manner as working example 6 (2) to (6) was carried out using 3-(4-hexyloxyphenyl)propyl iodide instead of 2-(4-octylphenyl)ethyl iodide in working example 6 (2) to give the subject compound (4.37 g), melting at 60–61° C.

Rf value: 0.5 (chloroform:methanol=9:1)

$^1$H-NMR(400 MHz, CDCl$_3$) δ: 0.90 (3H, t, J=6.8 Hz), 1.33–1.80 (12H, m), 1.99 (3H, s), 2.57 (2H, m), 2.71 (1H, m), 3.54 (1H, m), 3.66 (1H, m), 3.92 (2H, t, J=6.8 Hz), 3.93 (1H, s), 5.63 (1H, d, J=8.7 Hz), 6.81 (2H, d, J=8.3 Hz), 7.06 (2H, d, J=8.3 Hz)

IR(KBr): 3288, 2933, 1695, 1648, 1516, 1244 cm$^{-1}$

MS(EI): 321(M$^+$)

Elemental analysis

| Calculated | C; 70.99, H; 9.72, N; 4.36 |
|---|---|
| Found | C; 71.14, H; 9.69, N; 4.38 |

WORKING EXAMPLE 19

(±)-2-(3,5-dinitrobenzamido)-4-(4-heptyloxyphenyl)-2-methylbutanol

To 2-Amino-2-methyl-4-(4-heptyloxyphenyl)butanol hydrochloride (562 mg) and potassium hydrogencarbonate (512 mg), water (40 ml) and ethyl acetate (40 ml) were added and the mixture was allowed to suspend. 3,5-Dinitrobenzoyl chloride (412 mg) was added thereto and the mixture was stirred at room temperature for 15 minutes. After the ethyl acetate layer was separated, the aqueous layer was extracted with ethyl acetate and the ethyl acetate layer was combined each other. The organic layer was washed with a saturated brine and dried over anhydrous sodium sulfate. The solvent was distilled away and the powder obtained was recrystallized from a mixed solvent of ethyl acetate and hexane to give the subject compound (670 mg) as white crystals, melting at 132–133° C.

Rf value: 0.52 (ethyl acetate:hexane=2:3)

$^1$H-NMR(CDCl$_3$) δ: 0.90 (3H, t, J=6.8 Hz), 1.31 (8H, m), 1.50 (3H, s), 1.69 (2H, quint, J=7.3 Hz), 2.06 (1H, m), 2.33 (1H, m), 2.70 (1H, m), 2.78 (1H, m), 3.49 (1H, t, J=6.3 Hz), 3.75 (2H, m), 3.76 (1H, dd, J=11.2, 6.3 Hz), 3.88 (1H, dd, J=11.2, 6.3 Hz), 6.11 (1H, br.s), 6.70 (2H, d, J=8.7 Hz), 7.11 (2H, d, J=8.7 Hz), 8.64 (2H, d, J=1.9 Hz), 9.12 (1H, t, J=1.9 Hz)

IR(KBr): 3250, 3102, 2928, 2857, 1642, 1537, 1511, 1344, 1239, 1052, 919, 731 cm$^{-1}$

MS(EI): 487(M$^+$), 456, 251, 218, 147, 107

Elemental analysis

| Calculated | C; 61.58, H; 6.82, N; 8.62 |
|---|---|
| Found | C; 61.39, H; 6.80, N; 8.61 |

WORKING EXAMPLE 20

(−)-2-(3,5-Dinitrobenzamido)-4-(4-heptyloxyphenyl)-2-methylbutanol (±)-2-(3,5-Dinitrobenzamido)-4-(4-heptyloxyphenyl)-2-methylbutanol (900 mg) was separated to high performance liquid chromatography (column; CHIRALCEL OD, eluent; hexane:ethanol=55:45, flow rate; 4.6 ml/minute) to give the subject compound (370 mg) as a white powder, melting at 150–151° C.

[α]$_D$=−18.0° (c=0.83, chloroform, 24° C.).

WORKING EXAMPLE 21

(+)-2-Amino-4-(4-heptyloxyphenyl)-2-methylbutanol hydrochloride ½ hydrate (−)-2-(3,5-Dinitrobenzamido)-4-(4-heptyloxyphenyl)-2-methylbutanol (400 mg) was dissolved in a mixed solvent of methanol (20 ml) and tetrahydrofuran (15 ml), thereto was added a 2M aqueous lithium hydroxide solution (10 ml) and the mixture was refluxed under heating for 15 minutes while stirring. The reaction mixture was concentrated under reduced pressure, water (50 ml) was added thereto and the mixture was extracted with ethyl acetate. The ethyl acetate layer was washed with a saturated brine, dried over anhydrous sodium sulfate and the solvent was distilled away. To the residue obtained were added methanol (10 ml) and a 1M solution of hydrochloric acid in ether, and the solvent was distilled away. The residue obtained was suspended in ether (5 ml) and filtered to give the subject compound (70 mg) as yellow amorphous.

Rf value: 0.49 (chloroform:methanol=4:1)

$^1$H-NMR(CD$_3$OD) δ: 0.90 (3H, t, J=6.9 Hz), 1.32 (3H, s), 1.32 (6H, m), 1.46 (2H, m), 1.74 (2H, quint, J=7.6 Hz), 1.84 (1H, m), 1.91 (1H, m), 2.60 (2H, m), 3.51 (1H, d, J=11.7 Hz), 3.61 (1H, d, J=11.7 Hz), 3.92 (2H, t, J=6.6 Hz), 6.82 (2H, d, J=8.8 Hz), 7.11 (2H, d, J=8.8 Hz)

IR(KBr): 3433, 3301,3013, 2939, 2858, 1614, 1538, 1513, 1242, 1050, 827 cm$^{-1}$

MS(EI): 293(M$^+$), 276, 262, 245, 205, 147, 107

Elemental analysis

| | |
|---|---|
| Calculated | C; 63.79, H; 9.81, N; 4.13 |
| Found | C; 63.72, H; 9.69, N; 4.21 |

$[α]_D$=+3.3° (c=0.42, chloroform, 25° C.).

WORKING EXAMPLE 22

(+)-2-(3,5-Dinitrobenzamido)-4-(4-heptyloxyphenyl)-2-methylbutanol (±)-2-(3,5-Dinitrobenzamido)-4-(4-heptyloxyphenyl)-2-methylbutanol was separated in the same manner as working example 20 to give the subject compound as a white powder, melting at 150–151° C.

$[α]_D$=+17.2° (c=1.15, chloroform, 24° C.)

WORKING EXAMPLE 23

(−)-2-Amino-4-(4-heptyloxyphenyl)-2-methylbutanol ⅖ hydrate (+)-2-(3,5-Dinitrobenzamido)-4-(4-heptyloxyphenyl)-2-methylbutanol was treated in the same manner as working example 21 to give the subject compound as a yellow amorphous.

Rf value: 0.48 (chloroform:methanol=4:1)

$^1$H-NMR(CD$_3$OD) δ: 0.90 (3H, t, J=7.1 Hz), 1.32 (3H, s), 1.32 (6H, m), 1.46 (2H, m), 1.74 (2H, quint, J=7.3 Hz), 1.84 (1H, m), 1.91 (1H, m), 2.59 (2H, m), 3.51 (1H, d, J=11.7 Hz), 3.61 (1H, d, J=11.7 Hz), 3.92 (2H, t, J=6.4 Hz), 6.82 (2H, d, J=8.8 Hz), 7.11 (2H, d, J=8.8 Hz)

IR(KBr): 3437, 3299, 3012, 2927, 2858, 1614, 1538, 1513, 1242, 1050, 827 cm$^{-1}$

MS(EI): 293(M$^+$), 276, 262, 245, 205, 147, 107

Elemental analysis

| | |
|---|---|
| Calculated | C; 64.13, H; 9.81, N; 4.15 |
| Found | C; 64.25, H; 9.78, N; 4.18 |

$[α]_D$=−3.6° (c=0.31, chloroform, 25° C.)

WORKING EXAMPLE 24

2-Amino-2-methyl-4-(4-nonyloxyphenyl)butanol hydrochloride ⅓hydrate (1) 4-Methyl-4-[2-(4-nonyloxyphenyl)ethyl]-2-oxazolidinone In working example 1 (6), nonyl bromide was used instead of heptyl bromide and the reaction was treated in the same manner to give the subject compound as white crystals, melting at 68–69° C.

Rf value: 0.54 (ethyl acetate:hexane=1:1)

$^1$H-NMR(CDCl$_3$) δ: 0.88 (3H, t, J=6.9 Hz), 1.28 (12H, m), 1.40 (3H, s), 1.43 (2H, m), 1.77 (2H, quint, J=7.6 Hz), 1.89 (2H, m), 2.62 (2H, m), 3.93 (2H, t, J=6.6 Hz), 4.06 (1H, d, J=8.8 Hz), 4.17 (1H, d, J=8.8 Hz), 4.86 (1H, br.s), 6.83 (2H, d, J=8.6 Hz), 7.07 (2H, d, J=8.6 Hz)

IR(KBr): 3254, 2922, 2853, 1755, 1740, 1512, 1242, 1041 cm$^{-1}$

MS(EI): 347(M$^+$), 190, 120, 107, 100

Elemental analysis

| | |
|---|---|
| Calculated | C; 72.58, H; 9.57, N; 4.03 |
| Found | C; 72.73, H; 9.61, N; 3.94 |

(2) 2-Amino-2-methyl-4-(4-nonyloxyphenyl)butanol hydrochloride ⅓hydrate

4-Methyl-4-[2-(4-nonyloxyphenyl)ethyl]-2-oxazolidinone was used in the same manner as working example 1 (7) to give the subject compound as white crystals, melting at 157–159° C.

Rf value: 0.17 (chloroform:methanol=4:1)

$^1$H-NMR(DMSO-d$_6$) δ: 0.85 (3H, t, J=6.9 Hz), 1.18 (3H, s), 1.24–1.38 (12H, m), 1.65–1.74 (4H, m), 2.49 (2H, m), 3.43 (2H, m), 3.89 (2H, t, J=6.4 Hz), 5.50 (1H, t, J=4.9 Hz), 6.83 (2H, d, J=8.3 Hz), 7.09 (2H, d, J=8.3 Hz), 7.74 (3H, br.s)

IR(KBr): 3428, 3351,3016, 2923, 2855, 1513, 1242, 1062 cm$^{-1}$

MS(EI): 321(M$^+$), 304, 290, 273, 233, 147, 107

Elemental analysis

| | |
|---|---|
| Calculated | C; 66.44, H; 10.15, N; 3.87 |
| Found | C; 66.68, H; 10.32, N; 3.87 |

WORKING EXAMPLE 25

2-Amino-2-methyl-4-(4-undecyloxyphenyl)butanol hydrochloride ¼hydrate (1) 4-Methyl-4-[2-(4-undecyloxyphenyl)ethyl]-2-oxazolidinone In working example 1 (6), undecyl bromide was used instead of heptyl bromide and the reaction was treated in the same manner to give the subject compound as white crystals, melting at 70–71° C.

Rf value: 0.70 (ethyl acetate:hexane=1:1)

¹H-NMR(CDCl₃) δ: 0.88 (3H, t, J=6.9 Hz), 1.27 (16H, m), 1.41 (3H, s), 1.44 (2H, m), 1.77 (2H, quint, J=7.3 Hz), 1.89 (2H, m), 2.62 (2H, m), 3.92 (2H, t, J=6.6 Hz), 4.06 (1H, d, J=8.3 Hz), 4.16 (1H, d, J=8.3 Hz), 4.83 (1H, br.s) 6.83 (2H, d, J=8.6 Hz), 7.07 (1H, d, J=8.7 Hz)

IR(KBr): 3314, 2956, 2921, 2853, 1754, 1717, 1512, 1399, 1242, 1045, 1032 cm⁻¹

MS(EI): 375(M⁺), 274, 221, 190, 120, 107, 100

Elemental analysis

| | |
|---|---|
| Calculated | C; 73.56, H; 9.93, N; 3.73 |
| Found | C; 73.63, H; 9.98, N; 3.68 |

(2) 2-Amino-2-methyl-4-(4-undecyloxyphenyl)butanol hydrochloride ¼hydrate

4-Methyl-4-[2-(4-undecyloxyphenyl)ethyl]-2-oxazolidinone was used in the same manner as working example 1 (7) to give the subject compound as white crystals, melting at 153–155° C.

Rf value: 0.26 (chloroform, methanol=4:1)

¹H-NMR(DMSO-d₆) δ: 0.84 (3H, t, J=6.8 Hz), 1.17 (3H, s), 1.24–1.38 (16H, m), 1.65–1.74 (4H, m), 2.49 (2H, m), 3.46 (2H, m), 3.89 (2H, t, J=6.4 Hz), 5.50 (1H, t, J=5.3 Hz), 6.83 (2H, d, J=8.3 Hz), 7.08 (2H, d, J=8.3 Hz), 7.70 (3H, br.s)

IR(KBr): 3336, 3012, 2923, 2853, 1512, 1243, 1052 cm⁻¹

MS(EI): 349(M⁺), 332, 318, 301, 261, 147, 107

Elemental analysis

| | |
|---|---|
| Calculated | C; 67.66, H; 10.45, N; 3.59 |
| Found | C; 67.45, H; 10.28, N; 3.52 |

WORKING EXAMPLE 26

2-Amino-2-methyl-4-(4-(4-phenylbutyloxy)phenyl) butanol hydrochloride (1) 4-Phenylbutyl iodide 4-Phenylbutanol (50.0 g) and triethylamine (40.5 g) were dissolved in methylene chloride (1000 ml), methanesulfonyl chloride (49.6 g) was dropwise added thereto over 15 minutes at room temperature and the mixture was further stirred for 10 minutes. The reaction solution was subjected to silica gel chromatography eluted by methylene chloride and the solvent of portions collected was distilled away to give a yellowish oil. The oil was dissolved in 2-butanone (1000 ml), sodium iodide (64.9 g) was added thereto and the mixture was refluxed under heating for 5 hours while stirring. The reaction solution was filtered off and concentrated under reduced pressure. The residue obtained was dissolved in ethyl acetate (1000 ml), the mixture was washed with an aqueous sodium thiosulfate solution and a saturated brine and dried over anhydrous sodium sulfate. The solvent was distilled away to give the subject compound (86.5 g) as a brown oil.

Rf value: 0.55 (hexane)

¹H-NMR(CDCl₃) δ: 1.74 (2H, quint, J=7.6 Hz), 1.86 (2H, m), 2.64 (2H, t, J=7.6 Hz), 3.20 (2H, t, J=7.1 Hz), 7.17–7.30 (5H, m)

IR(neat): 3084, 3061, 3025, 2934, 2856, 1738, 1603, 1496, 1453, 1208, 747, 698 cm⁻¹

MS(EI): 260(M⁺), 133, 92, 77.

(2) 2-(4-(4-Phenylbutyloxy)phenyl)ethanol

Sodium ethoxide (26.5 g) was dissolved in ethanol (1000 ml) and 2-(4-hydroxyphenyl)ethanol (49.2 g) was added thereto. Then, thereto was added a solution of 4-phenylbutyl iodide (84.3 g) in tetrahydrofuran (50 ml) and the mixture was refluxed under heating for 5 hours while stirring. Water (700 ml) was added to the reaction mixture and the mixture was concentrated under reduced pressure and extracted with ethyl acetate. The ethyl acetate layer was washed with a 2M aqueous potassium hydroxide solution and a saturated brine and dried over anhydrous sodium sulfate. The solvent was distilled away to give the subject compound (83.9 g) as brown oil.

Rf value: 0.29 (ethyl acetate:hexane=3:7)

¹H-NMR(CDCl₃) δ: 1.36 (1H, t, J=6.4 Hz), 1.81 (4H, m), 2.69 (2H, t, J=7.0 Hz), 2.81 (2H, t, J=6.4 Hz), 3.82 (2H, q, J=6.4 Hz), 3.95 (2H, t, J=5.9 Hz), 6.84 (2H, d, J=8.6 Hz), 7.13 (2H, d, J=8.6 Hz), 7.17–7.30 (5H, m)

IR(neat): 3360, 3026, 2939, 2865, 1612, 1512, 1244, 1047, 824, 749, 699 cm⁻¹

MS(EI): 270(M⁺), 239, 138, 107, 91, 77.

(3) 2-(4-(4-Phenylbutyloxy)phenyl)ethyl iodide 2-(4-(4-Phenylbutyloxy)phenyl)ethanol was used in the same manner as working example 26 (1) to give the subject compound as a yellowish oil. Rf value: 0.56 (ethyl acetate:hexane=1:19)

¹H-NMR(CDCl₃) δ: 1.81 (4H, m), 2.69 (2H, t, J=7.1Hz), i3.11 (2H, t, J=7.8 Hz), 3.31 (2H, t, J=7.8 Hz), 3.95 (2H, t, J=6.1 Hz), 6.83 (2H, d, J=8.3 Hz), 7.09 (2H, d, J=8.3 Hz), 7.17–7.30 (5H, m)

IR(neat): 3027, 2939, 2863, 1737, 1611, 1511, 1245, 1176, 748, 699 cm⁻¹

MS(EI): 380(M⁺), 253, 121, 91, 77, 65.

(4) 2-(2-(4-(4-Phenylbutyloxy)phenyl)ethyl)-2-methylmalonic acid diethyl ester

In working example 1 (1), 2-(4-(4-phenylbutyloxy) phenyl)ethyl iodide was used instead of 2-(4-benzyloxyphenyl)ethyl iodide to give the subject compound as a yellowish oil.

Rf value: 0.38 (ethyl acetate:hexane=1:9)

¹H-NMR(CDCl₃) δ: 1.26 (6H, t, J=7.2 Hz), 1.48 (3H, s), 1.80 (4H, m), 2.13 (2H, m), 2.50 (2H, m), 2.68 (2H, t, J=7.3 Hz), 3.94 (2H, t, J=5.9 Hz), 4.19 (4H, q, J=7.2 Hz), 6.80 (2H, d, J=8.8 Hz), 7.08 (2H, d, J=8.8 Hz), 7.18–7.30 (5H, m)

IR(neat): 3062, 3027, 2982, 2940, 2866, 1731, 1512, 1245, 1179, 1110, 1029, 826, 748, 700 cm⁻¹

MS(EI): 426(M⁺), 381, 307, 252, 174, 120, 91.

(5) 2-Ethoxycarbonyl-2-methyl-4-(4-(4-phenylbutyloxy) phenyl)butanoic acid

To a solution of 2-(2-(4-(4-phenylbutyloxy)phenyl)ethyl)-2-methylmalonic acid diethyl ester (5.35 g) in ethanol (30 ml), a solution of potassium hydroxide (0.71 g) in ethanol (15 ml) was dropwise added over 30 minutes and the mixture was stirred at 45° C. for 16 hours. The reaction solution was concentrated under reduced pressure and water (300 ml) was added thereto. The aqueous layer was washed with ether, acidified with 2M hydrochloric acid and extracted with ethyl acetate. The ethyl acetate layer was washed with a saturated brine and dried over anhydrous sodium sulfate. The solvent was distilled away to give the subject compound (5.20 g) as a yellowish oil.

Rf value: 0.47 (ethyl acetate:hexane:acetic acid=49:49:2)

¹H-NMR(CDCl₃) δ: 1.29 (3H, t, J=7.1 Hz), 1.54 (3H, s), 1.80 (4H, m), 2.17 (2H, m), 2.52 (2H, m), 2.68 (2H, t, J=7.1 Hz), 3.94 (2H, t, J=5.9 Hz), 4.22 (2H, m), 6.80 (2H, d, J=8.3 Hz), 7.07 (2H, d, J=8.3 Hz), 7.18–7.30 (5H, m)

IR(neat): 3476, 3187, 3029, 2986, 2941, 2866, 2637, 1733, 1714, 1512, 1244, 1178, 749, 700 cm⁻¹

MS(EI): 398(M⁺), 354, 252, 120, 91.

(6) Ethyl 2-methoxycarbonylamino-2-methyl-4-(4-(4-phenylbutyloxy)phenyl)butanoate In working example 1 (3), 2-ethoxycarbonyl-2-methyl-4-(4-(4-phenylbutyloxy)phenyl)butanoic acid was used instead of potassium 2-ethoxycarbonyl-2-methyl-4-(4-benzyloxyphenyl)butanoate to give the subject compound as a yellowish oil.

Rf value: 0.10 (ethyl acetate:hexane=1:9)
$^1$H-NMR(CDCl$_3$) δ: 1.28 (3H, t, J=7.2 Hz), 1.60 (3H, s), 1.80 (4H, m), 2.07 (1H, m), 2.31 (1H, m), 2.54 (2H, m), 2.68 (2H, t, J=6.8 Hz), 3.65 (3H, s), 3.93 (2H, t, J=5.9 Hz), 4.18 (2H, m), 5.67 (1H, br.s), 6.78 (2H, d, J=8.5 Hz) 7.03 (2H, 2H, d, J=8.5 Hz), 7.16–7.30 (5H, m)
IR(neat): 3420, 3364, 3061,3028, 2984, 2941,2865, 1733, 1511, 1244, 1076, 827, 750, 700 cm$^{-1}$
MS(EI): 427(M$^+$), 239, 175, 129, 107, 91.

(7) 4-Methyl-4-(2-(4-(4-phenylbutyloxy)phenyl)ethyl)-2-oxazolidinone

To a solution of ethyl 2-methoxycarbonylamino-2-methyl-4-(4-(4-phenylbutyloxy)phenyl)butanoate (3.42 g) in tetrahydrofuran (70 ml), lithium borohydride (0.35 g) was added and the mixture was refluxed under heating for 90 minutes while stirring. 2M Hydrochloric acid (10 ml) and water (100 ml) were added thereto under ice-cooling and the mixture was extracted with ethyl acetate. The ethyl acetate layer was washed with a saturated brine and dried over anhydrous sodium sulfate. The solvent was distilled away to give the subject compound (2.97 g) as a colorless oil.

Rf value: 0.30 (ethyl acetate:hexane=2:3)
$^1$H-NMR(CDCl$_3$) δ: 1.40 (3H, s), 1.81 (4H, m), 1.88 (2H, m), 2.62 (2H, m), 2.69 (2H, t, J=7.3 Hz), 3.94 (2H, t, J=5.9 Hz), 4.06 (1H, d, J=8.3 Hz), 4.16 (1H, d, J=8.3 Hz), 4.94 (1H, br.s), 6.82 (2H, d, J=8.3 Hz), 7.07 (2H, d, J=8.3 Hz), 7.17–7.30 (5H, m)
IR(neat): 3400, 3274, 3062, 3028, 2940, 2864, 1751, 1733, 1512, 1244, 1045, 827, 749, 700 cm$^{-1}$
MS(EI): 353(M$^+$), 239, 190, 161, 148, 133, 120, 107, 100, 91.

(8) 2-Amino-2-methyl-4-(4-(4-phenylbutyloxy)phenyl) butanol hydrochloride

4-Methyl-4-(2-(4-(4-phenylbutyloxy)phenyl)ethyl)-2-oxazolidinone was used in the same manner as working example 1 (7) to give the subject compound as white crystals, melting at 145–147° C.

Rf value: 0.21 (chloroform:methanol=4:1)
$^1$H-NMR(CD$_3$OD) δ: 1.32 (3H, s), 1.77 (4H, m), 1.83 (1H, m), 1.91 (1H, m), 2.59 (2H, m), 2.67 (2H, t, J=7.3 Hz), 3.51 (1H, d, J=11.5 Hz), 3.61 (1H, d, J=11.5 Hz), 6.82 (2H, d, J=8.6 Hz), 7.10 (2H, d, J=8.6 Hz), 7.14–7.26 (5H, m)
IR(KBr): 3345, 3028, 2934, 1598, 1513, 1242, 1062, 745, 700 cm$^{-1}$
MS(EI): 327(M$^+$), 310, 296, 279, 239, 147, 107, 91
Elemental analysis

| | |
|---|---|
| Calculated | C; 69.31, H; 8.31, N; 3.85, Cl; 9.74 |
| Found | C; 69.06, H; 8.40, N; 3.84, Cl; 9.69 |

WORKING EXAMPLE 27

2-Amino-2-ethyl-4-(4-heptyloxyphenyl)butanol hydrochloride (1) 2-(4-Heptyloxyphenyl)ethanol In working example 26 (2), heptyl bromide was used instead of 4-phenylbutyl iodide to give the subject compound as a yellowish oil.

Rf value: 0.44 (ethyl acetate:hexane=3:7)
$^1$H-NMR(CDCl$_3$) δ: 0.89 (3H, t, J=6.9 Hz), 1.31 (7H, m), 1.45 (2H, m), 1.77 (2H, quint, J=6.6 Hz), 2.81 (2H, t, J=6.6 Hz), 3.82 (2H, q, J=6.3 Hz), 3.93 (2H, t, J=6.6 Hz), 6.85 (2H, d, J=8.5 Hz), 7.13 (2H, d, J=8.5 Hz)
IR(neat): 3355, 2931,2859, 1613, 1512, 1244, 1046, 824 cm$^{-1}$
MS(EI): 236(M$^+$), 205, 138, 107.

(2) 2-(4-Heptyloxyphenyl)ethyl iodide 2-(4-Heptyloxyphenyl)ethanol was used in the same manner as working example 26 (1) to give the subject compound as a yellowish oil.

Rf value: 0.63 (ethyl acetate:hexane=1:19)
$^1$H-NMR(CDCl$_3$) δ: 0.89 (3H, t, J=6.9 Hz), 1.31 (6H, m), 1.45 (2H, m), 1.77 (2H, quint, J=6.8 Hz), 3.11 (2H, t, J=7.8 Hz), 3.31 (2H, t, J=7.8 Hz), 3.93 (2H, t, J=6.5 Hz), 6.84 (2H, d, J=8.3 Hz), 7.09 (2H, d, J=8.3 Hz)
IR(neat): 2928, 2857, 1611, 1511, 1245, 1176, 1027, 826 cm$^{-1}$
MS(EI): 346(M$^+$), 219, 121.

(3) 2-Ethyl-2-(2-(4-heptyloxyphenyl)ethyl)malonic acid diethyl ester

In working example 1 (1), ethylmalonic acid diethyl ester instead of methylmalonic acid diethyl ester and 2-(4-heptyloxyphenyl)ethyl iodide instead of 2-(4-benzyloxyphenyl)ethyl iodide were used to give the subject compound as a colorless oil.

Rf value: 0.46 (ethyl acetate:hexane=1:9)
$^1$H-NMR(CDCl$_3$) δ: 0.87 (3H, t, J=7.8 Hz), 0.89 (3H, t, J=6.8 Hz), 1.26 (6H, t, J=7.1 Hz), 1.30 (6H, m), 1.42 (2H, m), 1.76 (2H, quint, J=6.8 Hz), 2.01 (2H, q, J=7.8 Hz), 2.14 (2H, m), 2.43 (2H, m), 3.92 (2H, t, J=6.8 Hz), 4.19 (4H, q, J=7.1 Hz), 6.81 (2H, d, J=8.8 Hz), 7.07 (2H, d, J=8.8 Hz)
IR(neat): 2933, 2859, 1735, 1512, 1243, 1178, 1036, 826 cm$^{-1}$
MS(EI): 406(M$^+$), 361,287, 218, 120.

(4) 2-Ethoxycarbonyl-2-ethyl-4-(4-he ptyloxyphenyl) butanoic acid

2-Ethyl-2-(2-(4-heptyloxyphenyl)ethyl)malonic acid diethyl ester was used in the same manner as working example 26 (5) to give the subject compound as a yellowish oil.

Rf value: 0.59 (ethyl acetate:hexane:acetic acid=49:49:2)
$^1$H-NMR(CDCl$_3$) δ: 0.88 (3H, t, J=6.7 Hz), 0.89 (3H, t, J=6.8 Hz), 1.30 (6H, m), 1.32 (3H, t, J=6.8 Hz), 1.44 (2H, m), 1.76 (2H, quint, J=6.9 Hz), 1.90–2.60 (6H, m), 3.92 (2H, t, J=6.9 Hz), 4.23 (2H, m), 6.80 (2H, d, J=8.3 Hz), 7.04 (2H, d, J=8.3 Hz)
IR(neat): 3487, 3168, 2933, 2859, 2632, 1535, 1713, 1513, 1243, 1178, 1036, 826 cm$^{-1}$
MS(EI): 378(M$^+$), 334, 287, 218, 120, 107.

(5) Ethyl 2-ethyl-2-methoxycarbonylamino-4-(4-heptyloxyphenyl)butanoate

In working example 1 (3), 2-ethoxycarbonyl-2-ethyl-4-(4-heptyloxyphenyl)butanoic acid instead of potassium 2-ethoxycarbonyl-2-methyl-4-(4-benzyloxyphenyl) butanoate was used to give the subject compound as a yellowish oil.

Rf value: 0.34 (ethyl acetate:hexane=1:9)
$^1$H-NMR(CDCl$_3$) δ: 0.76 (3H, t, J=7.3 Hz), 0.89 (3H, t, J=7.3 Hz), 1.29 (3H,t, J=7.3 Hz), 1.31 (6H, m), 1.43 (2H, m), 1.75 (3H, m), 2.03 (1H, m), 2.24 (1H, m), 2.36 (1H, m), 2.56 (1H, m), 2.66 (1H, m), 3.65 (3H, br.s), 3.91 (2H, t, J=6.8 Hz), 4.17 (2H, m), 5.84 (1H, br.s), 6.79 (2H, d, J=8.3Hz), 7.03 (2H, d, J=8.3 Hz)
IR(neat): 3424, 2934, 2859, 1723, 1512, 1248, 1081, 1031,827 cm$^{-1}$
MS(EI): 407(M$^+$), 205, 189, 143, 107.

(6) 4-Ethyl-4-[2-(4-heptyloxyphenyl)ethyl]-2-oxazolidinone

Ethyl 2-ethyl-2-methoxycarbonylamino-4-(4-heptyloxyphenyl)butanoate was used in the same manner as working example 26 (7) to give the subject compound as colorless crystals, melting at 51–53° C.

Rf value: 0.25 (ethyl acetate:hexane=3:7)
$^1$H-NMR(CDCl$_3$) δ: 0.89 (3H, t, J=6.8 Hz), 0.97 (3H, t, J=7.3 Hz), 1.31 (6H, m), 1.44 (2H, m), 1.69 (2H, m), 1.77 (2H, quint, J=6.8 Hz), 1.87 (2H, m), 2.59 (2H, m), 3.93 (2H, t, J=6.8 Hz), 4.13 (2H, s), 4.84 (1H, br.s), 6.83 (2H, d, J=8.3 Hz), 7.07 (2H, d, J=8.3 Hz)
IR(KBr): 3266, 2931,2859, 1749, 1512, 1244, 1050, 828 cm$^{-1}$
MS(EI): 333(M$^+$), 256, 173, 159, 75.

(7) 2-Amino-2-ethyl-4-(4-heptyloxyphenyl)butanol hydrochloride

4-Ethyl-4-[2-(4-heptyloxyphenyl)ethyl]-2-oxazolidinone was used in the same manner as working example 1 (7) to give the subject compound as white crystals, melting at 108–110° C.

Rf value: 0.43 (chloroform:methanol=4:1)
$^1$H-NMR(CD$_3$OD) δ: 0.90 (3H, t, J=6.9 Hz), 1.00 (3H, t, J=7.3 Hz), 1.32 (6H, m), 1.46 (2H, m), 1.75 (4H, m), 1.85 (2H, m), 2.56 (2H, m), 3.60 (2H, s), 3.92 (2H, t, J=6.3 Hz), 6.83 (2H, d, J=8.8 Hz), 7.11 (2H, d, J=8.8 Hz)
IR(KBr): 3359, 3183, 2928, 2871, 1614, 1514, 1245, 1045, 825 cm-$^1$
MS(EI): 307(M$^+$), 276, 259, 205, 107
Elemental analysis

| | |
|---|---|
| Calculated | C; 66.35, H; 9.96, N; 4.07, Cl; 10.31 |
| Found | C; 66.08, H; 10.07, N; 4.07, Cl; 10.16 |

WORKING EXAMPLE 28

2-Amino-2-[2-(4-heptyloxyphenyl)ethyl]pentanol (1) 2-[2-(4-Heptyloxyphenyl)ethyl]-2-propylmalonic acid diethyl ester Sodium hydride (60%, 11.9 g) was suspended in dimethylformamide (800 ml) and thereto was dropwise added a solution of propylmalonic acid diethyl ester (54.6 g) in dimethylformamide (50 ml) over 15 minutes. The mixture was stirred at 40° C. for 30 minutes, and thereto was dropwise added a solution of 2-(4-heptyloxyphenyl)ethyl iodide (112.2 g) obtained in working example 27 (2) in tetrahydrofuran (100 ml) over 30 minutes and the whole mixture was further stirred for 3 hours. Ice-water (3000 ml) was added to the reaction solution and the mixture was extracted with ethyl acetate. The ethyl acetate layer was washed with 0.2M hydrochloric acid and a saturated brine in order and dried over anhydrous sodium sulfate. The solvent was distilled away to give the subject compound (136.2 g) as a colorless oil.

Rf value: 0.52 (ethyl acetate:hexane=1:9)
$^1$H-NMR(CDCl$_3$) δ: 0.89 (3H, t, J=6.8 Hz), 0.94 (3H, t, J=7.3 Hz) 1.26 (6H, t, J=7.3 Hz), 1.30 (8H, m), 1.44 (2H, m), 1.76 (2H, quint, J=6.8 Hz), 1.93 (2H, m), 2.14 (2H, m), 2.44 (2H, m), 3.92 (2H, t, J=6.8 Hz), 4.19 (4H, q, J=7.3 Hz), 6.81 (2H, d, J=8.3 Hz), 7.07 (2H, d, J=8.3 Hz)
IR(neat): 2960, 2933, 2873, 1733, 1512, 1241, 1178, 1027, 827 cm$^{-1}$
MS(EI): 420(M$^+$), 375, 301,218, 202, 173, 120, 107.

(2) 2-Ethoxycarbonyl-2-[2-(4-heptyloxyphenyl)ethyl] pentanoic acid

To a solution of 2-[2-(4-heptyloxyphenyl)ethyl]-2-propylmalonic acid diethyl ester (136.2 g) in ethanol (500 ml), potassium hydroxide (85%, 26.7 g) was added and the mixture was refluxed under heating for 3 hours while stirring. The solvent was distilled away, ice-water (3L) was added thereto and the mixture was washed with hexane. Concentrated hydrochloric acid (25 ml) was added thereto to acidify and the mixture was extracted with ethyl acetate. The ethyl acetate layer was washed with a saturated brine and dried over anhydrous sodium sulfate. The solvent was distilled away to give the subject compound (134.9 g) as a yellowish oil.

Rf value: 0.65 (ethyl acetate:hexane:acetic acid=49:49:2)
$^1$H-NMR(CDCl$_3$) δ: 0.89 (3H, t, J=6.8 Hz), 0.91 (3H, t, J=7.3 Hz), 1.30 (8H, m), 1.32 (3H, t, J=7.2 Hz), 1.44 (2H, m), 1.76 (2H, quint, J=6.9 Hz), 1.85 (1H, m), 1.99 (1H, m), 2.14 (1H, m), 2.29 (1H, m), 2.36 (1H, m), 2.56 (1H, m), 3.92 (2H, t, J=6.9 Hz), 4.22 (2H, m), 6.80 (2H, d, J=8.3H), 7.04 (2H, d, J=8.3 Hz)
IR(neat): 3181,2961,2933, 2873, 2634, 1733, 1713, 1513, 1243, 1178, 1046, 825 cm$^{-1}$
MS(EI): 392(M$^+$), 218, 120, 107.

(3) Ethyl 2-[2-(4-heptyloxyphenyl)ethyl]-2-methoxycarbonylaminoheptanoate

To a solution of 2-ethoxycarbonyl-2-[2-(4-heptyloxyphenyl)ethyl]-pentanoic acid (134.9 g) in tetrahydrofuran (600 ml), triethylamine (35.5 g) and ethyl chloroformate (38.1 g) were added at -15° C. and the mixture was stirred for 30 minutes. A saturated aqueous sodium azide (35.1 g) solution was added thereto and the mixture was stirred for 30 minutes. Water (1000 ml) was added thereto and the mixture was extracted with ethyl acetate. The ethyl acetate layer was washed with a saturated brine, dried over anhydrous sodium sulfate and the solvent was distilled away. The residue obtained was dissolved in benzene (500 ml) and the mixture was refluxed under heating for 30 minutes. Methanol (500 ml) and p-toluenesulfonic acid (0.20 g) were added to the mixture and the whole mixture was refluxed under heating for 8 hours while stirring. The solvent was distilled away and the residue obtained was purified by silica gel column chromatography (eluent; hexane:ethyl acetate= 19:1) to give the subject compound (52.5 g) as a yellowish oil.

Rf value: 0.33 (ethyl acetate:hexane=1:9)
$^1$H-NMR(CDCl$_3$) δ: 0.87 (3H, t, J=6.8 Hz), 0.89 (3H, t, J=6.0 Hz), 1.28 (3H, t, J=7.1 Hz), 1.30 (8H, m), 1.44 (2H, m), 1.69 (1H. m), 1.76 (2H, quint, J=6.8Hz), 2.03 (1H, m), 2.23 (1H, m), 2.32 (1H, m), 2.55 (1H, m), 2.66 (1H, m, 3.65 (3H, br.s), 3.91 (2H, t, J=6.8 Hz), 4.17 (2H, m), 5.84 (1H, br.s), 6.79 (2H, d, J=8.3 Hz), 7.03 (2H, d, J=8.3 Hz)
IR(neat): 3424, 2959, 2933, 2872, 1723, 1511, 1237, 1085, 1037, 827, 779 cm$^{-1}$
MS(EI): 421(M+Y, 205, 157, 107.

(4) 4-[2-(4-Heptyloxyphenyl)ethyl]-4-propyl-2-oxazolidinone

To a solution of ethyl 2-[2-(4-heptyloxyphenyl)ethyl]-2-methoxycarbonylaminoheptanoate (1.83 g) in tetrahydrofuran (60 ml), lithium borohydride (0.19 g) was added and the mixture was refluxed under heating for 8 hours while stirring. The reaction mixture was ice-cooled, and 2M hydrochloric acid (4 ml) and water (100 ml) were added thereto and the mixture was extracted with ethyl acetate. The ethyl acetate layer was washed with a saturated brine and dried over anhydrous sodium sulfate. The solvent was distilled away to give the subject compound (1.60 g) as a colorless oil.

Rf value: 0.48 (ethyl acetate:hexane=2:3)
$^1$H-NMR(CDCl$_3$) δ: 0.89 (3H, t, J=6.9 Hz), 0.98 (3H, t, J=7.3 Hz), 1.31–1.43 (10H, m), 1.63 (2H, m), 1.77 (2H, m), 1.87 (2H, m), 2.59 (2H, m), 3.92 (2H, t, J=6.8 Hz), 4.13 (2H, s), 5.02 (1H, br.s), 6.83 (2H, d, J=8.3 Hz), 7.07 (2H, d, J=8.3 Hz)

IR(neat): 3264, 2933, 2872, 1751, 1512, 1244, 1036, 825 cm$^{-1}$

MS(EI): 347(M$^+$), 318, 304, 205, 128, 107.

(5) 2-Amino-2-[2-(4-heptyloxyphenyl)ethyl]pentanol

4-[2-(4-Heptyloxyphenyl)ethyl]-4-propyl-2-oxazolidinone (1.54 g) was dissolved in a mixed solvent of tetrahydrofuran (20 ml) and methanol (50 ml), a 5M aqueous potassium hydroxide solution (55 ml) was added thereto and the mixture was refluxed under heating for 21 hours while stirring. The reaction mixture was concentrated under reduced pressure and extracted with ethyl acetate. The ethyl acetate layer was washed with a saturated brine and dried over anhydrous sodium sulfate. The solvent was distilled away and the residue obtained was crystallized from a mixed solvent of diisopropyl ether and hexane to give the subject compound (0.56 g) as a white powder, melting at 48–50° C.

Rf value: 0.46 (chloroform:methanol=4:1)

$^1$H-NMR(CDCl$_3$) δ: 0.89 (3H, t, J=6.8 Hz), 0.95 (3H, t, J=6.8 Hz), 1.30–1.73 (14H, m), 1.76 (2H, m), 2.53 (2H, m), 3.36 (2H, s), 3.92 (2H, t, J=6.6 Hz), 6.81 (2H, d, J=8.3 Hz), 7.09 (2H, d, J=8.3 Hz), IR(KBr): 3337, 3277, 3132, 2956, 2936, 2859, 1612, 1513, 1248, 1059, 1019, 837 cm$^{-1}$

MS(EI): 321(M$^+$), 290, 205, 107

Elemental analysis

| | |
|---|---|
| Calculated | C; 74.72, H; 10.97, N; 4.36 |
| Found | C; 74.57, H; 11.24, N; 4.34 |

WORKING EXAMPLE 29

(±)-2-(3,5-Dinitrobenzamido)-2-[2-(4-heptyloxyphenyl)ethyl]pentanol

2-Amino-2-[2-(4-heptyloxyphenyl)ethyl]pentanol was used in the same manner as working example 19 to give the subject compound as a white powder, melting at 104–108° C.

Rf value: 0.66 (ethyl acetate:hexane=2:3)

$^1$H-NMR(CDCl$_3$) δ: 0.90 (3H, t, J=6.8 Hz), 1.02 (3H, t, J=7.3 Hz), 1.31 (10H, m), 1.70 (2H, m), 1.80 (1H, m), 1.90 (1H, m), 2.09 (1H, m), 2.21 (1H, m), 2.64 (1H, m), 2.75 (1H, m), 3.75 (2H, m), 3.84 (1H, d, J=11.7 Hz), 3.92 (1H, d, J=11.7 Hz), 6.04 (1H, br.s), 6.70 (2H, d, J=8.8 Hz), 7.11 (2H, d, J=8.8Hz), 8.63 (2H, d, J=2.0 Hz), 9.12 (1H, t, J=2.0 Hz)

IR(KBr): 3246, 3103, 2926, 2870, 1639, 1540, 1514, 1345, 1243, 1046, 731, 717 cm$^{-1}$

MS(EI): 515(M$^+$), 484, 290, 205, 107, 81.

WORKING EXAMPLE 30

(−)-2-(3,5-Dinitrobenzamido)-2-[2-(4-heptyloxyphenyl)ethyl]pentanol (±)-2-(3,5-Dinitrobenzamido)-2-[2-(4-heptyloxyphenyl)ethyl]pentanol was used in the same manner as working example 20 to give the subject compound as a white powder, melting at 115–116° C.

[α]$_D$=−20.7° (c=0.98, chloroform, 24° C.)

WORKING EXAMPLE 31

(R)-2-amino-2-[2-(4-heptyloxyphenyl)ethyl]pentanol hydrochloride (−)-2-(3,5-Dinitrobenzamido)-2-[2-(4-heptyloxyphenyl) ethyl]pentanol (170 mg) was dissolved in a mixed solvent of tetrahydrofuran (15 ml) and methanol (10 ml), a 2M aqueous lithium hydroxide solution (10 ml) was added thereto and the mixture was refluxed under heating for 45 minutes while stirring. The reaction mixture was concentrated under reduced pressure, water (100 ml) was added thereto and the mixture was extracted with ethyl acetate. The ethyl acetate layer was washed with a saturated brine, dried over anhydrous sodium sulfate and the solvent was distilled away. The residue obtained was dissolved in methanol (20 ml), a 1M solution of hydrochloric acid in ether (8 ml) was added thereto and the solvent was distilled away. The residue obtained was crystallized in ether to give the subject compound (108 mg) as yellow crystals, melting at 89–90° C.

[α]$_D$=+1.68° (c=0.51, ethanol, 24° C.)

WORKING EXAMPLE 32

(+)-2-(3,5-Dinitrobenzamido)-2-[2-(4-heptyloxyphenyl)ethyl]pentanol (±)-2-(3,5-Dinitrobenzamido)-2-[2-(4-heptyloxyphenyl) ethyl]pentanol was used in the same manner as working example 20 to give the subject compound as a white powder, melting at 114–115° C.

[α]$_D$=+18.2° (c=0.71, chloroform, 24° C.)

WORKING EXAMPLE 33

(S)-2-Amino-2-[2-(4-heptyloxyphenyl)ethyl] pentanol hydrochloride (+)-2-(3,5-Dinitrobenzamido)-2-[2-(4-heptyloxyphenyl) ethyl]pentanol was used in the same manner as working example 31 to give the subject compound as yellow crystals, melting at 90–91° C.

[α]$_D$=+1.68° (c=0.51, ethanol, 24° C.)

WORKING EXAMPLE 34

2-Acetamido-2-methyl-4-(4-octanoylphenyl)butyl acetate (1) 2-Methyl-2-(2-phenylethyl)malonic acid diethyl ester In working example 1 (1), phenetyl bromide was used instead of 2-(4-benzyloxyphenyl)ethyl iodide to give the subject compound as a colorless oil.

Rf value: 0.45 (ethyl acetate:hexane=1:9)

$^1$H-NMR(CDCl$_3$) δ: 1.26 (6H, t, J=7.3 Hz), 1.50 (3H, s), 2.17 (2H, m), 2.58 (2H, m), 4.19 (4H, q, J=7.3 Hz), 7.20 (3H, m), 7.28 (2H, m)

IR(neat): 3029, 2984, 2941, 1733, 1455, 1260, 1183, 1108, 1030, 861, 750, 700 cm$^{-1}$

MS(EI): 277, 250, 174, 128, 105, 91.

(2) 2-Ethoxycarbonyl-2-methyl-4-phenylbutanoic acid

2-Methyl-2-(2-phenylethyl)malonic acid diethyl ester was used in the same manner as working example 26 (5) to give the subject compound as a yellowish oil.

Rf value: 0.59 (ethyl acetate:hexane:acetic acid=49:49:2)

$^1$H-NMR(CDCl$_3$) δ: 1.29 (3H, t, J=7.3 Hz), 1.55 (3H, s), 2.21 (2H, m), 2.60 (2H, m), 4.22 (2H, m), 7.19 (3H, m), 7.28 (2H, m)

IR(neat): 3179, 3028, 2986, 2943, 2938, 1735, 1707, 1245, 1113, 749, 699 cm$^{-1}$

MS(EI): 251(M$^+$), 146, 128, 100, 91.

(3) Ethyl 2-methoxycarbonylamino-2-methyl-4-phenylbutanoate

2-Ethoxycarbonyl-2-methyl-4-phenylbutanoic acid was used in the same manner as working example 1 (3) to give the subject compound as a colorless oil.

Rf value: 0.13 (ethyl acetate:hexane=1:9)

$^1$H-NMR(CDCl$_3$) δ: 1.29 (3H, t, J=7.3 Hz), 1.61 (3H, s), 2.05 (1H, m), 2.38 (1H, m), 2.59 (2H, m), 3.66 (3H, s), 4.17 (2H, m), 5.70 (1H, br.s), 7.15 (3H, m), 7.25 (2H, m)

IR(neat): 3420, 3363, 3028, 2984, 2944, 1733, 1509, 1263, 1085, 781, 749, 700 cm$^{-1}$

MS(EI): 279(M$^+$), 206, 175, 129, 91.

(4) 2-Amino-2-methyl-4-phenylbutanol

Ethyl 2-methoxycarbonylamino-2-methyl-4-phenylbutanoate was used in the same manner as working example 26 (7), and then working example 28 (5) to give the subject compound as a white powder, melting at 59–60° C.

Rf value: 0.19 (chloroform:methanol=4:1)

$^1$H-NMR(CDCl$_3$) δ: 1.14 (3H, s), 1.65 (4H, m), 2.65 (2H, t, J=8.8 Hz), 3.33 (1H, d, J=10.8 Hz), 3.39 (1H, d, J=10.8 Hz), 7.21 (3H, m), 7.28 (2H, m)

IR(KBr): 3333, 3265, 3159, 3027, 2946, 2919, 2731, 1603, 1454, 1057, 972, 925, 744, 698 cm$^{-1}$

MS(EI): 180(M+H)+, 148, 131, 91, 74.

(5) 2-Acetamido-2-methyl-4-phenylbutyl acetate

To 2-amino-2-methyl-4-phenylbutanol (8.01 g), pyridine (50 ml) and acetic anhydride (42.5 ml) were added and the mixture was left standing at room temperature for 16 hours. To the resultant solution, a saturated aqueous sodium hydrogencarbonate solution (400 ml) which ice was put in, was added and the mixture was extracted with ethyl acetate. The ethyl acetate layer was washed with 1M hydrochloric acid, a saturated aqueous sodium hydrogencarbonate solution and a saturated brine, dried over anhydrous sodium sulfate and the solvent was distilled away to give the subject compound (12.2 g) as pale yellow crystals, melting at 75–78° C.

Rf value: 0.19 (ethyl acetate:hexane=1:1)

$^1$H-NMR(CDCl$_3$) δ: 1.38 (3H, s), 1.92 (3H, s), 1.94 (1H, m), 2.09 (3H, s), 2.21 (1H, m), 2.61 (2H, m), 4.18 (1H, d, J=11.3 Hz), 4.34 (1H, d, J=11.3 Hz), 5.37 (1H, br.s), 7.20 (3H, m), 7.28 (2H, m)

IR(KBr): 3308, 3064, 2980, 2938, 1741, 1656, 1549, 1373, 1243, 1046, 748, 701 cm$^{-1}$

MS(EI): 263(M$^+$), 190, 148, 99, 91.

(6) 2-Acetamido-2-methyl-4-(4-octanoylphenyl)butyl acetate

To a suspension of anhydrous aluminum chloride (6.1 g) in dichloroethane (70 ml), a solution of octanoyl chloride (3.7 g) in dichloroethane (10 ml) was dropwise added at room temperature and the mixture was stirred for 30 minutes. Thereto was dropwise added a solution of 2-acetamido-2-methyl-4-phenylbutyl acetate (2.0 g) in dichloroethane (10 ml) and the whole mixture was further stirred for 2 hours. Ice-water (250 ml) was added thereto and the mixture was extracted with methylene chloride. The methylene chloride layer was washed with 1M hydrochloric acid, a saturated aqueous sodium hydrogencarbonate solution and a saturated brine, dried over anhydrous sodium sulfate and the solvent was distilled away. The residue obtained was purified by silica gel column chromatography (eluent; ethyl acetate:hexane=1:1) and recrystallized from a mixed solvent of ethyl acetate and hexane to give the subject compound (1.5 g) as white crystals, melting at 81–83° C.

Rf value: 0.18 (ethyl acetate:hexane=1:1)

$^1$H-NMR(CDCl$_3$) δ: 0.88 (3H, t, J=6.9 Hz), 1.29 (8H, m), 1.37 (3H, s), 1.72 (2H, quint, J=7.4 Hz), 1.95 (3H, s), 2.01 (1H, m), 2.10 (3H, s) 2.26 (1H, m), 2.65 (2H, t, J=8.6 Hz), 2.93 (2H, t, J=7.4 Hz), 4.16 (1H, d, J=11.3 Hz), 4.34 (1H, d, J=11.3 Hz), 5.38 (1H, br.s), 7.27 (2H, d, J=8.3 Hz), 7.87 (2H, d, J=8.3 Hz)

IR(KBr): 3293, 3202, 3084, 2949, 2929, 2851, 1733, 1681, 1644, 1560, 1378, 1259, 1059, 814, 722 cm$^{-1}$

MS(EI): 389(M$^+$), 330, 274, 99

Elemental analysis

| | |
|---|---|
| Calculated | C; 70.79, H; 9.06, N; 3.60 |
| Found | C; 70.68, H; 9.17, N; 3.61 |

WORKING EXAMPLE 35

2-Acetamido-4-(4-decanoylphenyl)-2-methylbutyl acetate

In working example 34 (6), decanoyl chloride was used instead of octanoyl chloride to give the subject compound as white crystals, melting at 72–75° C.

Rf value: 0.15 (ethyl acetate:hexane=1:1)

$^1$H-NMR(CDCl$_3$) δ: 0.88 (3H, t, J=6.8 Hz), 1.27 (12H, m), 1.37 (3H, s), 1.71 (2H, m), 1.95 (3H, s), 1.98 (1H, m), 2.10 (3H, s), 2.26 (1H, m), 2.65 (2H, m), 2.92 (2H, m), 4.16 (1H, d, J=11.3 Hz), 4.34 (1H, d, J=11.3 Hz), 5.38 (1H, br.s), 7.26 (2H, d, J=8.3 Hz), 7.87 (2H, d, J=8.3 Hz)

IR(KBr): 3294, 3202, 3084, 2948, 2927, 2849, 1733, 1681, 1644, 1560, 1378, 1257, 1059, 810, 722 cm$^{-1}$

MS(EI): 417(M$^+$), 358, 302, 99

Elemental analysis

| | |
|---|---|
| Calculated | C; 71.91, H; 9.41, N; 3.35 |
| Found | C; 71.76, H; 9.49, N; 3.35 |

WORKING EXAMPLE 36

3-Acetamido-4-(4-dodecanoylphenyl)-2-methylbutyl acetate

In working example 34 (6), dodecanoyl chloride was used instead of octanoyl chloride to give the subject compound as white crystals, melting at 68–73° C.

Rf value: 0.74 (chloroform:methanol=9:1)

$^1$H-NMR(CDCl$_3$) δ: 0.88 (3H, t, J=6.8 Hz), 1.26 (16H, m), 1.37 (3H, s), 1.72 (2H, quint, J=7.3 Hz), 1.95 (3H, s), 1.96 (1H, m), 2.10 (3H, s), 2.27 (1H, d, J=2.65 (2H, m), 2.93 (2H, t, J=7.3 Hz), 4.16 (1H, d, J=11.3 Hz), 4.35 (1H, d, J=11.3 Hz), 5.40 (1H, br.s), 7.27 (2H, d, J=8.3 Hz), 7.87 (2H, d, J=8.3 Hz)

IR(KBr): 3293, 3202, 3084, 2925, 2848, 1733, 1680, 1644, 1561, 1471, 1378, 1260, 1060, 810, 723 cm$^{-1}$

MS(EI): 445 (M$^+$), 386, 330, 99.

WORKING EXAMPLE 37

2-Acetamido-2-methyl-4-(4-octylphenyl)butyl acetate

2-Acetamido-2-methyl-4-(4-octanoylphenyl)butyl acetate (1.40 g) was dissolved in trifluoroacetic acid (20 ml), and triethylsilane (1.25 g) was dropwise added thereto at room temperature and the mixture was further stirred for an hour. The reaction mixture was concentrated under reduced pressure and thereto was added a saturated aqueous sodium hydrogen-carbonate solution (100 ml) and the mixture was extracted with ethyl acetate. The ethyl acetate layer was washed with a saturated aqueous sodium hydrogencarbonate solution and a saturated brine, dried over anhydrous sodium sulfate and the solvent was distilled away. The residue obtained was recrystallized from ethyl acetate and hexane to give the subject compound (1.06 g) as white crystals, melting at 65° C.

Rf value: 0.40 (ethyl acetate:hexane=1:1)

$^1$H-NMR(CDCl$_3$) δ: 0.88 (3H, t, J=6.8 Hz), 1.26 (10H, m), 1.38 (3H, s), 1.56 (2H, m), 1.90 (3H, s), 1.92 (1H, m), 2.09 (3H, s), 2.20 (1H, m), 2.56 (4H, m), 4.19 (1H, d, J=11.2 Hz), 4.34 (1H, d, J=11.2 Hz), 5.32 (1H, br.s), 7.09 (4H, s)

IR(KBr): 3292, 3203, 3087, 2951, 2924, 2851, 1733, 1645, 1561, 1469, 1378, 1259, 1059, 813, 721 cm$^{-1}$

MS(EI): 375(M$^+$), 302, 260, 243, 216, 143, 99

Elemental analysis

| | |
|---|---|
| Calculated | C; 73.56, H; 9.93, N; 3.73 |
| Found | C; 73.47, H; 9.88, N; 3.74 |

WORKING EXAMPLE 38

2-Acetamido-4-(4-decylphenyl)-2-methylbutyl acetate

2-Acetamido-4-(4-decanoylphenyl)-2-methylbutyl acetate was used in the same manner as working example 37 to give the subject compound as white crystals, melting at 64–65° C.

Rf value: 0.41 (ethyl acetate:hexane=1:1)

$^1$H-NMR(CDCl$_3$) δ: 0.88 (3H, t, J=6.8 Hz), 1.26 (14H, m), 1.38 (3H, s), 1.58 (2H, m), 1.90 (3H, s), 1.94 (1H, m), 2.09 (3H, s), 2.20 (1H, m), 2.56 (4H, m), 4.19 (1H, d, J=11.2 Hz), 4.33 (1H, d, J=11.2 Hz), 5.32 (1H, br.s), 7.09 (4H, s)

IR(KBr): 3294, 3203, 3086, 2951, 2920, 2850, 1733, 1645, 1561, 1469, 1378, 1259, 1059, 812, 721 cm$^{-1}$

MS(EI): 403(M$^+$), 330, 288, 143, 117, 105, 91

Elemental analysis

| | |
|---|---|
| Calculated | C; 74.40, H; 10.24, N; 3.47 |
| Found | C; 74.39, H; 10.39, N; 3.49 |

WORKING EXAMPLE 39

2-Acetamido-4-(4-dodecylphenyl)-2-methylbutyl acetate

2-Acetamido-4-(4-dodecanoylphenyl)-2-methylbutyl acetate was used in the same manner as working example 37 to give the subject compound as white crystals, melting at 64–67° C.

Rf value: 0.46 (ethyl acetate:hexane=1:1)

$^1$H-NMR(CDCl$_3$) δ: 0.88 (3H, t, J=6.8 Hz), 1.25 (18H, m), 1.38 (3H, s), 1.57 (2H, m), 1.90 (3H, s), 1.92 (1H, m), 2.09 (3H, s), 2.20 (1H, m), 2.56 (4H, m), 4.19 (1H, d, J=11.2 Hz), 4.33 (1H, d, J=11.2 Hz), 5.32 (1H, br.s), 7.09 (4H, s)

IR(KBr): 3292, 3202, 3087, 2951, 2920, 2849, 1733, 1645, 1561, 1470, 1379, 1260, 1060, 812, 720 cm$^{-1}$

MS(EI): 431(M$^+$), 358, 316, 143, 99

Elemental analysis

| | |
|---|---|
| Calculated | C; 75.13, H; 10.51, N; 3.24 |
| Found | C; 74.84, H; 10.61, N; 3.34 |

WORKING EXAMPLE 40

2-Amino-2-methyl-4-(4-octylphenyl)butanol hydrochloride

2-Acetamido-2-methyl-4-(4-octylphenyl)butyl acetate (0.99 g) was dissolved in a mixed solvent of methanol (70 ml) and tetrahydrofuran (70 ml). A 2M aqueous lithium hydroxide solution (70 ml) was added thereto and the mixture was refluxed under heating for an hour while stirring. The reaction mixture was concentrated under reduced pressure, water (200 ml) was added thereto and the mixture was extracted with ethyl acetate. The ethyl acetate layer was washed with a saturated brine, dried over anhydrous sodium sulfate and the solvent was distilled away. The residue obtained was dissolved in ethanol (130 ml), a 1M solution of hydrochloric acid in ether (10 ml) was added thereto and the solvent was distilled away. The residue obtained was recrystallized from a mixed solvent of ethanol and hexane to give the subject compound (0.51 g) as white crystals, melting at 171–173° C.

Rf value: 0.27 (chloroform:methanol=4:1)

$^1$H-NMR(CD$_3$OD) δ: 0.88 (3H, t, J=7.1 Hz), 1.30 (10H, m), 1.33 (3H, s), 1.57 (2H, m), 1.89 (2H, m), 2.56 (2H, t, J=7.6 Hz), 2.62 (2H, m), 3.52 (1H, d, J=11.8 Hz), 3.62 (1H, d, J=11.8 Hz), 7.10 (4H, m)

IR(KBr): 3373, 3077, 3019, 2927, 2854, 1589, 1568, 1061 cm$^{-1}$

MS(EI): 291(M$^+$), 260, 243, 203, 105

Elemental analysis

| | |
|---|---|
| Calculated | C; 69.59, H; 10.45, N; 4.27 |
| Found | C; 69.36, H; 10.42, N; 4.26 |

WORKING EXAMPLE 41

2-Amino-4-(4-decylphenyl)-2-methylbutanol hydrochloride

2-Acetamido-4-(4-decylphenyl)-2-methylbutyl acetate was used in the same manner as working example 40 to give the subject compound as white crystals, melting at 161–163° C.

Rf value: 0.31 (chloroform:methanol=4:1)

$^1$H-NMR(CD$_3$OD) δ: 0.89 (3H, t, J=6.9 Hz), 1.27 (14H, m), 1.33 (3H, s), 1.57 (2H, m), 1.89 (2H, m), 2.56 (2H, t, J=7.6 Hz), 2.63 (2H, m), 3.52 (1H, d, J=11.7 Hz), 3.62 (1H, d, J=11.7 Hz), 7.11 (4H, m)

IR(KBr): 3351, 3083, 3020, 2923, 2852, 1597, 1512, 1061 cm$^{-1}$

MS(EI): 319 (M⁺), 288, 105
Elemental analysis

| | |
|---|---|
| Calculated | C; 70.85, H; 10.76, N; 3.93 |
| Found | C; 70.78, H; 10.70, N; 3.98 |

WORKING EXAMPLE 42

2-Amino-4-(4-dodecylphenyl)-2-methylbutanol hydrochloride

2-Acetamido-4-(4-dodecylphenyl)-2-methylbutyl acetate was used in the same manner as working example 40 to give the subject compound as white crystals, melting at 161–162° C.

Rf value: 0.53 (chlorofrom:methanol=4:1)
¹H-NMR(CD₃OD) δ: 0.89 (3H, t, J=7.1 Hz), 1.27 (18H, m), 1.33 (3H, s), 1.57 (2H, m), 1.89 (2H, m), 2.56 (2H, t, J=7.6 Hz), 2.62 (2H, m), 3.52 (1H, d, J=11.8 Hz), 3.62 (1H, d, J=11.8 Hz), 7.11 (4H, m)
IR(KBr): 3349, 3019, 2922, 2852, 1597, 1512, 1468, 1062 cm⁻¹
MS(EI): 347(M⁺), 316, 105
Elemental analysis

| | |
|---|---|
| Calculated | C; 71.93, H; 11.02, N; 3.65 |
| Found | C; 71.81, H; 11.11, N; 3.63 |

WORKING EXAMPLE 43

2-Acetamido-6-(4-hexanoylphenyl)-2-methylhexyl acetate (1) 2-Methyl-2-(4-phenylbutyl)malonic acid diethyl ester In working example 1 (1), 4-phenylbutyl iodide was used instead of 2-(4-benzyloxyphenyl)ethyl iodide to give the subject compound as a colorless oil.

Rf value: 0.50 (ethyl acetate:hexane=1:9)
¹H-NMR(CDCl₃) δ: 1.22 (6H, t, J=7.3 Hz), 1.27 (2H, m), 1.39 (3H, s), 1.64 (2H, quint, J=7.8 Hz), 1.89 (2H, m), 2.61 (2H, t, J=7.8 Hz), 4.16 (4H, q, J=7.3 Hz), 7.17 (3H, m), 7.26 (2H, m)
IR(neat): 3028, 2983, 2938, 2862, 1733, 1253, 1162, 1111, 748, 700 cm⁻¹
MS(EI): 306(M⁺), 260, 186, 174, 158, 130, 115, 91.

(2) 2-Ethoxycarbonyl-2-methyl-6-phenylhexanoic acid

2-Methyl-2-(4-phenylbutyl)malonic acid diethyl ester was used in the. same manner as working example 26 (5) to give the subject compound as a yellowish oil.

Rf value: 0.60 (ethyl acetate:hexane:acetic acid=49:49:2)
¹H-NMR(CDCl₃) δ: 1.25 (3H, t, J=7.3 Hz), 1.31 (2H, m), 1.45 (3H, s), 1.64 (2H, quint, J=7.8 Hz), 2.61 (2H, t, J=7.8 Hz), 4.21 (2H, q, J=7.3 Hz), 7.16 (3H, m), 7.26 (2H, m)
IR(neat): 3028, 2986, 2938, 2863, 2649, 1733, 1699, 1454, 1249, 1179, 1118, 748, 700 cm⁻¹
MS(EI): 278(M⁺), 260, 186, 158, 146, 130, 91.

(3) Ethyl 2-methoxycarbonylamino-2-methyl-6-phenylhexanoate

2-Ethoxycarbonyl-2-methyl-6-phenylhexanoic acid was used in the same manner as working example 1 (3) to give the subject compound as a yellowish oil.

Rf value: 0.24 (ethyl acetate:hexane=1:9)
¹H-NMR(CDCl₃) δ: 1.09 (1H, m), 1.24 (3H, t, J=7.3 Hz), 1.31 (1H, m), 1.55 (3H, s), 1.59 (2H, m), 1.78 (1H, m), 2.18 (1H, m), 2.58 (2H, m), 3.64 (3H, s), 4.18 (2H, q, J=7.3 Hz), 5.56(1H, br.s), 7.16 (3H, m), 7.26 (2H, m)
IR(KBr): 3423, 3355, 3062, 3027, 2984, 2940, 2862, 1733, 1717, 1506, 1454, 1262, 1091, 781, 748, 700 cm⁻¹
MS(EI): 307 (M⁺), 234, 91.

(4) 2-Amino-2-methyl-6-phenylhexanol

Ethyl 2-methoxycarbonylamino-2-methyl-6-phenylhexanoate was used in the same manner as working example 26 (7), and then working example 28 (5) to give the subject compound as pale red crystals, melting at 54–550° C.

Rf value: 0.35 (chloroform:methanol=4:1)
¹H-NMR(CDCl₃) δ: 1.04 (3H, s), 1.35 (4H, m), 1.63 (5H, m), 2.63 (2H, t, J=7.8 Hz), 3.26 (1H, d, J=10.3 Hz), 3.31 (1H, d, J=10.3Hz), 7.18 (3H, m), 7.28 (2H, m)
IR(KBr): 3326, 3278, 3085, 2931,2765, 1607, 1497, 1452, 1021, 736, 697 cm⁻¹
MS(EI): 207(M⁺), 176, 117, 91, 74.

(5) 2-Acetamido-2-methyl-6-phenylhexyl acetate

2-Amino-2-methyl-6-phenylhexanol was used in the same manner as working example 34 (5) to give the subject compound as pale yellow crystals, melting at 65–67° C.

Rf value: 0.27 (ethyl acetate:hexane=1:1)
¹H-NMR(CDCl₃) δ: 1.28 (3H, s), 1.30 (2H, m), 1.63 (3H, m), 1.89 (1H, m), 1.92 (3H, s), 2.07 (3H, s), 2.61 (2H, t, J=7.8 Hz), 4.12 (1H, d, J=11.2 Hz), 4.27 (1H, d, J=11.2 Hz), 5.32 (1H, br.s), 7.17 (3H, m), 7.27 (2H, m)
IR(KBr): 3307, 3065, 3027, 2938, 2861, 1733, 1662, 1558, 1373, 1243, 1043, 752, 700 cm⁻¹
MS(EI): 291(M⁺), 218, 176, 91.

(6) 2-Acetamido-6-(4-hexanoylphenyl)-2-methylhexyl acetate

In working example 34 (6), hexanoyl chloride instead of octanoyl chloride, and 2-acetamido-2-methyl-6-phenylhexyl acetate instead of 2-acetamido-2-methyl-4-phenylbutyl acetate were respectively used to give the subject compound as white crystals, melting at 61–63° C.

Rf value: 0.22 (ethyl acetate:hexane=1:1)
¹H-NMR(CDCl₃) δ: 0.91 (3H, t, J=6.9 Hz), 1.27 (3H, s), 1.36 (6H, m), 1.60–1.75 (5H, m), 1.91 (1H, m), 1.93 (3H, s), 2.08 (3H, s), 2.67 (2H, t, J=7.1 Hz), 2.93 (2H, t, J=7.6 Hz), 4.10 (1H, d, J=11.3 Hz), 4.27 (1H, d, J=11.3 Hz), 5.32 (1H, br.s), 7.24 (2H, d, J=8.3 Hz), 7.88 (2H, d, J=8.3 Hz)
IR(KBr): 3367, 3316, 3076, 2934, 2862, 1739, 1683, 1373, 1243, 1042, 755 cm⁻¹
MS(EI): 389(M⁺), 316, 274.

WORKING EXAMPLE 44

2-Acetamido-2-methyl-6-(4-octanoylphenyl)hexyl acetate

In working example 43 (6), octanoyl chloride was used instead of hexanoyl chloride to give the subject compound as white crystals, melting at 63–66° C.

Rf value: 0.24 (ethyl acetate:hexane=1:1)
¹H-NMR(CDCl₃) δ: 0.88 (3H, t, J=7.1 Hz), 1.28 (3H, s), 1.29 (1OH, m), 1.60–1.76 (5H, m), 1.92 (1H, m), 1.93 (3H, s), 2.08 (3H, s), 2.67 (2H, t, J=7.8 Hz), 2.93 (2H, t, J=7.6 Hz), 4.10 (1H, d, J=11.3 Hz), 4.27 (1H, d, J=11.3 Hz), 5.34 (1H, br.s), 7.24 (2H, d, J=8.3 Hz), 7.88 (2H, d, J=8.3 Hz)
IR(KBr): 3345, 3322, 2931,2859, 1739, 1683, 1607, 1549, 1467, 1373, 1241, 1043, 755 cm⁻¹
MS(EI): 417(M⁺), 344, 302.

WORKING EXAMPLE 45

2-Acetamido-6-(4-decanoylphenyl)-2-methylhexyl acetate

In working example 43 (6), decanoyl chloride was used instead of hexanoyl chloride to give the subject compound as white crystals, melting at 61–64° C.

Rf value: 0.24 (ethyl acetate:hexane=1:1)

$^1$H-NMR(CDCl$_3$) δ: 0.88 (3H, t, J=7.1 Hz), 1.26 (14H, m), 1.28 (3H, s), 1.62–1.74 (5H, m), 1.92 (1H, m), 1.93 (3H, s), 2.08 (3H, s), 2.67 (2H, t, J=7.8 Hz), 2.93 (2H, t, J=7.6 Hz), 4.10 (1H, d, J=11.3 Hz), 4.27 (1H, d, J=11.3 Hz), 5.32 (1H, br.s), 7.24 (2H, d, J=8.3 Hz), 7.88 (2H, d, J=8.3 Hz)

IR(KBr): 3366, 3310, 3075, 2927, 2856, 1743, 1683, 1549, 1467, 1373, 1241, 1042, 756 cm$^{-1}$

MS(EI): 445(M$^+$), 385, 372, 330, 98.

WORKING EXAMPLE 46

2-Acetamido-6-(4-hexylphenyl)-2-methylhexyl acetate

2-Acetamido-6-(4-hexanoylphenyl)-2-methylhexyl acetate was used in the same manner as working example 37 to give the subject compound as a yellowish oil.

Rf value: 0.39(ethyl acetate:hexane=1:1)

$^1$H-NMR(CDCl$_3$) δ: 0.88 (3H, t, J=6.8 Hz), 1.28 (3H, s), 1.30 (8H, m), 1.60 (5H, m), 1.88 (1H, m), 1.92 (3H, s), 2.07 (3H, s), 2.57 (4H, m), 4.13 (1H, d, J=11.2 Hz), 4.28 (1H, d, J=11.2 Hz), 5.30 (1H, br.s), 7.07 (414, m)

IR(neat): 3307, 3077, 2929, 2858, 1747, 1652, 1558, 1372, 1242, 1042, 757 cm$^{-1}$

MS(EI): 375(M$^+$), 302, 260, 188.

WORKING EXAMPLE 47

2-Acetamido-2-methyl-6-(4-octylphenyl) hexyl acetate

2-Acetamido-2-methyl-6-(4-octanoylphenyl)hexyl acetate was used in the same manner as working example 37 to give the subject compound as a yellowish oil.

Rf value: 0.53 (ethyl acetate:hexane=1:1)

$^1$H-NMR(CDCl$_3$) δ: 0.88 (3H, t, J=6.8 Hz), 1.28 (3H, s), 1.30 (12H, m), 1.61 (5H, m), 1.90 (1H, m), 1.93 (3H, s), 2.07 (3H, s), 2.57 (4H, m), 4.13 (1H, d, J=11.2 Hz), 4.28 (1H, d, J=11.2 Hz), 5.30 (1H, br.s), 7.07 (4H, m)

IR(neat): 3302, 3082, 2929, 2856, 1748, 1652, 1554, 1467, 1373, 1242, 1042 cm$^{-1}$

MS(EI): 403(M$^+$), 330, 288, 216.

WORKING EXAMPLE 48

2-Acetamido-6-(4-decylphenyl)-2-methylhexyl acetate

2-Acetamido-6-(4-decanoylphenyl)-2-methylhexyl acetate was used in the same manner as working example 37 to give the subject compound as a yellowish oil.

Rf value: 0.51 (ethyl acetate:hexane=1:1)

$^1$H-NMR(CDCl$_3$) δ: 0.88 (3H, t, J=7.1 Hz), 1.26 (16H, m), 1.29 (3H, s), 1.60 (5H, m), 1.88 (1H, m), 1.93 (3H, s), 2.07 (3H, s), 2.57 (4H, m), 4.13 (1H, d, J=11.0 Hz), 4.27 (1H, d, J=11.0 Hz), 5.30 (1H, br.s), 7.07 (4H, m)

IR(neat): 3307, 3081, 2927, 2855, 1747, 1653, 1555, 1466, 1373, 1241, 1041, 721 cm$^{-1}$

MS(EI): 431(M$^+$), 358, 316, 244, 171.

WORKING EXAMPLE 49

2-Amino-6-(4-hexylphenyl)-2-methylhexanol hydrochloride

2-Acetamido-6-(4-hexylphenyl)-2-methylhexyl acetate was used in the same manner as working example 40 to give the subject compound as white crystals, melting at 109–111° C.

Rf value: 0.46 (chloroform:methanol=4:1)

$^1$H-NMR(CD$_3$OD) δ: 0.88 (3H, t, J=6.6 Hz), 1.21 (3H, s), 1.29–1.39 (8H, m), 1.55–1.68 (6H, m), 2.54 (2H, t, J=7.6 Hz), 2.60 (2H, t, J=7.6 Hz), 3.44 (1H, d, J=11.3 Hz), 3.51 (1H, d, J=11.3 Hz), 7.06 (4H, s)

IR(KBr): 3355, 3007, 2927, 2856, 1599, 1506, 1068, 832 cm$^{-1}$

MS(EI): 291(M$^+$), 260, 175, 117, 74

Elemental analysis

| | |
|---|---|
| Calculated | C; 69.59, H; 10.45, N; 4.27 |
| Found | C; 69.53, H; 10.64, N; 4.30 |

WORKING EXAMPLE 50

2-Amino-2-methyl-6-(4-octylphenyl)hexanol hydrochloride ¼ hydride

2-Acetamido-2-methyl-6-(4-octylphenyl)hexyl acetate was used in the same manner as working example 40 to give the subject compound as white crystals, melting at 99–100° C.

Rf value: 0.43 (chloroform:methanol=4:1)

$^1$H-NMR(CD$_3$OD) δ: 0.89 (3H, t, J=6.9 Hz), 1.21 (3H, s), 1.27–1.41 (12H, m), 1.56–1.68 (6H, m), 2.55 (2H, t, J=7.6 Hz), 2.61 (2H, t, J=7.6 Hz), 3.44 (1H, d, J=11.5 Hz), 3.51 (1H, d, J=11.5 Hz), 7.07 (4H, s)

IR(KBr): 3437, 3325, 3019, 2927, 2855, 1617, 1515, 1059 cm$^{-1}$

MS(EI): 319(M$^+$), 288, 74

Elemental analysis

| | |
|---|---|
| Calculated | C; 69.97, H; 10.76, N; 3.93 |
| Found | C; 69.93, H; 10.87, N; 3.88 |

WORKING EXAMPLE 51

2-Amino-6-(4-decylphenyl)-2-methylhexanol hydrochloride

2-Acetamido-6-(4-decylphenyl)-2-methylhexyl acetate was used in the same manner as working example 40 to give the subject compound as white crystals, melting at 93–96° C.

Rf value: 0.43 (chloroform:methanol=4:1)

$^1$H-NMR(CD$_3$OD) δ: 0.89 (3H, t, J=6.8 Hz), 1.21 (3H, s), 1.27–1.41 (16H, m), 1.56–1.68 (6H, m), 2.55 (2H, t, J=7.6 Hz), 2.61 (2H, t, J=7.6 Hz), 3.44 (1H, d, J=11.5 Hz), 3.51 (1H, d, J=11.5 Hz), 7.07 (4H, s)

IR(KBr): 3432, 3352, 3017, 2925, 2854, 1618, 1515, 1468, 1060, 830, 722 cm$^{-1}$

MS(EI): 347(M$^+$), 316, 288, 74

Elemental analysis

| | |
|---|---|
| Calculated | C; 71.93, H; 11.02, N; 3.65 |
| Found | C; 71.66, H; 11.24, N; 3.68 |

WORKING EXAMPLE 52

2-Amino-2-(2-(2-heptyloxyphenyl)ethyl)pentanol hydrochloride (1) 2-(2-Benzyloxyphenyl)ethanol To a solution of sodium ethoxide (10.8 g) in ethanol (500 ml), 2-(2-hydroxyphenyl)ethanol (20.0 g) and benzyl bromide (24.8 g) were added and the mixture was refluxed under heating for 2 hours. The solvent was distilled away under reduced pressure, water was added thereto and the mixture was extracted with ethyl acetate. The organic layer was washed with a 2M aqueous potassium hydroxide solution and a saturated brine and dried over sodium sulfate. The solvent was distilled away under reduced pressure and the residue was subjected to silica gel chromatography (eluent; hexane-ethyl acetate=8:1) to give the subject compound (27.2 g).

$^1$H-NMR(400 MHz, CDCl$_3$) δ: 1.60 (1H, t, J=5.9 Hz), 2.97 (2H, t, J=6.6 Hz), 3.87 (2H, q, J=6.4 Hz), 5.09 (2H, s), 6.93–6.95 (2H, m), 7.20–7.23 (2H, m), 7.39–7.42 (5H, m).

(2) 2-(2-Benzyloxyphenyl)ethyl iodide 2-(2-Benzyloxyphenyl)ethanol was used in the same manner as working example 26 (1) to give the subject compound.

$^1$H-NMR(400 MHz, CDCl$_3$) δ: 3.25 (2H, t, J=7.8 Hz), 3.40 (2H, t, J=7.8 Hz), 5.10 (2H, s), 6.91–6.94 (2H, m), 7.15–7.24 (2H, m), 7.33–7.42 (5H, m);

(3) Diethyl 2-(2-(2-benzyloxyphenyl)ethyl)-2-propylmalonate

To a suspension of sodium hydride (1.3 g) in dimethylformamide (15 ml), a solution of diethyl propylmalonate (6.6 g) in dimethylformamide (45 ml) was added under ice-cooling and the mixture was stirred at room temperature for an hour. To the solution was added a solution of 2-(2-benzyloxyphenylpethyl iodide (10 g) in dimethylformamide (30 ml), the mixture was stirred at the same temperature for an hour and left standing overnight. The reaction mixture was poured into water and extracted with ethyl acetate. The organic layer was washed with an aqueous sodium hydrogencarbonate solution and a saturated brine and dried over magnesium sulfate. The solvent was distilled away under reduced pressure and the residue was subjected to silica gel chromatography (eluent; hexane-ethyl acetate=8:1) to give the subject compound (10 g).

$^1$H-NMR(400 MHz, CDCl$_3$) δ: 0.80 (3H, t, J=8 Hz), 1.04–1.23 (2H, m), 1.18 (6H, t, J=8 Hz), 1.87–1.91 (2H, m), 2.12–2.17 (2H, m), 2.49–2.54 (2H, m), 4.00–4.15 (4H, m), 5.03 (2H, s), 6.86–6.89 (2H, m), 7.12 (2H, t, J=8 Hz), 7.29–7.41 (5H, m).

(4) 2-(2-(2-Benzyloxyphenyl)ethyl)-2-ethoxycarbonylpentanoic acid

To a solution of diethyl 2-(2-(2-benzyloxyphenyl)ethyl)-2-propylmalonate (10 g) in ethanol (50 ml), a solution of potassium hydroxide (1.9 g) in ethanol (180 ml) was added and the mixture was refluxed under heating for 6.5 hours. Ethanol (45 ml) was added thereto and the mixture was stirred at room temperature for 4 days. The reaction mixture was poured into a dilute hydrochloric acid and extracted with ethyl acetate. The organic layer was washed with a saturated brine and dried over sodium sulfate. The solvent was distilled away under reduced pressure and the residue was subjected to silica gel chromatography (eluent; chloroform-methnaol=12:1) to give the subject compound (5.7 g).

$^1$H-NMR(400 MHz, CDCl$_3$) δ: 0.86 (3H, t, J=8 Hz), 1.15 (3H, t, J=8 Hz), 1.05–1.25 (2H, m), 1.75–1.84 (1H, m), 1.95–2.05 (1H, m), 2.10–2.30 (2H, m, 2.60 (3H, t, J=8 Hz), 3.84–3.96 (1H, m), 4.06–4.17 (1H, m), 5.06 (2H, s), 6.87–6.89 (2H, m), 7.10–7.18 (2H, m), 7.27–7.44 (5H, m).

(5) Ethyl 2-(2-(2-benzyloxyphenyl)ethyl)-2-methoxycarbonylaminopentanoate

To a solution of 2-(2-(2-benzyloxyphenyl)ethyl)-2-ethoxycarbonylpentanoic acid (5.7 g) in tetrahydrofuran (100 ml), triethyl-amine (2.5 ml) and a solution of ethyl chloroformate (1.9 g) in tetrahydro-furan (3 ml) were added under ice-cooling and the mixture was stirred at the same temperature for 30 minutes. Then, sodium azide (1.2 g) and water (5 ml) were added thereto and the mixture was stirred at room temperature for 2 hours. The reaction mixture was poured into water and extracted with ethyl acetate. The organic layer was washed with a saturated brine, dried over sodium sulfate and the solvent was distilled away under reduced pressure.

The residue obtained was dissolved in benzene (90 ml), the solution was refluxed under heating for an hour and methanol (40 ml) and catalytic amount of paratoluene-sulfonic acid were added thereto and the mixture was left standing overnight. The reaction mixture was concentrated under reduced pressure and the residue was subjected to silica gel chromatography (eluent; hexane-ethyl acetate=4:1) to give the subject compound (2.3 g).

$^1$H-NMR(400 MHz, CDCl$_3$) δ: 0.85 (3H, t, J=8 Hz), 1.14 (3H, t, J=8 Hz), 1.17–1.36 (2H, m), 1.60–1.78 (1H, m), 2.00–2.16 (1H, m), 2.20–2.38 (1H, m), 2.40–2.54 (1H, m), 2.50–2.64 (2H, m), 3.59 (3H, s), 3.82–3.98 (1H, m), 4.00–4.16 (1H, m), 5.06 (2H, s), 5.81 (1H, s), 6.87 (2H, t, J=8 Hz), 7.06–7.18 (2H, m), 7.27–7.44 (5H, m).

(6) 2-Amino-2-(2-(2-benzyloxyphenyl)ethyl)pentanol

To a solution of ethyl 2-(2-(2-benzyloxyphenyl)ethyl)-2-methoxycarbonylaminopentanoate (2.3 g) in tetrahydrofuran (50 ml), under a nitrogen atmosphere, lithium borohydride (0.24 g) was added and the mixture was refluxed under heating for 2.5 hours. Then, a 2N dilute hydrochloric acid (5.5 ml) was added thereto and the mixture was stirred at room temperature for 30 minutes. The reaction mixture was poured into water and extracted with ethyl acetate. The organic layer was washed with a saturated brine, dried over sodium sulfate and the solvent was distilled away under reduced pressure. The residue obtained was dissolved in methanol (30 ml), and tetrahydrofuran (1 ml) and a 5N aqueous potassium hydroxide solution (10 ml) were added thereto and the mixture was refluxed under heating for 4 days. The reaction solution was poured into water and extracted with ethyl acetate. The organic layer was washed with a saturated brine, dried over sodium sulfate and the solvent was distilled away under reduced pressure. The reaction mixture was concentrated under reduced pressure to give the subject compound (1.1 g).

$^1$H-NMR(400 MHz, CDCl$_3$) δ: 0.84 (3H, t, J=8 Hz), 1.20–1.32 (4H, m), 1.32–1.50 (2H, m), 2.50–2.66 (2H, m), 3.29 (2H, s), 5.05 (2H, s), 6.88–6.96 (2H, m), 7.12–7.22 (2H, m), 7.27–7.48 (5H, m).

(7) 2-Acetamido-2-(2-(2-benzyloxyphenyl)ethyl)pentyl acetate

To a solution of 2-amino-2-(2-(2-benzyloxyphenyl)ethyl) pentanol (1.1 g) in methylene chloride (35 ml), triethylamine (1.2 ml) and acetyl chloride (0.5 ml) were added and the mixture was stirred at room temperature for 6 hours. The reaction mixture was poured into ice-water and extracted with ethyl acetate. The organic layer was washed with a dilute hydrochloric acid, an aqueous sodium hydrogencarbonate solution and a saturated brine and dried over magnesium sulfate. The solvent was distilled away under reduced pressure and the residue was subjected to silica gel chromatography (eluent; hexane-ethyl acetate=1:1) to give the subject compound (0.90 g).

¹H-NMR(400 MHz, CDCl₃) δ: 0.83 (3H, t, J=8 Hz), 1.20–1.28 (4H, m), 1.75 (3H, s), 1.60–1.90 (2H, m), 2.02 (3H, s), 2.57–2.63 (2H, m), 4.12 (1H, dd, J=20, 12 Hz), 4.33 (1H, dd, J=20, 12 Hz), 5.06 (2H, s), 5.18 (1H, s), 6.84–6.96 (2H, m), 7.10–7.22 (2H, m), 7.30–7.45 (5H, m).

(8) 2-Acetamido-2-(2-(2-hydroxyphenyl)ethyl)pentyl acetate

To a solution of 2-acetamido-2-(2-(2-benzyloxyphenyl) ethyl)pentyl acetate (0.90 g) in ethanol (45 ml), 10% palladium-carbon (0.40 g) was added and the mixture was subjected to catalytic reduction at room temperature for 6 hours. Catalyst was filtered off from the reaction solution and the solvent was distilled away under reduced pressure to give the subject compound (0.65 g).

¹H-NMR(400 MHz, CDCl₃) δ: 0.93 (3H, t, J=8 Hz), 1.24–1.40 (4H, m), 1.55–1.80 (2H, m), 2.04 (3H, s), 2.12 (3H, s), 2.50–2.63 (2H, m), 4.05–4.23 (2H, m), 5.66 (1H, s), 6.79–6.88 (3H, m), 7.04 (1H, d, J=8 Hz), 7.13 (1H, t, J=8 Hz).

(9) 2-Acetamido-2-(2-(2-heptyloxyphenyl)ethyl)pentyl acetate

To a suspension of sodium hydride (85 mg) in dimethylformamide (5 ml), a solution of 2-acetamido-2-(2-(2-hydroxyphenyl)ethyl)pentyl acetate (0.65 g) in dimethylformamide (5 ml) was added under ice-cooling and the mixture was stirred at room temperature for an hour. To the solution, a solution of heptyl bromide (0.42 g) in tetrahydrofuran (4 ml) was added. The mixture was stirred at the same temperature for 6 hours and left standing overnight. The reaction mixture was poured into water and extracted with ethyl acetate. The organic layer was washed with an aqueous sodium hydrogencarbonate solution and a saturated brine and dried over magnesium sulfate. The solvent was distilled away under reduced pressure and the residue was subjected to silica gel chromatography (eluent; chloroform-methanol= 12:1) to give the subject compound (0.36 g).

¹H-NMR(400 MHz, CDCl₃) δ: 0.89 (3H, t, J=8 Hz), 0.93 (3H, t, J=8 Hz), 1.22–1.40 (10H, m), 1.40–1.55 (2H, m), 1.50–1.70 (2H, m), 1.80–2.10 (2H, m), 1.93 (3H, s), 2.07 (3H, s), 2.58 (2H, t, J=8 Hz), 3.96 (2H, t, J=8 Hz), 4.35–4.40 (2H, m), 5.25 (1H, s), 6.81–6.88 (2H, m), 7.10–7.17 (2H, m).

(10) 2-Amino-2-(2-(2-heptyloxyphenyl)ethyl)pentanol hydrochloride

To a solution of 2-acetamido-2-(2-(2-heptyloxyphenyl) ethyl)pentyl acetate (0.36 g) in methanol (20 ml), lithium hydroxide monohydrate (0.43 g) and water (5 ml) were added and the mixture was refluxed under heating for 7 hours. The reaction mixture was poured into water and extracted with ethyl acetate. The organic layer was washed with a saturated brine, dried over sodium sulfate and the solvent was distilled away under reduced pressure. Thereto was added a solution of hydrochloric acid in ether to form hydrochloride, crystallization from hexane and recrystallization from ethyl acetate gave the subject compound (0.28 g).

¹H-NMR(400 MHz, DMSO) δ: 0.86 (3H, t, J=8 Hz), 0.90 (3H, t, J=8 Hz), 1.20–1.46 (10H, m), 1.50–1.60 (2H, m), 1.62–1.78 (4H, m), 2.50–2.60 (2H, m), 3.40–3.50 (2H, m), 3.93 (2H, t, J=8 Hz), 5.47 (1H, t, J=4 Hz), 6.85 (1H, t, J=8 Hz), 6.92 (1H, d, J=8 Hz), 7.11–7.17 (2H, m), 7.70–7.85 (3H, bs)

IR(KBr) cm⁻¹: 3254, 3115, 2924, 2870, 1602, 1497, 1242
MS: 322(M⁺+1), 304, 290, 278, 205
Elemental analysis

| | |
|---|---|
| Calculated | C; 67.10, H; 10.14, N; 3.91 |
| Found | C; 66.70, H; 10.28, N; 3.91 |

WORKING EXAMPLE 53

2-Amino-4-(2-heptyloxyphenyl)-2-methylbutanol hydrochloride (1) Diethyl 2-(2-(2-benzyloxyphenyl)ethyl)-2-methylmalonate 2-Methylmalonic acid diethyl ester and 2-(2-benzyloxyphenyl)ethyl iodide were used in the same manner as working example 52 (3) to give the subject compound.

¹H-NMR(400 MHz, CDCl₃) δ: 1.21 (6H, t, J=8 Hz), 1.45 (;3H, s), 2.14–2.18 (2H, m), 2.60–2.64 (2H, m), 4.09–4.17 (4H, m), 5.07 (2H, s), 6.88–6.91 (2H, m), 7.14–7.18 (2H, m), 7.29–7.44 (5H, m).

(2) 4-(2-Benzyloxyphenyl)-2-ethoxycarbonyl-2-methylbutanoic acid

Diethyl 2-(2-(2-benzyloxyphenyl)ethyl)-2-methylmalonate was used in the same manner as working example 52 (4) to give the subject compound.

¹H-NMR(400 MHz, CDCl₃) δ: 1.18 (3H, t, J=8 Hz), 1.48 (3H, s), 2.10–2.22 (2H, m), 2.62 (2H, t, J=8 Hz), 4.00–4.14 (2H, m), 5.04 (2H, s), 6.85–6.89 (2H, m), 7.10–7.16 (2H, m), 7.28–7.42 (5H, m).

(3) Ethyl 4-(2-benzyloxyphenyl)-2-methoxycarbonylamino-2-methylbutanoate 4-(2-Benzyloxyphenyl)-2-ethoxycarbonyl-2-methylbutanoic acid was used in the same manner as working example 52 (5) to give the subject compound.

¹H-NMR(400 MHz, CDCl₃) δ: 1.17 (3H, t, J=8 Hz), 1.58 (3H, s), 2.05–2.15 (1H, m), 2.30–2.43 (1H, m), 2.47–2.57 (1H, m), 2.60–2.70 (1H, m), 3.59 (3H, s), 3.95–4.15 (2H, m), 5.08 (2H, s), 5.57–6.63 (1H, bs), 6.86–6.89 (2H, m), 7.10–7.16 (2H, m), 7.28–7.44 (5H, m).

(4) 4-(2-(2-Benzyloxyphenyl)ethyl)-4-methyl-2-oxazolidinone

To a solution of ethyl 4-(2-benzyloxyphenyl)-2-methoxycarbonylamino-2-methylbutanoate (5.2 g) in tetrahydrofuran (135 ml), under a nitrogen atmosphere, lithium borohydride (0.59 g) was added and the mixture was refluxed under heating for an hour. Then, a 2N hydrochloric acid (6.6 ml) was added thereto and the mixture was stirred at room temperature for 30 minutes. The reaction mixture was poured into water and extracted with ethyl acetate. The organic layer was washed with an aqueous sodium hydrogencarbonate solution and a saturated brine and dried over sodium sulfate. The solvent was distilled away under reduced pressure to give the subject compound (4.6 g).

¹H-NMR(400 MHz, CDCl₃) δ: 1.31 (3H, s), 1.85 (2H, t, J=8 Hz), 2.57–2.77 (2H, m), 4.04 (2H, dd, J=64, 8 Hz), 5.07 (2H, s), 6.89–6.95 (2H, m), 7.12–7.26 (2H, m), 7.35–7.42 (5H, m).

(5) 4-(2-(2-Hydroxyphenyl)ethyl)-4-methyl-2-oxazolidinone

To a solution of 4-(2-(2-benzyloxyphenyl)ethyl)-4-methyl-2-oxazolidinone (4.60 g) in ethanol (200 ml), 10% palladium-carbon (0.60 g) was added and the mixture was subjected to catalytic reduction at room temperature for 6 hours. Catalyst was filtered off form the reaction solution and the solvent was distilled away under reduced pressure. The residue was crystallized from ether-isopropyl ether to give the subject compound (2.0 g).

¹H-NMR(400 MHz, CDCl3) δ: 1.38 (3H, s), 1.91 (2H, t, J=8 Hz), 2.62–2.77 (2H, m), 4.16 (2H, dd, J=60, 8 Hz), 5.65 (1H, s), 5.90 (1H, s), 6.78 (1H, d, J=8 Hz), 6.86 (1H, t, J=8 Hz), 7.05–7.12 (2H, m).

(6) 4-(2-(2-Heptyloxyphenyl)ethyl)-4-methyl-2-oxazolidinone

To a suspension of sodium hydride (90 mg) in dimethylformamide (1 ml), under ice-cooling, a solution of 4-(2-(2-hydroxyphenyl)ethyl)-4-methyl-2-oxazolidinone (0.50 g) in dimethylformamide (2 ml) was added and the mixture was stirred at room temperature for 2 hours. To the solution, a solution of heptyl bromide (0.47 g) in tetrahydrofuran (2 ml) was added and the mixture was stirred at the same temperature for 5.5 hours. The reaction mixture was poured into water and extracted with ethyl acetate. The organic layer was washed with a saturated brine and dried over magnesium sulfate. The solvent was distilled away under reduced pressure and the residue was subjected to silica gel chromatography (eluent; hexane ethyl acetate=1:1) to give the subject compound (0.60 g).

¹H-NMR(400 MHz, CDCl₃) δ: 0.90 (3H, t, J=8 Hz), 1.40 (3H, s), 1.20–1.55 (8H, m), 1.75–1.90 (4H, m), 2.57–2.73 (2H, m), 3.97 (2H, t, J=8 Hz), 4.15 (2H, dd, J=56, 8 Hz), 4.85 (1H, s), 6.83–6.89 (2H, m), 7.10–7.20 (2H, m).

(7) 2-Amino-4-(2-heptyloxyphenyl)-2-methylbutanol hydrochloride

To a solution of 4-(2-(2-heptyloxyphenyl)ethyl)-4-methyl-2-oxazolidinone (0.60 g) in methanol (20 ml), tetrahydrofuran (3 ml) and a 5N aqueous potassium hydroxide solution (3.4 ml) were added and the mixture was refluxed under heating for 6 days. The reaction mixture was poured into water and extracted with ethyl acetate. The organic layer was washed with a saturated brine, dried over sodium sulfate and the solvent was distilled away under reduced pressure. Thereto was added a solution of hydrochloric acid in ether to form hydrochloride. The salt was crystallized from ethyl acetate-hexane and recrystallized from ethyl acetate to give the subject compound (0.47 g).

¹H-NMR(400 MHz, DMSO) δ: 0.86 (3H, t, J=8 Hz), 1.21 (3H, s), 1.23–1.38 (6H, m), 1.40–1.50 (2H, m), 1.65–1.76 (4H, m), 2.54 (2H, t, J=8 Hz), 3.40–3.49 (2H, m), 3.93 (2H, t, J=8 Hz), 5.49 (1H, t, J=4 Hz), 6.84 (1H, t, J=8Hz), 6.91 (1H, d, J=8 Hz), 7.11–7.16 (2H, m), 7.84–7.95 (3H, bs)

IR(KBr) cm⁻¹: 3196, 2934, 2688, 1601, 1534, 1498, 1243
MS: 293(M⁺), 262, 245, 205, 147
Elemental analysis

| | |
|---|---|
| Calculated | C; 65.53, H; 9.78, N; 4.25 |
| Found | C; 65.38, H; 9.86, N; 4.22 |

WORKING EXAMPLE 54

2-Amino-2-methyl-4-(2-nonyloxyphenyl)butanol hydrochloride 1/8hydrate (1) 4-Methyl-4-(2-(2-nonyloxyphenyl)ethyl)-2-oxazolidinone In working example 53 (6), nonyl bromide instead of heptyl bromide was used in the same manner to give the subject compound.

¹H-NMR(400 MHz, CDCl₃) δ: 0.89 (3H, t, J=8 Hz), 1.39 (3H, s), 1.20–1.55 (12H, m), 1.75–1.89 (4H, m), 2.60–2.75 (2H, m), 3.97 (2H, t, J=8 Hz), 4.14 (2H, dd, J=56, 8 Hz), 4.84 (1H, s), 6.83–6.89 (2H, m), 7.09–7.11 (1H, m), 7.16–7.20 (1H, m).

(2) 2-Amino-2-methyl-4-(2-nonyloxyphenyl)butanol hydrochloride 1/8hydrate

4-Methyl-4-(2-(2-nonyloxyphenyl)ethyl)-2-oxazolidinone was used in the same manner as working example 53 (7) to give the subject compound.

¹H-NMR(400 MHz, DMSO) δ: 0.85 (3H, t, J=8 Hz), 1.20 (3H, s), 1.23–1.36 (10H, m), 1.38–1.48 (2H, m), 1.65–1.77 (4H, m), 2.50–2.62 (2H, m), 3.38–3.39 (2H, m), 3.93 (2H, t, J=8 Hz), 5.46–5.48 (1H, bs), 6.84 (1H, t, J=8 Hz), 691 (1H, d, J=8 Hz), 7.10–7.17 (2H, m), 7.62–7.83 (3H, bs)

IR(KBr) cm⁻¹: 3188, 2923, 2855, 2685, 1601, 1498, 1243
MS: 321(M⁺), 306, 290, 273, 163
Elemental analysis

| | |
|---|---|
| Calculated | C; 66.69, H; 10.14, N; 3.89 |
| Found | C; 66.68, H; 10.28, N; 3.93 |

WORKING EXAMPLE 55

2-Amino-2-[2-(3-heptyloxyphenyl)ethyl]pentanol hydrochloride (1) 2-(3-Benzyloxyphenyl)ethanol 2-(3-Hydroxyphenyl)ethanol was used in the same manner as working example 52 (1) to give the subject compound.

¹H-NMR(400 MHz, CDCl₃) δ: 1.37 (1H, t, J=6.3 Hz), 2.85 (2H, t, J=6.3 Hz), 3.86 (2H, q, J=6.3 Hz), 5.06 (2H, s), 6.83–6.87 (3H, m), 7.22–7.45 (6H, m).

(2) 2-(3-Benzyloxyphenyl)ethyl iodide 2-(3-Benzyloxyphenyl)ethanol was used in the same manner as working example 52 (2) to give the subject compound.

¹H-NMR(400 MHz, CDCl₃) δ: 3.15 (2H, t, J=7.7 Hz), 3.34 (2H, t, J=7.7 Hz), 5.06 (2H, s), 6.79–6.90 (3H, m), 7.21–7.44 (6H, m).

(3) 2-[2-(3-Benzyloxyphenyl)ethyl]-2-propylmalonic acid diethyl ester 2-(3-Benzyloxyphenyl)ethyl iodide was used in the same manner as working example 52 (3) to give the subject compound.

¹H-NMR(400 MHz, CDCl₃) δ: 0.94 (3H, t, J=7.4 Hz), 1.21–1.28 (2H, m), 1.26 (6H, t, J=7.3 Hz), 1.93 (2H, m), 2.18 (2H, m), 2.48 (2H, m), 4.19 (4H, q, J=7.3 Hz), 5.05 (2H, s), 6.79 (3H, m), 7.20 (1H, t, J=7.8 Hz), 7.31–7.45 (5H, m).

(4) 2-[2-(3-Benzyloxyphenyl)ethyl]-2-ethoxycarbonylpentanoic acid

2-[2-(3-Benzyloxyphenyl)ethyl]-2-propylmalonic acid diethyl ester was used in the same manner as working example 52 (4) to give the subject compound.

¹H-NMR(400 MHz, CDCl₃) δ: 0.91 (3H, t, J=7.4 Hz), 1.29 (3H, t, J=7.3 Hz), 1.21–1.28 (2H, m), 1.86 (1H, m), 1.99 (1H, m), 2.18 (1H, m), 2.30 (1H, m), 2.40 (1H, m), 2.58 (1H, m), 4.23 (2H, m), 5.04 (2H, s), 6.78 (3H, m), 7.19 (1H, t, J=7.8 Hz), 7.32–7.44 (5H, m).

(5) Ethyl 2-[2-(3-benzyloxyphenyl)ethyl]-2-methoxycarbonylaminopentanoate

2-[2-(3-Benzyloxyphenyl)ethyl]-2-ethoxycarbonylpentanoic acid was used in the same manner as working example 52 (5) to give the subject compound.

¹H-NMR(400 MHz, CDCl₃) δ: 0.86 (3H, t, J=7.3 Hz), 0.97 (1H, m), 1.26 (3H, t, J=7.3 Hz), 1.30 (1H, m), 1.68 (1H, m), 2.05 (1H, m), 2.25 (2H, m), 2.57 (1H, m), 2.68 (1H, m), 3.63 (3H, s), 4.17 (2H, m), 5.02 (2H, s), 5.83 (1H, s), 6.75 (3H, m), 7.15 (1H, t, J=7.8 Hz), 7.29–7.43 (5H, m).

(6) 2-Acetamido-2-[2-(3-benzyloxyphenyl)ethyl]pentyl acetate

Ethyl 2-[2-(3-benzyloxyphenyl)ethyl]-2-methoxycarbonylaminopentanoate was used in the same manner as working example 52 (6) and (7) to give the subject compound.

$^1$H-NMR(400 MHz, CDCl$_3$) δ: 0.91 (3H, t, J=7.3 Hz), 1.26 (2H, m), 1.71 (2H, m), 1.91 (3H, s), 1.94 (1H, m), 2.07 (3H, s), 2.10 (1H, m), 2.52 (2H, t, J=8.3 Hz), 4.27 (1H, d, J=11.2), 4.31 (1H, d, J=11.2), 5.03 (2H, s), 5.23 (1H, s), (6.78 (3H, m), 7.17 (1H, t, J=7.8 Hz), 7.30–7.43 (5H, m).

(7) 2-Acetamido-2-[2-(3-hydroxyphenyl)ethyl]pentyl acetate

2-Acetamido-2-[2-(3-benzyloxyphenyl)ethyl]pentyl acetate was used in the same manner as working example 52 (8) to give the subject compound.

$^1$H-NMR(400 MHz, CDCl$_3$) δ: 0.93 (3H, t, J=7.3 Hz), 1.25 (2H, m), 1.73 (2H, m), 1.92 (3H, s), 1.94 (1H, m), 2.08 (3H, s), 2.10 (1H, m), 2.53 (2H, t, J=8.3 Hz), 4.26 (1H, d, J=11.2), 4.31 (1H, d, J=11.2), 5.56 (1H, s), 6.72 (3H, m), 7.15 (1H, t, J=7.8 Hz).

(8) 2-Acetamido-2-[2-(3-heptyloxyphenyl)ethyl]pentyl acetate

2-Acetamido-2-[2-(3-hydroxyphenyl)ethyl]pentyl acetate was used in the same manner as working example 52 (9) to give the subject compound.

$^1$H-NMR(400 MHz, CDCl$_3$) δ: 0.87 (3H, t, J=7.3 Hz), 0.91 (3H, t, J=7.3 Hz), 1.22–1.40 (10H, m), 1.73 (4H, m), 1.80–2.10 (2H, m), 1.91 (3H, s), 2.49 (3H, s), 2.51 (2H, t, J=8.3 Hz), 3.91 (2H, t, J=6.8 Hz), 4.28 (1H, d, J=11.2), 4.30 (1H, d, J=11.2), 5.21 (1H, s), 6.71 (3H, m), 7.15 (1H, t, J=7.8 Hz).

(9) 2-Amino-2-[2-(3-heptyloxyphenyl)ethyl]pentanol hydrochloride

2-Acetamido-2-[2-(3-heptyloxyphenyl)ethyl]pentyl acetate was used in the same manner as working example 52 (10) to give the subject compound as a yellowish oily substance.

$^1$H-NMR(400 MHz, DMSO) δ: 0.85 (6H, m), 1.22–1.38 (10H, m), 1.68 (4H, m), 1.90 (2H, m), 2.62 (2H, m), 3.65 (2H, s), 3.87 (2H, t, J=6.8 Hz), 5.70 (3H, bs), 6.65–6.76 (3H, m), 7.08 (1H, t, J=7.8 Hz)

IR(neat): 3354, 2933, 1584, 1261, 1159, 1056, 774, 696 cm$^{-1}$

MS(EI): 321(M$^+$)

Elemental analysis

| Calculated | C; 66.77, H; 10.14, N; 3.89 |
| Found | C; 66.52, H; 10.18, N; 3.86 |

WORKING EXAMPLE 56

2-Amino-2-[2-(3-octyloxyphenyl)ethyl]pentanol hydrochloride

2-Acetamido-2-[2-(3-hydroxyphenyl)ethyl]pentyl acetate and octyl bromide were used in the same manner as working example 52 (9) and (10) to give the subject compound as a yellowish oily substance.

$^1$H-NMR(400 MHz, DMSO) δ: 0.85 (6H, m), 1.19–1.36 (12H, m), 1.68 (4H, m), 1.89 (2H, m), 2.61 (2H, m), 3.63 (2H, s), 3.87 (2H, t, J=6.8 Hz), 5.80 (3H, bs), 6.64–6.76 (3H, m), 7.08 (1H, t, J=7.8 Hz)

IR(neat): 3355, 2932, 1584, 1261, 1159, 1051, 775, 695 cm$^{-1}$

MS(EI): 335(M$^+$)

Elemental analysis

| Calculated | C; 67.81, H; 10.30, N; 3.77 |
| Found | C; 67.58, H; 10.41, N; 3.72 |

WORKING EXAMPLE 57

2-Amino-4-(3-heptyloxyphenyl)-2-methylbutanol hydrochloride (1) 2-[2-(3-Benzyloxyphenyl)ethyl]-2-Methylmalonic acid diethyl ester 2-(3-Benzyloxyphenyl)ethyl iodide and 2-Methylmalonic acid diethyl ester were used in the same manner as working example 52 (3) to give the subject compound.

$^1$H-NMR(400 MHz, CDCl$_3$) δ: 1.26 (6H, t, J=7.3 Hz), 1.49 (3H, s), 2.16 (2H, m), 2.55 (2H, m), 4.19 (4H, q, J=7.3 Hz), 5.05 (2H, s), 6.81 (3H, m), 7.20 (1H, t, J=7.8 Hz), 7.32–7.45 (5H, m).

(2) 4-(3-Benzyloxyphenyl)-2-ethoxycarbonyl-2-methylbutanoic acid

2-[2-(3-Benzyloxyphenyl)ethyl]-2-Methylmalonic acid diethyl ester was used in the same manner as working example 52 (4) to give the subject compound.

$^1$H-NMR(400 MHz, CDCl$_3$) δ: 1.29 (3H, t, J=7.3 Hz), 1.53 (3H, s), 2.18 (2H, m), 2.58 (2H, m), 4.23 (2H, m), 5.04 (2H, s), 6.78 (3H, m), 7.19 (1H, t, J=7.8 Hz), 7.32–7.44 (5H, m).

(3) Ethyl 4-(3-Benzyloxyphenyl)-2-methoxycarbonylamino-2-methylbutanoate 4-(3-Benzyloxyphenyl)-2-ethoxycarbonyl-2-methylbutanoic acid was used in the same manner as working example 52 (5) to give the subject compound.

$^1$H-NMR(400 MHz, CDCl$_3$) δ: 1.26 (3H, t, J=7.3 Hz), 1.59 (3H, s), 2.09 (1H, m), 2.34 (1H, m), 2.57 (2H, m), 3.64 (3H, s), 4.17 (2H, m), 5.02 (2H, s), 5.67 (1H, s), 6.76 (3H, m), 7.16 (1H, t, J=7.8 Hz), 7.29–7.43 (5H, m).

(4) 2-Acetamido-4-(3-benzyloxyphenyl)-2-methylbutyl acetate

Ethyl 4-(3-Benzyloxyphenyl)-2-methoxycarbonylamino-2-methylbutanoate was used in the same manner as working example 52 (6) and (7) to give the subject compound.

$^1$H-NMR(400 MHz, CDCl$_3$) δ: 1.34 (3H, s), 1.89 (3H, s), 1.93 (1H, m), 2.07 (3H, s), 2.18 (1H, m), 2.56 (2H, t, J=8.3 Hz), 4.16 (H, d, J=11.2), 4.31 (1H d, J=11.2), 5.03 (2H, s), 5.36 (1H, s), 6.78 (3H, m), 7.17 (1H, t, J=7.8 Hz), 7.30–7.42 (5H, m).

(5) 2-Acetamido-4-(3-hydroxyphenyl)-2-methylbutyl acetate

2-Acetamido-4-(3-benzyloxyphenyl)-2-methylbutyl acetate was used in the same manner as working example 52 (8) to give the subject compound.

$^1$H-NMR(400 MHz, CDCl$_3$) δ: 1.33 (3H, s), 1.88 (3H, s), 1.94 (1H, m), 2.06 (3H, s), 2.20 (1H, m), 2.52 (2H, t, J=8.3 Hz), 4.14 (1H, d, J=11.2), 4.32 (1H, d, J=11.2), 5.59 (1H, s), 6.68 (3H, m), 7.09 (1H, t, J=7.8 Hz).

(6) 2-Acetamido-4-(3-heptyloxyphenyl)-2-methylbutyl acetate

2-Acetamido-4-(3-hydroxyphenyl)-2-methylbutyl acetate was used in the same manner as working example 52 (9) to give the subject compound.

$^1$H-NMR(400 MHz, CDCl$_3$) δ: 0.87 (3H, t, J=6.8 Hz), 1.35 (3H, s), 1.24–1.43 (8H, m), 1.89 (3H, s), 1.92 (1H, m), 2.07 (3H, s), 2.19 (1H, m), 2.55 (2H, t, J=8.3 Hz), 3.91 (2H, t, J=6.8), 4.16 (1H, d, J=11.2), 4.31 (1H, d, J=11.2), 5.35 (1H, s), 6.71 (3H, m), 7.15 (1H, t, J=7.8 Hz).

(7) 2-Amino-4-(3-heptyloxyphenyl)-2-methylbutanol hydrochloride

2-Acetamido-4-(3-heptyloxyphenyl)-2-methylbutyl acetate was used in the same manner as working example 52 (10) to give the subject compound as white crystals, melting at 133–136° C.

$^1$H-NMR(400 MHz, CDCl$_3$) δ: 0.86 (3H, t, J=6.8 Hz), 1.54 (3H, s), 1.26–1.37 (8H, m), 1.70 (2H, quint, J=6.8 Hz), 2.0 (2H, m), 2.6 (2H, m), 3.60 (1H, d, J=12.2 Hz), 3.65 (1H, d, J=12.2 Hz), 3.86 (2H, t, J=6.8 Hz), 6.64–6.74 (3H, m), 7.03 (1H, t, J=7.8 Hz), 8.04 (3H, s)

IR(neat): 3360, 2922, 1611, 1268, 1164, 1063, 771,697 cm$^{-1}$

MS(EI): 293(M$^+$)

Elemental analysis

| | |
|---|---|
| Calculated | C; 65.53, H; 9.78, N; 4.25 |
| Found | C; 65.25, H; 9.92, N; 4.20 |

WORKING EXAMPLE 58

2-Amino-4-(3-octyloxyphenyl)-2-methylbutanol hydrochloride

2-Acetamido-4-(3-hydroxyphenyl)-2-methylbutyl acetate and octyl bromide were used in the same manner as working example 52 (9) and (10) to give the subject compound as white crystals, melting at 130–132° C.

$^1$H-NMR(400 MHz, CDCl$_3$) δ: 0.86 (3H, t, J=6.8 Hz), 1.34 (3H, s), 1.25–1.39 (10H, m), 1.70 (2H, quint, J=6.8 Hz), 2.0 (2H, m), 2.6 (2H, m), 3.61 (1H, d, J=12.2 Hz), 3.65 (1H, d, J=12.2 Hz), 3.86 (2H, t, J=6.8 Hz), 6.64–6.74 (3H, m), 7.07 (1H, t, J=7.8 Hz), 8.04 (3H, s)

IR(neat): 3357, 2921, 1584, 1270, 1165, 1064, 773, 697 cm$^{-1}$

MS(EI): 307(M$^+$)

Elemental analysis

| | |
|---|---|
| Calculated | C; 66.01, H; 9.97, N; 4.05 |
| Found | C; 65.94, H; 10.16, N; 4.04 |

WORKING EXAMPLE 59

2-Amino-2-[2-(4-heptyloxyphenyl)ethyl]hexanol 1/10hydrate (1) 2-[2-(4-heptyloxyphenyl)ethyl]-2-butylmalonic acid diethyl ester In working example 1 (1), butylmalonic acid diethyl ester instead of methylmalonic acid, and 2-(4-heptyloxyphenyl) ethyl iodide instead of 2-(4-benzyloxyphenyl)ethyl iodide were used to give the subject compound as a yellowish oil.

Rf value: 0.33 (ethyl acetate:hexane=1:9)

$^1$H-NMR(CDCl$_3$) δ: 0.89 (3H, t, J=6.9 Hz), 0.90 (3H, t, J=7.3 Hz), 1.16–1.36 (10H, m), 1.26 (6H, t, J=7.3 Hz), 1.43–1.46 (2H, m), 1.74–1.78 (2H, m), 1.92–1.97 (2H, m), 2.12–2.16 (2H, m), 2.41–2.46 (2H, m), 3.92 (2H, t, J=6.6 Hz), 4.19 (4H, q, J=7.3 Hz), 6.81 (2H, d, J=8.6 Hz), 7.07 (2H, d, J=8.6 Hz)

IR(neat): 2957, 2930, 2860, 1732, 1612, 1512, 1468, 1245, 1177, 1027, 827 cm$^{-1}$

MS(EI): 434(M$^+$), 346, 218, 173, 121, 107.

(2) 2-Ethoxycarbonyl-2-[2-(4-heptyloxyphenyl)ethyl] hexanoic acid

2-[2-(4-Heptyloxyphenyl)ethyl]-2-butylmalonic acid diethyl ester was used in the same manner as working example 26 (5) to give the subject compound as a yellowish oil.

Rf value: 0.63 (ethyl acetate:hexane:acetic acid=49:49:2)

$^1$H-NMR(CDCl$_3$) δ: 0.88 (3H, t, J=7.1 Hz), 0.89 (3H, t, J=6.3 Hz), 1.09–1.12 (2H, m), 1.24–1.35 (8H, m), 1.32 (3H, t, J=7.3 Hz), 1.40–1.46 (2H, m), 1.76 (2H, quint, J=7.6 Hz), 1.85–1.91 (1H, m), 2.00–2.06 (1H, m), 2.11–2.18 (1H, m), 2.25–2.33 (1H, m), 2.32–2.39 (1H, m), 2.52–2.58 (1H, m), 3.92 (2H, t, J=6.6 Hz), 4.17–4.27 (2H, m), 6.80 (2H, d, J=8.6 Hz), 7.04 (2H, d, J=8.6 Hz)

IR(neat): 3188, 2959, 2932, 2861, 2675, 1733, 1713, 1512, 1469, 1244, 1178, 1025, 826 cm$^{-1}$

MS(EI): 406(M$^+$), 218, 173, 120, 107.

(3) Ethyl 2-[2-(4-heptyloxyphenyl)ethyl)]-2-methoxycarbonylaminohexanoate

In working example 1 (3), 2-ethoxycarbonyl-2-[2-(4-heptyloxyphenyl)-ethyl)]hexanoic acid instead of potassium 2-ethoxycarbonyl-2-methyl-4-(4-benzyloxyphenyl) butanoate was used to give the subject compound as a yellowish oil.

Rf value: 0.32 (ethyl acetate:hexane=1:9)

$^1$H-NMR(CDCl$_3$) δ: 0.86 (3H, t, J=7.1 Hz), 0.89 (3H, t, J=6.8 Hz), 1.24–1.31 (10H, m), 1.29 (3H, t, J=6.6 Hz), 1.42–1.46 (2H, m), 1.72–1.79 (3H, m), 2.05 (1H, m), 2.20–2.33 (2H, m), 2.51–2.67 (2H, m), 3.65 (3H, br.s), 3.91 (2H, t, J=6.6 Hz), 4.11–4.22 (2H, m), 5.84 (1H, br.s), 6.79 (2H, d, J=8.6 Hz), 7.03 (2H, d, J=8.6 Hz)

IR(neat): 3424, 2957, 2933, 1723, 1514, 1468, 1245, 1086, 1042, 827 cm$^{-1}$

MS(EI): 435(M$^+$), 217.

(4) 2-Amino-2-[2-(4-heptyloxyphenyl)ethyl]hexanol 1/10hydrate

Ethyl 2-[2-(4-heptyloxyphenyl)ethyl]-2-methoxycarbonylaminohexanoate was used in the same manners as working example 26 (7), and then working example 28 (5) to give the subject compound as a white powder, melting at 47–49° C.

Rf value: 0.61 (chloroform:methanol=4:1)

$^1$H-NMR(D)MSO-d$_6$) δ: 0.85 (3H, t, J=6.8 Hz), 0.87 (3H, t, J=5.4 Hz), 1.25–1.45 (16H, m), 1.67 (2H, quint, J=7.4 Hz), 2.42–2.48 (2H, m), 3.29 (2H, s), 3.88 (2H, t, J=6.4 Hz), 6.79 (2H, d, J=8.5 Hz), 7.09 (2H, d, J=8.5 Hz)

IR(KBr): 3328, 3280, 3124, 3031, 2956, 2933, 2858, 1613, 1513, 1249, 1073, 1042, 825 cm$^{-1}$

MS(EI): 335(M$^+$), 304, 205, 116, 107

Elemental analysis

| | |
|---|---|
| Calculated | C; 74.77, H; 11.11, N; 4.15 |
| Found | C; 74.62, H; 11.37, N; 4.16 |

WORKING EXAMPLE 60

2-Amino-2-isopropyl-4-(4-heptyloxyphenyl)butanol hydrochloride 1/2hydrate (1) 2-[2-(4-Heptyloxyphenyl)ethyl]-2-isopropylmalonic acid diethyl ester In working example 1 (1), isoprpylmalonic acid diethyl ester instead of Methylmalonic acid diethyl ester, and 2-(4-heptyloxyphenyl)ethyl iodide instead of 2-(4-benzyloxyphenyl)ethyl iodide were used to give the subject compound as a yellowish oil.

Rf value: 0.53 (ethyl acetate:hexane=1:9)

$^1$H-NMR(CDCl$_3$) δ: 0.89 (3H, t, J=6.8 Hz), 1.01 (6H, d, J=6.8 Hz), 1.25–1.32 (6H, m), 1.29 (6H, t, J=7.1 Hz), 1.42–1.44 (2H, m), 1.74–1.78 (2H, quint, J=7.4 Hz), 2.10–2.15 (2H, m), 2.38 (1H, sept, J=6.8 Hz), 2.46–2.51 (2H, m), 3.92 (2H, t, J=6.6 Hz), 4.22 (4H, q, J=7.1 Hz), 6.81 (2H, d, J=8.6 Hz), 7.08 (2H, d, J=8.6 Hz)

IR(neat): 2964, 2935, 2873, 1730, 1512, 1243, 1177, 1037, 829 cm$^{-1}$.

(2) 2-Ethoxycarbonyl-2-[2-(4-heptyloxyphenyl)ethyl]-3-methylbutanoic acid

2-[2-(4-Heptyloxyphenyl)ethyl]-2-isopropylmalonic acid diethyl ester was used in the same manner as working example 26 (5) to give the subject compound as a brown oil.

Rf value: 0.74 (ethyl acetate:hexane:acetic acid=49:49:2)

$^1$H-NMR(CDCl$_3$) δ: 0.89 (3H, t, J=6.9 Hz), 1.01 (3H, d, J=6.8 Hz), 1.01 (3H, d, J=6.8 Hz), 1.26–1.44 (8H, m), 1.76 (2H, quint, J=6.6 Hz), 2.11–2.18 (1H, m), 2.26–2.38 (1H, m), 2.46–2.57 (2H, m), 3.92 (2H, t, J=6.6 Hz), 4.23–4.32 (2H, m), 6.81 (2H, d, J=8.8H), 7.05 (2H, d, J=8.8 Hz)

IR(neat): 3203, 2933, 2860, 1733, 1699, 1512, 1243, 1176, 1057, 828 cm$^{-1}$

MS(EI): 392(M$^+$), 218, 202, 187, 120, 107.

(3) Ethyl 2-[2-(4-heptyloxyphenyl)ethyl]-2-methoxycarbonylamino-3-methylbutanoate In working example 1 (3), 2-ethoxycarbonyl-2-[2-(4-heptyloxyphenyl)-ethyl]-3-methylbutanoic acid instead of potassium 2-ethoxycarbonyl-2-methyl-4-(4-benzyloxyphenyl)butanoate was used to give the subject compound as a yellowish oil.

Rf value: 0.30 (ethyl acetate:hexane=1:9)

$^1$H-NMR(CDCl$_3$) δ: 0.89 (3H, t, J=6.8 Hz), 0.89 (3H, d, J=6.9 Hz), 0.97 (3H, d, J=6.9 Hz), 1.25–1.33 (6H, m), 1.31 (3H, t, J=7.1 Hz), 1.42–1.44 (2H, m), 1.76 (2H, quint, J=6.6 Hz), 2.15–2.20 (2H, m), 2.46–2.55 (2H, m), 2.82 (1H, m), 3.66 (3H, br.s), 3.91 (2H, t, J=6.6 Hz), 4.15–4.24 (2H, m), 5.93 (1H, br.s), 6.80 (2H, d, J=8.8 Hz), 7.06 (2H, d, J=8.8 Hz)

IR(neat): 3421, 2934, 2859, 1723, 1514, 1247, 1182, 1058, 826 cm$^{-1}$

MS(EI): 421(M$^+$), 389, 316, 203, 157, 107.

(4) 2-Amino-2-isopropyl-4-(4-heptyloxyphenyl)butanol hydrochloride 1/2hydrate

Ethyl 2-[2-(4-heptyloxyphenyl)ethyl]-2-methoxycarbonylamino-3-methylbutanoate was used in the same manner as working example 26 (7), and then working example 1 (7) to give the subject compound as a yellow amorphous.

Rf value: 0.59 (chloroform:methanol=9:1)

$^1$H-NMR(DMSO-d$_6$) δ: 0.85 (3H, t, J=6.8 Hz), 0.92 (6H, d, J=6.8 Hz), 1.26–1.38 (8H, m), 1.63–1.70 (2H, m), 1.70–1.75 (2H, m), 2.08–2.11 (1H, m), 2.54 (2H, m), 3.52–3.57 (2H, m), 3.89 (2H, t, J=6.6 Hz), 5.39 (1H, m), 6.83 (2H, d, J=8.6 Hz), 7.11 (2H, d, J=8.6 Hz), 7.89 (3H, br.s)

IR(KBr): 3349, 3185, 2923, 2852, 2616, 1614, 1512, 1472, 1242, 1060, 828 cm$^{-1}$

MS(EI): 321(M$^+$), 290, 278, 205, 107

Elemental analysis

| | |
|---|---|
| Calculated | C; 65.46, H; 10.26, N; 3.82 |
| Found | C; 65.13, H; 10.00, N; 3.86 |

WORKING EXAMPLE 61

2-Acetamido-2-[2-(4-heptyloxyphenyl)ethyl]-4-pentenyl acetate (1) 2-Allyl-2-[2-(4-heptyloxyphenyl)ethyl]malonic acid diethyl ester In working example 1 (1), allylmalonic acid diethyl ester instead of methylmalonic acid diethyl ester, and 2-(4-heptyloxyphenyl)ethyl iodide instead of 2-(4-benzyloxyphenyl)ethyl iodide were used to give the subject compound as a yellowish oil.

Rf value: 0.57 (ethyl acetate:hexane=1:9)

$^1$H-NMR(CDCl$_3$) δ: 0.89 (3H, t, J=6.9 Hz), 1.26 (6H, t, J=7.2 Hz), 1.29–1.36 (6H, m), 1.40–1.46 (2H, m), 1.76 (2H, quint, J=6.8 Hz), 2.11–2.16 (2H, m), 2.44–2.48 (2H, m), 2.73 (2H, d, J=7.3 Hz), 3.92 (2H, t, J=6.8 Hz), 4.20 (4H, q, J=7.2 Hz), 5.10–5.12 (1H, m), 5.12–5.17 (1H, m), 5.65–5.72 (1H, m), 6.81 (2H, d, J=8.8 Hz), 7.06 (2H, d, J=8.8 Hz)

IR(neat): 3079, 2932, 2859, 1733, 1512, 1243, 1178, 1027, 827 cm$^{-1}$

MS(EI): 418(M$^+$), 373, 346, 218, 200, 120, 107.

(2) 2-Ethoxycarbonyl-2-[2-(4-heptyloxyphenyl)ethyl]-4-pentenoic acid

2-Allyl-2-[2-(4-heptyloxyphenyl)ethyl]malonic acid diethyl ester was used in the same manner as working example 26 (5) to give the subject compound as a brown oil.

Rf value: 0.61 (ethyl acetate:hexane:acetic acid=49:49:2)

$^1$H-NMR(CDCl$_3$) δ: 0.89 (3H, t, J=6.9 Hz), 1.30–1.33 (6H, m), 1.31 (3H, t, J=7.1 Hz), 1.42–1.44 (2H, m), 1.76 (2H, quint, J=6.9 Hz), 2.12–2.19 (1H, m), 2.25–2.33 (1H, m), 2.36–2.43 (1H, m), 2.53–2.62 (1H, m), 2.60–2.65 (1H, m), 2.78–2.83 (1H, m), 3.92 (2H, t, J=6.9 Hz), 4.17–4.27 (2H, m), 5.11–5.16 (2H, m), 5.60–5.68 (1H, m), 6.81 (2H, d, J=8.8H), 7.04 (2H, d, J=8.8 Hz)

IR(neat): 3080, 2931, 2859, 1733, 1717, 1512, 1242, 1178, 1025, 922, 826 cm$^{-1}$

MS(EI): 390(M$^+$), 346, 218, 120, 107.

(3) Ethyl 2-[2-(4-heptyloxyphenyl)ethyl]-2-methoxycarbonylamino-4-pentenoate

In working example 1 (3), 2-ethoxycarbonyl-2-[2-(4-heptyloxyphenyl)-ethyl]-4-pentenoic acid instead of potassium 2-ethoxycarbonyl-2-methyl-4-(4-benzyloxyphenyl)butanoate was used to give the subject compound as a yellowish oil.

Rf value: 0.30 (ethyl acetate:hexane=1:9)

$^1$H-NMR(CDCls ) δ: 0.89 (3H, t, J=6.8 Hz), 1.28 (3H, t, J=7.1 Hz), 1.31–1.36 (6H, m), 1.40–1.46 (2H, m), 1.76 (2H, quint, J=6.8 Hz), 2.02–2.10 (1H, m), 2.23–2.30 (1H, m), 2.46–2.54 (1H, m), 2.53–2.60 (1H, m), 2.66 (1H, m), 3.11 (1H, m), 3.66 (3H, br.s), 3.91 (2H, t, J=6.8 Hz), 4.12–4.21 (2H, m), 5.05–5.09 (2H, m), 5.56–5.65 (1H, m), 5.79 (1H, br.s), 6.79 (2H, d, J=8.3 Hz), 7.03 (2H, d, J=8.3 Hz)

IR(neat): 3423, 3080, 2933, 2859, 1733, 1506, 1232, 1179, 1049, 922, 827 cm$^{-1}$

MS(EI): 419(M$^+$), 201, 155, 107.

(4) 2-Acetamido-2-[2-(4-heptyloxyphenyl)ethyl]-4-pentenyl acetate

Ethyl 2-[2-(4-heptyloxyphenyl)ethyl]-2-methoxycarbonylamino-4-pentenoate was used in the same manners as working example 26 (7), working example 28 (5) and working example 34 (5) to give the subject compound as a brown oil.

Rf value: 0.46 (ethyl acetate:hexane=1:1)

$^1$H-NMR(CDCl$_3$) δ: 0.89 (3H, t, J=6.9 Hz), 1.30 (6H, m), 1.44 (2H, m), 1.76 (2H, quint, J=6.4 Hz), 1.94 (3H, s), 1.99–2.06 (2H, m), 2.09 (3H, s), 2.51–2.55 (2H, m), 2.59–2.64 (2H, m), 3.92 (2H, t, J=6.4 Hz), 4.29 (1H, d, J=11.2 Hz), 4.32 (1H, d, J=11.2 Hz), 5.14–5.18 (2H, m), 5.31 (1H, br.s), 5.72–5.80 (1H, m), 6.81 (2H, d, J=8.3 Hz), 7.07 (2H, d, J=8.3 Hz)

IR(neat): 3301, 3076, 2929, 2859, 1746, 1658, 1512, 1243, 1041, 918, 821 cm$^{-1}$

MS(EI): 403(M$^+$), 205, 107.

WORKING EXAMPLE 62

2-Amino-2-[2-(4-heptyloxyphenyl)ethyl]-4-penten-1-ol

2-Acetamido-2-[2-(4-heptyloxyphenyl)ethyl]-4-pentenyl acetate was used in the same manner as working example 28 (5) to give the subject compound as a pale brown amorphous.

Rf value: 0.47 (chloroform:methanol=4:1)

$^1$H-NMR(CDCl$_3$) δ: 0.89 (3H, t, J=6.9 Hz), 1.27–1.72 (10H, m), 1.72–1.80 (2H, m), 2.19 (1H, dd, J=13.7, 7.8 Hz), 2.26 (1H, dd, J=14.1, 7.8 Hz), 2.57 (2H, m), 3.39 (2H, s), 3.92 (2H, t, J=6.6 Hz), 5.14–5.18 (2H, m), 5.81–5.88 (1H, m), 6.81 (2H, d, J=8.6 Hz), 7.08 (2H, d, J=8.6 Hz)

IR(KBr): 3349, 3314, 3282, 3067, 2923, 2856, 2751, 1612, 1512, 1246, 1045, 910 cm$^{-1}$

MS(EI): 319(M$^+$), 288, 278, 205, 107

Elemental analysis

| | |
|---|---|
| Calculated | C; 75.19, H; 10.41, N; 4.38 |
| Found | C; 74.87, H; 10.54, N; 4.27 |

WORKING EXAMPLE 63

2-Amino-4-(4-heptyloxyphenyl)-2-phenylmethylbutanol 1/20hydrate (1) 2-[2-(4-Heptyloxyphenyl)ethyl]-2-phenylmethylmalonic acid diethyl ester In working example 1 (1), benzylmalonic acid diethyl ester instead of Methylmalonic acid diethyl ester, and 2-(4-heptyloxyphenyl)ethyl iodide instead of 2-(4-benzyloxyphenyl)ethyl iodide were used to give the subject compound as a yellowish oil.

Rf value: 0.36 (ethyl acetate:hexane=1:9)

$^1$H-NMR(CDCl$_3$) δ: 0.89 (3H, t, J=6.8 Hz), 1.25 (6H, t, J=7.3 Hz), 1.26–1.30 (6H, m), 1.43 (2H, m), 1.76 (2H, quint, J=6.8 Hz), 2.03–2.07 (2H, m), 2.52–2.57 (2H, m), 3.32 (2H, s), 3.91 (2H, t, J=6.8 Hz), 4.13–4.23 (4H, m), 6.80 (2H, d, J=8.8 Hz), 7.04 (2H, d, J=8.8 Hz)

IR(neat): 3031, 2933, 2859, 1733, 1512, 1244, 1177, 1029, 701 cm$^{-1}$

MS(EI): 468(M$^+$), 423, 377, 250, 218, 204, 158, 120, 107.

(2) 2-Ethoxycarbonyl-4-(4-heptyloxyphenyl)-2-phenylmethylbutanoic acid

2-[2-(4-Heptyloxyphenyl)ethyl]-2-phenylmethylmalonic acid diethyl ester was used in the same manner as working example 26 (5) to give the subject compound as a yellowish oil.

Rf value: 0.48 (ethyl acetate:hexane:acetic acid=49:49:2)

$^1$H-NMR(CDCl$_3$) δ: 0.89 (3H, t, J=6.9 Hz), 1.30–1.35 (6H, m), 1.33 (3H, t, J=7.3 Hz), 1.40–1.44 (2H, m), 1.76 (2H, quint, J=6.8 Hz), 2.19–2.24 (1H, m), 2.34–2.42 (2H, m), 2.52–2.64 (1H, m), 3.16 (1H, d, J=13.5 Hz), 3.42 (1H, d, J=13.5 Hz), 3.92 (2H, t, J=6.8 Hz), 4.16–4.22 (2H, m), 6.81 (2H, d, J=8.6H), 7.04 (2H, d, J=8.6 Hz), 7.09–7.13 (2H, m), 7.22–7.32 (3H, m)

IR(neat): 3473, 3032, 2932, 2859, 2645, 1733, 1708, 1512, 1245, 1178, 1029, 743, 701 cm$^{-1}$

MS(EI): 440(M$^+$), 396, 250, 218, 120, 107.

(3) Ethyl 4-(4-heptyloxyphenyl)-2-methoxycarbonylamino-2-phenylmethylbutanoate

In working example 1 (3), 2-ethoxycarbonyl-4-(4-heptyloxyphenyl)-2-phenylmethyibutanoic acid instead of potassium 2-ethokycarbonyl- 2-methyl-4-(4-benzyloxyphenyl)butanoate was used to give the subject compound as a yellowish oil.

Rf value: 0.31 (ethyl acetate:hexane=1:9)

$^1$H-NMR(CDCl$_3$) δ: 0.89 (3H, t, J=6.9 Hz), 1.28–1.37 (6H, m), 1.30 (3H, t, J=7.1 Hz), 1.40–1.46 (2H, m), 1.76 (2H, quint, J=6.9 Hz), 2.15–2.31 (2H, m), 2.56–2.63 (1H, m), 2.84 (1H, m), 3.06 (1H, d, J=13.4 Hz), 3.64 (1H, d, J=13.4 Hz), 3.71 (3H, br.s), 3.92 (2H, t, J=6.9 Hz), 4.10–4.20 (2H, m), 5.66 (1H, br.s), 6.80 (2H, d, J=8.8 Hz), 7.01–7.03 (2H, m), 7.05 (2H, d, J=8.8 Hz), 7.19–7.29 (3H, m)

IR(neat): 3422, 3031, 2933, 2859, 1733, 1512, 1243, 1080, 1052, 745, 702 cm$^{-1}$

MS(EI): 469(M$^+$), 251, 205, 107.

(4) 2-Amino-4-(4-heptyloxyphenyl)-2-phenylmethylbutanol 1/20hydtare

Ethyl 4-(4-heptyloxyphenyl)-2-methoxycarbonylamino-2-phenylmethylbutanoate was used in the same manners as working example 26 (7) and then working example 28 (5) to give the subject compound as white crystals, melting at 93–94° C.

Rf value: 0.52 (chloroform:methanol=4:1)

$^1$H-NMR(CDCl$_3$) δ: 0.89 (3H, t, J=6.9 Hz), 1.30–1.44 (8H, m), 1.62–1.67 (2H, m), 1.76 (2H, quint, J=6.9 Hz), 2.66 (2H, t, J=8.6 Hz), 2.76 (1H, d, J=13.4 Hz), 2.79 (1H, d, J=13.4 Hz), 3.38 (1H, d, J=10.5 Hz), 3.40 (1H, d, J=10.5 Hz), 3.92 (2H, t, J=6.9 Hz), 6.82 (2H, d, J=8.8 Hz), 7.09 (2H, d, J=8.8 Hz), 7.23–7.33 (5H, m)

IR(KBr): 3338, 3279, 3088, 3029, 2952, 2927, 2870, 2749, 1511, 1243, 1045, 807, 700 cm$^{-1}$

MS(EI): 369(M$^+$), 278, 205, 107

Elemental analysis

| | |
|---|---|
| Calculated | C; 77.82, H; 8.55, N; 3.78 |
| Found | C; 77.59, H; 9.78, N; 3.74 |

WORKING EXAMPLE 64

2-Amino-2-[2-(4-octylphenyl)ethyl]-1,5-pentanediol hydrochloride 1/4hydrate (1) 2-[3-(tetrahydropyran-2-yloxy)propyl]malonic acid diethyl ester In working example 1 (1), malonic acid diethyl ester instead of methylmalonic acid diethyl ester, and 3-(tetrahydropyran-2-yloxy)propyl bromide prepared from 3-bromopropanol instead of 2-(4-benzyloxyphenyl)ethyl iodide were used to give the subject compound as a colorless oil.

Rf value: 0.41 (ethyl acetate:hexane=1:4)

$^1$H-NMR(CDCl$_3$) δ: 1.27 (6H, t, J=7.3 Hz), 1.50–1.84 (8H, m), 1.97–2.02 (2H, m), 3.37–3.43 (2H, m), 3.47–3.53 (1H, m), 3.73–3.79 (1H, m), 3.82–3.88 (1H, m), 4.19 (2H, q, J=7.3 Hz), 4.20 (2H, q, J=7.3 Hz), 4.58 (1H, t, J=3.7 Hz)

IR(neat): 2943, 2872, 1732, 1156, 1034 cm$^{-1}$

MS(EI): 217, 201, 173, 127, 85.

(2) 2-[2-(4-Octylphenyl)ethyl]-2-[3-(tetrahydropyran-2-yloxy)propyl]malonic acid diethyl ester In working example 1 (1), 2-[3-(tetrahydropyran-2-yloxy)propyl]malonic acid diethyl ester instead of methylmalonic acid diethyl ester, and 2-(4-octylphenyl)ethyl iodide instead of 2-(4-benzyloxyphenyl)ethyl iodide were used to give the subject compound as a yellowish oil.

Rf value: 0.48 (ethyl acetate:hexane=1:4)

$^1$H-NMR(CDCl$_3$) δ: 0.88 (3H, t, J=6.8 Hz), 1.26 (6H, t, J=7.1 Hz), 1.27–1.29 (10H, m), 1.50–1.58 (8H, m), 1.68–1.73 (1H, m), 1.81–1.84 (1H, m), 2.02–2.06 (2H, m), 2.16–2.21 (2H, m), 2.46–2.50 (2H, m), 2.54–2.58 (2H, m), 3.36–3.42 (1H, m), 3.47–3.52 (1H, m), 3.72–3.77 (1H, m), 3.83–3.88 (1H, m), 4.19 (4H, q, J=7.1 Hz), 4.57–4.59 (1H, m), 7.08 (4H, s)

IR(neat): 2927, 2856, 1732, 1514, 1455, 1200, 1034 cm$^{-1}$
MS(EI): 417, 218, 85.

(3) 2-Ethoxycarbonyl-2-[2-(4-octylphenyl)ethyl]-5-(tetrahydropyran-2-yloxy)-pentanoic acid 2-[2-(4-Octylphenyl)ethyl]-2-[3-(tetrahydropyran-2-yloxy)propyl]malonic acid diethyl ester was used in the same manner as working example 26 (5) to give the subject compound as a yellow-green oil.

Rf value: 0.56 (ethyl acetate:hexane:acetic acid=49:49:2)
$^1$H-NMR(CDCl$_3$) δ: 0.88 (3H, t, J=6.8 Hz), 1.21–1.28 (10H, m), 1.31 (3H, t, J=7.3 Hz), 1.43–1.57 (8H, m), 1.69–1.72 (1H, m), 1.79–1.81 (1H, m), 1.97–2.12 (2H, m), 2.14–2.22 (1H, m), 2.28–2.35 (1H, m), 2.38–2.46 (1H, m), 2.47–2.63 (3H, m), 3.31–3.40 (1H, m), 3.47–3.50 (1H, m), 3.66–3.76 (1H, m), 3.80–3.85 (1H, m), 4.14–4.27 (2H, m), 4.55–4.59 (1H, m), 7.04–7.09 (4H, m)

IR(neat): 3160, 2927, 2856, 1733, 1717, 1455, 1200, 1034 cm$^{-1}$.

(4) Ethyl 2-methoxycarbonylamino-2-[2-(4-octylphenyl)ethyl]-5-(tetrahydropyran-2-yloxy)pentanoate In working example 1 (3), 2-ethoxycarbonyl-2-[2-(4-octylphenyl)ethyl]-5-(tetrahydropyran-2-yloxy)pentanoic acid instead of potassium 2-ethoxycarbonyl-2-methyl-4-(4-benzyloxyphenyl)butanoate was used to give the subject compound as a yellowish oil.

Rf value: 0.27 (ethyl acetate:hexane=1:4)
$^1$H-NMR(CDCl$_3$) δ: 0.88 (3H, t, J=6.8 Hz), 1.24–1.30 (12H, m), 1.28 (3H, t, J=7.3 Hz), 1.50–1.64 (6H, m), 1.67–1.72 (1H, m), 1.78–1.88 (2H, m), 2.05–2.12 (1H, m), 2.25–2.36 (2H, m), 2.52–2.56 (2H, m), 2.56–2.70 (2H, m), 3.31–3.39 (1H, m), 3.47–3.49 (1H, m), 3.64 (3H, br.s), 3.67–3.72 (1H, m), 3.81–3.85 (1H, m), 4.10–4.21 (2H, m), 4.54 (1H, m), 5.87 (1H, br.s), 7.03 (2H, d, J=8.3 Hz), 7.07 (2H, d, J=8.3 Hz)

IR(neat): 3423, 3381, 2928, 2856, 1721, 1502, 1201, 1080, 1032, 816, 780 cm$^{-1}$
MS(EI): 519(M$^+$), 219, 173, 85.

(5) 2-Amino-2-[2-(4-octylphenyl)ethyl]-5-(tetrahydropyran-2-yloxy)pentanol

Ethyl 2-methoxycarbonylamino-2-[2-(4-octylphenyl)ethyl]-5-(tetrahydropyran-2-yloxy)pentanoate was used in the same manners as working example 26 (7), and then working example 28 (5) to give the subject compound as a yellowish oil.

Rf value: 0.56 (chloroform:methanol=4:1)
$^1$H-NMR(CDCl$_3$) δ: 0.88 (3H, t, J=7.1 Hz), 1.26–1.30 (10H, m), 1.54–1.80 (14H, m), 2.53–2.62 (4H, m), 3.46–3.52 (4H, m), 3.76 (1H, m), 3.87 (1H, m), 4.58 (1H, m), 7.08 (2H, d, J=8.5 Hz), 7.10 (2H, d, J=8.5 Hz)

IR(KBr): 3348, 2924, 2856, 1514, 1454, 1120, 1075, 1032, 813 cm$^{-1}$
MS(EI): 419(M$^+$), 304, 287, 105, 85.

(6) 2-Amino-2-[2-(4-octylphenyl)ethyl]pentan-1,5-diol hydrochloride 1/4hydrate

To a solution of 2-amino-2-[2-(4-octylphenyl)ethyl]-5-(tetrahydropyran-2-yloxy)pentanol (0.80 g) in methanol (100 ml), 1M hydrochloric acid-ether (3 ml) was added and the mixture was stirred at room temperature for 30 minutes. Water (200 ml) was added thereto and the mixture was washed with ether. The mixture was made alkaline with a 1M aqueous potassium hydroxide solution and extracted with ethyl acetate. The ethyl acetate layer was washed with a saturated brine, dried over anhydrous sodium sulfate and the solvent was distilled away. The residue obtained was dissolved in ethanol (30 ml), a solution of 1M hydrochloric acid in ether (3 ml) was added thereto and the solvent was distilled away. Ether (10 ml) was added to the residue obtained and the suspension was filtered off to give the subject compound (0.23 g) as a red-violet viscous substance.

Rf value: 0.32 (chloroform:methanol=4:1)
$^1$H-NMR(DMSO-d$_6$) δ: 0.84 (3H, t, J=6.9 Hz), 1.23–1.25 (10H, m), 1.46–1.52 (4H, m), 1.58–1.63 (2H, m), 1.71–1.75 (2H, m), 2.51–2.55 (2H, m), 3.39–3.42 (2H, m), 3.45–3.47 (2H, m), 4.59 (1H, t, J=5.1 Hz), 5.48 (1H, t, J=4.9 Hz), 7.09 (4H, s), 7.85 (3H, br.s)

IR(neat): 3346, 3009, 2924, 2854, 1609, 1515, 1456, 1057 cm$^{-1}$
MS(EI): 335(M$^+$), 304, 203, 105. Elemental analysis

| | |
|---|---|
| Calculated | C; 66.99, H; 10.31, N; 3.72 |
| Found | C; 67.00, H; 10.42, N; 3.62 |

WORKING EXAMPLE 65

2-Amino-2-cyclopropylmethyl-4-(4-heptyloxyphenyl)-butanol hydrochloride (1) 2-[2-(4-Heptyloxyphenyl)ethyl]malonic acid diethyl ester In working example 1 (1), malonic acid diethyl ester instead of methylmalonic acid diethyl ester, and 2-(4-heptyloxyphenyl)ethyl iodide instead of 2-(4-benzyloxyphenyl)ethyl iodide were used to give the subject compound as a yellowish oil.

Rf value: 0.36 (ethyl acetate:hexane=1:9)
$^1$H-NMR(CDCl$_3$) δ: 0.89 (3H, t, J=6.9 Hz), 1.24–1.37 (6H, m), 1.27 (6H, t, J=7.3 Hz), 1.41–1.46 (2H, m), 1.77 (2H, quint, J=6.9 Hz), 2.18 (2H, q, J=7.6 Hz) 2.59 (2H, t, J=7.6 Hz), 3.32 (1H, t, J=7.8 Hz), 3.92 (2H, t, J=6.9 Hz), 4.20 (4H, q, J=7.3 Hz), 6.82 (2H, d, J=8.3 Hz), 7.08 (2H, d, J=8.3 Hz)

IR(neat): 2932, 2860, 1733, 1513, 1244, 1177, 1043, 828 cm$^{-1}$
MS(EI): 378(M$^+$), 333, 218, 120, 107.

(2) 2-Cyclopropylmethyl-2-[2-(4-heptyloxyphenyl)ethyl]malonic acid diethyl ester In working example 1 (1), 2-[2-(4-heptyloxyphenyl)ethyl]malonic acid diethyl ester instead of Methylmalonic acid diethyl ester, and cyclopropylmethyl bromide instead of 2-(4-benzyloxyphenyl)ethyl iodide were used to give the subject compound as a yellowish oil.

Rf value: 0.44 (ethyl acetate:hexane=1:9)
$^1$H-NMR(CDCl$_3$) δ: 0.06–0.09 (2H, m), 0.42–0.47 (2H, m), 0.65 (1H, m), 0.89 (3H, t, J=6.6 Hz), 1.26 (6H, t, J=7.1 Hz), 1.28–1.34 (6H, m), 1.40–1.44 (2H, m), 1.76 (2H, quint, J=6.8 Hz), 1.92 (2H, d, J=6.9 Hz), 2.26–2.30 (2H, m), 2.43–2.50 (2H, m), 3.92 (2H, t, J=6.8 Hz), 4.11–4.25 (4H, m), 6.81 (2H, d, J=8.8 Hz), 7.08 (2H, d, J=8.8 Hz)

IR(neat): 3080, 2932, 2859, 1735, 1513, 1243, 1178, 1028, 826 cm$^{-1}$
MS(EI): 432(M$^+$), 387, 218, 120, 107.

(3) 2-Cyclopropylmethyl-2-ethoxycarbonyl-4-(4-heptyloxyphenyl)butanoic acid

2-Cyclopropylmethyl-2-[2-(4-heptyloxyphenyl)ethyl]malonic acid diethyl ester was used in the same manner as working example 26 (5) to give the subject compound as a yellow-green oil.

Rf value: 0.64 (ethyl acetate:hexane:acetic acid=49:49:2)

IR(neat): 3081, 2933, 2859, 1738, 1713, 1613, 1514, 1469, 1251, 1023, 826 cm$^{-1}$

MS(EI): 404(M$^+$), 392, 360, 218, 205, 120, 107.

(4) Ethyl 2-cyclopropylmethyl-4-(4-heptyloxyphenyl)-2-methoxycarbonylaminobutanoate In working example 1 (3), 2-cyclopropylmethyl-2-ethoxycarbonyl-4-(4-heptyloxyphenyl)butanoic acid instead of potassium 2-ethoxycarbonyl-2-methyl-4-(4-benzyloxyphenyl)butanoate was used to give the subject compound as a brown oil.

Rf value: 0.33 (ethyl acetate:hexane=1:9)

$^1$H-NMR(CDCl$_3$) δ: 0.01–0.09 (1H, m), 0.10–0.13 (1H, m), 0.38–0.43 (1H, m), 0.44–0.48 (1H, m), 0.59–0.61 (1H, m), 0.93 (3H, t, J=6.9 Hz), 1.30–1.56 (9H, m), 1.80 (2H, quint, J=6.9 Hz), 2.05–2.11 (1H, m), 2.25–2.32 (1H, m), 2.46–2.51 (1H, m), 2.57–2.65 (1H, m), 2.67–2.71 (1H, m), 3.71 (3H, br.s), 3.96 (2H, t, J=6.9 Hz), 4.16–4.27 (2H, m), 6.03 (1H, br.s), 6.83 (2H, d, J=8.8 Hz), 7.07 (2H, d, J=8.8 Hz)

IR(neat): 3424, 3081, 2929, 2859, 1733, 1505, 1239, 1055, 825 cm$^{-1}$

MS(EI): 433(M$^+$), 215, 205, 169, 107.

(5) 2-Amino-2-cyclopropylmethyl-4-(4-heptyloxyphenyl)butanol hydrochloride

Ethyl 2-cyclopropylmethyl-4-(4-heptyloxyphenyl)-2-methoxycarbonylaminobutanoate was used in the same manners as working example 26 (7) and then working example 1 (7) to give the subject compound as a brown viscous oil.

Rf value: 0.53 (chloroform:methanol=4:1)

$^1$H-NMR(DMSO-d$_6$) δ: 0.13–0.14 (2H, m), 0.45–0.47 (2H, m), 0.73 (1H, m), 0.85 (3H, t, J=6.8 Hz), 1.26–1.40 (8H, m), 1.52 (2H, d, J=6.9 Hz), 1.67 (2H, quint, J=6.8 Hz), 1.80–1.85 (2H, m), 2.51–2.54 (2H, m), 3.52–3.55 (2H, m), 3.90 (2H, t, J=6.8 Hz), 5.47 (1H, t, J=4.7 Hz), 6.83 (2H, d, J=8.6 Hz), 7.10 (2H, d, J=8.6 Hz), 7.91 (3H, br.s)

IR(neat): 3348, 3228, 2933, 2852, 1616, 1506, 1243, 1056, 827 cm$^{-1}$;

WORKING EXAMPLE 66

2-Amino-4-(4-heptyloxy-3-methoxyphenyl)-2-methylbutanol 1/10hydrate (1) 2-[2-(4-Heptyloxy-3-methoxyphenyl)ethyl]-2-methylmalonic acid dimethyl ester In working example 1 (1), methylmalonic acid dimethyl ester instead of methylmalonic acid diethyl ester, and 2-(4-heptyloxy-3-methoxyphenyl)ethyl iodide instead of 2-(4-benzyloxyphenyl)ethyl iodide were used to give the subject compound as a colorless oil.

Rf value: 0.39 (ethyl acetate:hexane=1:5)

$^1$H-NMR(CDCl$_3$) δ: 0.88 (3H, t, J=7.1 Hz), 1.20–1.60 (8H, m), 1.50 (3H, s), 1.81 (2H, tt, J=6.9, 6.9 Hz), 2.16 (2H, m), 2.51 (2H, m), 3.73 (6H, s, ), 3.86 (3H, s), 3.97 (2H, t, J=6.9 Hz), 6.69 (1H, d, J=8.7 Hz), 6.70 (1H, s), 6.79 (1H, d, J=8.7 Hz)

IR(neat): 2933, 2859, 1735, 1515 cm$^{-1}$

MS(EI): 394(M$^+$).

(2) 4-(4-Heptyloxy-3-methoxyphenyl)-2-methyl-2-methoxycarbonylbutanoic acid.

2-[2-(4-Heptyloxy-3-methoxyphenyl)ethyl]-2-methylmalonic acid dimethyl ester was used in the same manner as working example 26 (5) to give the subject compound as a yellow-green oil.

Rf value: 0.55 (ethyl acetate:hexane:acetic acid=49:49:2)

$^1$H-NMR(CDCl$_3$) δ: 0.88 (3H, t, J=6.9 Hz), 1.20–1.60 (8H, m), 1.55 (3H, s), 1.81 (2H, tt, J=6.9, 6.9 Hz), 2.21 (2H, m), 2.53 (2H, m), 3.76 (3H, s, ), 3.85 (3H, s), 3.97 (2H, t, J=6.9 Hz), 6.69 (1H, d, J=8.7 Hz), 6.70 (1H, s), 6.79 (1H, d, J=8.7 Hz)

IR(neat): 3244, 2933, 2859, 1736, 1515 cm$^{-1}$

MS(EI): 380(M$^+$).

(3) Methyl 4-(4-heptyloxy-3-methoxyphenyl)-2-methyl-2-methoxycarbonylaminobutanoate In working example 1 (3), 4-(4-heptyloxy-3-methoxyphenyl)-2-methyl-2-methoxycarbonylbutanoic acid instead of potassium 2-ethoxycarbonyl-2-methyl-4-(4-benzyloxyphenyl)butanoate was used to give the subject compound as a colorless oil.

Rf value: 0.13 (ethyl acetate:hexane=1:5)

$^1$H-NMR(CDCl$_3$) δ: 0.88 (3H, t, J=6.9 Hz), 1.20–1.55 (8H, m), 1.61 (3H, s), 1.81 (2H, tt, J=6.9, 6.9 Hz), 2.11 (1H, m), 2.36 (1H, m), 2.55 (2H, m), 3.66 (3H, s), 3.72 (3H, s, ), 3.85 (3H, s), 3.97 (2H, t, J=6.9 Hz), 5.63 (1H, br.s), 6.65 (1H, d, J=8.7 Hz), 6.66 (1H, s), 6.77 (1H, d, J=8.7 Hz)

IR(neat): 3421, 3363, 2933, 2859, 1732, 1514 cm$^{-1}$

MS(EI): 409(M$^+$).

(4) 2-Amino-4-(4-heptyloxy-3-methoxyphenyl)-2-methylbutanol 1/10hydrate

Methyl 4-(4-heptyloxy-3-methoxyphenyl)-2-methyl-2-methoxycarbonylaminobutanoate was used in the same manners as working example 26 (7) and then working example 28 (5) to give the subject compound as a white amorphous.

Rf value: 0.32 (chloroform:methanol:acetic acid:water=70:20:6:4)

$^1$H-NMR(CDCl$_3$) δ: 0.88 (3H, t, J=6.9 Hz), 1.14 (3H, s), 1.20–1.55 (8H, m), 1.55–1.90 (7H, m), 2.59 (2H, t, J=8.8 Hz), 3.33 (1H, d, J=12.0 Hz), 3.39 (1H, d, J=12.0 Hz), 3.86 (3H, s), 3.97 (2H, t, J=6.9 Hz), 6.71 (1H, d, J=8.3 Hz), 6.72 (1H, s), 6.79 (1H, d, J=8.3 Hz)

MS(EI):323(M$^+$)

Elemental analysis

| | |
|---|---|
| Calculated | C; 70.16, H; 10.29, N; 4.31 |
| Found | C; 70.11, H; 10.35, N; 4.34 |

WORKING EXAMPLE 67

2-Amino-2-(2-(4-heptyloxyphenyl)ethyl)-pent-4-yn-1-ol (1) Ethyl 2-(2-(4-heptyloxyphenyl)ethyl)-2-methoxycarbonylaminopent-4-ynoate In working example 1 (1), 2-[2-(4-heptyloxyphenyl)ethyl]malonic acid diethyl ester instead of methylmalonic acid diethyl ester, and 2-propargyl-2-[2-(4-heptyloxyphenyl)ethyl]malonic acid diethyl ester obtained using 3-bromo-1-propyne instead of 2-(4-benzyloxyphenyl)ethyl iodide were used and the reaction was carried out in the same manners as working example 26 (5) and then working example 1 (3) (Curtius rearrangement reaction) to give the subject compound as a colorless oil.

Rf value:0.27 (ethyl acetate: hexane=1:5)

$^1$H-NMR(CDCl$_3$) δ: 0.87 (3H, t, J–7.1 Hz), 1.28 (3H, t, J=7.1 Hz), 1.10–1.39 (8H, m), 1.40 (2H, m), 1.73 (2H, tt, J=6.6, 6.6 Hz), 1.95 (1H, t, J=2.5 Hz), 2.05 (1H, m), 2.31 (1H, m), 2.52 (1H, m), 2.73 (1H, dd, J=17.1, 2.5 Hz), 3.24 (1H, dd, J=17.1, 2.5 Hz), 3.66 (3H, s,), 3.89 (2H, t, J=6.6 Hz), 4.19 (2H, m), 5.83 (1H, br.s), 6.77 (2H, d, J=8.3 Hz), 7.00 (2H, d, J=8.3 Hz)

IR(neat): 3421, 3310, 2932, 2859, 1724, 1512 cm$^{-1}$.

(2) 2-Amino-2-(2-(4-heptyloxyphenyl)ethyl)-pent-4-yn-1-ol

Ethyl 2-(2-(4-heptyloxyphenyl)ethyl)-2-methoxycarbonylaminopent-4-ynoate was used and the reaction was carried out in the same manners as working example 26 (7) and then working example 28 (5) to give the subject compound.

Rf value: 0.18 (chloroform:methanol=9:1)
IR(neat): 3290, 2931, 2858, 1613, 1512 cm$^{-1}$.

WORKING EXAMPLE 68

Two diastereomers of 2-[(S)-α-methoxy-α-trifluoromethylphenylacetylamino]-4-(4-octylphenyl)butanol 2-Amino-4-(4-octylphenyl)butanol (30 mg), N,N-dimethyl-p-aminopyridine (52.6 mg), anhydrous triethylamine (34.2 μl) and anhydrous methylene chloride (1 ml) were mixed and the mixture was stirred under a nitrogen atmosphere at room temperature. Thereto was added (S)-α-methoxy-α-trifluoromethylphenylacetyl chloride (50.4 μl) and the mixture was stirred at room temperature for 10 hours. The reaction mixture was concentrated under reduced pressure and the residue obtained was purified by thin layer chromatography (eluent; chloroform:methanol=9:1) to give the two diastereomer mixtures. Moreover, the mixture was purified by high performance liquid chromatography (eluent; methanol:water=88:12, flow rate; 8.0 ml/minute) to give the subject oily substance (31.6 mg) of 67.8 mununtes at retention time and the subject oily substance (31.9 mg) of 71.6 minutes at retention time.

WORKING EXAMPLE 69

Two diastereomers of 2-[(R)-α-methoxy-α-trifluoromethylphenylacetylamino]-4-(4-octylphenyl)butanol 2-Amino-4-(4-octylphenyl)butanol (10 mg), N,N-dimethyl-p-aminopyridine (17.5 mg), anhydrous triethylamine (11.4 μl) and anhydrous methylene chloride (1 ml) were mixed and the mixture was stirred under a nitrogen atmosphere at room temperature. Thereto was added (R)-α-methoxy-α-trifluoromethylphenylacetyl chloride (16.8 μl) and the mixture was stirred at room temperature for 10 hours. The reaction mixture was concentrated under reduced pressure and the residue obtained was purified by thin layer chromatography (eluent; chloroform:methanol=9:1) to give the two diastereomer mixtures. Moreover, the mixture was purified by high performance liquid chromatography (eluent; methanol:water=88:12, flow rate; 8.0 ml/minute) to give the subject oily substance (9.8 mg) of 67.8 mununtes at retention time and the subject oily substance (9.6 mg) of 71.6 minutes at retention time.

WORKING EXAMPLE 70

(S)-2-Amino-4-(4-octylphenyl)butanol

The oily substance (20 mg) of 67.8 minutes at retention time obtained in working example 69 was, under a nitrogen atmosphere, dissolved in a 3.5M solution of sodium methoxide in anhydrous methanol (4 ml) at room temperature and the mixture was refluxed under heating for 20 hours. The reaction mixture was diluted with ice-water (10 ml) and extracted with chloroform. The organic layer was washed with a saturated aqueous sodium hydrogencarbonate solution and dried over anhydrous sodium sulfate. The solvent was concentrated under reduced pressure and the residue obtained was purified by thin layer chromatography (eluent; chloroform:methanol=7:1) to give the subject compound (5.5 mg) as a white wax-like solid, melting at 54–57° C.
$[\alpha]_D^{30}$=+0.52 (c=1.88, chloroform)

WORKING EXAMPLE 71

(R)-2-Amino-4-(4-octylphenyl)butanol

The oily substance (20 mg) of 71.6 minutes at retention time obtained in working example 69 was, under a nitrogen atmosphere, dissolved in a 3.5M solution of sodium methoxide in anhydrous methanol (4 ml) at room temperature and the mixture was refluxed under heating for 20 hours. The reaction mixture was diluted with ice-water (10 ml) and extracted with chloroform. The organic layer was washed with a saturated aqueous sodium hydrogencarbonate solution and dried over anhydrous sodium sulfate. The solvent was concentrated under reduced pressure and the residue obtained was purified by thin layer chromatography (eluent; chloroform:methanol=7:1) to give the subject compound (5.6 mg) as a white wax-like solid, melting at 54–57° C.
$[\alpha]_D^{30}$=−0.81 (c=1.73, chloroform)

WORKING EXAMPLE 72

3-Acetamido-3-acetyloxymethyl-5-(4-heptyloxyphenyl)pentyl acetate (1) 2-[2-(4-Heptyloxyphenyl)ethyl] -2-tert-butyldiphenylsilyloxyethylmalonic acid diethyl ester In working example 1 (1), 2-[2-(4-heptyloxyphenyl) ethyl]malonic acid diethyl ester obtained in working example 65 (1) instead of methylmalonic acid diethyl ester, and 2-tert-butyldiphenylsilyloxyethyl iodide prepared from 2-iodoethanol instead of 2-(4-benzyloxyphenyl)ethyl iodide were used to give the subject compound as a pale yellow-green oil.

Rf value: 0.47 (ethyl acetate:hexane=1:9)
$^1$H-NMR(CDCl$_3$) δ: 0.87 (3H, t, J=7.1 Hz), 1.00 (9H, s), 1.18 (6H, t, J=7.1 Hz), 1.27–1.49 (8H, m), 1.74 (2H, quint, J=6.9 Hz), 2.10–2.15 (2H, m), 2.28–2.36 (4H, m), 3.65 (2H, t, J=7.1 Hz), 3.90 (2H, t, J=6.9 Hz), 4.07 (2H, dq, J=10.7, 7.3 Hz), 4.12 (2H, dq, J=10.7, 6.9 Hz), 6.76 (2H, d, J=8.8 Hz), 6.95 (2H, d, J=8.8 Hz), 7.32–7.41 (6H, m), 7.62–7.64 (4H, m)

IR(neat): 3072, 3049, 3030, 2957, 2932, 2859, 1733, 1512, 1244, 1178, 1112, 1030, 825, 741, 703 cm$^{-1}$ MS(EI): 603[(M-t-Bu)$^+$], 227, 199, 173, 107.

(2) 2-Ethoxycarbonyl-2-[2-(4-heptyloxyphenyl)ethyl]-γ-butyrolactone

To a solution of 2-[2-(4-heptyloxyphenyl)ethyl]-2-tert-butyldiphenylsilyloxyethylmalonic acid diethyl ester (45.3 g) in tetrahydrofuran (450 ml), under ice-cooling, a 1M solution of tetrabutylammmonium fluoride in tetrahydrofuran (82.2 ml) was dropwise added and the mixture was stirred at room temperature for 4 hours. The solvent was distilled away and water (500 ml) was added thereto and the mixture was extracted with ethyl acetate. The ethyl acetate layer was washed with a saturated brine, dried over anhydrous sodium sulfate and the solvent was distilled away. The residue obtained was purified by silica gel chromatography (eluent; ethyl acetate:hexane=15:85) to give the subject compound (27.8 g) as a colorless oil.

Rf value: 0.36 (ethyl acetate:hexane=1:4)
$^1$H-NMR(CDCl$_3$) δ: 0.87 (3H, t, J=6.9 Hz), 1.26–1.34 (6H, m), 1.28 (3H, t, J=7.1 Hz), 1.38–1.44 (2H, m), 1.74 (2H, quint, J=6.8 Hz), 2.02 (1H, ddd, J=13.7, 11.7, 4.9 Hz), 2.24 (1H, dt, J=12.9, 8.8 Hz), 2.37 (1H, ddd, J=13.7, 11.7, 4.9 Hz), 2.51 (1H, ddd, J=13.7, 11.7, 4.9 Hz), 2.65 (1H, ddd, J=13.7, 11.7, 4.9 Hz), 2.76 (1H, dt, J=12.9, 5.3 Hz), 3.90 (2H, t, J=6.8 Hz), 4.22 (2H, dq, J=2.2, 7.1 Hz), 4.33 (2H, dd, J=8.8, 5.3 Hz), 6.80 (2H, d, J=8.8 Hz), 7.07 (2H, d, J=8.8 Hz)

IR(neat): 2929, 2859, 1774, 1735, 1513, 1244, 1176, 1031, 827 cm$^{-1}$

MS(EI): 376(M$^+$), 218, 120.

(3) 2-[2-(4-Heptyloxyphenyl)ethyl]-γ-butyrolactone-2-carboxylic acid

To a solution of 2-ethoxycarbonyl-2-[2-(4-heptyloxyphenyl)ethyl]-γ-butyrolactone (27.7 g) in acetone (300 ml), under ice-cooling, a 0.25M aqueous sodium hydroxide solution (295 ml) was added and the mixture was stirred for 5 minutes. The solvent was distilled away, water (300 ml) was added thereto and the mixture was extracted with ethyl acetate. The ethyl acetate layer was washed with a saturated brine, dried over anhydrous sodium sulfate and the solvent was distilled away to give the subject compound (27.5 g) as a white amorphous.

Rf value: 0.68 (ethyl acetate:hexane:acetic acid=49:49:2)

$^1$H-NMR(CDCl$_3$) δ: 0.87 (3H, t, J=6.8 Hz), 1.28–1.34 (6H, m), 1.38–1.44 (2H, m), 1.74 (2H, quint, J=6.8 Hz), 2.01–2.10 (1H, m), 2.16–2.40 (2H, m), 2.52–2.59 (1H, m), 2.66–2.74 (1H, m), 2.76–2.83 (1H, m), 3.90 (2H, t, J=6.8 Hz), 4.33–4.43 (2H, m), 6.80 (2H, d, J=8.8 Hz), 7.07 (2H, d, J=8.8 Hz)

IR(neat): 3083, 2935, 2857, 2595, 1767, 1723, 1514, 1247, 1162, 1025, 826 cm$^{-1}$

MS(EI): 348(M$^+$), 304, 218, 121, 107, 86.

(4) 2-[2-(4-Heptyloxyphenyl)ethyl]-2-methoxycarbonylamino-γ-butyrolactone

In working example 1 (3), 2-[2-(4-heptyloxyphenyl)ethyl]-γ-butyrolactone-2-carboxylic acid instead of potassium 2-ethoxycarbonyl-2-methyl-4-(4-benzyloxyphenyl)butanoate was used to give the subject compound as a yellowish oil.

Rf value: 0.11 (ethyl acetate:hexane=1:4)

$^1$H-NMR(CDCl$_3$) δ: 0.87 (3H, t, J=6.8 Hz), 1.28–1:34 (6H, m), 1.38–1.44 (2H, m), 1.74 (2H, quint, J=6.9 Hz), 1.94–2.02 (1H, m), 2.14–2.22 (1H, m), 2.50–2.54 (1H, m), 2.64 (2H, t, J=8.6 Hz), 2.67–2.75 (1H, m), 3.65 (3H, br.s), 3.90 (2H, t, J=6.9 Hz), 4.25 (1H, dt, J=9.3, 7.1 Hz), 4.47 (1H, br.t, J=9.3 Hz), 5.22 (1H, br.s), 6.80 (2H, d, J=8.8 Hz), 7.05 (2H, d, J=8.8 Hz)

IR(neat): 3531, 3346, 2932, 2859, 1771, 1733, 1613, 1506, 1456, 1381, 1254, 1030, 828, 781 cm$^{-1}$ MS(FAB, positive): 378[(M+H)$^+$].

(5) 3-Acetyloxymethyl-5-(4-heptyloxyphenyl)-3-methoxycarbonylaminopentyl acetate 2-[2-(4-Heptyloxyphenyl)ethyl]-2-methoxycarbonylamino-γ-butyrolactone was used in the same manner as working example 8 (1) to give the subject compound as white crystals, melting at 75–76° C.

Rf value: 0.35 (ethyl acetate:hexane=3:7)

$^1$H-NMR(CDCl$_3$) δ: 0.87 (3H, t, J=6.8 Hz), 1.28–1.34 (6H, m), 1.38–1.44 (2H, m), 1.74 (2H, quint, J=6.8 Hz), 1.96–2.00 (2H, m), 2.02 (3H, s), 2.08 (3H, s), 2.13 (2H, t, J=6.8 Hz), 2.52 (2H, dd, J=10.7, 6.4 Hz), 3.62 (3H, br.s), 3.90 (2H, t, J=6.8 Hz), 4.16 (2H, t, J=6.8 Hz), 4.25 (2H, s), 4.83 (1H, br.s), 6.79 (2H, d, J=8.3 Hz), 7.04 (2H, d, J=8.3 Hz)

IR(neat): 3359, 2933, 2859, 1733, 1717, 1699, 1538, 1471, 1368, 1224, 1089, 1045, 826, 781 cm$^{-1}$

MS(EI): 465(M$^+$), 433, 330, 205, 107.

(6) 3-Acetamido-3-acetyloxymethyl-5-(4-heptyloxyphenyl) pentyl acetate

3-Acetyloxymethyl-5-(4-heptyloxyphenyl)-3-methoxycarbonylaminopentyl acetate was used in the same manner as working example 8 (2) to give the subject compound as a colorless oil.

Rf value: 0.23 (ethyl acetate:hexane=2:3); 1H-NMR (CDCl$_3$) δ: 0.87 (3H, t, J=6.9 Hz), 1.26–1.34 (6H, m), 1.40–1.44 (2H, m), 1.74 (2H, quint, J=6.8 Hz), 1.92 (3H, s), 2.02 (3H, s), 2.03–2.06 (2H, m), 2.08 (3H, s), 2.19 (2H, t, J=6.9 Hz), 2.51 (2H, m), 3.90 (2H, t, J=6.8 Hz), 415 (2H, t, J=6.9 Hz), 4.30 (2H, s), 5.54 (1H, br.s), 6.79 (2H, d, J=8.8 Hz), 7.05 (2H, d, J=8.8 Hz)

IR(neat): 3308, 3073, 2932, 2860, 1739, 1733, 1662, 1514, 1369, 1244, 1039, 826 cm$^{-1}$

MS(EI): 449(M$^+$), 330, 218, 171, 111.

WORKING EXAMPLE 73

2-Amino-2-[2-(4-heptyloxyphenyl)ethyl]butane-1,4-diol

3-Acetamido-3-acetyloxymethyl-5-(4-heptyloxyphenyl) pentyl acetate (10.0 g) obtained in working example 72 was dissolved in tetrahydrofuran (50 ml) and methanol (50 ml), a 2M aqueous lithium hydroxide solution (80 ml) was added thereto and the mixture was refluxed under heating for 2 hours while stirring. The solvent was distilled away, water (200 ml) was added thereto and the mixture was extracted with ethyl acetate. The ethyl acetate layer was washed with a saturated brine, dried over anhydrous sodium sulfate and the solvent was distilled away. The powder obtained was recrystallized from ethyl acetate and hexane to give the subject compound (6.71 g) as white crystals, melting at 64–65° C.

Rf value: 0.23 (chloroform:methanol=4:1)

$^1$H-NMR(DMSO-d$_6$) δ: 0.86 (3H, t, J=6.8 Hz), 1.26–1.38 (8H, m), 1.47–1.51 (4H, m), 1.67(2H, quint, J=6.8 Hz), 2.44–2.47 (2H, m), 3.19 (2H, br, s), 3.54 (2H, t, J=6.6 Hz), 3.88 (2H, t, J=6.8 Hz), 4.59 (1H, br.s), 6.79 (2H, d, J=8.6 Hz), 7.05 (2H, d, J=8.6 Hz)

IR(KBr): 3360, 3268, 3068, 2927, 2858, 2673, 1612, 1575, 1513, 1468, 1242, 1066, 1044, 831, 798 cm$^{-1}$

Elemental analysis

| | |
|---|---|
| Calculated | C; 70.55, H; 10.28, N; 4.33 |
| Found | C; 70.42, H; 10.47; N; 4.26 |

WORKING EXAMPLE 74

2-Amino-4-fluoro-2-[2-(4-heptyloxyphenyl)ethyl]-butanol hydrochloride (1) 4-[2-(4-Heptyloxyphenyl)ethyl]-4-(2-hydroxyethyl)-2-methyl-2-oxazoline To a solution of 2-amino-2-[2-(4-heptyloxyphenyl)ethyl]butane-1,4-diol (0.50 g) obtained in working example 73 in dimethylformamide (60 ml), N, N-diisopropylethylamine (0.88 g) and triethyl orthoacetate (1.10 g) were added and the mixture was stirred at 115° C. for 2.5 hours. Water (300 ml) was added thereto and the mixture was extracted with ethyl acetate. The ethyl acetate layer was washed with a 1M hydrochloric acid, a saturated aqueous sodium hydrogencarbonate and a saturated brine in order, and dried over anhydrous sodium sulfate. The solvent was distilled away and the residue obtained was purified by silica gel column chromatography (eluent; chloroform:methanol=97:3) to give the subject compound (1.66 g) as a yellowish oil.

Rf value: 0.46 (chloroform:methanol=9:1)

$^1$H-NMR(CDCl$_3$) δ: 0.87 (3H, t, J=6.9 Hz), 1.28–1.34 (6H, m), 1.38–1.44 (2H, m), 1.74 (2H, quint, J=6.9 Hz), 1.80–1.95 (4H, m), 1.95 (3H, s), 2.41–2.50 (2H, m), 3.68–3.72 (1H, m), 3.86–3.90 (1H, m), 3.90 (2H, t, J=6.9 Hz), 3.92 (1H, d, J=8.6 Hz), 4.14 (1H, d, J=8.6 Hz), 6.79 (2H, t, J=8.7 Hz), 7.06 (2H, d, J=8.7 Hz)

IR(neat): 3348, 2927, 2858, 1669, 1515, 1387, 1248, 1039, 992, 825, 751 cm$^{-1}$

MS(EI): 347(M$^+$), 205, 129.

(2) 4-(2-Fluoroethyl)-4-[2-(4-heptyloxyphenyl)ethyl]-2-methyl-2-oxazoline

To a solution of 4-[2-(4-heptyloxyphenyl)ethyl]-4-(2-hydroxyethyl)-2-methyl-2-oxazoline (500 mg) in tetrahydrofuran (20 ml), paratosyl fluoride (502 mg), molecular sieves 4A (5 g) and a 1M solution of tetrabutylammonium fluoride in tetrahydrofuran (4.3 ml) were added and the mixture was refluxed under heating for 23 hours while stirring. The reaction mixture was filtered off, ethyl acetate (100 ml) was added to the filtrate The organic layer was washed with a 0.5 M hydrochloric acid, a saturated aqueous sodium hydrogencarbonate solution and a saturated brine in order, and dried over anhydrous sodium sulfate. The solvent was distilled away and the residue obtained was purified by preparative thin layer chromatography (eluent; ethyl acetate:hexane=35:65) to give the subject compound (250 mg) as a yellowish oil.

Rf value: 0.29 (ethyl acetate:hexane=3:7)

$^1$H-NMR(CDCl$_3$) δ: 0.87 (3H, t, J=6.9 Hz), 1.28–1.33 (6H, m), 1.38–1.44 (2H, m), 1.74 (2H, m), 1.79–1.86 (2H, m), 1.99 (3H, s), 2.00 (2H, ddt, J=25.3, 6.6, 2.4 Hz), 2.47–2.57 (2H, m), 3.90 (2H, t, J=6.6 Hz), 4.04 (2H, d, J=8.8 Hz), 4.10 (2H, d, J=8.8 Hz), 4.57 (2H, ddt, J=47.3, 2.3, 5.9 Hz), 6.79 (2H, d, J=8.8 Hz), 7.06 (2H, d, J=8.8 Hz)

IR(neat): 2931, 2859, 1674, 1514, 1243, 992, 825 cm$^{-1}$

MS(EI): 349 (M$^+$), 131, 89.

(3) 2-Amino-4-fluoro-2-[2-(4-heptyloxyphenyl)ethyl] butanol hydrochloride

To a solution of 4-(2-fluoroethyl)-4-[2-(4-heptyloxyphenyl)ethyl]-2-methyl-2-oxazoline (220 mg) in ethanol (9 ml), concentrated hydrochloric acid (3 ml) was added and the mixture was refluxed under heating for an hour while stirring. The solvent was distilled away and the residue obtained was recrystallized from ethyl acetate and hexane to give the subject compound (140 mg) as white crystals, melting at 126–127° C.

Rf value: 0.47 (chloroform:methanol=4:1)

$^1$H-NMR(DMSO-d$_6$) δ: 0.86 (3H, t, J=6.8 Hz), 1.26–1.38 (8H, m), 1.67 (2H, quint, J=6.8 Hz), 1.76–1.80 (2H, m), 2.04 (2H, dt, J=26.9, 5.9 Hz), 2.51–2.54 (2H, m), 3.51 (2H, d, J=4.8 Hz), 3.89 (2H, t, J=6.8 Hz), 4.64 (2H, dt, J=47.3, 5.9 Hz), 5.57 (1H, t, J=4.8 Hz), 6.83 (2H, d, J=8.5 Hz), 7.09 (2H, d, J=8.5Hz), 8.00 (3H, br.s)

IR(KBr): 3447, 3265, 3029, 2942, 2857, 2598, 1614, 1515, 1247, 1045, 828 cm$^{-1}$

MS(EI): 325(M$^+$), 294, 205, 107. Elemental analysis

| Calculated | C; 63.05, H; 9.19, N; 3.87 |
| Found | C; 62.68, H; 9.25, N; 3.81 |

WORKING EXAMPLE 75

2-Amino-4-chloro-2-[2-(4-heptyloxyphenyl)ethyl]-butanol hydrochloride (1) 4-(2-Chloroethyl)-4-[2-(4-heptyloxyphenyl)ethyl]-2-methyl-2-oxazoline To a solution of 4-[2-(4-heptyloxyphenyl)ethyl]-4-(2-hydroxyethyl)-2-methyl-2-oxazoline (300 mg) obtained in working example 74 (1) in methylene chloride (15 ml), triphenylphosphine (270 mg) and N-chlorosuccinimide (138 mg) were added and the mixture was refluxed under heating for 20 minutes while stirring. A 5% aqueous sodium hydrogencarbonate solution (50 ml) was added thereto and the mixture was extracted with methylene chloride. The methylene chloride layer was washed with a saturated brine and dried over anhydrous sodium sulfate. The solvent was distilled away and the residue obtained was purified by silica gel chromatography (eluent; ethyl acetate:hexane=1:4) to give the subject compound (190 mg) as a colorless oil.

Rf value: 0.58 (ethyl acetate:hexane=3:7)

$^1$H-NMR(CDCl$_3$) δ: 0.87 (3H, t, J=6.9 Hz), 1.28–1.34 (6H, m), 1.38–1.44 (2H, m), 1.70–1.77 (2H, m), 1.74–1.88 (2H, m), 1.98 (3H, s), 2.03 (1H, ddd, J=13.7, 9.3, 5.8 Hz), 2.14 (1H, ddd, J=16.1, 9.8, 6.3 Hz), 2.43–2.55 (2H, m), 3.49–3.59 (2H, m), 3.90 (2H, t, J=6.6 Hz), 4.04 (2H, s), 6.79 (2H, d, J=8.8 Hz), 7.05 (2H, d, J=8.8 Hz)

IR(neat): 3030, 2927, 2860, 1674, 1515, 1471, 1386, 1243, 992, 824 cm$^{-1}$

MS(EI): 367[(M+2)$^+$], 365(M$^+$), 147, 120, 107.

(2) 2-Amino-4-chloro-2-[2-(4-heptyloxyphenyl)ethyl] butanol hydrochloride 4-(2-Chloroethyl)-4-[2-(4-heptyloxyphenyl)ethyl]-2-methyl-2-oxazoline was used in the same manner as working example 74 (3) to give the subject compound as a pale yellow amorphous.

Rf value: 0.65 (chloroform:methanol=4:1)

$^1$H-NMR(DMSO-d$_6$) δ: 0.86 (3H, t, J=6.8 Hz), 1.26–1.38 (8H, m), 1.67 (2H, quint, J=6.9 Hz), 1.74–1.79 (2H, m), 2.09–2.13 (2H, m), 2.50–2.55 (2H, m), 3.50 (2H, d, J=4.9 Hz), 3.74 (2H, t, J=8.3 Hz), 3.89 (2H, t, J=6.9 Hz), 5.59 (1H, t, J=4.9 Hz), 6.83 (2H, d, J=8.6 Hz), 7.12 (2H, d, J=8.6 Hz), 8.12 (3H, br.s)

IR(KBr): 3443, 3318, 3036, 2933, 2860, 2587, 1614, 1515, 1244, 1044, 824, 728, 660 cm$^{-1}$

MS(EI): 305, 288, 246, 107

Elemental analysis

| Calculated | C; 60.31, H; 8.79, N; 3.70 |
| Found | C; 60.00, H; 9.01, N; 3.68 |

WORKING EXAMPLE 76

2-Amino-4-(4-heptyloxyphenyl)-2-(2-methylpropyl) butanol hydrochloride (1) 2-[2-(4-Heptyloxyphenyl)ethyl]-2-(2-methylpropyl) malonic acid diethyl ester In working example 1 (1), isobutylmalonic acid diethyl ester instead of methylmalonic acid diethyl ester, and 2-(4-heptyloxyphenyl)ethyl iodide obtained in working example 27 (2) instead of 2-(4-benzyloxyphenyl)ethyl iodide were used to give the subject compound as a yellowish oil.

Rf value: 0.58 (ethyl acetate:hexane=1:9)

$^1$H-NMR(CDCl$_3$) δ: 0.87 (3H, t, J=6.6 Hz), 0.88 (6H, d, J=6.4 Hz), 1.24 (6H, t, J=7.3 Hz), 1.28–1.34 (6H, m), 1.38–1.44 (2H, m), 1.66 (1H, m), 1.72 (2H, quint, J=6.8 Hz), 1.94 (2H, d, J=6.4 Hz), 2.14–2.19 (2H, m), 2.37–2.42 (2H, m), 3.90 (2H, t, J=6.8 Hz), 4.16 (4H, dq, J=1.2, 7.3 Hz), 6.79 (2H, d, J=8.6 Hz), 7.05 (2H, d, J=8.6 Hz)

IR(neat): 2957, 2933, 2871, 1731, 1513, 1240, 1178, 1029, 826 cm$^{-1}$

MS(EI): 434(M$^+$), 315, 218, 173.

(2) 2-Ethoxycarbonyl-2-[2-(4-heptyloxyphenyl)ethyl]-4-methylpentanoic acid

2-[2-(4-Heptyloxyphenyl)ethyl]-2-(2-methylpropyl) malonic acid diethyl ester was used in the same manner as working example 26 (5) to give the subject compound as a yellowish oil.

Rf value: 0.70 (ethyl acetate:hexane:acetic acid=49:49:2)
$^1$H-NMR(CDCl$_3$) δ: 0.83 (3H, d, J=6.8 Hz), 0.87 (3H, t, J=6.9 Hz), 0.87 (3H, d, J=6.3 Hz), 1.28–1.36 (6H, m), 1.31 (3H, t, J=7.4 Hz), 1.38–1.43 (2H, m), 1.57 (1H, m), 1.74 (2H, quint, J=6.9 Hz), 1.83 (1H, dd, J=14.2, 6.6 Hz), 2.03 (1H, dd, J=14.2, 6.8 Hz), 2.07–2.13 (1H, m), 2.22–2.33 (2H, m), 2.50–2.55 (1H, m), 3.89 (2H, t, J=6.9 Hz), 4.20 (2H, dq, J=3.5, 7.4 Hz), 6.78 (2H, d, J=8.8 Hz), 7.00 (2H, d, J=8.8 Hz)
IR(neat): 2959, 2932, 2872, 1733, 1714, 1512, 1243, 1178, 1051, 827 cm$^{-1}$
MS(EI): 406(M$^+$), 218, 120, 107.

(3) Ethyl 2-[2-(4-heptyloxyphenyl)ethyl]-2-methoxycarbonylamino-4-methylpentanoate In working example 1 (3), 2-ethoxycarbonyl-2-[2-(4-heptyloxyphenyl)-ethyl]-4-methylpentanoic acid instead of potassium 2-ethoxycarbonyl-2-methyl-4-(4-benzyloxyphenyl)butanoate was used to give the subject compound as a yellowish oil.
Rf value: 0.36 (ethyl acetate:hexane=1:9)
$^1$H-NMR(CDCl$_3$) δ: 0.76 (3H, d, J=6.9 Hz), 0.87 (3H, t, J=6.4 Hz), 0.87 (3H, d, J=6.3 Hz), 1.28 (3H, t, J=7.3 Hz), 1.28–1.34 (6H, m), 1.39–1.41 (1H, m), 1.61–1.66 (1H, m), 1.73 (2H, quint, J=6.8 Hz), 1.95–1.98 (1H, m), 2.13–2.21 (1H, m), 2.35 (1H, dd, J=13.7, 5.2 Hz), 2.47–2.54 (1H, m), 2.65 (1H, m), 3.63 (3H, s), 3.89 (3H, t, J=6.8 Hz), 4.15 (2H, q, J=7.3 Hz), 5.92 (1H, s), 6.76 (2H, d, J=8.8 Hz), 7.00 (2H, d, J=8.8 Hz)
IR(neat): 3424, 2958, 2935, 2871, 1733, 1506, 1237, 1178, 1086, 1046, 829 cm$^{-1}$
MS(EI): 435(M$^+$), 217, 171, 107.

(4) 2-Amino-4-(4-heptyloxyphenyl)-2-(2-methylpropyl) butanol hydrochloride

Ethyl 2-[2-(4-heptyloxyphenyl)ethyl]-2-methoxycarbonylamino-4-methylpentanoate was used in the same manners as working example 26 (7) and then working example 1 (7) to give the subject compound as a yellow amorphous.
Rf value: 0.56 (chloroform:methanol=4:1)
$^1$H-NMR(DMSO-d$_6$) δ: 0.86 (3H, t, J=6.8 Hz), 0.94 (6H, d, J=6.3 Hz), 1.26–1.38 (8H, m), 1.52 (2H, d, J=5.3 Hz), 1.67 (2H, quint, J=6.9 Hz), 1.75–1.79 (3H, m), 2.49–2.53 (2H, m), 3.48 (2H, br.s), 3.90 (2H, t, J=6.4 Hz), 5.49 (1H, t, J=4.4 Hz), 6.83 (2H, d, J=8.8 Hz), 7.09 (2H, d, J=8.8 Hz), 7.88 (3H, br.s)
IR(KBr): 3468, 3378, 3252, 2952, 2924, 2871, 2634, 1614, 1514, 1244, 1044, 825 cm$^{-1}$
MS(EI): 335(M$^+$), 304, 205, 107.

WORKING EXAMPLE 77

2-Acetamido-2-[2-(4-octanoylphenyl)ethyl]pentyl acetate (1) 2-(2-Phenylethyl)-2-propylmalonic acid diethyl ester In working example 1 (1), propylmalonic acid diethyl ester instead of methylmalonic acid diethyl ester, and phenethyl bromide instead of 2-(4-benzyloxyphenyl)ethyl iodide were used to give the subject compound as a colorless oil.
Rf value: 0.53 (ethyl acetate:hexane=1:9)
$^1$H-NMR(CDCl$_3$) δ: 0.92 (3H, t, J=7.3 Hz), 1.19–1.22 (2H, m), 1.24 (6H, t, J=7.2 Hz), 1.90–1.94 (2H, m), 2.14–2.19 (2H, m), 2.46–2.50 (2H, m), 4.17 (4H, q, J=7.2 Hz), 7.15–7.18 (3H, m), 7.24–7.28 (2H, m)
IR(neat): 3064, 3029, 2965, 2875, 1733, 1455, 1238, 1211, 1180, 1031, 750, 700 cm$^{-1}$
MS(EI): 307[(M+1)$^+$], 202, 173, 91.

(2) 2-Ethoxycarbonyl-2-(2-phenylethyl)pentanoic acid 2-(2-Phenylethyl)-2-propylmalonic acid diethyl ester was used in the same manner as workig example 26 (5) to give the subject compound as a yellowish oil.

Rf value: 0.68 (ethyl acetate:hexane:acetic acid=49:49:2)
$^1$H-NMR(CDCl$_3$) δ: 0.89 (3H, t, J=7.3 Hz), 1.14–1.19 (1H, m), 1.30 (3H, t, J=7.3 Hz), 1.42 (1H, m), 1.85 (1H, dt, J=4.9, 12.7 Hz), 1.96 (1H, dt, J=5.4, 12.2 Hz), 2.16 (1H, dt, J=5.4, 12.6 Hz), 2.30 (1H, dt, J=4.9, 12.5 Hz), 2.41 (1H, dt, J=5.4, 12.2 Hz), 2.59 (1H, dt, J=5.4, 12.6 Hz), 4.20 (2H, dq, J=10.7, 7.3 Hz), 7.11–7.27 (5H, m)
IR(neat): 3485, 3159, 3029, 2965, 2876, 2629, 1733, 1717, 1455, 1236, 747, 700 cm$^{-1}$
MS(EI): 278(M$^+$), 174, 145, 127, 91.

(3) Ethyl 2-methoxycarbonylamino-2-(2-phenylethyl) pentanoate

In working example 1 (3), 2-ethoxycarbonyl-2-(2-phenylethyl)pentanoic acid instead of potassium 2-ethoxycarbonyl-2-methyl-4-(4-benzyloxyphenyl)-butanoate was used to give the subject compound as a yellowish oil.
Rf value: 0.42 (ethyl acetate:hexane=1:9)
$^1$H-NMR(CDCl$_3$) δ: 0.86 (3H, t, J=7.4 Hz), 0.96–1.04 (1H, m), 1.27 (3H, t, J=7.3 Hz), 1.28–1.37 (1H, m), 1.65–1.72 (1H, m), 2.01–2.09 (1H, m), 2.25–2.32 (2H, m), 2.56–2.63 (1H, m), 2.69 (1H, m), 3.63 (3H, m), 4.09–4.21 (2H, m), 5.82 (1H, br.s), 7.10–7.25 (5H, m)
IR(neat): 3423, 3086, 3063, 3028, 2962, 2874, 1720, 1508, 1375, 1341, 1235, 1032, 748, 700 cm$^{-1}$
MS(EI): 308[(M+1)$^+$], 234, 203, 157, 91.

(4) 2-Acetamido-2-(2-phenylethyl)pentyl acetate

Ethyl 2-methoxycarbonylamino-2-(2-phenylethyl) pentanoate was used in the same manners as working example 26 (7), working example 28 (5) and then working example 34 (5) to give the subject compound as white crystals, melting at 74–76° C.
Rf value: 0.37 (ethyl acetate:hexane=2:3)
$^1$H-NMR(CDCl$_3$) δ: 0.92 (3H, t, J=7.1 Hz), 1.22–1.34 (2H, m), 1.65–1.81 (2H, m), 1.91 (3H, s), 1.94–2.04 (1H, m), 2.07 (3H, s), 2.09–2.15 (1H, m), 2.55 (2H, t, J=8.6 Hz), 4.28 (1H, d, J=11.2 Hz), 4.31 (1H, d, J=11.2 Hz), 5.22 (1H, br.s), 7.15–7.21 (3H, m), 7.24–7.27 (2H, m)
IR(neat): 3313, 3064, 3028, 2961, 2935, 2874, 1733, 1652, 1558, 1455, 1372, 1231, 1042, 750, 699 cm$^{-1}$
MS(EI): 291(M$^+$), 218, 176, 127, 91.

(5) 2-Acetamido-2-[2-(4-octanoylphenyl)ethyl]pentyl acetate

In working example 34 (6), 2-acetamido-2-(2-phenylethyl)pentyl acetate instead of 2-acetamido-2-methyl-4-phenylbutyl acetate was used to give the subject compound as a yellowish oil.
Rf value: 0.36 (ethyl acetate:hexane=2:3)
$^1$H-NMR(CDCl$_3$) δ: 0.86 (3H, t, J=6.9 Hz), 0.92 (3H, t, J=7.3 Hz), 1.26–1.34 (10H, m), 1.66–1.74 (4H, m), 1.93 (3H, s), 1.96–2.00 (1H, m), 2.08 (3H, s), 2.11–2.18 (1H, m), 2.59 (2H, t, J=8.5 Hz), 2.90 (2H, t, J=7.6 Hz), 4.25 (1H, d, J=11.7 Hz), 4.30 (1H, d, J=11.7 Hz), 5.27 (1H, s), 7.24 (2H, d, J=8.3 Hz), 7.85 (2H, d, J=8.3 Hz)
IR(neat): 3585, 3321, 3218, 3070, 2956, 2936, 2857, 1739, 1674, 1652, 1538, 1455, 1372, 1228, 1042, 724 cm$^{-1}$
MS(EI): 471(M$^+$), 302, 127, 99.

WORKING EXAMPLE 78

2-Amino-2-[2-(4-octanoylphenyl)ethyl]pentanol

2-Acetamido-2-[2-(4-octanoylphenyl)ethyl]pentyl acetate (374.5 mg) obtained in working example 77 and lithium hydroxide monohydrate (376 mg) were dissolved in methanol (4.5 mg), tetrahydrofuran (3 ml) and water (4.5 mg) and the mixture was refluxed under heating for 3 hours while stirring. The mixture was diluted with water (50 ml)

and extracted with ethyl acetate. The ethyl acetate layer was dried over anhydrous sodium sulfate, the solvent was distilled away and the crude crystals obtained was recrystallized from hexane and ethyl acetate to give the subject compound (45 mg) as white crystals, melting at 62–63° C.

Rf value: 0.34 (chloroform:methanol=4:1)

$^1$H-NMR(CDCl$_3$) δ: 0.88 (3H, t, J=6.9 Hz), 0.96 (3H, t, J=6.9 Hz), 1.35 (12H, m), 1.40–1.80 (7H, m), 2.65 (2H, t, J=8.8 Hz), 2.93 (2H, t, J=6.8 Hz), 3.39 (2H, 2d, Jgem=10.7 Hz), 7.27 (2H, d, J=8.3 Hz), 7.88 (2H, d, J=8.3 Hz)

IR(KBr): 2957, 2927, 2851, 1679, 1607 cm$^{-1}$

MS(EI): 333(M$^+$), 302

Elemental analysis

| Calculated | C; 75.63, H; 10.58, N; 4.20 |
| Found | C; 75.49, H; 10.73, N; 4.07 |

WORKING EXAMPLE 79

2-Acetamido-2-[2-[4-(1-hydroxyoctyl)phenyl]ethyl]-pentyl acetate

To a solution of 2-acetamido-2-[2-(4-octanoylphenyl) ethyl]pentyl acetate (2.0 g) obtained in working example 77 in ethanol (60 ml), sodium borohydride (91 mg) was added and the mixture was stirred at room temperature for 30 minutes. Water (50 ml) was added to the reaction mixture under ice-cooling, the mixture was neutralized with a 2M hydrochloric acid and the solvent was distilled away. Water (100 ml) was added to the residue obtained and the mixture was extracted with chloroform. The chloroform layer was washed with a saturated brine and dried over anhydrous sodium sulfate. The solvent was distilled away and the residue obtained was purified by silica gel column chromatography (eluent; chloroform:methanol=19:1) to give the subject compound as a yellowish oil.

Rf value: 0.38(chloroform:methanol=19:1)

$^1$H-NMR(CDCl$_3$) δ: 0.84 (3H, t, J=6.8 Hz), 0.92 (3H, t, J=7.3 Hz), 1.25–1.38 (12H, m), 1.67–1.76 (4H, m), 1.92 (3H, s), 1.92–1.99 (1H, m), 2.07 (3H, s), 2.07–2.14 (1H, m), 2.53 (2H, t, J=8.6 Hz), 4.27 (1H, d, J=11.2 Hz), 4.30 (1H, d, J=11.2 Hz), 4.61 (1H, m), 5.22 (1H, br.s), 7.14 (2H, d, J=8.3 Hz), 7.23 (2H, d, J=8.3 Hz)

IR(neat): 3311, 3082, 3009, 2960, 2925, 2857, 1733, 1652, 1558, 1456, 1372, 1237, 1043, 755 cm$^{-1}$

MS(EI): 401[(M-H$_2$O)$^+$], 342, 201, 127, 99.

WORKING EXAMPLE 80

2-Amino-2-[2-[4-(1-hydroxyoctyl)phenyl]ethyl] pentanol 1/2hydrate

2-Acetamido-2-[2-[4-(1-hydroxyoctyl)phenyl]ethyl] pentyl acetate (360 mg) obtained in working example 79 was dissolved in tetrahydrofuran (35 ml) and methanol (40 ml), a 2M aqueous lithium hydroxide solution (35 m) was added thereto and the mixture was refluxed under heating for an hour while stirring. The solvent was distilled away, water (150 ml) was added thereto and the mixture was extracted with ethyl acetate. The ethyl acetate layer was washed with a saturated brine, dried over anhydrous sodium sulfate and the solvent was distilled away to give the subject compound (272 mg) as a yellowish oil.

Rf value: 0.36 (chloroform:methanol=4:1)

$^1$H-NMR(CDCl$_3$) δ: 0.84 (3H, t, J=6.8 Hz), 0.92 (3H, t, J=6.8 Hz), 1.23–1.46 (14H, m), 1.52–1.78 (4H, m), 2.07 (4H, br.s), 2.55 (2H, t, J=8.6 Hz), 3.35 (2H, s), 4.59 (2H, t, J=6.6 Hz), 7.13 (2H, d, J=8.3 Hz), 7.22 (2H, d, J=8.3 Hz)

IR(neat): 3354, 3018, 2931, 2859, 1589, 1514, 1464, 1050, 755 cm$^{-1}$

MS(EI): 335(M$^+$), 304

Elemental analysis

| Calculated | C; 74.18, H; 11.12, N; 4.12 |
| Found | C; 73.93, H; 11.23, N; 4.03 |

WORKING EXAMPLE 81

2-Acetamido-2-[2-(4-octylphenyl)ethyl]pentyl acetate

2-Acetamido-2-[2-(4-octanoylphenyl)ethyl]pentyl acetate (696.2 mg) was subjected to reduction in the same manner as working example 2 (7) to give the subject compound (365.5 mg) as a colorless oily substance.

Rf value: 0.26 (ethyl acetate:hexane=1:2)

$^1$H-NMR (CDCl$_3$) δ: 0.88 (3H, t, J=6.8 Hz), 0.93 (3H, t, J=7.4 Hz), 1.26–1.33 (12H, m), 1.58–1.60 (2H, m), 1.66–1.83 (2H, m), 1.92 (3H, s), 1.92–1.99 (1H, m), 2.05–2.14 (1H, m), 2.09 (3H, s), 2.51–2.57 (4H, m), 4.31 (1H, d, J=11.2 Hz), 4.33 (1H, d, J=11.2 Hz), 5.22 (1H, br.s), 7.08 (4H, s)

IR (neat, cm$^{-1}$): 3307, 3079, 3009, 2959, 2927, 2856, 1746, 1652, 1549, 1467, 1372, 1236, 1042, 757.

WORKING EXAMPLE 82

2-Amino-2-[2-(4-octylphenyl)ethyl]pentanol hydrochloride

2-Acetamido-2-[2-(4-octylphenyl)ethyl]pentyl acetate (341.1 mg) was subjected to hydrolysis in the same manner as working example 2 (8) to give the subject compound (240 mg).

Rf value: 0.58 (chloroform:methanol=4:1)

$^1$H-NMR (DMSO-d$_6$) δ: 0.84 (3H, t, J=6.9 Hz), 0.88 (3H, t, J=7.1 Hz), 1.22–1.34 (12H, m), 1.52–1.53 (4H, m), 1.71–1.75 (2H, m), 2.52–2.54 (4H, m), 3.45 (2H, br. s), 5.47 (1H, br. s), 7.09 (4H, s), 7.86 (3H, br. s)

IR (neat, cm$^{-1}$): 3355, 3224, 2963, 2854, 1607, 1514, 1466, 1067.

WORKING EXAMPLE 83

2-Amino-5-(4-hexyloxyphenyl)pentanol hydrochloride

2-Acetamido-5-(4-hexyloxyphenyl)pentanol (0.32 g) obtained in working example 18 was dissolved in a mixed solvent of methanol-water (1:1, 20 ml), lithium hydroxide monohydrate (0.13 g) was added thereto and the mixture was stirred at 60° C. for 10 hours. Ice-water was poured into the reaction mixture, the mixture was extracted with ethyl acetate and the organic layer was dried over anhydrous sodium sulfate. The solvent was distilled away and the yellowish oily substance obtained was dissolved in 30% hydrochloric acid-methanol. The solution was concentrated under reduced pressure to give a pale yellow powder. This was recrystallized from a mixed solvent of ethyl acetate-methanol to give the subject compound (0.25 g) as white crystals, melting at 158–159° C.

Rf value: 0.3 (chloroform:methanol=5:1)

$^1$H-NMR(400 MHz, DMSO-$d_6$) δ: 0.88 (3H, t, J=6.8 Hz), 1.30–1.72 (12H, m), 2.57 (2H, m), 3.05 (1H, m), 3.48 (1H, m), 3.57 (1H, m), 3.90 (2H, t, J=6.3 Hz), 5.25 (1H, t, J=4.8 Hz), 6.82 (2H, d, J=8.3 Hz), 7.09 (2H, d, J=8.3 Hz), 7.73 (3H, s)

IR(KBr): 3221, 2933, 1514, 1246, 1055 cm$^{-1}$

MS(EI): 279(M$^+$)

Elemental analysis

|  |  |
|---|---|
| Calculated | C; 64.64, H; 9.57, N; 4.43 |
| Found | C; 64.42, H; 9.70, N; 4.39 |

WORKING EXAMPLE 84

2-Amino-4-(4-heptyloxyphenyl)butanol hydrochloride (1) 2-Acetamido-4-(4-benzyloxyphenyl)butanol In working example 6 (1), 2-(4-benzyloxyphenyl)ethanol instead of 2-(4-octylphenyl)ethanol was used in the same manner as process (1) to (6) to give the subject compound (9.48 g).

$^1$H-NMR(400 MHz, CDCl$_3$) δ: 1.43–1.68 (1H, m), 1.70–1.90 (1H, m), 1.97 (3H, s), 2.40 (1H, bs), 2.55–2.66 (2H, m), 3.50–3.60 (1H, m), 3.60–3.70 (1H, m), 3.90–4.00 (1H, m), 5.04 (2H, s), 5.52 (1H, bs), 6.90 (2H, d, J=8 Hz), 7.09 (2H, d, J=8 Hz), 7.26–7.44 (5H, m).

(2) 2-Acetamido-4-(4-benzyloxyphenyl)butyl acetate

To a solution of 2-acetamido-4-(4-benzyloxyphenyl) butanol (9.48 g) in pyridine (100 ml), acetic anhydride (22.2 ml) was added and the mixture was stirred at room temperature for 5 hours. Then, the solution was poured into water and extracted with ethyl acetate. The extract was washed with a dilute hydrochloric acid, a dilute aqueous sodium hydrogencarbonate solution and a saturated brine, dried over magnesium sulfate and the solvent was distilled away under reduced pressure. The residue obtained was crystallized from ethyl acetate-hexane to give the subject compound (8.32 g).

$^1$H-NMR(400 MHz, CDCl$_3$) δ: 1.40–1.70 (2H, m), 1.98 (3H, s), 2.05 (3H, s), 2.50–2.63 (2H, m), 4.09 (2H, ddd, J=48, 8, 4 Hz), 4.20–4.30 (1H, m), 5.04 (2H, s), 5.39–5.45 (1H, m), 6.90 (2H, d, J=8 Hz), 7.07 (2H, d, J=8 Hz), 7.26–7.44 (5H, m).

(3) 2-Acetamido-4-(4-hydroxyphenyl)butyl acetate

To a solution of 2-acetamido-4-(4-benzyloxyphenyl)butyl acetate (8.32 g) in ethanol (150 ml), 10% palladium-carbon (1 g) was added and the mixture was stirred, under a hydrogen atmosphere, at room temperature for 8.5 hours. Then, the catalyst was filtered off and the solvent was distilled away under reduced pressure. Ethanol (200 ml) and 10% palladium-carbon (1 g) were added to the residue and the mixture was further stirred, under a hydrogen atmosphere, at room temperature for 3.5 hours. The catalyst was filtered off from the reaction solution and the solvent was distilled away under reduced pressure. The residue was subjected to silica gel chromatography (eluent; ethyl acetate-hexane=1:4) to give the subject compound (5.80 g).

$^1$H-NMR(400 MHz, CDCl$_3$) δ: 1.40–1.70 (2H, m), 1.99 (3H, s), 2.06 (3H, s), 2.50–2.63 (2H, m), 3.98–4.06 (2H, m), 4.10–4.18 (2H, m), 4.18–4.26 (1H, m), 5.45–5.57 (1H, m), 6.76 (2H, dd, J=8, 4 Hz), 7.03 (2H, dd, J=8, 4 Hz).

(4) 2-Acetamido-4-(4-heptyloxyphenyl)butyl acetate

To a suspension of sodium hydride (0.076 g) in dimethylformamide (1 ml) and tetrahydrofuran (1 ml), under a nitrogen atmosphere, a solution of 2-acetamido-4-(4-hydroxyphenyl)butyl acetate (0.51 g) in dimethylformamide (2 ml) was added and the mixture was stirred at room temperature for 50 minutes. Then, to the solution, heptyl bromide (0.35 g) and catalytic amount of potassium iodide were added and the mixture was stirred at 60° C. for 4 hours and 40 minutes. Then, the reaction mixture was poured into water and extracted with ethyl acetate. The extract was washed with a dilute aqueous sodium hydrogencarbonate solution and a saturated brine, dried over sodium sulfate and the solvent was distilled away under reduced pressure. The residue obtained was subjected to silica gel chromatography (eluent; ethyl acetate-hexane=4:1) to give the subject compound (0.30 g).

$^1$H-NMR(400 MHz, CDCl$_3$) δ: 0.89 (3H, t, J=8 Hz), 1.20–1.65 (10H, m), 1.70–1.80 (2H, m), 1.97 (3H, s), 2.06 (3H, s), 2.47–2.63 (2H, m), 3.92 (3H, t, J=8 Hz), 3.98–4.15 (5H, m), 5.34–5.45 (2H, m), 6.81 (2H, d, J=8 Hz), 7.06 (2H, d, J=8 Hz).

(5) 2-Amino-4-(4-heptyloxyphenyl)butanol hydrochloride

To a solution of 2-acetamido-4-(4-heptyloxyphenyl)butyl acetate (0.30 g) in methanol (20 ml), an aqueous lithium hydroxide monohydrate (0.35 g) solution (5 ml) was added and the mixture was refluxed under heating for 10.5 hours. Then, the reaction mixture was poured into water and extracted with ethyl acetate. The extract was washed with water and a saturated brine, dried over sodium sulfate and the solvent was distilled away under reduced pressure. A solution of hydrochloric acid in ether was added to the residue obtained and the solution was crystallized from methanol-ethyl acetate to give the subject compound (0.18 g), melting at 205–210° C. (decomposition).

Rf value: 0.2 (chloroform:methanol=8:1)

$^1$H-NMR(400 MHz, DMSO-$d_6$) δ: 0.86 (3H, t, J=8 Hz), 1.20–1.80 (12H, m), 2.50–2.57 (2H, m), 2.97–3.08 (1H, m), 3.30–3.50 (2H, m), 3.50–3.62 (1H, m), 3.89 (2H, t, J=8 Hz), 5.20–5.30 (1H, m), 6.83 (2H, t, J=8 Hz), 7.09 (2H, t, J=8 Hz), 7.77 (3H, bs)

IR(KBr): 3221, 2925, 1580, 1242, 1056 cm$^{-1}$

MS(EI): 279(M$^+$)

Elemental analysis

|  |  |
|---|---|
| Calculated | C; 64.64, H; 9.57, N; 4.44 |
| Found | C; 64.56, H; 9.73, N; 4.30 |

WORKING EXAMPLE 85

2-Amino-2-[2-[4-(1-acetamidooctyl)phenyl]ethyl]-pentanol (1) 2-Acetamido-2-[2-[4-(1-acetamidooctyl)phenyl]ethyl]pentyl acetate To a solution of 2-acetamido-2-[2-[4-(1-hydroxyoctyl) phenyl]ethyl]pentyl acetate (1.15 g) obtained in working example 79, phthalimide (400 mg) and triphenylphosphine (720 mg) in tetrahydrofuran (10 ml), a solution of diethyl azodicarboxylate (480 mg) in tetrahydrofuran (2 ml) was dropwise added at room temperature and the mixture was further stirred for 19 hours. The solvent was distilled away and the residue obtained was purified by silica gel column chromatography (eluent; chloroform:methanol=19:1) to give a white amorphous. This was dissolved in ethanol (20 ml), hydrazine (330 mg) was added thereto and the mixture was refluxed under heating for 1.5 hours while stirring. Concentrated hydrochloric acid (3 ml) was added thereto and the mixture was filtered off and the filtrate obtained was made alkaline with a 1M aqueous sodium hydroxide solution. Water (200 ml) was added thereto and the mixture was extracted with ethyl acetate. The ethyl acetate layer was washed with a saturated brine, dried over anhydrous sodium sulfate and the solvent was distilled away. The residue obtained was acetylated with acetic anhydride and pyridine according to a usual method and purified by silica gel column chromatography (eluent; chloroform:methanol=9:1) to give the subject compound (175 mg) as a yellowish oil.

Rf value: 0.44 (chloroform:methanol=9:1)

$^1$H-NMR(CDCl$_3$) δ: 0.86 (3H, t, J=6.9 Hz), 0.94 (3H, t, J=7.3 Hz), 1.23–1.33 (12H, m), 1.66–1.77 (4H, m), 1.90–2.00 (1H, m), 1.93 (3H, 2s), 1.97 (3H, s), 2.09 (3H, s), 2.09–2.16 (1H, m), 2.54 (2H, t, J=8.6 Hz), 4.28 (1H, d, J=11.7 Hz), 4.31 (1H, d, J=11.7 Hz), 4.90 (1H, q, J=7.8Hz), 5.24 (1H, br, s), 5.60 (1H, d, J=8.8 Hz), 7.14 (2H, d, J=8.3 Hz), 7.18 (2H, d, J=8.3 Hz)

IR(neat): 3294, 3078, 2959, 2931, 2858, 1743, 1652, 1549, 1456, 1373, 1237, 1042, 757 cm$^{-1}$.

(2) 2-Amino-2-[2-[4-(1-acetamidooctyl)phenyl]ethyl]pentanol

2-Acetamido-2-[2-[4-(1-acetamidooctyl)phenyl]ethyl]pentyl acetate (160 mg) was dissolved in methanol (5 ml) and tetrahydrofuran (5 ml), a 2M aqeuous lithium hydroxide solution (5 ml) was added thereto and the mixture was refluxed under heating for an hour while stirring. The solvent was distilled away, water (100 ml) was added thereto and the mixture was extracted with ethyl acetate. The ethyl acetate layer was washed with a saturated brine, dried over anhydrous sodium sulfate and the solvent was distilled away to give the subject compound (121 mg) as a yellowish oil.

Rf value: 0.43 (chloroform:methanol=4:1)

$^1$H-NMR(CDCl$_3$) δ: 0.86 (3H, t, J=6.9 Hz), 0.95 (3H, t, J=6.9 Hz), 1.23–1.35 (12H, m), 1.43–1.74 (9H, m), 1.97 (3H, s), 2.58 (2H, t, J=8.8 Hz), 3.38 (2H,s), 4.91 (1H, q, J=7.8 Hz), 5.64 (1H, d, J=8.8 Hz), 7.16 (2H, d, J=8.3 Hz), 7.18 (2H, d, J=8.3 Hz)

IR(neat): 3316, 3081, 2962, 2924, 2854, 1652, 1558, 1455, 1304, 1061 cm$^{-1}$.

WORKING EXAMPLE 86

2-Amino-2-[2-[4-(1-aminooctyl)phenyl]ethyl]pentanol

2-Amino-2-[2-[4-(1-acetamidooctyl)phenyl]ethyl]pentanol obtained in working example 85 is subjected to hydrolysis with alkali to give the subject compound.

WORKING EXAMPLE 87

2-Amino-2-methyl-4-(4-octanoylphenyl)butanol

2-Acetamido-2-methyl-4-(4-octanoylphenyl)butyl acetate obtained in working example 34 was hydrolyzed in a similar manner to that described in working example 78 to give the subject compound as a white powder, melting at 88–89° C.

$^1$H-NMR (CDCl$_3$) δ: 0.88 (3H, t, J=6.9 Hz), 1.15 (3H, s), 1.18–1.36 (8H, m), 1.63–1.79 (4H, m), 2.71 (2H, t, J=8.6 Hz), 2.93 (2H, t, J=7.6 Hz), 3.35 (1H, d, J=11.3 Hz), 3.40 (1H, d, J=11.3 Hz), 7.28 (2H, d, J=8.1 Hz), 7.88 (2H, d, J=8.1 Hz)

IR (KBr, cm$^{-1}$): 3333, 3263, 3089, 2936, 2851, 2733, 1683, 1609, 1057

MS (EI): 305 (M$^+$), 274. Elemental analysis

| Calculated | C; 74.71, H; 10.23, N; 4.59 |
| Found | C; 74.40, H; 10.18, N; 4.51 |

WORKING EXAMPLE 88

2-Amino-4-[4-(1-hydroxyoctyl)phenyl]-2-methylbutanol

2-Acetamido-2-methyl-4-(4-octanoylphenyl)butyl acetate obtained in working example 34 was reduced in a similar manner to that described in working example 79 and hydrolyzed in a similar manner to that described in working example 80 to give the subject compound as a yellowish oily substance.

$^1$H-NMR (CDCl$_3$) δ: 0.87 (3H, t, J=6.8 Hz), 1.13 (3H, s), 1.24–1.43 (10H, m), 1.61–1.78 (4H, m), 2.64 (2H, t, J=8.8 Hz), 3.32 (1H, d, J=10.5 Hz), 3.38 (1H, d, J=10.5 Hz), 4.63 (1H, t, J=6.6 Hz), 7.18 (2H, d, J=8.3 Hz), 7.26 (2H, d, J=8.3 Hz)

IR (neat, cm$^{-1}$): 3347, 2928, 2856, 1464, 1053

MS (EI): 307 (M$^+$), 276.

WORKING EXAMPLE 89

2-Amino-2-ethyl-4-(4-octanoylphenyl)butanol

2-Acetamido-2-ethyl-4-(4-octanoylphenyl)butyl acetate obtained in working example 97 was hydrolyzed in a similar manner to that described in working example 78 to give the subject compound as white crystals, melting at 75–76° C.

$^1$H-NMR (CDCl$_3$) δ: 0.88 (3H, t, J=6.9 Hz), 0.92 (3H, t, J=7.6 Hz), 1.29–1.46 (10H, m), 1.51–1.62 (2H, m), 1.68–1.77 (4H, m), 2.63–2.67 (2H, m), 2.93 (2H, t, J=7.6 Hz), 3.37 (1H, d, J=10.8 Hz), 3.39 (1H, d, J=10.8 Hz), 7.28 (2H, d, J=8.3 Hz), 7.88 (2H, d, J=8.3 Hz)

IR (KBr, cm$^{-1}$): 3339, 3287, 3081, 2920, 2849, 1678, 1608, 970

MS (EI): 319 (M$^+$), 288

Elemental analysis

| Calculated | C; 75.19, H; 10.41, N; 4.38 |
| Found | C; 74.90, H; 10.61, N; 4.38 |

WORKING EXAMPLE 90

2-Amino-2-ethyl-4-(4-octylphenyl)butanol

In working example 77, 2-acetamido-2-ethyl-4-(4-octanoylphenyl)butyl acetate obtained by using ethylmalonic acid diethyl ester instead of propylmalonic acid diethyl ester, is subjected to reduction in the same manner as working example 2 (7) and then hydrolysis in the same manner as working example 78 to give the subject compound.

WORKING EXAMPLE 91

2-Amino-2-ethyl-4-[4-(1-hydroxyoctyl)phenyl]butanol

In working example 77, 2-acetamido-2-ethyl-4-(4-octanoylphenyl)butyl acetate obtained by using ethylmalonic acid diethyl ester instead of propylmalonic acid diethyl ester, is treated in the same manners as working example 79 and then working example 80 to give the subject compound.

WORKING EXAMPLE 92

2-Amino-4-[4-(1-aminoocyl)phenyl]-2-ethylbutanol

In working example 77, 2-acetamido-2-ethyl-4-(4-octanoylphenyl)butyl acetate obtained by using ethylmalonic acid diethyl ester instead of propylmalonic acid diethyl ester, is treated in the same manners as working example 79, working example 85 and then working example 86 to give the subject compound.

The following compounds can be produced in the same manners as aforementioned examples.

WORKING EXAMPLE 93

2-Amino-4-(4-heptyloxy-3-hydroxyphenyl)-2-methylbutanol

WORKING EXAMPLE 94

2-Amino-2-ethyl-4-(4-heptyloxy-3-hydroxyphenyl)-butanol

WORKING EXAMPLE 95

2-Amino-2-[2-(4-heptyloxy-3-hydroxyphenyl)ethyl]-pentanol

WORKING EXAMPLE 96

3-Amino-3-[2-(4-octylphenyl)ethyl]pentane-1,5-diol

3-Acetamido-5-acetoxy-3-[2-(4-octylphenyl)ethyl]pentyl acetate obtained in working example 102 was hydrolyzed in a similar manner to that described in working example 78 to give the subject compound as a white powder, melting at 57–59° C.

$^1$H-NMR (CDCl$_3$) δ: 0.88 (3H, t, J=6.8 Hz), 1.27–1.30 (10H, m), 1.57–1.59 (2H, m), 1.70–1.82 (6H, m), 2.53–2.59 (4H, m), 3.88 (4H, t, J=5.9 Hz), 7.10 (4H, s)

IR (KBr, cm$^{-1}$): 3375, 3326, 3267, 3061, 2922, 2849, 1050, 1015

MS (EI): 335 (M$^+$), 290, 118.

WORKING EXAMPLE 97

2-Acetamido-2-ethyl-4-(4-octanoylphenyl)butyl acetate

The subject compound was obtained as a colorless oily substance starting from diethyl ethylmalonate and 2-phenylethyl bromide using a similar method to that described in working example 34.

$^1$H-NMR (CDCl$_3$) δ: 0.88 (3H, t, J=6.9 Hz), 0.90 (3H, t, J=7.3 Hz), 1.28–1.36 (4H, m), 1.72 (2H, qui., J=7.3 Hz), 1.82 (2H, dq, J=7.3, 1.4 Hz), 1.96 (3H, s), 1.96–2.03 (1H, m), 2.10 (3H, s), 2.13–2.20 (1H, m), 2.61 (2H, t, J=8.6 Hz), 2.93 (2H, t, J=7.6 Hz), 4.28 (1H, t, J=11.3 Hz), 4.33 (1H, t, J=11.3 Hz), 5.28 (1H, br. s), 7.26 (2H, d, J=8.3 Hz), 7.87 (2H, d, J=8.3 Hz)

IR (neat, cm$^{-1}$): 3310, 3078, 2956, 2931, 2858, 1739, 1683, 1652, 1549, 1462, 1372, 1238, 1046

MS (EI): 403 (M$^+$), 288, 113.

WORKING EXAMPLE 98

2-Acetamido-2-ethyl-4-(4-octylphenyl)butyl acetate

2-Acetamido-2-ethyl-4-(4-octanoylphenyl)butyl acetate obtained in working example 89 was reduced in a similar manner to that described in working example 37 to give the subject compound as a colorless oily substance.

$^1$H-NMR (CDCl$_3$) δ: 0.88 (3H, t, J=6.8 Hz), 0.89 (3H, t, J=7.6 Hz), 1.26–1.30 (10H, m), 1.58 (2H, m), 1.75–1.90 (2H, m), 1.90–1.98 (1H, m), 1.93 (3H, s), 2.05–2.13 (1H, m), 2.09 (3H, s), 2.51–2.58 (4H, m), 4.31 (1H, d, J=11.3 Hz), 4.33 (1H, d, J=11.3 Hz), 5.20 (1H, br. s), 7.09 (4H, s)

IR (neat, cm$^{-1}$): 3307, 3079, 2957, 2928, 2856, 1746, 1652, 1554, 1461, 1372, 1237, 1047, 757

MS (EI): 389 (M$^+$), 316, 113.

WORKING EXAMPLE 99

2-Amino-2-ethyl-4-(4-octylphenyl)butanol hydrochloride

2-Acetamido-2-ethyl-4-(4-octylphenyl)butyl acetate obtained in working example 98 was hydrolyzed in a similar manner to that described in working example 1 (7) to give the subject compound as a white powder, melting at 107–109° C.

$^1$H-NMR (DMSO-d$_6$) δ: 0.84 (3H, t, J=6.9 Hz), 0.88 (3H, t, J=7.6 Hz), 1.23–1.25 (10H, m), 1.50–1.53 (2H, m), 1.62 (2H, q, J=7.6 Hz), 1.70–1.75 (2H, m), 2.50–2.55 (4H, m), 3.46 (2H, d, J=5.4 Hz), 5.46 (1H, t, J=5.4 Hz), 7.09 (4H, s), 7.91 (3H, br. s)

IR (KBr, cm$^{-1}$): 3185, 3131, 2923, 2604, 1618, 1515, 1455, 1071

MS (EI): 305 (M$^+$), 274.

WORKING EXAMPLE 100

3-Acetamido-5-acetoxy-3-[2-(4-octanoylphenyl) ethyl]-pentyl acetate (1) Dimethyl 1,3-acetonedicarboxylate ethylene acetal A solution of dimethyl 1,3-acetonedicarboxylate (50 g), ethyleneglycol (48 ml) and p-toluenesulfonic acid monohydrate (0.57 g) in benzene (450 ml) was refluxed under heating removing water for 10 hours while stirring. The benzene layer was washed with a saturated aqueous sodium hydrogencarbonate solution and a saturated brine. The solvent was distilled away and the residue obtained was purified by silica gel column chromatography (eluent; n-hexane:ethyl acetate=3:2) to give the subject compound (31 g) as a colorless oily substance.

$^1$H-NMR (CDCl$_3$) δ: 2.96 (4H, s), 3.70 (6H, s), 4.02 (4H, s)

IR (neat, cm$^{-1}$): 2993, 2956, 2898, 1739, 1439, 1330, 1199, 1102, 1036.

(2) 1,5-Dibenzyloxy-3-pentanone

To a solution of dimethyl 1,3-acetonedicarboxylate ethylene acetal (31 g) in tetrahydrofuran (500 ml) was added lithium aluminum hydride (6.47 g) under ice-cooling and the mixture was stirred at room temperature for an hour. Thereto was added a saturated aqueous sodium sulfate solution (200 ml) with stirring under ice-cooling. The resulting mixture was filtered through celite and the filtrate was concentrated. A solution of thus obtained residue in dimethylformamide (150 ml) was added to a suspension of 60% sodium hydride (10.2 g) in dimethylformamide (250 ml). Thereto was added a solution of benzyl bromide (52.3 g) in tetrahydrofuran (100 ml). The mixture was stirred at room temperature for an hour, poured into ice-water, and extracted with ethyl acetate. The ethyl acetate layer was washed with a saturated brine, dried over anhydrous sodium sulfate, and concentrated. The residue obtained was dissolved in acetone (200 ml), tetrahydrofuran (200 ml) and 1 N hydrochloric acid (200 ml), and the solution was stirred at room temperature for 6 hours. After the organic solvents were distilled away, the aqueous layer was extracted with ethyl acetate. The ethyl acetate layer was washed with a saturated aqueous sodium hydrogencarbonate solution and a saturated brine, dried over anhydrous sodium sulfate and concentrated. The residue obtained was purified by silica gel column chromatography (eluent; n-hexane:ethyl acetate=7:3) to give the subject compound (15.4 g) as a pale yellowish oily substance.

$^1$H-NMR (CDCl$_3$) δ: 2.75 (4H, t, J=6.3 Hz), 3.75 (4H, t, J=6.3 Hz), 4.50 (4H, s), 7.23–7.33 (10H, m)

IR (neat, cm$^{-1}$): 3088, 3064, 3031, 2866, 1717, 1454, 1367, 1103, 737, 698.

(3) 1,5-Dibenzyloxy-3-(2-phenylethyl)-3-pentanol

To a solution of 1,5-dibenzyloxy-3-pentanone (13.9 g) in tetrahydrofuran (150 ml) was dropwise added a solution of 2-phenylethyl-magnesium bromide, which was prepared from 2-phenylethyl bromide (24 g) and magnesium (3.1 g), in tetrahydrofuran (100 ml) under ice-cooling. The mixture was stirred under ice-cooling for 90 minutes, poured into a saturated aqueous ammonium chloride solution, and extracted with ethyl acetate. The ethyl acetate layer was washed with a saturated aqueous sodium hydrogencarbonate solution and a saturated brine, dried over anhydrous sodium sulfate, and concentrated. The residue obtained was purified by silica gel column chromatography (eluent; n-hexane:ethyl acetate=4:1) to give the subject compound (8.1 g) as a colorless oily substance.

$^1$H-NMR (CDCl$_3$) δ: 1.75–1.80 (2H, m), 1.92 (4H, t, J=6.3 Hz), 2.61–2.66 (2H, m), 3.69 (4H, t, J=6.3 Hz), 4.50 (4H, s), 4.70 (1H, br. s), 7.09–7.38 (15H, m)

IR (neat, cm$^{-1}$): 3458, 3063, 3029, 2941, 2865, 1496, 1454, 1098, 735, 696.

(4) N-[1,1-Bis(2-benzyloxyethyl)-3-phenylpropyl] acetamide

Sulfuric acid (4.2 g) was added to a solution of 1,5-dibenzyloxy-3-(2-phenylethyl)-3-pentanol (5.8 g) in acetonitrile (50 ml) under ice-cooling and the mixture was stirred at room temperature for 3 hours. The mixture was poured into ice-water and extracted with ethyl acetate. The ethyl acetate layer was washed with a saturated aqueous sodium hydrogencarbonate solution and a saturated brine, dried over anhydrous sodium sulfate and concentrated. The residue obtained was purified by silica gel column chromatography (eluent; n-hexane:ethyl acetate=7:3) to give the subject compound (2.2 g) as a yellowish oily substance.

$^1$H-NMR (CDCl$_3$) δ: 1.75 (3H, s), 2.07–2.22 (6H, m), 2.52–2.56 (2H, m), 3.62–3.68 (4H, m), 4.47 (4H, s), 6.64 (1H, br. s), 7.12–7.36 (10H, m)

IR (neat, cm$^{-1}$): 3317, 3063, 3029, 2935, 2864, 1652, 1538, 1454, 1368, 1100, 739, 698

MS (EI): 446 ((M+1)$^+$), 91.

(5) 3-Acetamido-5-acetoxy-3-(2-phenylethyl)pentyl acetate

N-[1,1-bis(2-benzyloxyethyl)-3-phenypropyl]acetamide (2.2 g) in acetic acid (40 ml) was added to a suspension of 10% palladium-carbon (250 mg) in acetic acid (40 ml). The mixture was stirred at room temperature under a hydrogen pressure of 15 atm. for 7 hours. The reaction mixture was filtered and concentrated. The residue obtained was dissolved in pyridine (20 ml) and acetic anhydride (20 ml). The solution was allowed to stand overnight, poured into ice-water, and extracted with ethyl acetate. The ethyl acetate layer was washed with 2N hydrochloric acid, a saturated aqueous sodium hydrogencarbonate solution and a saturated brine, dried over anhydrous sodium sulfate and concentrated. The residue obtained was purified by silica gel column chromatography (eluent; n-hexane:ethyl acetate= 1:1) to give the subject compound (1.5 g) as white crystals, melting at 73–74° C.

$^1$H-NMR (CDCl$_3$) δ: 1.93 (3H, s), 2.02–2.06 (2H, m), 2.05 (6H, s), 2.13 (2H, dt, J=14.4, 7.1 Hz), 2.27 (2H, dt, J=14.4, 7.1 Hz), 2.59–2.63 (2H, m), 4.17 (4H, t, J=7.1 Hz), 5.41 (1H, br. s), 7.18–7.30 (5H, m)

IR (neat, cm$^{-1}$): 3309, 3064, 3028, 2962, 1739, 1652, 1549, 1368, 1238, 1037, 747, 701

MS (EI): 349 (M$^+$), 202, 185, 160, 112.

(6) 3-Acetamido-5-acetoxy-3-[2-(4-octanoylphenyl)ethyl] pentyl acetate

3-Acetamido-5-acetoxy-3-(2-phenylethyl)pentyl acetate was used instead of 2-acetamido-2-methyl-4-phenylbutyl acetate in working example 34 (6) to give the subject compound as a pale yellowish oily substance.

$^1$H-NMR (CDCl$_3$) δ: 0.88 (3H, t, J=6.9 Hz), 1.28–1.35 (8H, m), 1.70–1.74 (2H, m), 1.95 (3H, s), 2.05 (6H, s), 2.02–2.26 (6H, m), 2.63–2.67 (2H, m), 2.93 (2H, t, J=7.6 Hz), 4.18 (4H, t, J=6.6 Hz), 5.50 (1H, br. s), 7.27 (2H, d, J=7.8 Hz), 7.88 (2H, d, J=7.8 Hz)

IR (neat, cm$^{-1}$): 3321, 3064, 2931, 2858, 1733, 1683, 1652, 1607, 1538, 1456, 1372, 1229, 1036

MS (EI): 475 (M$^+$), 416, 286, 185, 112.

WORKING EXAMPLE 101

3-Amino-3-[2-(4-octanoylphenyl)ethyl]pentane-1,5-diol

3-Acetamido-5-acetoxy-3-[2-(4-octanoylphenyl)ethyl] pentyl acetate obtained in working example 100 was hydrolyzed in a similar manner to that described in working example 78 to give the subject compound as a white powder, melting at 83–86° C.

$^1$H-NMR (CDCl$_3$) δ: 0.88 (3H, t, J=6.9 Hz), 1.29–1.36 (8H, m), 1.71–1.85 (8H, m), 2.62 (4H, br. s), 2.62–2.67 (2H, m), 2.94 (2H, t, J=7.6 Hz), 3.89 (4H, t, J=5.4 Hz), 7.27 (2H, d, J=8.3 Hz), 7.89 (2H, d, J=8.3 Hz)

IR (KBr, cm$^{-1}$): 3373, 3324, 3266, 3051, 2937, 2848, 2757, 1683, 1610, 1055, 1015.

WORKING EXAMPLE 102

3-Acetamido-5-acetoxy-3-[2-(4-octylphenyl)ethyl]-pentyl acetate

3-Acetamido-5-acetoxy-3-[2-(4-octanoylphenyl)ethyl] pentyl acetate obtained in working example 100 was reduced in a similar manner to that described in working example 37 to give the subject compound as a colorless oily substance.

$^1$H-NMR (CDCl$_3$) δ: 0.88 (3H, t, J=6.8 Hz), 1.26–1.29 (10H, m), 1.56–1.59 (2H, m), 1.91 (3H, s), 1.99–2.05 (2H, m), 2.05 (6H, s), 2.13 (2H, dt, J=14.6, 6.8 Hz), 2.27 (2H, dt, J=14.6, 6.8 Hz), 2.55 (2H, t, J=6.9 Hz), 2.57 (2H, t, J=7.8 Hz), 4.16 (4H, t, J=6.8 Hz), 5.39 (1H, br. s), 7.09 (4H, s)

IR (neat, cm$^{-1}$): 3313, 3053, 2956, 2928, 2856, 1733, 1652, 1538, 1456, 1368, 1239, 1037

MS (EI): 461 (M$^+$), 185, 112.

WORKING EXAMPLE 103

3-Acetamido-3-methyl-5-(4-octanoylphenyl)pentyl acetate

Ethyl acetoacetate was used instead of dimethyl 1,3-acetonedicarboxylate in working example 100 to give the subject compound as a pale yellow powder, melting at 83–84° C.

¹H-NMR (CDCl₃) δ: 0.88 (3H, t, J=6.9 Hz), 1.24–1.35 (8H, m), 1.35 (3H, s), 1.72 (2H, qui., J=7.3 Hz), 1.91–2.00 (2H, m), 1.93 (3H, s), 2.05 (3H, s), 2.21–2.36 (2H, m), 2.59–2.65 (2H, m), 2.92 (2H, t, J=7.3 Hz), 4.11–4.19 (2H, m), 5.34 (1H, br. s), 7.27 (2H, d, J=7.8 Hz), 7.87 (2H, d, J=7.8 Hz)

IR (KBr, cm⁻¹): 3275, 3077, 2948, 2929, 2851, 1741, 1680, 1643, 1559, 1372, 1265, 1040

MS (EI): 403 (M⁺), 334, 113

Elemental analysis

| | |
|---|---|
| Calculated | C; 71.43, H; 9.24, N; 3.47 |
| Found | C; 71.09, H; 9.36, N; 3.46 |

WORKING EXAMPLE 104

3-Amino-3-methyl-5-(4-octanoylphenyl)pentanolhydrochloride

3-Acetamido-3-methyl-5-(4-octanoylphenyl)pentyl acetate obtained in working example 103 was hydrolyzed in a similar manner to that described in working example 1 (7) to give the subject compound as a white powder, melting at 163–165° C.

¹H-NMR (DMSO-d₆) δ: 0.85 (3H, t, J=6.8 Hz), 1.24–1.30 (8H, m), 1.30 (3H, s), 1.57–1.60 (2H, m), 1.76–1.86 (4H, m), 2.70 (2H, t, J=8.6 Hz), 2.96 (2H, t, J=7.3 Hz), 3.60 (2H, t, J=6.4 Hz), 4.92 (1H, br. s), 7.36 (2H, d, J=8.3 Hz), 7.89 (2H, d, J=8.3 Hz), 8.04 (3H, br. s)

IR (KBr, cm⁻¹): 3292, 3181, 3074, 2923, 2854, 1676, 1607, 1182

MS (EI): 319 (M⁺), 274, 88

Elemental analysis

| | |
|---|---|
| Calculated | C; 67.49, H; 9.63, N; 3.94 |
| Found | C; 67.16, H; 9.73, N; 3.97 |

WORKING EXAMPLE 105

3-Acetamido-3-methyl-5-(4-octylphenyl)pentyl acetate

3-Acetamido-3-methyl-5-(4-octanoylphenyl)pentyl acetate obtained in working example 103 was reduced in a similar manner to that described in working example 37 to give the subject compound as white crystals, melting at 62–63° C.

¹H-NMR (CDCl₃) δ: 0.88 (3H, t, J=6.8 Hz), 1.26–1.29 (10H, m), 1.36 (3H, s), 1.56–1.66 (2H, m), 1.86–1.93 (1H, m), 1.89 (3H, s), 1.98–2.06 (1H, m), 2.04 (3H, s), 2.14–2.22 (1H, m), 2.25–2.32 (1H, m), 2.50–2.58 (4H, m), 4.15 (2H, td, J=6.9, 1.0 Hz), 5.28 (1H, br. s), 7.09 (4H, s)

IR (KBr, cm⁻¹): 3275, 3078, 2950, 2923, 2851, 1742, 1646, 1561, 1264, 1040

MS (EI): 389 (M⁺), 255, 157, 113

Elemental analysis

| | |
|---|---|
| Calculated | C; 73.99, H; 10.09, N; 3.60 |
| Found | C; 73.86, H; 10.21, N; 3.56 |

WORKING EXAMPLE 106

3-Amino-3-methyl-5-(4-octylphenyl)pentanol hydrochloride

3-Acetamido-3-methyl-5-(4-octylphenyl)pentyl acetate obtained in working example 105 was hydrolyzed in a similar manner to that described in working example 1 (7) to give the subject compound as a white powder, melting at 137–141° C.

¹H-NMR (DMSO-d₆) δ: 0.84 (3H, t, J=6.9 Hz), 1.23–1.25 (10H, m), 1.28 (3H, s), 1.50–1.53 (2H, m), 1.73–1.87 (4H, m), 2.52–2.59 (4H, m), 3.59 (2H, t, J=6.1 Hz), 4.92 (1H, br. s), 7.09 (4H, s), 8.00 (3H, br. s)

IR (KBr, cm⁻¹): 3120, 2956, 2854, 1525, 1073

MS (EI): 305 (M⁺), 260, 88

Elemental analysis

| | |
|---|---|
| Calculated | C; 70.25, H; 10.61, N; 4.10 |
| Found | C; 69.92, H; 10.77, N; 4.15 |

WORKING EXAMPLE 107

3-Acetamido-3-ethyl-5-(4-octanoylphenyl)pentyl acetate

Methyl propionylacetate was used instead of dimethyl 1,3-acetonedicarboxylate in working example 100 to give the subject compound as a yellowish oily substance.

¹H-NMR (CDCl₃) δ: 0.88 (3H, t, J=6.9 Hz), 0.90 (3H, t, J=7.3 Hz), 1.28–1.36 (8H, m), 1.68–1.83 (4H, m), 1.88–1.98 (1H, m), 1.95 (3H, s), 2.04 (3H, s), 2.04–2.14 (1H, m), 2.16–2.27 (2H, m), 2.59 (2H, t, J=8.6 Hz), 2.93 (2H, t, J=7.3 Hz), 4.13 (2H, td, J=7.3, 2.4 Hz), 5.16 (1H, br. s), 7.27 (2H, d, J=8.3 Hz), 7.87 (2H, d, J=8.3 Hz)

IR (neat, cm⁻¹): 3316, 3067, 2960, 2931, 2858, 1739, 1683, 1652, 1607, 1538, 1456, 1368, 1236, 1037

MS (EI): 417 (M⁺), 358, 286, 127.

WORKING EXAMPLE 108

3-Amino-3-ethyl-5-(4-octanoylphenyl)pentanol hydrochloride 1/10hydrate

3-Acetamido-3-ethyl-5-(4-octanoylphenyl)pentyl acetate obtained in working example 107 was hydrolyzed in a similar manner to that described in working example 1 (7) to give the subject compound as a white powder, melting at 81–84° C.

¹H-NMR (DMSO-d₆) δ: 0.85 (3H, t, J=6.8 Hz), 0.90 (3H, t, J=7.5 Hz), 1.24–1.29 (8H, m), 1.57–1.60 (2H, m), 1.68 (2H, q, J=7.5 Hz), 1.79 (2H, t, J=6.6 Hz), 1.83 (2H, dd, J=11.9, 5.7 Hz), 2.68 (2H, dd, J=11.7, 5.3 Hz), 2.96 (2H, t, J=7.3 Hz), 3.59–3.60 (2H, m), 4.93 (1H, br. s), 7.37 (2H, d, J=8.3 Hz), 7.89 (2H, d, J=8.3 Hz), 8.03 (3H, br. s)

IR (KBr, cm$^{-1}$): 3230, 3055, 2927, 2859, 1681, 1608, 1525, 1182

MS (EI): 333 (M$^+$), 304, 288, 102.

WORKING EXAMPLE 109

3-Acetamido-3-ethyl-5-(4-octylphenyl)pentyl acetate

3-Acetamido-3-ethyl-5-(4-octanoylphenyl)pentyl acetate obtained in working example 107 was reduced in a similar manner to that described in working example 37 to give the subject compound as white crystals, melting at 66–69° C.

$^1$H-NMR (CDCl$_3$) δ: 0.87 (3H, t, J=6.4 Hz), 0.88 (3H, t, J=7.4 Hz), 1.24–1.29 (10H, m), 1.56–1.61 (2H, m), 1.64–1.73 (1H, m), 1.81–1.89 (1H, m), 1.91 (3H, s), 2.04 (3H, s), 2.08–2.24 (2H, m), 2.47–2.57 (4H, m), 4.09–4.14 (2H, m), 5.06 (1H, br. s), 7.09 (4H, s)

IR (neat, cm$^{-1}$): 3309, 3075, 2960, 2927, 2856, 1739, 1652, 1549, 1458, 1368, 1244, 1037

MS (EI): 403 (M$^+$), 255, 127

Elemental analysis

| | |
|---|---|
| Calculated | C; 74.40, H; 10.24, N; 3.47 |
| Found | C; 74.16, H; 10.43, N; 3.53 |

WORKING EXAMPLE 110

3-Amino-3-ethyl-5-(4-octylphenyl)pentanol hydrochloride

3-Acetamido-3-ethyl-5-(4-octylphenyl)pentyl acetate obtained in working example 109 was hydrolyzed in a similar manner to that described in working example 1 (7) to give the subject compound as a white powder, melting at 108–110° C.

$^1$H-NMR (DMSO-d$_6$) δ: 0.84 (3H, t, J=6.9 Hz), 0.90 (3H, t, J=7.5 Hz), 1.22–1.25 (10H, m), 1.50–1.53 (2H, m), 1.66 (2H, q, J=7.5 Hz), 1.76–1.80 (4H, m), 2.52–2.57 (4H, m), 3.59 (2H, t, J=7.5 Hz), 4.92 (1H, br. s), 7.09 (2H, d, J=8.3 Hz), 7.10 (2H, d, J=8.3 Hz), 8.00 (3H, br. s)

IR (KBr, cm$^{-1}$): 3278, 2964, 2927, 2855, 1535, 1028

MS (EI): 319 (M$^+$), 290, 102

Elemental analysis

| | |
|---|---|
| Calculated | C; 70.85, H; 10.76, N; 3.93 |
| Found | C; 70.60, H; 10.92, N; 3.92 |

WORKING EXAMPLE 111

2-Acetamido-2-[2-(4-octylphenyl)ethyl]pentyl acetate

2-Acetamido-2-[2-(4-octanoylphenyl)ethyl]pentyl acetate obtained in working example 77 was reduced in a similar manner to that described in working example 37 to give the subject compound as a colorless oily substance.

$^1$H-NMR (CDCl$_3$) δ: 0.88 (3H, t, J=6.8 Hz), 0.93 (3H, t, J=7.4 Hz), 1.26–1.33 (12H, m), 1.58–1.60 (2H, m), 1.66–1.83 (2H, m), 1.92 (3H, s), 1.92–1.99 (1H, m), 2.05–2.14 (1H, m), 2.09 (3H, s), 2.51–2.57 (4H, m), 4.31 (1H, d, J=11.2 Hz), 4.33 (1H, d, J=11.2 Hz), 5.22 (1H, br. s), 7.08 (4H, s)

IR (neat, cm$^{-1}$): 3307, 3079, 3009, 2959, 2927, 2856, 1746, 1652, 1549, 1467, 1372, 1236, 1042, 757

MS (EI): 403 (M$^+$), 117.

WORKING EXAMPLE 112

2-Amino-2-[2-(4-octylphenyl)ethyl]pentanol hydrochloride

2-Acetamido-2-[2-(4-octylphenyl)ethyl]pentyl acetate obtained in working example 111 was hydrolyzed in a similar manner to that described in working example 1 (7) to give the subject compound as a yellowish oily substance.

$^1$H-NMR (DMSO-d$_6$) δ: 0.84 (3H, t, J=6.9 Hz), 0.88 (3H, t, J=7.1 Hz), 1.22–1.34 (12H, m), 1.52–1.53 (4H, m), 1.71–1.75 (2H, m), 2.52–2.54 (4H, m), 3.45 (2H, br. s), 5.47 (1H, br. s), 7.09 (4H, s), 7.86 (3H, br. s)

IR (neat, cm$^{-1}$): 3355, 3224, 2963, 2854, 1607, 1514, 1466, 1067

MS (EI): 320 (M$^+$), 288, 203, 105.

WORKING EXAMPLE 113

2-Amino-2-[2-(4-octyloxyphenyl)ethyl]pentanol 2-(4-Octyloxyphenyl)ethyl iodide was used instead of 2-(4-heptyloxyphenyl)ethyl iodide in working example 28 to give the subject compound as a white powder, melting at 43–47° C.

$^1$H-NMR (CDCl$_3$) δ: 0.89 (3H, t, J=6.9 Hz), 0.95 (3H, t, J=6.9 Hz), 1.28–1.49 (12H, m), 1.52–1.80 (6H, m), 2.49–2.55 (4H, m), 3.36 (2H, s), 3.92 (2H, t, J=6.6 Hz), 6.81 (2H, d, J=8.3 Hz), 7.09 (2H, d, J=8.3 Hz)

IR (KBr, cm$^{-1}$): 3337, 3279, 3120, 2957, 2928, 2854, 1513, 1247

MS (EI): 335 (M$^+$), 304, 219, 107

Elemental analysis

| | |
|---|---|
| Calculated | C; 75.17, H; 11.11, N; 4.17 |
| Found | C; 75.37, H; 11.08, N; 4.02 |

WORKING EXAMPLE 114

2-(3,5-Dinitrobenzamido)-2-[2-(4-heptyloxyphenyl)-ethyl]butane-1,4-diol

2-Amino-2-[2-(4-heptyloxyphenyl)ethyl]butane-1,4-diol obtained in working example 73 was acylated in a similar manner to that described in working example 19 to give the subject compound as a yellowish oily substance.

$^1$H-NMR (CDCl$_3$) δ: 0.89 (3H, t, J=6.8 Hz), 1.30–1.44 (8H, m), 1.73 (2H, qui., J=7.1 Hz), 1.93–2.00 (1H, m), 2.03–2.09 (1H, m), 2.17–2.22 (1H, m), 2.45–2.57 (2H, m), 2.67–2.75 (1H, m), 3.86 (2H, t, J=7.1 Hz), 3.87–3.92 (2H, m), 4.01–4.05 (2H, m), 6.77 (2H, d, J=8.8 Hz), 7.11 (2H, d, J=8.8 Hz), 8.08 (1H, br. s), 8.90 (2H, d, J=2.0 Hz), 9.14 (1H, t, J=2.0 Hz)

IR (neat, cm$^{-1}$): 3334, 3105, 2955, 2925, 2860, 1629, 1560, 1343, 1238, 1074

MS (EI): 517 (M$^+$), 486, 281, 205, 107.

WORKING EXAMPLE 115

(+)-2-(3,5-Dinitrobenzamido)-2-[2-(4-heptyloxyphenyl)ethyl]butane-1,4-diol (±)-2-(3,5-Dinitrobenzamido)-2-[2-(4-heptyloxyphenyl)ethyl]butane-1,4-diol in working example 114 was optically resolved in a similar manner to that described in working example 20 to give the subject compound as a white powder, melting at 116–117° C.

$[\alpha]_D^{23}$=+15.2° (c=0.46, chloroform)

WORKING EXAMPLE 116

(−)-2-(3,5-Dinitrobenzamido)-2-[2-(4-heptyloxyphenyl)ethyl]butane-1,4-diol (±)-2-(3,5-Dinitrobenzamido)-2-[2-(4-heptyloxyphenyl)ethyl]butane-1,4-diol in working example 114 was optically resolved in a similar manner to that described in working example 20 to give the subject compound as a white powder, melting at 114–115° C.

$[\alpha]_D^{26}$=−13.8° (c=0.46, chloroform)

WORKING EXAMPLE 117

(+)-2-Amino-2-[2-(4-heptyloxyphenyl)ethyl]butane-1,4-diol (+)-2-(3,5-Dinitrobenzamido)-2-[2-(4-heptyloxyphenyl)ethyl]butane-1,4-diol obtained in working example 115 was hydrolyzed in a similar manner to that described in working example 21 to give the subject compound as a yellow powder, melting at 78–79° C.

$[\alpha]_D^{26}$=+4.01° (c=0.49, chloroform)

WORKING EXAMPLE 118

(−)-2-Amino-2-[2-(4-heptyloxyphenyl)ethyl]butane-1,4-diol (−)-2-(3,5-Dinitrobenzamido)-2-[2-(4-heptyloxyphenyl)ethyl]butane-1,4-diol obtained in working example 116 was hydrolyzed in a similar manner to that described in working example 21 to give the subject compound as a yellow powder, melting at 77–79° C.

$[\alpha]_D^{27}$=−4.08° (c=0.40, chloroform)

WORKING EXAMPLE 119

2-Amino-2-fluoromethyl-4-(4-octylphenyl)butanol hydrochloride

2-Amino-2-[2-(4-octylphenyl)ethyl]propane-1,3-diol reported in WO94/08943 and methanesulfonyl fluoride were used instead of 2-amino-2-[2-(4-heptyloxyphenyl)ethyl]butane-1,4-diol and p-toluenesulfonyl fluoride, respectively in working example 74 to give the subject compound as a white powder, melting at 181–184° C. (decomposition).

$^1$H-NMR (DMSO-d$_6$) δ: 0.84 (3H, t, J=6.9 Hz), 1.23–1.25 (10H, m), 1.52–1.54 (2H, m), 1.81–1.85 (2H, m), 2.56–2.66 (4H, m), 3.54–3.58 (2H, m), 4.60 (2H, d, J=46.4 Hz), 5.61 (1H, t, J=5.1 Hz), 7.10 (4H, s), 8.32(3H, br. s)

IR (KBr, cm$^{-1}$): 3415, 3332, 2958, 2924, 2854, 1541, 1051, 1020

MS (EI): 309 (M$^+$), 278, 203, 105.

WORKING EXAMPLE 120

2-Amino-2-chloromethyl-4-(4-octylphenyl)butanol hydrochloride

Three successive treatments similar to those described in working example 74 (1), 75 (1) and 74 (3) were done on 2-amino-2-[2-(4-octylphenyl)-ethyl]propane-1,3-diol reported in WO94/08943 to give the subject compound as a white powder, melting at 148–151° C.

$^1$H-NMR (DMSO-d$_6$) δ: 0.84 (3H, t, J=6.6 Hz), 1.23–1.25 (10H, m), 1.50–1.53 (2H, m), 1.84–1.88 (2H, m), 2.54–2.66 (4H, m), 3.56–3.63 (2H, m), 3.87 (1H, d, J=12.2 Hz), 3.89 (1H, d, J=12.2 Hz), 5.68 (1H, t, J=4.9 Hz), 7.10 (4H, s), 8.26 (3H, br. s)

IR (KBr, cm$^{-1}$): 3367, 3004, 2923, 2854, 1516, 1500, 1070

MS (EI): 325 (M$^+$), 294, 218, 203, 105.

WORKING EXAMPLE 121

2-Amino-2-ethyl-4-(4-(4-phenylbutyloxy)phenyl)-butanol hydrochloride 1/4 hydrate (1) Diethyl 2-ethyl-2-(2-(4-(4-phenylbutyloxy)phenyl)ethyl)malonate To a suspension of sodium hydride (4.3 g) in dimethylformamide (212 ml) was added diethyl ethylmalonate (20 g) at 0° C. and the mixture was stirred at room temperature for an hour. To the solution, 2-(4-(4-phenyl-butyloxy)phenyl) ethyl iodide (40 g) was dropwise added at 0° C., and the mixture was stirred for 20 minutes and allowed to stand at room temperature overnight. The reaction mixture was poured into water and extracted with ethyl acetate. The ethyl acetate layer was washed with water and a saturated brine and dried over anhydrous magnesium sulfate. The solvent was distilled away under reduced pressure and the residue obtained was purified by silica gel column chromatography (eluent; n-hexane:ethyl acetate=9:1) to give the subject compound (46 g).

$^1$H-NMR (270 MHz, CDCl$_3$) δ: 0.87 (3H, t, J=7.3 Hz), 1.26 (6H, t, J=7.3 Hz), 1.76–1.83 (2H, m), 2.11–2.17 (2H, m), 2.40–2.46 (2H, m), 2.65–2.71 (2H, m), 3.89–3.94 (2H, m), 4.08–4.38 (4H, m), 6.80 (2H, dd, J=9.2, 2.6 Hz), 7.07 (2H, dd, J=8.5, 2.6 Hz), 7.19 (3H, d, J=6.6 Hz), 7.28–7.31 (2H, m)

IR (neat, cm$^{-1}$): 3028, 2976, 2939, 2868, 1730, 1612, 1583

MS (EI): 440 (M$^+$), 395, 321, 252, 188, 173.

(2) 2-Ethoxycarbonyl-2-ethyl-4-(4-(4-phenylbutyloxy) phenyl)butanoic acid

Potassium hydroxide (14 g) was added to a solution of diethyl 2-ethyl-2-(2-(4-(4-phenylbutyloxy)phenyl)ethyl) malonate (46 g) in ethanol (300 ml) and the mixture was refluxed under heating for 3.5 hours. The reaction mixture was poured into water and washed with isopropyl ether. After being acidified to pH 1 with concentrated hydrochloric acid, the aqueous layer was extracted with ethyl acetate. The ethyl acetate layer was washed with a saturated brine and dried over anhydrous sodium sulfate, and the solvent was distilled away under reduced pressure to give the subject compound (23 g).

$^1$H-NMR (270 MHz, CDCl$_3$) δ: 0.88 (3H, t, J=7.9 Hz), 1.33 (3H, t, J=6.6 Hz), 1.74–1.82 (4H, m), 1.91–2.59 (6H, m), 2.65–2.70 (2H, m), 3.91–3.97 (2H, m), 4.13–4.31 (2H, m), 6.76 (2H, d, J=8.6 Hz), 7.04 (2H, d, J=8.6 Hz), 7.12–7.32 (5H, m)

IR(neat, cm$^{-1}$): 3028, 2974, 2941, 2868, 1709, 1612, 1583

MS(EI): 412(M$^+$), 368, 239, 161.

(3) Ethyl 2-ethyl-2-methoxycarbonylamino-4-(4-(4-phenylbutyloxy)phenyl)-butanoate Ethyl chloroformate (7.4 g) was added to a solution of 2-ethoxy-carbonyl-2-ethyl-4-(4-(4-phenylbutyloxy)phenyl) butanoic acid (23 g) and triethylamine (9.5 ml) in acetone (224 ml) at 0° C. and the mixture was stirred at 0° C. for 70 minutes. A solution of sodium azide (4.4 g) in water (30 ml) was added thereto and the whole mixture was stirred at 0° C. for 45 minutes. The reaction mixture was poured into ice-water and extracted with ethyl acetate. The ethyl acetate layer was washed with water and a saturated brine, dried over anhydrous magnesium sulfate and the solvent was distilled away under reduced pressure. The residue obtained was dissolved in benzene (200 ml) and the solution was refluxed under heating for 70 minutes. Methanol (50 ml) and p-toluenesulfonic acid monohydrate (catalytic amount) were added to the solution. The mixture was further refluxed under heating for 10 minutes and allowed to stand at room temperature overnight. The solvent was distilled away and the residue obtained was purified by silica gel column chromatography (eluent; ethyl acetate:n-hexane=1:4) to give the subject compound (5.7 g).

$^1$H-NMR (270 MHz, CDCl$_3$) δ: 0.76 (3H, t, J=7.9 Hz), 1.28 (3H, t, J=7.3 Hz), 1.70–1.85 (6H, m), 2.18–2.71 (4H, m), 3.65 (3H, s), 3.91–3.95 (2H, m), 4.08–4.26 (2H, m), 5.79 (1H, s), 6.77 (2H, d, J=8.6 Hz), 7.03 (2H, d, J=8.6 Hz), 7.18–7.32 (5H, m)

IR (neat, cm$^{-1}$): 3423, 3028, 2974, 2941, 2864, 2861, 1720

MS (EI): 441 (M$^+$), 336, 310, 248, 239, 189.

(4) 4-Ethyl-4-(2-(4-(4-phenylbutyloxy)phenyl)ethyl) oxazolidin-2-one

Lithium borohydride (0.83 g) was added to a solution of ethyl 2-ethyl-2-methoxycarbonylamino-4-(4(4-phenylbutyloxy)phenyl)butanoate (5.6 g) in tetrahydrofuran (130 ml) and the mixture was refluxed under heating for 4 hours and allowed to stand at room temperature overnight. 2M Hydrochloric acid (11 ml) and water (400 ml) were added to the reaction mixture under ice-cooling and the mixture was extracted with ethyl acetate. The ethyl acetate layer was washed with a saturated brine, dried over anhydrous sodium sulfate and the solvent was distilled away under reduced pressure. The residue obtained was purified by silica gel column chromatography (eluent; ethyl acetate:n-hexane=1:1) to give the subject compound (3.0 g).

$^1$H-NMR (270 MHz, CDCl$_3$) δ: 0.96 (3H, t, J=7.3 Hz), 1.61–1.89 (8H, m), 2.39–2.81 (4H, m), 3.91–3.96 (2H, m), 4.09–4.20 (2H, m), 5.30 (1H, s), 6.75–6.84 (2H, m), 6.99–7.10 (2H, m), 7.15–7.31 (5H, m)

IR (neat, cm$^{-1}$): 3292, 3061, 3026, 2939, 2864, 1749

MS (EI): 368 ((M+1)$^+$), 338, 324, 281, 252.

(5) 2-Amino-2-ethyl-4-(4-(4-phenylbutyloxy)phenyl) butanol hydrochloride 1/4 hydrate A solution of potassium hydroxide (5.8 g) in water (20 ml) was added to a solution of 4-ethyl-4-(2-(4-(4-phenylbutyloxy)phenyl)ethyl)oxazolidin-2-one (3.0 g) in methanol (60 ml) and tetrahydrofuran (50 ml). The mixture was refluxed under heating for 18.5 hours while stirring. The reaction mixture was poured into water and extracted with ethyl acetate. The ethyl acetate layer was washed with saturated brine and dried over anhydrous sodium sulfate. The solvent was distilled away under reduced pressure to give a pale brown, oily substance. The oily substance was subjected to silica gel column chromatography (eluent; ethyl acetate then methanol) and the solvent was distilled away to give a pale brown residue. The obtained residue was dissolved in methanol and thereto was added a 1M solution of hydrochloric acid in ether. The solution was concentrated under reduced pressure, and the obtained crude crystals were recrystallized from isopropyl ether and hexane to give the subject compound (0.63 g) as white crystals, melting at 101–103° C.

$^1$H-NMR (270 MHz, DMSO-d$_6$) δ: 0.90 (3H, t, J=7.3 Hz), 1.59–1.77 (8H, m), 2.49–2.54 (2H, m), 2.61–2.66 (2H, m), 3.47(2H, d, J=4.6 Hz), 3.93(2H, br. s), 5.46 (1H, t, J=4.6 Hz), 6.84 (2H, d, J=8.6 Hz), 7.12 (2H, d, J=8.6 Hz), 7.16–7.31 (5H, m), 7.98 (3H, br. s)

IR (KBr, cm$^{-1}$): 3385, 3130, 3022, 2943, 2870, 2607, 1612

MS (EI): 341 (M$^+$), 310, 293, 239, 161

Elemental analysis

| Calculated | C; 69.09, H; 8.57, N; 3.66 |
|---|---|
| Found | C; 68.77, H; 8.46, N; 3.71 |

WORKING EXAMPLE 122

(−)-2-Amino-2-ethyl-4-(4-(4-phenylbutyloxy) phenyl)-butanol hydrochloride and (+)-2-Amino-2-ethyl-4-(4-(4-phenylbutyloxy)-phenyl)butanol hydrochloride (1) Diethyl 2-ethyl-2-(2-(4-benzyloxyphenyl)ethyl) malonate Diethyl ethylmalonate (50 g) was added to a suspension of sodium hydride (11 g) in dimethylformamide (200 ml) and tetrahydrofuran (50 ml), at 0° C., and the mixture was stirred at room temperature for 35 minutes. A solution of 2-(4-benzyloxyphenyl)ethyl iodide (90 g) was added to the reaction mixture at 0° C. and the whole mixture was stirred at 0° C. for 20 minutes and allowed to stand at room temperature overnight. The resultant mixture was poured into water and extracted with ethyl acetate. The ethyl acetate layer was washed with water and a saturated brine and dried over anhydrous magnesium sulfate. The solvent was distilled away under reduced pressure and the residue obtained was purified by silica gel column chromatography (eluent; ethyl acetate:n-hexane=1:9) to give the subject compound (100 g).

$^1$H-NMR (270 MHz, CDCl$_3$) δ: 0.87 (3H, t, J=7.3 Hz), 1.26 (6H, t, J=7.3 Hz), 1.88–2.05 (2H, m), 2.11–2.17 (2H, m), 2.41–2.47 (2H, m), 4.06–4.28 (4H, m), 5.04 (2H, s), 6.89 (2H, d, J=8.6 Hz), 7.09 (2H, d, J=8.6 Hz), 7.29–7.47 (5H, m)

IR(neat, cm$^{-1}$): 3064, 2977, 2939, 2879, 1729, 1610, 1583

MS (EI): 398 (M$^+$), 353, 307, 279, 188, 173.

(2) 2-Ethoxycarbonyl-2-ethyl-4-(2-(4-benzyloxyphenyl) ethyl)butanoic acid

To a solution of potassium hydroxide (31 g) in ethanol (100 ml) was added a solution of diethyl 2-ethyl-2-(2-(4-benzyloxyphenyl)ethyl)malonate (100 g) in ethanol (100 ml) and the mixture was refluxed under heating for 5.25 hours. The reaction mixture was poured into water and washed with isopropyl ether. After being acidified to pH 1 with concentrated hydrochloric acid, the aqueous layer was extracted with ethyl acetate. The ethyl acetate layer was washed with water and a saturated brine and dried over anhydrous sodium sulfate. The solvent was distilled away under reduced pressure to give the subject compound (95 g).

$^1$H-NMR (270 MHz, CDCl$_3$) δ: 0.89 (3H, t, J=7.3 Hz), 1.29 (3H, t, J=6.6 Hz), 1.92–2.30 (4H, m), 2.36–2.59 (2H, m), 4.14–4.29 (2H, m), 5.04 (2H, s), 6.89 (2H, d, J=8.6 Hz), 7.07 (2H, d, J=8.6 Hz), 7.28–7.44 (5H, m)

IR (neat, cm$^{-1}$): 3032, 2976, 2939, 1730, 1709, 1612, 1583

MS (EI): 370 (M$^+$), 353, 326, 279, 210.

(3) Ethyl 2-ethyl-2-methoxycarbonylamino-4-(4-benzyloxyphenyl)butanoate

Triethylamine (45 ml) and ethyl chloroformate (21 ml) were added to a solution of 2-ethoxycarbonyl-2-ethyl-4-(2-(4-benzyloxyphenyl)ethyl)-butanoic acid (85 g) in tetrahydrofuran (430 ml) at 0° C. and the mixture was stirred at 0° C. for 35 minutes. A solution of sodium azide (14 g) in water (10 ml) was added thereto and the whole mixture was stirred at 0° C. for 3 hours. The reaction mixture was poured into ice-water and extracted with ethyl acetate. The ethyl acetate layer was washed with water and a saturated brine, dried over anhydrous sodium sulfate and the solvent was distilled away under reduced pressure to give a pale brown oily substance. The oily substance obtained was dissolved in benzene (300 ml) and the solution was refluxed under heating for 170 minutes. Methanol (50 ml) and p-toluenesulfonic acid monohydrate (catalytic amount) were added thereto and the mixture was further refluxed under heating for 10 minutes and allowed to stand at room temperature overnight. Ethyl acetate was added to the reaction mixture, and the mixture was washed with water and a saturated brine and dried over anhydrous sodium sulfate. The solvent was distilled away under reduced pressure and the residue obtained was purified by silica gel column chromatography (eluent; n-hexane:ethyl acetate=4:1) to give the subject compound (31 g).

$^1$H-NMR (270 MHz, CDCl$_3$) δ: 0.76 (3H, t, J=7.9 Hz), 1.27 (3H, t, J=7.3 Hz), 1.72–1.83 (1H, m), 1.98–2.09 (1H, m), 2.20–2.39 (2H, m), 2.50–2.70 (2H, m), 3.65 (3H, s), 4.06–4.24 (2H, m), 5.03 (2H, s), 5.83 (1H, s), 6.87 (2H, d, J=8.6 Hz), 7.04 (2H, d, J=8.6 Hz), 7.27–7.44 (5H, m)

IR (neat, cm$^{-1}$): 3421, 3032, 2976, 2939, 2877, 1720, 1612

MS (EI): 498 (M$^+$), 367, 342, 313, 268, 236.

(4) 4-Ethyl-4-(2-(4-benzyloxyphenyl)ethyl)oxazolidin-2-one

Lithium borohydride (3.2 g) was added to a solution of ethyl 2-ethyl-2-methoxycarbonylamino-4-(4-benzyloxyphenyl)butanoate (29 g) in tetrahydrofuran (370 ml) and the mixture was refluxed under heating for 5 hours. 2 M Hydrochloric acid (40 ml) was added to the reaction mixture and the mixture was stirred for 2.5 hours. Ethyl acetate was added to the reaction mixture, the mixture was washed with water and a saturated brine and dried over anhydrous sodium sulfate. The solvent was distilled away under reduced pressure. Treatment of the residue with hexane and ethyl acetate gave the subject compound (11 g). Then, the mother liquid was concentrated under reduced pressure and the obtained residue was purified by silica gel column chromatography (eluent; ethyl acetate:n-hexane=1:2) to give the subject compound (11 g).

$^1$H-NMR (270 MHz, CDCl$_3$) δ: 0.97 (3H, t, J=7.3 Hz), 1.64–1.73 (2H, m), 1.84–1.90 (2H, m), 2.56–2.62 (2H, m), 4.12 (2H, s), 5.04 (2H, s), 5.41 (1H, s), 6.91 (2H, d, J=8.6 Hz), 7.08 (2H, d, J=8.6 Hz), 7.31–7.45 (5H, m)

IR (neat, cm$^{-1}$): 3437, 3215, 3124, 2972, 2913, 1754

MS (EI): 325 (M$^+$), 264, 197, 107.

(5) 4-(2-(4-Benzyloxyphenyl)ethyl)-3-tert-butoxycarbonyl-4-ethyloxazolidin-2-one To a suspension of sodium hydride (2.5 g) in dimethylformamide (30 ml) was added a solution of 4-ethyl-4-(2-(4-benzyloxyphenyl)ethyl)-oxazolidin-2-one (19 g) in dimethylformamide (250 ml) at 0° C. and the mixture was stirred at room temperature for an hour. Di-tert-butyl-dicarbonate (15 g) was added to the solution at 0° C. and the mixture was stirred at 0° C. for 2 hours. Ethyl acetate was added to the reaction mixture and the mixture was washed with water and a saturated brine and dried over anhydrous magnesium sulfate. The solvent was distilled away under reduced pressure and the residue obtained was purified by silica gel column chromatography (eluent; ethyl acetate:n-hexane=1:2) to give the subject compound (18 g).

$^1$H-NMR (270 MHz, CDCl$_3$) δ: 0.92 (3H, t, J=7.3 Hz), 1.56 (9H, s), 1.58–1.85 (2H, m), 2.08–2.68 (4H, m), 4.03–4.22 (2H, m), 5.04 (2H, s), 6.91 (2H, d, J=8.6 Hz), 7.06 (2H, d, J=8.6 Hz), 7.28–7.44 (5H, m)

IR (neat, cm$^{-1}$): 3032, 2976, 2933, 1813, 1790, 1724, 1612

MS (EI): 425 (M$^+$), 367, 353, 325, 294.

(6) 4-(4-Benzyloxyphenyl)-2-tert-butoxycarbonylamino-2-ethylbutanol

To a solution of 4-(2-(4-benzyloxyphenyl)ethyl)-3-tert-butoxycarbonyl-4-ethyloxazolidin-2-one (18 g) in methanol (432 ml) was added a solution of lithium hydroxide monohydrate (9.1 g) in water (50 ml) and the mixture was stirred at room temperature for 3 hours. Ethyl acetate was added to the reaction mixture and the mixture was washed with water and a saturated brine and dried over anhydrous sodium sulfate. The solvent was distilled away under reduced pressure to give the subject compound (24 g).

$^1$H-NMR (270 MHz, CDCl$_3$) δ: 0.92 (3H, t, J=7.3 Hz), 1.44 (9H, s), 1.65 (2H, dd, J=15, 7.6 Hz), 1.76–1.95 (2H, m), 2.44–2.63 (2H, m), 3.72 (2H, s), 4.56 (1H, br. s), 5.04 (2H, s), 6.89 (2H, d, J=8.6 Hz), 7.10 (2H, d, J=8.6 Hz), 7.29–7.44 (5H, m)

IR (KBr, cm$^{-1}$): 3275, 3068, 2974, 2945, 2859, 1673, 1558

MS (EI): 399 (M$^+$), 386, 368, 327, 295.

(7) 4-(4-Benzyloxyphenyl)-2-tert-butoxycarbonylamino-2-ethylbutyl acetate

A solution of 4-(4-benzyloxyphenyl)-2-tert-butoxycarbonylamino-2-ethylbutanol (24 g) in pyridine (200 ml) and acetic anhydride (32 ml) was allowed to stand at room temperature overnight. Ethyl acetate was added to the reaction mixture and the mixture was washed with water, a dilute hydrochloric acid, an aqueous sodium hydrogencarbonate solution and a saturated brine in order, and dried over anhydrous magnesium sulfate. The solvent was distilled away under reduced pressure and the residue obtained was purified by silica gel column chromatography (eluent; ethyl acetate:n-hexane=1:1) to give the subject compound (13 g).

$^1$H-NMR (270 MHz, CDCl$_3$) δ: 0.89 (3H, t, J=7.3 Hz), 1.45 (9H, s), 1.61–2.06 (4H, m), 2.04 (3H, s), 2.51 (2H, t, J=8.6 Hz), 4.22 (2H, dd, J=16, 11 Hz), 4.42 (1H, br. s), 5.04 (2H, s), 6.89 (2H, d, J=8.6 Hz), 7.09 (2H, d, J=8.6 Hz), 7.28–7.44 (5H, m)

IR (KBr, cm$^{-1}$): 3375, 2974, 2935, 1741, 1718, 1612, 1583

MS (EI): 441 M$^+$), 385, 312, 264, 233.

(8) 2-tert-Butoxycarbonylamino-2-ethyl-4-(4-hydroxyphenyl)butyl acetate

To a solution of 4-(4-benzyloxyphenyl)-2-tert-butoxycarbonylamino-2-ethylbutyl acetate (7 g) in ethyl acetate (80 ml) were added a 1 M solution of hydrochloric acid in ether (1 ml) and 10% palladium-carbon (0.4 g) and the suspension was subjected to catalytic reduction under an oridinary atmosphere at room temperature for 160 minutes. Catalyst was filtered off from the reaction mixture and the solvent was distilled away under reduced pressure. The residue obtained was dissolved in ethyl acetate (50 ml) and ethanol (50 ml). To the solution were added 10% palladium-carbon (0.4 g) and a 1 M solution of hydrochloric acid in ether (1 ml) and the suspension was subjected to catalytic reduction under an ordinary atmosphere at room temperature for 140 minutes. Catalyst was filtered off from the reaction mixture and the filtrate was concentrated under reduced pressure to give the subject compound (7.2 g).

$^1$H-NMR (270 MHz, CDCl$_3$) δ: 0.89 (3H, t, J=7.3 Hz), 1.45 (9H, s), 1.63–2.09 (4H, m), 2.09 (3H, s), 2.49 (2H, t, J=8.6 Hz), 4.22 (2H, dd, J=18, 11 Hz), 4.45 (1H, br. s), 6.75 (2H, d, J=8.6 Hz), 7.02 (2H, d, J=8.6 Hz)

IR(KBr, cm$^{-1}$): 3377, 2974, 2937, 1716, 1614, 1515

MS (EI): 351 (M$^+$), 312, 295, 278, 252.

(9) 2-tert-Butoxycarbonylamino-2-ethyl-4-(4-(4-phenylbutyloxy)phenyl)butyl acetate To a suspension of sodium hydride (0.65 g) in dimethylformamide (16 ml) was added a solution of 2-tert-butoxycarbonylamino-2-ethyl-4-(4-hydroxyphenyl)butyl acetate (6.0 g) in dimethylformamide (50 ml) at 0° C. and the mixture was stirred at room temperature for an hour. 4-Phenyl-butyl iodide (90 g) was added to the solution at 0° C. and the mixture was allowed to stand at room temperature overnight. The reaction mixture was poured into water and extracted with ethyl acetate. The ethyl acetate layer was washed with water and a saturated brine and dried over anhydrous sodium sulfate. The solvent was distilled away under reduced pressure and the residue obtained was purified by silica gel column chromatography (eluent; n-hexane:ethyl acetate=1:1) to give the subject compound (3.6 g).

$^1$H-NMR (270 MHz, CDCl$_3$) δ: 0.89 (3H, t, J=7.3 Hz), 1.45 (9H, s), 1.65–2.01 (8H, m), 2.08 (3H, s), 2.50 (2H, t, J=8.6 Hz), 2.67 (2H, t, J=6.6 Hz), 3.94 (2H, t, J=5.94 Hz), 4.22 (2H, dd, J=16, 11 Hz), 4.42 (1H, br. s), 6.80 (2H, d, J=8.6 Hz) 7.07 (2H, d, J=8.6 Hz), 7.16 (3H, t, J=7.3 Hz), 7.26–7.31 (2H, m)

IR (KBr, cm$^{-1}$): 3369, 3062, 3028, 2973, 1743, 1720

MS (EI): 483 (M$^+$), 440, 427, 409, 306.

(10) 2-tert-Butoxycarbonylamino-2-ethyl-4-(4-(4-phenylbutyloxy)phenyl)-butanol

To a solution of 2-tert-butoxycarbonylamino-2-ethyl-4-(4-(4-phenylbutyloxy)phenyl)butyl acetate (3.4 g) in methanol (50 ml) was added a solution of lithium hydroxide monohydrate (0.33 g) in water (10 ml) and the mixture was stirred at room temperature for 20 minutes. The reaction mixture was poured into water and extracted with ethyl acetate. The ethyl acetate layer was washed with a saturated brine and dried over anhydrous sodium sulfate. The solvent was distilled away under reduced pressure to give the subject compound (3.6 g).

$^1$H-NMR (270 MHz, CDCl$_3$) δ: 0.91 (3H, t, J=7.3 Hz), 1.44 (9H, s), 1.50 (2H, dd, J=15, 7.3 Hz), 1.72–1.94 (6H, m), 2.41–2.62 (2H, m), 2.68 (2H, t, J=7.3 Hz), 3.71 (2H, s), 3.94 (2H, t, J=5.9 Hz), 4.56 (1H, br. s), 6.80 (2H, d, J=8.6 Hz), 7.08 (2H, d, J=8.6 Hz), 7.15–7.41 (5H, m)

IR (KBr, cm$^{-1}$): 3263, 3068, 3028, 2980, 1680, 1614

MS (EI): 441 (M$^+$), 427, 410, 367, 354.

(11) 2-Amino-2-ethyl-4-(4-(4-phenylbutyloxy)phenyl) butanol hydrochloride

To a solution of 2-tert-butoxycarbonylamino-2-ethyl-4-(4-(4-phenylbutyloxy)phenyl)butanol (3.2 g) in tetrahydrofuran (10 ml) was added a solution of 4M hydrochloric acid in dioxane (10 ml) and the mixture was stirred for 3 hours. The solvent was distilled away to give the subject compound (3 g).

$^1$H-NMR (270 MHz, DMSO-d$_6$) δ: 0.90 (3H, t, J=7.3 Hz), 1.59–1.77 (8H, m), 2.49–2.54 (2H, m), 2.61–2.66 (2H, m), 3.47 (2H, d, J=4.6 Hz), 3.93 (2H, br. s), 5.46 (1H, t, J=4.6 Hz), 6.84 (2H, d, J=8.6 Hz), 7.12 (2H, d, J=8.6 Hz), 7.16–7.31 (5H, m), 7.98 (3H, br. s)

IR (KBr, cm$^{-1}$): 3385, 3130, 3022, 2943, 2870, 2607, 1612

MS (EI): 325 (M$^+$), 310, 239, 161, 147.

(12) 2-Ethyl-2-(3,5-dinitrobenzamido)-4-(4-(4-phenylbutyloxy)phenyl)-butanol

To a solution of 2-amino-2-ethyl-4-(4-(4-phenylbutyloxy) phenyl)butanol hydrochloride (3.0 g) in ethyl acetate (100 ml) were added a solution of potassium hydrogencarbonate (1.6 g) in water (50 ml) and 3,5-dinitrobenzoyl chloride (3.6 g). The mixture was stirred vigorously at room temperature for 2.5 hours and extracted with ethyl acetate. The ethyl acetate layer was washed with an aqueous sodium hydrogencarbonate solution and a saturated brine, dried over anhydrous sodium sulfate and the solvent was distilled away under reduced pressure. The yellow residue obtained was subjected to the same procedure as mentioned above, and the resulting residue was purified by silica gel column chromatography (eluent; n-hexane:ethyl acetate=2:1) to give the subject compound (1.5 g) and 2-ethyl-2-(3,5-dinitrobenzamido)-4-(4-(4-phenylbutyloxy)phenyl)butyl 3,5-dinitrobenzoate (2.9 g) as a by-product. To a solution of the by-product (2.7 g) in a mixed solvent of methanol (50 ml) and tetrahydrofuran (30 ml) was added a solution of lithium hydroxide monohydrate (0.15 g) in water (10 ml) and the mixture was stirred at room temperature for 30 minutes. The reaction mixture was poured into water and extracted with ethyl acetate, the ethyl acetate layer was washed with water and a saturated brine and dried over anhydrous sodium sulfate. The solvent was distilled away under reduced pressure and the residue obtained was purified by silica gel column chromatography (eluent; n-hexane:ethyl acetate=1:1) to give the subject compound (2.4 g). The combined subject compound was recrystallized from ethyl acetate and hexane to give the subject compound (2.6 g) as pure white crystals, melting at 121–122° C.

$^1$H-NMR (270 MHz, CDCl$_3$) δ: 1.00 (3H, t, J=7.3 Hz), 1.73–1.76 (4H, m), 1.83–2.25 (4H, m), 2.57–2.78 (4H, m), 3.61–3.94 (4H, m), 6.07 (1H, s), 6.69 (2H, d, J=8.6 Hz), 7.11 (2H, d, J=8.6 Hz), 7.16–7.31 (5H,m), 8.65 (2H, d, J=2.6 Hz), 9.09 (2H, t, J=2.0 Hz)

IR (KBr, cm$^{-1}$): 3255, 3101, 3032, 2974, 1639, 1571

MS (EI): 535 (M$^+$), 504, 372, 324, 293.

(13) Optical resolution of 2-ethyl-2-(3,5-dinitrobenzamido)-4-(4-(4-phenylbutyloxy)phenyl)butanol Racemic 2-ethyl-2-(3,5-dinitrobenzamido)-4-(4-(4-phenylbutyloxy)-phenyl)butanol was optically resolved by high performance liquid chromatography using an optically active carrier to give an enantiomer (enantiomer A: retention time=30 minutes, 0.50 g) and the other enantiomer (enantiomer B: retention time=39 minutes, 0.50 g). The resolution conditions were as follows: optically active carrier; CHIRAL CELL OD (trademark, Daicel Chemical Industries), mobile phase; ethanol/hexane=1:1, detected at 254 nm, flow rate; 7 ml/minute. Enantiomer A was recrystallized from ethanol/hexane to give the optically pure enantiomer (100% ee; 0.39 g). Enantiomer B was recrystallized from ethanol/hexane to give the optically almost pure enantiomer (99% ee; 0.40 g).

(14) (−)-2-Amino-2-ethyl-4-(4-(4-phenylbutyloxy)phenyl) butanol hydrochloride

To a solution of the enantiomer A (0.38 g) in methanol (30 ml) and tetrahydrofuran (12 ml) was added a solution of lithium hydroxide monohydrate (0.10 g) in water (5 ml) and the mixture was stirred at room temperature for an hour. The reaction mixture was concentrated and dissolved in ethyl acetate. The solution was washed with an aqueous sodium hydroxide solution and a saturated brine, dried over anhydrous sodium sulfate, and the solvent was distilled away under reduced pressure. The pale brown oily substance obtained was dissolved in methanol and 1 M solution of hydrochloric acid in ether. The solvent was distilled away and the crude material obtained was recrystallized from methanol and ethyl acetate to give the subject compound (0.21 g), melting at 126–127° C.

$[α]_D^{26}$=−13.12 (c=0.1, chloroform)

$^1$H-NMR (400 MHz, DMSO-d$_6$) δ: 0.88 (3H, t, J=7.3 Hz), 1.59–1.70 (8H, m), 2.46–2.50 (2H, m), 2.55–2.65 (2H, m), 3.45 (2H, d, J=4.4 Hz), 3.93 (2H, br.s), 5.46 (1H, t, J=4.8 Hz), 6.83 (2H, d, J=8.3 Hz), 7.09 (2H, d, J=8.8 Hz), 7.13–7.29 (5H, m), 7.81 (3H, br. s)

IR (KBr, cm$^{-1}$): 3130, 3022, 2942, 2870, 2605, 1614
MS (EI): 342 ((M+1)$^+$), 310, 293, 239, 161
Elemental analysis

| | |
|---|---|
| Calculated | C; 69.91, H; 8.53, N; 3.77 |
| Found | C; 70.20, H; 8.60, N; 3.64 |

(15) (+)-2-Amino-2-ethyl-4-(4-(4-phenylbutyloxy)phenyl) butanol hydrochloride

To a solution of the enantiomer B (0.40 g) in methanol (30 ml) and tetrahydrofuran (12 ml) was added a solution of lithium hydroxide monohydrate (0:10 g) in water (5 ml) and the mixture was stirred at room temperature for an hour. The reaction mixture was concentrated and dissolved in ethyl acetate. The solution was washed with an aqueous sodium hydroxide solution and a saturated brine, dried over anhydrous sodium sulfate, and the solvent was distilled away under reduced pressure. The pale brown oily substance obtained was dissolved in methanol and 1 M solution of hydrochloric acid in ether. The solvent was distilled away and the crude material obtained was recrystallized from methanol and ethyl acetate to give the subject compound (0.22 g), melting at 126–127° C.

$[\alpha]_D^{26}$=+11.45 (c=0.1, chloroform)
$^1$H-NMR (400 MHz, DMSO-d$_6$) δ: 0.88 (3H, t, J=7.3 Hz), 1.55–1.69 (8H, m), 2.46–2.50 (2H, m), 2.55–2.65 (2H, m), 3.45 (2H, br. s), 3.93 (2H, br. s), 5.42 (1H, br. s), 6.83 (2H, d, J=8.3 Hz), 7.09 (2H, d, J=8.8 Hz), 7.13–7.29 (5H, m), 7.81(3H, br. s)

IR (KBr, cm$^{-1}$): 3022, 2942, 2906, 1614, 1581, 1473
MS (EI): 342 ((M+1)$^+$), 310, 293, 239, 161
Elemental analysis

| | |
|---|---|
| Calculated | C; 69.91, H; 8.53, N; 3.77 |
| Found | C; 69.59, H; 8.61, N; 3.71 |

The action and effect of the present invention are explained in detail by illustrating experimental examples in the following.

For determining the immunosuppressive activity, various immune reactions using lymphocytes of mouse, rat or human can be measured. It may be determined with high sensitivity, for example, by an allogenic mixed lymphocyte reaction (allogenic MLR) of mouse, rat or human.

The allogenic MLR is a blastogenesis of lymphocytes induced by a mixed culture of lymphocytes derived from two kinds of cells which are allogenic and have different major histocompatibility antigens, such as spleen cells, lymph node cells and peripheral blood lymphocytes. The allogenic MLR is a phenomenon induced by and reflects the difference in major histocompatibility antigens of the donors of the lymphocytes, and a blastogenesis phenomenon of the lymphocytes is not developed by a mixed culture of the lymphocytes from monozygotic twins. Accordingly, allogenic MLR is widely used for the donor-recipient selection in organ transplantations.

When allogenic MLR is desired, one way-MLR, wherein the lymphocytes of one of them are used as stimulator cells upon X-ray irradiation or treatment with mitomycin C to inhibit proliferation and the blastogenesis of the other lymphocytes (responder cells) is determined, may be carried out.

Further, the immunosuppressive activity may be determined as an activity to inhibit induction of cytotoxic T cells having the major histocompatibility antigen restrictive property during arlogenic MLR.

Also, the immunosuppressive activity may be determined, besides allogenic MLR, as an activity to inhibit the blastogenesis of the lymphocytes induced by the stimulation of various mitogens such as concanavalin A, phytohemagglutinin and pokeweed mitogen or as an activity to inhibit the proliferation of the lymphocytes induced by a cytokine (e.g. interleukin 1,2, 3, 4, 5 or 6) having an activity to reinforce the proliferation or promote the differentiation of the lymphocytes such as T cells or B cells, or manifestation of such function. In addition, it is possible to evaluate the immunosuppressive activity according to the inhibition of the production of these cytokines from T cells or macrophages.

Alternatively, the activity may be evaluated as an activity to inhibit induction of allogenic cells-specific cytotoxic T cells induced in spleen cells of mouse previously immunized with, for example, allogenic cells by intraperitoneally, orally, intravenously, intradermally, subcutaneously or intramuscularly administering a compound to mice; as an activity to inhibit the production of an allogenic cells-specific antibody produced in the blood serum of mouse immunized with allogenic cells or the like. The activity may be also evaluated as an activity to inhibit rejection on organ transplantation among allogenic skin, heart, liver, kidney and so on, or graft-versus-host reaction (GvHR) and host-versus-graft reaction (HvGR) by administering a compound to rat, dog or the like. Moreover, the activity may be evaluated as an activity to inhibit delayed hypersensitivity reaction, adjuvant arthritis, experimental allergy encephalomyelitis, experimental autoimmune uveitis or the like by administering a compound to mouse, rat or the like.

Moreover, the immunosuppressive activity may be evaluated as an activity to inhibit, for example, production of an anti-DNA antibody, production of a rheumatoid factor, nephritis, abnormal proliferation of lymphocytes or urinary protein; or a macrobiotic effect by the administration of the compound to MRL/1pr mouse, NZB/WF$_1$ mouse, BXSB mouse, NOD mouse and the like which are spontaneous model animals with autoimmune diseases.

EXPERIMENTAL EXAMPLE 1

(Inhibition of allogenic mixed lymphocyte reaction in mouse)

The mouse allogenic mixed lymphocyte reaction (hereinafter referred to as mouse allogenic MLR) is carried out by a mixed culture of spleen cells of BALB/c mouse as responder cells and spleen cells of C57BL/6 mouse treated with mitmycin C as stimulator cells at the same ratio.

The reaction cells are prepared as follows. A spleen is removed from a 5–6 weeks old BALB/c mouse and a single cell suspension of spleen cells is obtained by the use of an RPMI1640 medium (containing kanamycin sulfate 60 μg/ml, penicillin G potassium 100 units/ml, N-2-hydroxyethylpiperadine-N'-2-ethanesulfonate 10 mM, 0.1% sodium hydrogencarbonate and L-glutamine 2 mM) supplemented with 5% heat-inactivated fetal calf serum (hereinafter referred to as FCS). After hemolysis treatment, the suspension is adjusted to a concentration of $10^7$ cells/ml by the use of an RPMI1640 medium containing $10^{-4}$ M 2-mercaptoethanol and 10% FCS and used as a reaction cell suspension.

The stimulator cells are prepared as follows. A spleen is removed from a 5–6 weeks old C57BL/6 mouse and a single cell suspension of spleen cell is obtained by the use of an RPMI1640 medium. After hemolysis treatment, the suspension is treated with 40 μg/ml mitomycin C at 37° C. for 60 minutes. After washing three times, the suspension is adjusted to a concentration of $10^7$ cells/ml by the use of an RPMI1640 medium containing $10^{-4}$ M 2-mercaptoethanol and 10% FCS and used as a stimulator cell suspension.

The responder cell suspension (50 μl) prepared by the method described above, the stimulator cell suspension (50 μl) prepared by the method described above and a test sample (100 μl) prepared by the use of an RPMI1640 medium containing 10% FCS are placed in a 96 well flat-bottomed micro test plate and cultured at 37° C. under 5% $CO_2$-95% air for 4 days.

The blastogenesis reaction of lymphocytes in mouse allogenic MLR is determined by a method using $^3$H-thymidine uptake as an index. Namely, after the culture, $^3$H-thymidine 18.5KBq/well is added and the cells are cultured for 4 hours. The cells are collected by a cell harvester and the radioactivity incorporated into the cells is determined by a liquid scintillation counter and used as an index for the lymphocyte blastogenesis in mouse allogenic MLR. The inhibition of mouse allogenic MLR is calculated by the formula below and evaluated accordingly.

Of the compounds of the present invention, the preferred show an $IC_{50}$ value (a concentration to inhibit by 50%) of from about 1 nM to about 50 nM in a mouse allogenic mixed lymphocyte reaction.

$$\text{Inhibition (\%)} = \left[1 - \frac{\left(\begin{array}{c}\text{cpm of MLR} \\ \text{with test sample}\end{array}\right) - \left(\begin{array}{c}\text{cpm of responder} \\ \text{cells alone}\end{array}\right)}{\left(\begin{array}{c}\text{cpm of MLR with-} \\ \text{out test sample}\end{array}\right) - \left(\begin{array}{c}\text{cpm of responder} \\ \text{cells alone}\end{array}\right)}\right] \times 100$$

EXPERIMENTAL EXAMPLE 2

(Inhibition of proliferation of interleukin 2 (IL-2)-dependent mouse T cell line CTLL-2 induced by IL-2)

An IL-2-dependent mouse T cell line CTLL-2 is prepared to a concentration of $2\times10^5$ cell/ml in an RPMI1640 medium containing 10% FCS. A cell suspension thereof (50 μl), recombinant human IL-2 (rh-IL-2) 40 U/ml (50 μl) and a test sample (100 μl) prepared by the use of an RPMI1640 medium containing 10% FCS are placed in a 96 well flat-bottomed micro testplate and cultured at 37° C. under 5% $CO_2$-95% air for 68 hours. After the culture, 100 μl of the supernatant of each well is removed and a 5 mg/ml MTT [3-(4,5-dimethylthiazol-2-yl)-2,5-diphenyltetrazolium bromide] solution is added to each well by 20 μl and the cells are incubated at 37° C. for 4 hours. Then, 0.01N hydrochloric acid solution (100 μl) containing 10% sodium dodecyl sulfate is added thereto and the cells are incubated at 37° C. overnight. The purple formazan crystals produced are dissolved and the absorbance at 570 nm is measured using a microplate absorbance photometer and used as an index of the proliferation of the IL-2-dependent CTLL-2 cells. The inhibition (%) of the IL-2-dependent proliferation is calculated by the following formula.

Of the compounds of the present invention, the preferred show an $IC_{50}$ value (a concentration to inhibit by 50%) of from about 1 nM to about 50 nM in the IL-2-dependent proliferation of mouse T cell line CTLL-2.

$$\text{Inhibition (\%)} = \left[1 - \frac{\left(\begin{array}{c}\text{absorbance when} \\ \text{test sample and} \\ \text{rh-IL-2 are added}\end{array}\right) - \left(\begin{array}{c}\text{absorbance when} \\ \text{rh-IL-2 is} \\ \text{not added}\end{array}\right)}{\left(\begin{array}{c}\text{absorbance when} \\ \text{rh-IL-2 alone} \\ \text{is added}\end{array}\right) - \left(\begin{array}{c}\text{absorbance when} \\ \text{rh-IL-2 is} \\ \text{not added}\end{array}\right)}\right] \times 100$$

EXPERIMENTAL EXAMPLE 3

(Inhibitory effect on delayed type hypersensitivity reaction in mice)

BALB/c mice at age of 5 weeks old are sensitized by subcutaneous injection with 0.1 ml of 0.25% methylated human serum albumin (MeHSA) solution. Four days after sensitization, the volume of right foot in mice are measured and thereafter 25 ul of 0.25% MeHSA solution is injected into the right foot pad in order to induce delayed hypersensitivity reaction (DTH reaction). After 24 hr of the injection, namely after 5 days of sensitization, the volume of right foot was measured again. The test compounds are examined by the differences of the foot volumes between at 5 days and 4 days, namely the swelling in the volume of right foot pad as a indicator of DTH reaction. In this time, the body weight, wet weight of thymus, and spleen and the number of peripheral white blood cells are also measured. Test compound are administered for 5 days from the day of sensitization. The suitable compounds in this invention shows statistically significant inhibitory effect on DTH reaction by administration at 0.1 to 10 mg/kg.

EXPERIMENTAL EXAMPLE 4

(Inhibitory effect on host versus graft reaction in rats)

The spleen is removed from male WKAH rats at ages of 4 to 5 weeks old and is used to obtain a single cell suspension of spleen cells using RPMI 1640 medium (containing kanamycin sulfate at 60 mg/ml, penicillin G potassium at 100 unit/ml, N-2-hydroxyethylpiperazine-N'-2-ethane sulfate at 10 mM, 0.1% sodium bicarbonate, and L-glutamine at 2 mM). After the treatment of lysing of red blood cells, the cells are washed at three times and are adjusted at $5\times10^7$ cells/ml with physiological saline. By injection into right hind foot pad of 100 ul of spleen cell suspension, the host versus graft reaction (HvG reaction) are induced. After 4 days of the injection with cells, both of right and left popliteal lymph nodes are removed and the weight of them are measured. The test compounds are examined by difference of the lymph node weights between right and left as a indicator of HvG reaction. In addition, after 4 days of the injection with cells, blood is obtained from tail vein of the rats and the number of peripheral white blood cells are measured using automatic hemocytometer for animal (MEK-5158, Nihonkouden Co. Ltd.). Test compounds are administered daily for 4 days after the injection with cells intravenously or orally.

Table 1 shows the results obtained from the above methods. The value in the table represents minimum effective dose (mg/kg).

TABLE 1

| Test compound | Inhibitory effect on HvG reaction | Reduction of peripheral white blood cells |
| --- | --- | --- |
| FTY720 | 0.1 | 0.03 |
| Compound of experiment 1 | 0.03 | 0.03 |
| Compound of experiment 3 | 0.03 | 0.03 |
| Compound of experiment 27 | 0.03 | 0.03 |
| Compound of experiment 31 | <0.3 | 3 |
| Compound of experiment 60 | 1 | 3 |
| Compound of experiment 66 | 3 | 3 |

It is presumed that infectious diseases are problems for immunosuppressant using maintenance therapy of organ transplantations or therapy of autoimmune diseases, when immunosuppressant shows the reduction of peripheral white blood cell number. Therefore, in general, for suitable immnuosuppressant, dose showing immunosuppressive activity is lower than the dose showing reduction on white blood cell number and such immunosuppressant is suggested to be highly safe. As indicated in the above result, the compounds in this invention, especially, example 1, 3, 27, 31, 60, 66 of experiments, are useful as a superior immunosuppressants because of the weakness of reduction of peripheral white blood cell number.

EXPERIMENTAL EXAMPLE 5
(Inhibitory effect on graft versus host reaction in rats)

There are two types of graft versus host reactions (GvH reaction) which are systemic and local GvH reactions. Systemic GvH reaction is induced by intravenous administration with cyclophosphamide at 150 mg/kg to 5-weeks old, female (LEWxBN)F1 rats and, by intravenously injection with $5 \times 10^7$ spleen cells from male LEW rats at age of 5 weeks old to them on the next day. Test compounds are examined by determining the survival time after the induction of systemic GvH reaction. Local GvH reaction is induced by subcutaneous injection of $2 \times 10^7$ spleen cells from 5-weeks old, male LEW rats into the right hind foot pad of female (LEWxBN)F1 rats at age of 5 weeks and after 7 days, popliteal lymph nodes are removed and their weights are measured. Test compound are orally administered daily for 30 days and 7 days from the day of cell injection in systemic and local GvH reactions, respectively.

EXPERIMENTAL EXAMPLE 6
(Inhibitory effect on antibody production against sheep red blood cells in mice)

Seven to eight weeks old, female BALB/c mice are immunized by intravenous injection with $1 \times 10^8$ of sheep red blood cells. After 4 days, the spleen is removed, and the number of anti-sheep red blood cell antibody producing cells are counted by direct hemolytic plaque forming assay using sheep red blood cells and guinea pig complement. In this case, the body weights, wet weights of thymus and spleen, and the number of spleen cells are also measured. Test compounds are orally administered daily for 4 days after the day of immunization.

EXPERIMENTAL EXAMPLE 8
(Inhibitory effect on collagen-induced arthritis in rats)

Seven to eight weeks old, male Sprague-Dawley rats are subcutaneously injected by division of 5 portions with 1 ml of emulsion which are prepared by mixing of 0.1 N acetic acid solution containing bovine type II collagen at 2 mg/ml with an equal volume of Freund' incomplete adjuvant. After 7 days, re-immunization is performed by subcutaneous injection with collagen emulsion prepared by the same method into the root of tail. The swelling of right hind foot pad in the rat is periodically measured by using foot volume measuring apparatus (TK-102; Neuroscience Co. Ltd.). Additionally, after 10 and 21 days of primary immunization with collagen, the blood is collected and anti-type II collagen antibody titer in the serum are measured by ELISA method. Test compounds are intravenously or orally administered daily for 21 days from the day of primary immunization.

EXPERIMENTAL EXAMPLE 9
(Inhibitory effect on experimental allergic encephalomyelitis in rats)

Eight weeks old, female LEW rats are immunized by subcutaneous injection to their right hind foot pad with 0.1 ml of emulsion of Freund' complete adjuvant containing 100 mg of myelin basic protein (MBP) purified from spinal cord of guinea pigs and 100 mg of died Mycobacterium tuberculosis H37 RA. Thereafter somatic symptoms after immunization are judged according to the standards of 6 levels.

Score 0: No symptoms
Score 1: Weakness of tail
Score 2: Weakness of hind legs
Score 3: Paralysis of hind leg in only one side
Score 4: Paralysis of both hind legs
Score 5: Incontinence of urine or death Additionally, after 20 days of immunization with MBP, the spinal cords are removed from the rats to make tissue section and the histology of them are investigated after staining by Hematoxylin-Eosin method. Test compounds are orally administered daily for 20 days after the day of immunization.

EXPERIMENTAL EXAMPLE 10
(Inhibitory effect on experimental autoimmune uveitis)

Eight weeks old, female LEW rats are immunized by subcutaneous injection to their right hind foot pad with 0.1 ml of emulsion of Freund' complete adjuvant containing 30 mg of soluble antigen (s-antigen) purified from bovine retina and 100 mg of died Mycobacterium tuberculosis H37 RA. Onset and seriousness of uveitis are periodically inspected after the immunization. Seriousness of uveitis are judged according to the following standards.

Score 0: No inflammation
Score 1: Weak, or light
Score 2: Medium
Score 3: Strong Additionally, After 15 days of immunization with s-antigen, eyes are removed from the rats to make tissue section and the histology of them are investigated after staining by Hematoxylin-Eosin method.

Score 0: No infiltration of inflammation-associated cells
Score 1: Slight infiltration
Score 2: Weak or light infiltration
Score 3: Medium infiltration and partial destruction of cells in retina
Score 4: Remarkable infiltration and complete destruction of cells in retina Test compounds are orally administered daily for 15 days after the day of immunization.

EXPERIMENTAL EXAMPLE 11
(Effect on survival of MRL/lpr mice as a model of systemic lupus erythematosus)

Test compounds are orally administered to male MRL/lpr mice. The administration is continued for 8 to 40 weeks of age at three times a week, namely on Monday, Wednesday and Friday. Mortality is recorded and, blood and urine obtained from the animals periodically are measured the titers of anti-nuclear antibodies and rheumatoid factor in the serum, and protein in the urine.

EXPERIMENTAL EXAMPLE 12
(Take-prolonging effect of skin graft on allogenic skin graft in rats)

A full-thickness graft (1.5×1.5 cm) of a 4 weeks-old male WKAH rat or LEW rat is grafted to a graft floor on the back of a 4 weeks-old male F344 rat by suture. The graft is covered with a sterile gauze and bound. The bandage is removed 5 days after the grafting and the skin graft is observed daily until it is rejected. The skin graft is considered to be rejected when 90% or more of the epithelium of the skin graft showed necrosis and turned brown. The number of days from the grafting to rejection is taken as a graft taking days. Test compounds are intraperitoneally, intravenously or orally administered once a day and 10 times from the grafting day to day 9.

When test compounds are not administered, an average taking days for grafting the skin of a WKAH rat to an F344 rat was 6.6±0.5 and that for grafting the skin of an LEW rat to an F344 rat was 8.2±0.4.

Of the compounds of the present invention, a preferred compound showed, when administered at 0.1–10 mg/kg, an average taking days of not less than 10 for grafting the skin of a WKAH rat to an F344 rat and not less than 20 for grafting the skin of an LEW rat to an F344 rat, thus showing a take-prolonging effect statistically significant as compared with the group without administration of the test compound.

EXPERIMENTAL EXAMPLE 13
(Take-prolonging effect on graft survival of cardiac graft on allogenic cardiac graft in rats)

The hearts from the male WKAH rats at 10 weeks of age are heterotopicaly transplanted in subcutaneous locations at cervixes of male ACI/N rats at 10 weeks of age using vascular anastomosis. The transplanted hearts are judged to be rejected in case of the cessation of heart beat, then survival time was calculated. Test compounds are orally administered for 15 days from the day of transplantation.

EXPERIMENTAL EXAMPLE 14
(Take-prolonging effect on graft survival of renal graft on allogenic renal graft in dogs)

Mongrel and beagle dogs are used as donors and recipients, respectively, and then prolonging effect on the survival of transplanted kidney are examined by performing surgery of renal transplantation. After the transplantation, blood obtained from the transplanted animals periodically is measured the levels of serum creatinine and blood urea nitrogen (BUN).

Formulation Examples:

| (1) Soft capsules (per capsule) | |
|---|---|
| Compound of the present invention | 30 mg |
| Polyethylene glycol 300 | 300 mg |
| Polysolbate 80 | 20 mg |
| Total | 350 mg |

Production method

Polyethylene glycol 300 and Polysolbate 80 are added to a compound of the present invention and the mixture is packed in a soft capsule.

(2) Injections (per 10 ml in one ampoule)

| Compound of the present invention | 0.3% |
|---|---|
| Polyethylene glycol 300 | 20% |
| Ethanol | 60% |
| Injectable distilled water | amount to make the total 10 ml |

Production method

Ethanol and Polyethylene glycol 300 are added to a compound of the present invention and injectable distilled water is added to reach the total amount.

Injections containing 30 ml of the compound of the present invention in one ampoule (10 ml) are thus obtained.

What is claimed is:

1. A benzene compound of the formula:

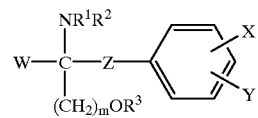

wherein,

W is $R^4O\,(CH_2)_n$;

X is a straight-chain alkyl having carbon atoms in the number of p or a straight-chain alkoxy having carbon atoms in the number of (p−1), wherein the straight-chain alkyl having carbon atoms in the number of p and the straight-chain alkoxy having carbon atoms in the number of (p−1) may have 1 to 3 substituents selected from the group consisting of an alkyl, hydroxy, an alkoxy, an acyloxy, amino, an alkylamino, an acylamino, oxo, a haloalkyl, a halogen and a phenyl which may have 1 to 3 substituents selected from the group consisting of an alkyl, hydroxy, an alkoxy, an acyl, an acyloxy, amino, an alkylamino, an acylamino, a haloalkyl and a halogen;

Y is hydrogen, an alkyl, hydroxy, an alkoxy, an acyl, an acyloxy, amino, an alkylamino, an acylamino, a haloalkyl or a halogen;

Z is a straight-chain alkylene having carbon atoms in the number of q;

p and q are the same or different and each is an integer of 1 to 20, with the proviso of $6 \leq p+q \leq 23$;

m is 1, 2 or 3;

n is 2 or 3;

$R^1$ and $R^2$ are the same or different and each is hydrogen, an alkyl or an acyl;

$R^3$ is hydrogen, an alkyl or an acyl; and $R^4$ is hydrogen, an alkyl or an acyl, an optically active isomer thereof or a salt thereof.

2. A benzene compound according to claim 1 of the formula:

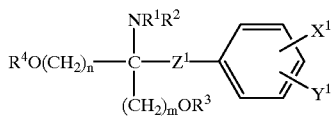

wherein
- $X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
- $Y^1$ is hydrogen, an alkyl, hydroxy or an alkoxy;
- $Z^1$ is a straight-chain alkylene having 2 to 4 carbon atoms;
- m is 1, 2 or 3;
- n is 2 or 3;
- $R^1$ and $R^2$ are the same or different and each is hydrogen, an alkyl or an acyl;
- $R^3$ is hydrogen, an alkyl or an acyl; and
- $R^4$ is hydrogen, an alkyl or an acyl, an optically active isomer thereof or a salt thereof.

3. The benzene compound of claim 2, having the formula:

(I-p)

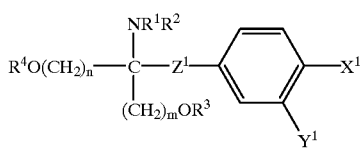

wherein
- $X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
- $Y^1$ is hydrogen, an alkyl, hydroxy or an alkoxy;
- $Z^1$ is a straight-chain alkylene having 2 to 4 carbon atoms;
- m is 1, 2 or 3; n is 2 or 3;
- $R^1$ and $R^2$ are the same or different and each is hydrogen, an alkyl or an acyl;
- $R^3$ is hydrogen, an alkyl or an acyl; and
- $R^4$ is hydrogen, an alkyl or an acyl, an optically active isomer thereof or a salt thereof.

4. The benzene compound of claim 3, having the formula:

(I-q)

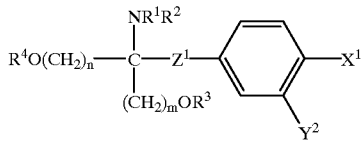

wherein
- $X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
- $Y^2$ is hydrogen, hydroxy or an alkoxy;
- $Z^1$ is a straight-chain alkylene having 2 to 4 carbon atoms;
- m is 1, 2 or 3; n is 2 or 3;
- $R^1$ and $R^2$ are the same or different and each is hydrogen, an alkyl or an acyl;
- $R^3$ is hydrogen, an alkyl or an acyl; and
- $R^4$ is hydrogen, an alkyl or an acyl, an optically active isomer thereof or a salt thereof.

5. The benzene compound of claim 4, having the formula:

(I-r)

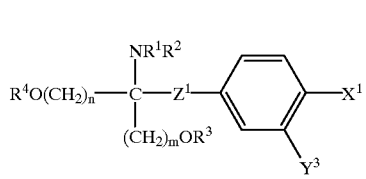

wherein
- $X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
- $Y^3$ is hydrogen or an alkoxy;
- $Z^1$ is a straight-chain alkylene having 2 to 4 carbon atoms;
- m is 1, 2 or 3; n is 2 or 3;
- $R^1$ and $R^2$ are the same or different and each is hydrogen, an alkyl or an acyl;
- $R^3$ is hydrogen, an alkyl or an acyl; and
- $R^4$ is hydrogen, an alkyl or an acyl, an optically active isomer thereof or a salt thereof.

6. The benzene compound of claim 3, having the formula:

(I-s)

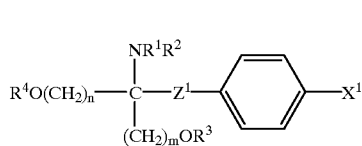

wherein
- $X^1$ is a straight-chain alkyl having 5 to 19 carbon atoms or a straight-chain alkoxy having 4 to 18 carbon atoms, wherein the straight-chain alkyl having 5 to 19 carbon atoms and the straight-chain alkoxy having 4 to 18 carbon atoms may have 1 to 3 substituents selected from the group consisting of hydroxy, an acyloxy, amino, an acylamino, oxo and phenyl;
- $Z^1$ is a straight-chain alkylene having 2 to 4 carbon atoms;
- m is 1, 2 or 3; n is 2 or 3;
- $R^1$ and $R^2$ are the same or different and each is hydrogen, an alkyl or an acyl;
- $R^3$ is hydrogen, an alkyl or an acyl; and
- $R^4$ is hydrogen, an alkyl or an acyl, an optically active isomer thereof or a salt thereof.

7. The benzene compound of claim 6, having the formula:

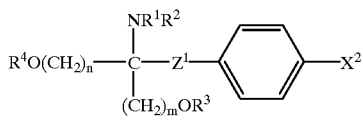

(I-t)

wherein
- $X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;
- $Z^1$ is a straight-chain alkylene having 2 to 4 carbon atoms;
- m is 1, 2 or 3; n is 2 or 3;
- $R^1$ and $R^2$ are the same or different and each is hydrogen, an alkyl or an acyl;
- $R^3$ is hydrogen, an alkyl or an acyl; and
- $R^4$ is hydrogen, an alkyl or an acyl, an optically active isomer thereof or a salt thereof.

8. The benzene compound of claim 7, having the formula:

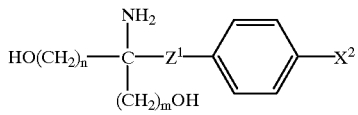

(I-u)

wherein
- $X^2$ is a straight-chain alkyl having 7 to 12 carbon atoms or a straight-chain alkoxy having 6 to 11 carbon atoms, wherein the straight-chain alkyl having 7 to 12 carbon atoms and the straight-chain alkoxy having 6 to 11 carbon atoms may have 1 to 3 substituents selected from the group consisting of hydroxy, an acyloxy, amino, an acylamino and oxo;
- $Z^1$ is a straight-chain alkylene having 2 to 4 carbon atoms;
- m is 1, 2 or 3; and n is 2 or 3, an optically active isomer thereof or a salt thereof.

9. The benzene compound of claim 8, which is selected from the group consisting of:
2-amino-2-[3-(4-heptylphenyl)propyl]butane-1,4-diol,
2-amino-2-[3-(4-nonylphenyl)propyl]butane-1,4-diol,
2-amino-2-[3-(4-undecylphenyl)propyl]butane-1,4-diol,
2-amino-2-[2-(4-octylphenyl)ethyl]butane-1,4-diol,
2-amino-2-[2-(4-decylphenyl)ethyl]butane-1,4-diol,
2-amino-2-[2-(4-dodecylphenyl)ethyl]butane-1,4-diol,
2-amino-2-[2-(4-heptyloxyphenyl)ethyl]butane-1,4-diol,
2-amino-2-[2-(4-octylphenyl)ethyl]pentane-1,5-diol,
3-amino-3-[2-(4-octylphenyl)ethyl]pentane-1,5-diol and
3-amino-3-[2-(4-octylphenyl)ethyl]hexane-1,6-diol,
an optically active isomer thereof or a salt thereof.

10. The benzene compound of claim 8, which is selected from the group consisting of:
2-amino-2-[3-(4-heptylphenyl)propyl]butane-1,4-diol,
2-amino-2-[3-(4-nonylphenyl)propyl]butane-1,4-diol,
2-amino-2-[3-(4-undecylphenyl)propyl]butane-1,4-diol,
2-amino-2-[2-(4-octylphenyl)ethyl]butane-1,4-diol,
2-amino-2-[2-(4-decylphenyl)ethyl]butane-1,4-diol,
2-amino-2-[2-(4-dodecylphenyl)ethyl]butane-1,4-diol,
2-amino-2-[2-(4-heptyloxyphenyl)ethyl]butane-1,4-diol,
2-amino-2-[2-(4-octylphenyl)ethyl]pentane-1,5-diol and
3-amino-3-[2-(4-octylphenyl)ethyl]hexane-1,6-diol,
an optically active isomer thereof or a salt thereof.

11. The benzene compound of claim 8, which is
2-amino-2-[3-(4-nonylphenyl)propyl]butane-1,4-diol,
an optically active isomer thereof or a salt thereof.

12. A pharmaceutical composition comprising the compound claimed 1.

13. A method for immunosuppression of an immune system of a mammal comprising administering to a mammal a therapeutically effective amount of a benzene compound of claim 1.

14. The method according to claim 13, wherein the immunosuppression comprises suppressing rejection in an organ or bone marrow transplantation.

15. The method according to claim 14, wherein the suppressing of rejection in an organ or bone marrow transplantation comprises preventing treatment of graft-versus-host diseases.

16. A method for the prevention or treatment of an autoimmune disease comprising administering to a mammal a therapeutically effective amount of a benzene compound of claim 1.

17. The method according to claim 10, wherein the autoimmune disease is rheumatoid arthritis.

18. The method according to claim 10, wherein the autoimmune disease is psoriasis or atopic dermatitis.

19. The method according to claim 10, wherein the autoimmune disease is bronchial asthma or pollinosis.

20. The method according to claim 10, wherein the autoimmune disease is Behcet's disease or uveitis.

21. The method according to claim 10, wherein the autoimmune disease is systemic lupus erythematosus.

22. The method according to claim 10, wherein the autoimmune disease is multiple sclerosis.

23. A method for the prevention or treatment of an allergy disease comprising administering to a mammal a therapeutically effective amount of a benzene compound of claim 1.

* * * * *